United States Patent
Yamamoto et al.

(10) Patent No.: US 10,633,590 B2
(45) Date of Patent: *Apr. 28, 2020

(54) LIQUID CRYSTAL COMPOSITION AND LIQUID CRYSTAL DISPLAY DEVICE INCLUDING THE SAME

(71) Applicant: DIC CORPORATION, Tokyo (JP)

(72) Inventors: Junko Yamamoto, Kita-adachi-gun (JP); Tomoaki Hara, Kita-adachi-gun (JP); Go Sudo, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 67 days.

This patent is subject to a terminal disclaimer.

(21) Appl. No.: 15/751,342

(22) PCT Filed: Aug. 25, 2016

(86) PCT No.: PCT/JP2016/074800
§ 371 (c)(1),
(2) Date: Feb. 8, 2018

(87) PCT Pub. No.: WO2017/038617
PCT Pub. Date: Mar. 9, 2017

(65) Prior Publication Data
US 2018/0230383 A1    Aug. 16, 2018

(30) Foreign Application Priority Data

Sep. 4, 2015 (JP) ................. 2015-174812

(51) Int. Cl.
| | |
|---|---|
| *C09K 19/34* | (2006.01) |
| *C09K 19/54* | (2006.01) |
| *C07D 207/09* | (2006.01) |
| *C07D 207/16* | (2006.01) |
| *C09K 19/30* | (2006.01) |
| *C09K 19/32* | (2006.01) |
| *G02F 1/137* | (2006.01) |
| *C09K 19/12* | (2006.01) |
| *C09K 19/04* | (2006.01) |

(52) U.S. Cl.
CPC ............ *C09K 19/54* (2013.01); *C07D 207/09* (2013.01); *C07D 207/16* (2013.01); *C09K 19/3003* (2013.01); *C09K 19/3066* (2013.01); *C09K 19/322* (2013.01); *C09K 19/3402* (2013.01); *G02F 1/137* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3019* (2013.01); *C09K 2019/3021* (2013.01); *C09K 2019/3025* (2013.01); *C09K 2019/3422* (2013.01); *G02F 2001/13706* (2013.01); *G02F 2001/13712* (2013.01)

(58) Field of Classification Search
CPC ..................................................... C09K 19/56
See application file for complete search history.

(56) References Cited

U.S. PATENT DOCUMENTS

| | | | |
|---|---|---|---|
| 3,020,288 A | | 2/1962 | Wragg et al. |
| 3,838,059 A | | 9/1974 | Shi-Yin Wong |
| 4,105,626 A | | 8/1978 | Brunetti et al. |
| 4,111,901 A | | 9/1978 | Hechenbleikner |
| 4,336,183 A | | 6/1982 | Nakahara et al. |
| 4,731,376 A | | 3/1988 | Hideg et al. |
| 4,946,880 A | * | 8/1990 | Costanzi .............. C07D 207/08 524/96 |

(Continued)

FOREIGN PATENT DOCUMENTS

| | | |
|---|---|---|
| EP | 2894476 A1 | 7/2015 |
| JP | 48-97780 A | 12/1973 |

(Continued)

OTHER PUBLICATIONS

International Search Report dated Nov. 8, 2016, issued in counterpart International Application No. PCT/JP2016/074800 (2 pages).
Notification of Reasons for Refusal dated Sep. 14, 2017, issued in counterpart Japanese Patent Application No. 2017-534626 w/English translation (9 pages).
Non-Final Office Action dated Jun. 14, 2019, issued in U.S. Appl. No. 15/745,804 (14 pages).
International Search Report dated Oct. 11, 2016, issued in application No. PCT/JP2016/071843 (counterpart to U.S. Appl. No. 15/745,804 (2 pages).

(Continued)

*Primary Examiner* — Chanceity N Robinson
(74) *Attorney, Agent, or Firm* — Westerman, Hattori, Daniels & Adrian, LLP

(57) ABSTRACT

The present application provides a liquid crystal composition with high dielectric constant anisotropy and a low viscosity, and to provide a liquid crystal display device with high contrast, high-speed responsivity, high light fastness, and high display quality without image sticking and display defects. The liquid crystal composition contains one or two or more compounds represented by the general formula (I). The liquid crystal composition is of great practical use as a liquid crystal composition for use in liquid crystal displays and is effective for high contrast, high-speed response, and high quality reliability.

(I)

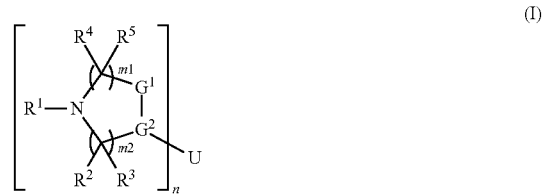

9 Claims, No Drawings

(56) References Cited

U.S. PATENT DOCUMENTS

| | | | |
|---|---|---|---|
| 5,032,600 A | 7/1991 | Hideg et al. | |
| 5,264,204 A | 11/1993 | Cacheris et al. | |
| 5,567,411 A | 10/1996 | Keana et al. | |
| 5,714,510 A | 2/1998 | Proctor | |
| 6,441,088 B1 | 8/2002 | Kaul et al. | |
| 9,604,932 B2 | 3/2017 | Salzman et al. | |
| 2003/0215390 A1 | 11/2003 | Rosen | |
| 2006/0011886 A1 | 1/2006 | Li et al. | |
| 2009/0233128 A1 | 9/2009 | Ito | |
| 2013/0037745 A1 | 2/2013 | Hung | |
| 2013/0248763 A1 | 9/2013 | Goebel et al. | |
| 2013/0258268 A1 | 10/2013 | Goebel et al. | |
| 2014/0110630 A1 | 4/2014 | Goebel et al. | |
| 2014/0111730 A1 | 4/2014 | Goebel et al. | |
| 2015/0192852 A1 | 7/2015 | Sato et al. | |
| 2015/0273087 A1 | 10/2015 | Rosen | |
| 2015/0376203 A1 | 12/2015 | Zhao | |
| 2016/0122647 A1 | 5/2016 | Furusato et al. | |
| 2016/0145491 A1 | 5/2016 | Furusato et al. | |
| 2016/0208172 A1* | 7/2016 | Gotoh | C09K 19/32 |
| 2016/0289189 A1 | 10/2016 | Gotoh et al. | |
| 2016/0376505 A1 | 12/2016 | Furusato et al. | |
| 2017/0209695 A1 | 7/2017 | Solomon | |
| 2018/0230383 A1 | 8/2018 | Yamamoto et al. | |

FOREIGN PATENT DOCUMENTS

| | | |
|---|---|---|
| JP | S51-143674 A | 12/1976 |
| JP | S56-11932 | 2/1981 |
| JP | 57-10663 A | 1/1982 |
| JP | S60-67587 A | 4/1985 |
| JP | 60-500668 A | 5/1985 |
| JP | 60-500669 A | 5/1985 |
| JP | 60-190786 A | 9/1985 |
| JP | 63-101389 A | 5/1988 |
| JP | 2-265966 A | 10/1990 |
| JP | 5-117324 A | 5/1993 |
| JP | 9-291282 A | 11/1997 |
| JP | 2002-256267 A | 9/2002 |
| JP | 2004-507607 A | 3/2004 |
| JP | 2004-524259 A | 8/2004 |
| JP | 2006-124544 A | 5/2006 |
| JP | 2006-206819 A | 8/2006 |
| JP | 2007-165197 A | 6/2007 |
| JP | 2012-515206 A | 7/2012 |
| JP | 2013-36038 A | 2/2013 |
| JP | 2014-505745 A | 3/2014 |
| JP | 2014-505746 A | 3/2014 |
| JP | 2014-84460 A | 5/2014 |
| JP | 2014-84462 A | 5/2014 |
| JP | 2014-91697 A | 5/2014 |
| JP | 2016-132678 A | 7/2016 |
| JP | 2017-523015 A | 8/2017 |
| WO | 93/22662 A1 | 11/1993 |
| WO | 2014/045783 A1 | 3/2014 |
| WO | 2014/066230 A1 | 5/2014 |
| WO | 2014/136059 A2 | 9/2014 |
| WO | 2014/208320 A1 | 12/2014 |
| WO | 2015/001916 A1 | 1/2015 |
| WO | 2015/076077 A1 | 5/2015 |
| WO | 2015/079797 A1 | 6/2015 |
| WO | 2015/107071 A1 | 7/2015 |
| WO | 2017/038552 A1 | 3/2017 |
| WO | 2017/038617 A1 | 3/2017 |

OTHER PUBLICATIONS

Office Action dated Jun. 15, 2017, issued in JP application No. 2017-527392 (counterpart to U.S. Appl. No. 15/745,804), w/ English translation. (8 pages).

Caproiu et al., "Synthesis and characterisation of several di-, tri-, and tetra- radicals linked by flexible or rigid linkers", ARKIVOC, 2008, No. 14, pp. 158-165, Cited in ISR dated Nov. 15, 2016 and JP Notification of Reasons for Refusal dated Aug. 3, 2017 (8 pages).

MATSUMOTO et al., "Modification of nitroxyl contrast agents with multiple spins and their proton TI relaxivity", Magnetic Resonance Imaging, 2008, vol. 26, No. 1, pp. 117-121, Cited in ISR dated Nov. 15, 2016 and JP Notification of Reasons for Refusal dated Aug. 3, 2017 (5 pages).

Bosman et al., "Five Generations of Nitroxyl-Functionalized Dendrimers", Macromolecules, 1997, vol. 30, No. 12, pp. 3606-3611, Cited in ISR dated Nov. 15, 2016 and JP Notification of Reasons for Refusal dated Aug. 3, 2017 (6 pages).

Gallez et al., "Evaluation of Nonionic Nitroxyl Lipids as Potential Organ-Specific Contrast Agents for Magnetic Resonance Imaging", Magnetic Resonance Imaging, 1992, vol. 10, No. 3, pp. 445-455, Cited in ISR dated Nov. 15, 2016 and JP Notification of Reasons for Refusal dated Aug. 3, 2017 (11 pages).

Valera et al., "A Modular Approach for the Synthesis of Nanometer-Sized Polynitroxide Multi-Spin Systems", The Journal of Organic Chemistry, 2014, vol. 79, No. 17, pp. 8313-8323, Cited in ISR dated Nov. 15, 2016 and JP Notification of Reasons for Refusal dated Aug. 3, 2017 (11 pages).

Schuetz et al., "4,4'',4Δ-(Methanetriyl)triphenyl tris-(2,2,5,5-tetramethyl-1-oxyl-3-pyrroline-3-carboxylate) benzene trisolvate", Acta Crystallographica Section E: Structure Reports Online, 2010, vol. 66, No. 4, pp. o729-o730, Cited in ISR dated Nov. 15, 2016 and JP Notification of Reasons for Refusal dated Aug. 3, 2017 (18 pages).

Sen et al., "Synthesis and Structure of Products of Hydroxylamine Acylation with 3-Carboxy-2,2,5,5-tetramethylpyrrolinoxyl Derivatives", Russian Journal of Organic Chemistry, 2009, vol. 45, No. 8, pp. 1189-1199, Cited in ISR dated Nov. 15, 2016 and JP Notification of Reasons for Refusal dated Aug. 3, 2017 (11 pages).

Jaszberenyi et al., "Synthesis, Equilibrium and Kinetic Properties of Gd3+ Complexes of Three DTPA-Bis(Amide) Derivatives Containing Stable Nitroxide Free Radical Substituents", European Journal of Inorganic Chemistry, 2003, No. 19, pp. 3601-3608, Cited in ISR dated Nov. 15, 2016 and JP Notification of Reasons for Refusal dated Aug. 3, 2017 (8 pages).

Martin et al., "Novel pH-Sensitive Nitroxide Di- and Tri-radical Spin Labels", Journal of the Chemical Society, Chemical Communications, 1995, No. 7, pp. 723-724, Cited in ISR dated Nov. 15, 2016 and JP Notification of Reasons for Refusal dated Aug. 3, 2017 (2 pages).

Brik, "Synthesis of Di and Polynitroxides by Favorskii Rearrangement of Polyamines on Cis—3,5-Dibromo—4-OXO-2,2,6,6-Tetramethylpiperidin-1-Oxyl", Synthetic Communications, 1990, vol. 20, No. 10, pp. 1487-1495, Cited in ISR dated Nov. 15, 2016 and JP Notification of Reasons for Refusal dated Aug. 3, 2017 (9 pages).

Brik et al., "Evaluation of MRI contrast by using polynitroxides: application to magnetic resonance imaging of lungs and liver" in French, Analusis, 1990, vol. 18, No. 3, pp. 179-184, Cited in ISR dated Nov. 15, 2016 and JP Notification of Reasons for Refusal dated Aug. 3, 2017 (6 pages).

Shapiro et al., "Iminoxyl biradicals with polyene bridges, Izvestiya Akademii Nauk SSSR" in Russian, Seriya Khimicheskaya, 1976, No. 9, pp. 2124-2127, Cited in ISR dated Nov. 15, 2016 and JP Notification of Reasons for Refusal dated Aug. 3, 2017 (4 pages).

Ferruti et al., "Synthesis of Mono-, Di-, and Polynitroxides. Classification of Electron Spin Resonance Spectra of Flexible Dinitroxides Dissolved in Liquids and Glasses", Journal of the American Chemical Society, Jun. 17, 1970, vol. 92, No. 12, pp. 3704-3713, Cited in ISR dated Nov. 15, 2016 and JP Notification of Reasons for Refusal dated Aug. 3, 2017 (10 pages).

Krinitskaya,L. A. et al, Individual iminoxyl polyradicals of hydrogenated pyrrole, Zhurnal Organicheskoi Khimii in Russian, 1966, vol. 2, No. 7, pp. 1301-1305, Cited in ISR dated Nov. 15, 2016 and JP Notification of Reasons for Refusal dated Aug. 3, 2017 (5 pages).

Corvaja et al., "Electron Spin Resonance Studies of Nitroxide Radicals and Biradicals in Nematic Solvents", Journal of the American Chemical Society, Jul. 1, 1970, vol. 92, No. 13, pp. 3919-3924, Cited in ISR dated Nov. 15, 2016 and JP Notification of Reasons for Refusal dated Aug. 3, 2017 (6 pages).

Yamaoka et al., "Spin-Labeled Metachromatic Dyes. I. ESR and Some Optical Properties of Spin-Labeled Proflavine in Solution,

(56) References Cited

OTHER PUBLICATIONS

Liquid Crystal, and Stretched Film", Chemistry Letters, 1976, No. 12, pp. 1351-1354, Cited in ISR dated Nov. 15, 2016 and JP Notification of Reasons for Refusal dated Aug. 3, 2017 (4 pages).
Setaka et al., "Orientation of Some Nitroxide Spin Labels in the Lamellar Mesophases of Aerosol-OT-Water and Decanol-Decanoate-Water Systems", Journal of the American Chemical Society, Oct. 15, 1975, vol. 97, No. 21, pp. 6013-6018, Cited in ISR dated Nov. 15, 2016 and JP Notification of Reasons for Refusal dated Aug. 3, 2017 (6 pages).
Hatano et al., "Facile Synthesis of 3-Methoxycarbonyl-2,2,5,5-Tetra-Methylpyrrolidine-1-Oxyl and Derivatives", Heterocycles, 2010, vol. 81, No. 2, pp. 349-356, Cited in ISR dated Nov. 15, 2016 and JP Notification of Reasons for Refusal dated Aug. 3, 2017 (8 pages).
Chemical Abstract, 1987, vol. 107, p. 672, 107:39524b, Kyazimov et. al., "Liquid-phase catalytic oxidation of dimethyl phthalate and allyl chloride", Neftekhimiya, 1986, vol. 26, No. 4, pp. 549-553, Cited in ISR and Japanese Notification of Reasons for Refusal (1 page).
International Search Report dated Nov. 15, 2016, issued in counterpart International Application No. PCT/JP2016/074474 (8 pages).
Notification of Reasons for Refusal dated Aug. 3, 2017, issued in counterpart JP Application No. 2017-529113, with English translation (12 pages).
Nakatsuji, Shinichi et al., "Organic biradical compounds with a mesogenic core and long alkoxy groups: preparation, structures and magnetic properties", Journal of Physical Organic Chemistry, 2006, vol. 19, pp. 333-340.
Non-Final Office Action dated Nov. 19, 2018, issued in U.S. Appl. No. 15/751,380 (7 pages).

\* cited by examiner

LIQUID CRYSTAL COMPOSITION AND LIQUID CRYSTAL DISPLAY DEVICE INCLUDING THE SAME

TECHNICAL FIELD

The present invention relates to a liquid crystal composition useful as an electrooptical liquid crystal display material.

BACKGROUND ART

Liquid crystal display devices are used in various measuring instruments, automotive panels, word processors, electronic notebooks, printers, computers, television sets, clocks and watches, and advertising boards, as well as clocks and watches and electronic calculators. Typical liquid crystal display modes include a twisted nematic (TN) mode, a super twisted nematic (STN) mode, a vertically aligned (VA) mode characterized by vertical alignment including a thin-film transistor (TFT), and an in-plane switching (IPS)/fringe field switching (FFS) mode characterized by horizontal alignment including a thin-film transistor (TFT).

Liquid crystal materials having a negative dielectric constant anisotropy ($\Delta\varepsilon$) are characteristically used in the IPS mode, an electrically controlled birefringence (ECB) mode, the VA mode, and a color super homeotropic (CSH) mode among such display modes. By contrast, liquid crystal compositions having a positive $\Delta\varepsilon$ are used in horizontal alignment displays of the TN mode, the STN mode, and the IPS mode. In recent years, a display drive mode has been reported that includes vertically aligning a liquid crystal composition having a positive $\Delta\varepsilon$ under no voltage application and applying an IPS mode/FFS mode electric field to the liquid crystal composition. In all these drive modes, there is a demand for low-voltage drive, high-speed response, and a wide operating temperature range. In other words, there is a demand for a high absolute $\Delta\varepsilon$, a low viscosity ($\eta$), and a high nematic phase-isotropic liquid phase transition temperature ($T_{ni}$). In order to set the product $\Delta n \times d$ of refractive index anisotropy ($\Delta n$) and cell gap (d) at a predetermined value, the $\Delta n$ of a liquid crystal composition must be adjusted in an appropriate range for the cell gap. Furthermore, liquid crystal display devices for use in television sets require a liquid crystal composition with a low $\gamma_1$ due to the importance of high-speed responsivity. Liquid crystal compositions are generally composed of several to tens of compounds to optimize the $\Delta\varepsilon$ and $\Delta n$ in each display device.

In addition to the demands on the physical properties of liquid crystal compositions, a liquid crystal composition for use in a liquid crystal display device should be stable toward external stimuli, such as water, air, heat, and light. A lack of stability toward external stimuli causes display defects of a liquid crystal display device, such as image sticking or variations in display. A high voltage holding ratio (VHR) is generally believed to be essential to prevent display defects, such as image sticking or variations in display. Thus, it is known that some liquid crystal compositions contain a particular compound in combination with, for example, an antioxidant, an ultraviolet absorber, or a light stabilizer (Patent Literature 1 and Patent Literature 2). Stability toward external stimuli is regarded as important in any application. Thus, further development of a liquid crystal composition that can achieve a high VHR is required.

Furthermore, liquid crystal compositions for use in liquid crystal television sets that require high-speed response need a sufficiently low $\eta$, a sufficiently low $\gamma_1$, a high elastic constant ($K_{33}$), and a high VHR without a decrease in $\Delta n$ and $T_{ni}$. Furthermore, there is a demand for a liquid crystal display device including such a liquid crystal composition with no or few display defects, such as image sticking or variations in display, and with high display quality and a high response speed.

CITATION LIST

Patent Literature

PTL 1: Japanese Unexamined Patent Application Publication No. 2014-84460
PTL 2: Japanese Unexamined Patent Application Publication No. 2014-84462

SUMMARY OF INVENTION

Technical Problem

It is an object of the present invention to provide a liquid crystal composition that is stable toward heat and light and can maintain a high voltage holding ratio and to provide a liquid crystal display device including the liquid crystal composition that has no or few display defects, such as image sticking or variations in display, and has high display quality.

Solution to Problem

The present inventors have completed the present invention by examining various liquid crystal compounds and various chemical substances and finding that a particular compound can be used to solve the problems described above.

The present invention provides a liquid crystal composition containing a compound represented by the general formula (I) and a liquid crystal display device including the liquid crystal composition.

[Chem. 1]

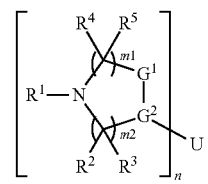

(I)

(In the formula, $R^1$ denotes a hydrogen atom, a hydroxy group, —O., or an alkyl group having 1 to 20 carbon atoms, one —$CH_2$— or two or more nonadjacent —$CH_2$— groups in the alkyl group not directly bonded to a nitrogen atom adjacent to $R^1$ may be independently substituted with —O—, —S—, —CO—, —CO—O—, —O—CO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —C≡C—, —Si(CH$_3$)$_2$—, a trans-1,4-cyclohexylene group, a 1,4-phenylene group, or a naphthalene-2,6-diyl group, and one or two or more hydrogen atoms in $R^1$ may be independently substituted with a fluorine atom, a chlorine atom, or a cyano group, $R^2$, $R^3$, $R^4$, and $R^5$ independently denote a hydrogen atom or an alkyl group having 1 to 8 carbon atoms, $R^R$, $R^3$, $R^4$, and $R^5$ bonded to a carbon atom directly bonded to the nitrogen atom in the ring structure denote an alkyl group, and if $R^2$ and $R^3$, or $R^4$ and $R^5$, or both denote an alkyl group, $R^2$ and $R^3$, or $R^1$ and $R^5$, or both may be bonded together to form a ring, -$G^1$-$G^2$- denotes a group represented by

[Chem. 2]

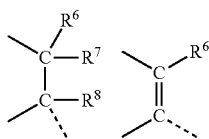

(In the formula, each broken line denotes a bond to U in the general formula (I), $R^6$, $R^7$, and $R^8$ independently denote a hydrogen atom, a hydroxy group, or an alkyl group having 1 to 20 carbon atoms, one —$CH_2$— or two or more nonadjacent —$CH_2$— groups in the alkyl group may be independently substituted with —O—, —S—, —CO—, —CO—O—, —O—CO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —C≡C—, —Si(CH$_3$)$_2$—, a trans-1,4-cyclohexylene group, a 1,4-phenylene group, or a naphthalene-2,6-diyl group, and one or two or more hydrogen atoms in the alkyl group may be independently substituted with a fluorine atom, a chlorine atom, or a cyano group.)

U denotes a hydrogen atom, a fluorine atom, a chlorine atom, a bromine atom, an iodine atom, a pentafluorosulfanyl group, a nitro group, an amino group, a hydroxy group, a mercapto group, or one of monovalent to decavalent organic groups, provided that U has a valence of n, m1 and m2 independently denote an integer in the range of 0 to 3, provided that m1+m2 denotes an integer of 1, 2, 4, 5, or 6, and n denotes an integer in the range of 1 to 10, and pluralities of $R^1$s, $R^2$s, $R^3$s, $R^4$s, $R^5$s, m1s, m2s, and -$G^1$-$G^2$- groups, if present, may be the same or different $R^1$s, $R^2$s, $R^3$s, $R^4$s, $R^5$s, m1s, m2s, and -$G^1$-$G^2$- groups, respectively.)

Advantageous Effects of Invention

A liquid crystal composition according to the present invention is stable toward heat and light and can maintain a high voltage holding ratio. Thus, a liquid crystal display device including the liquid crystal composition has no or few display defects, such as image sticking or variations in display, and high display quality.

DESCRIPTION OF EMBODIMENTS

A liquid crystal composition according to the present invention contains one or two or more compounds represented by the general formula (I).

[Chem. 3]

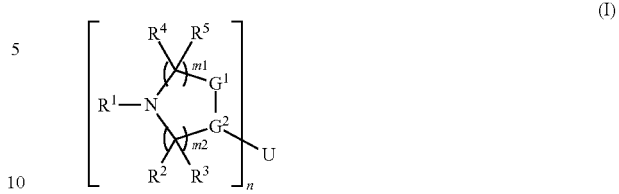

In the general formula (I), $R^1$ preferably denotes a hydrogen atom, an alkyl group having 1 to 20 carbon atoms, an alkoxy group having 1 to 20 carbon atoms, or an alkenyl group having 2 to 20 carbon atoms, more preferably an alkyl group having 1 to 12 carbon atoms, an alkoxy group having 1 to 12 carbon atoms, or an alkenyl group having 3 to 12 carbon atoms, in terms of compatibility in the liquid crystal composition. The alkyl group, alkoxy group, or alkenyl group is preferably in a linear or branched form, preferably in a linear form. A hydrogen atom or a linear alkyl group having 1 to 5 carbon atoms is particularly preferred in terms of manufacturability. In order to improve ability to prevent photodegradation, a hydrogen atom or a hydroxy group is preferred, and a hydrogen atom is particularly preferred.

Among $R^2$, $R^3$, $R^4$, and $R^5$, $R^2$, $R^3$, $R^4$, and $R^5$ bonded to the carbon atom directly bonded to the nitrogen atom in the ring structure preferably independently denote an alkyl group having 1 to 4 carbon atoms, particularly preferably a methyl group in terms of the availability of raw materials and the stability of the compound. Preferably, $R^2$ and $R^3$, or $R^4$ and $R^5$, or both are bonded together to form a ring structure to facilitate the removal of polar impurities introduced during production. If m1 and/or m2 is 2 or 3, $R^2$, $R^3$, $R^4$, and $R^5$ directly bonded to a carbon atom not directly bonded to the nitrogen atom in the ring structure preferably independently denote a hydrogen atom or an alkyl group having 1 to 8 carbon atoms, preferably a hydrogen atom or an alkyl group having 1 to 4 carbon atoms, particularly preferably a hydrogen atom or a methyl group in terms of the availability of raw materials and the stability of the compound.

$G$-$G^2$ denotes a group represented by

[Chem. 4]

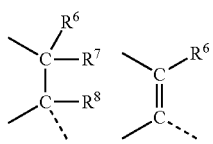

wherein $R^6$, $R^7$, and $R^8$ in the group preferably independently denote a hydrogen atom or an alkyl group having 1 to 12 carbon atoms, preferably a hydrogen atom or an alkyl group having 1 to 8 carbon atoms, preferably a hydrogen atom or an alkyl group having 1 to 4 carbon atoms, particularly preferably a hydrogen atom in terms of manufacturability. The alkyl group is preferably in a linear or branched form, preferably in a linear form. $G^1$-$G^2$ preferably denotes —$CH_2$—CH— or —CH=C— in terms of manufacturability, particularly preferably —$CH_2$—CH— in terms of the stability of the compound. In the case of m1=0 and m2=1, $R^6$, $R^7$, and $R^8$ preferably independently denote an alkyl group having 1 to 8 carbon atoms, more preferably an alkyl group having 1 to 4 carbon atoms, particularly preferably a methyl group in terms of the availability of raw materials and the stability of the compound. The variables m1 and m2 preferably independently denote an integer in the range of 1 to 3, preferably 1. The variable m1+m2 is preferably 2, 4, 5, or 6, preferably 2, 4, or 5, more preferably 2. If m1+m2 is 1, preferably, m1 is 0, and m2 is 1. If m1+m2 is 2, preferably, m1 is 1, and m2 is 1. If m1+m2 is 4, preferably. m1 is 2, and m2 is 2. If m1+m2 is 5, preferably, m1 is 2, and m2 is 3. If m1+m2 is 6, preferably, m1 is 3, and m2 is 3.

The variable n preferably denotes an integer in the range of 1 to 4 in terms of compatibility in the liquid crystal composition. In order to improve the storage stability of the liquid crystal composition, n is preferably 1 or 2. In order to improve ability to prevent photodegradation, n is preferably 3 or 4 due to an increased number of hindered amine structures per unit weight.

U preferably denotes a hydrogen atom or one of monovalent to tetravalent organic groups.

A compound represented by the general formula (I) is preferably one of the compounds represented by the general formulae (I-a) to (I-g).

[Chem. 5]

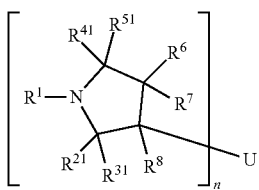
(I-a)

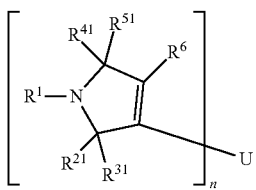
(I-b)

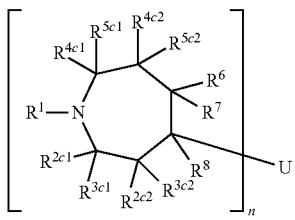
(I-c)

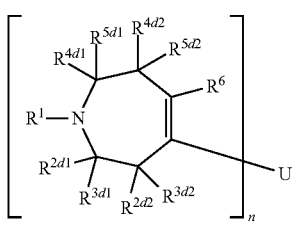
(I-d)

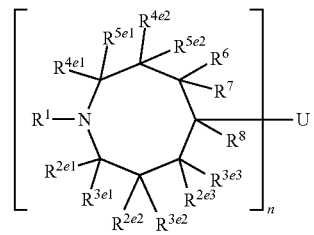
(I-e)

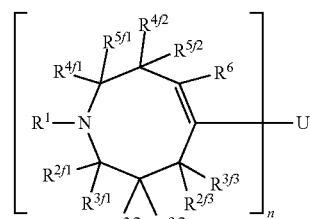
(I-f)

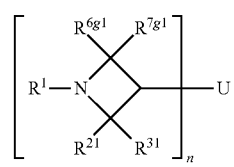
(I-g)

(In the formula, $R^1$, $R^6$ to $R^8$, n, and U have the same meaning as $R^1$, $R^\varepsilon$ to $R^8$, n, and U, respectively, in the general formula (I), $R^{21}$, $R^{31}$. $R^{41}$, $R^{51}$, $R^{2c1}$ to $R^{2f1}$, $R^{3c1}$ to $R^{3f1}$, $R^{4c1}$ to $R^{4f1}$, $R^{5c1}$ to $R^{5f1}$, $R^{6g1}$, and $R^{7g1}$ independently denote an alkyl group having 1 to 8 carbon atoms, and $R^{2c2}$ to $R^{2f2}$, $R^{3c2}$ to $R^{3f2}$, $R^{4c2}$ to $R^{4f2}$, $R^{5c2}$ to $R^{5f2}$, $R^{2e3}$, $R^{2f3}$, $R^{3e3}$, and $R^{3f3}$ independently denote a hydrogen atom or an alkyl group having 1 to 8 carbon atoms.)

In the general formula (I), U preferably denotes a group represented by the general formula (U-1).

[Chem. 6]

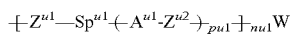
(U-1)

(In the formula, $Z^{u1}$ and $Z^{u2}$ independently denote —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, $A^{u1}$ denotes a group selected from the group consisting of
(a) a 1,4-cyclohexylene group (in which one —CH$_2$— or two or more nonadjacent —CH$_2$— groups may be substituted with —O—),
(b) a 1,4-phenylene group (in which one —CH= or two or more nonadjacent —CH= groups may be substituted with —N=), and
(c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl group or the 1,2,3,4-tetrahydronaphthalene-2,6-diyl group may be substituted with —N=), the groups (a), (b), and (c) may be independently substituted with a fluorine atom, a chlorine atom, a bromine atom, an iodine atom, a pentafluorosulfanyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —$CH_2$— or two or more nonadjacent —$CH_2$— groups in the alkyl group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—, $Sp^{u1}$ denotes a single bond or an alkylene group having 1 to 10 carbon atoms, and one —$CH_2$— or two or more nonadjacent —$CH_2$— groups in the alkylene group not directly bonded to $Z^{u1}$ adjacent to $Sp^{u1}$ may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—, W denotes a hydrogen atom, a fluorine atom, a chlorine atom, a bromine atom, an iodine atom, a pentafluorosulfanyl group, a nitro group, an amino group, a hydroxy group, a mercapto group, or one of monovalent to decavalent organic groups, provided that W has a valence of n in the general formula (I), pu1 denotes an integer in the range of 0 to 8.

nu1 denotes an integer in the range of 1 to 10, and nu1 is identical with n in the general formula (I), and pluralities of $Z^{u1}$s, $Z^{u2}$s, $Sp^{u1}$s, and $A^{u1}$s, if present, may be the same or different $Z^{u1}$s, $Z^{u2}$s, $Sp^{u1}$s, and $A^{u1}$s, respectively.)

In the general formula (U-1), $Z^{u1}$ and $Z^{u2}$ preferably denote —$CH_2O$—, —COO—, —OCO—, —CO—NH—, —COO—CH=CH—, —COO—$CH_2CH_2$—, —COO—$CH_2$—, —$CH_2$—OCO—, —CH=CH—, —C≡C—, or a single bond, more preferably —$CH_2O$—, —COO—, —CO—NH—, or a single bond, in terms of manufacturability.

$Sp^{u1}$ preferably denotes a single bond or an alkylene group having 1 to 8 carbon atoms, more preferably a single bond or an alkylene group having 1 to 6 carbon atoms, and one —$CH_2$— or two or more nonadjacent —$CH_2$— groups in the alkylene group not directly bonded to $Z^{u1}$ adjacent to $Sp^{u1}$ may be independently substituted with —O—, —COO—, —OCO—, —CH=CH—, or —C≡C—$Sp^{u1}$ preferably denotes a single bond in terms of the availability of raw materials and the ease of synthesis.

$A^{u1}$ preferably denotes a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups are preferably independently unsubstituted or may be substituted with a cyano group, a fluorine atom, a chlorine atom, a methyl group, or a methoxy group.

From the perspective of compatibility in the liquid crystal composition and manufacturability, pu1 preferably denotes an integer in the range of 0 to 3, preferably 1 to 3.

The variable nu1 is identical with n in the general formula (I). W preferably denotes a hydrogen atom or one of monovalent to tetravalent organic groups, provided that W has a valence of n in the general formula (I). For example, if n in the general formula (I) is 1, that is, if nu1 in the general formula (U-1) is 1, and W has a valence of 1, then the general formula (U-1) denotes the following.

$$\text{—}[Z^{u1}\text{—}Sp^{u1}\text{—}(A^{u1}\text{-}Z^{u2})_{pu1}]\text{—}W \quad \text{[Chem. 7]}$$

If n in the general formula (I) is 2, that is, if nu1 in the general formula (U-1) is 2, and W has a valence of 2, then the general formula (U-1) denotes the following.

$$\begin{array}{l}\text{—}[Z^{u1}\text{-}Sp^{u1}\text{—}(A^{u1}\text{-}Z^{u2})_{pu1}]\text{—}W \\ \text{—}[(Z^{u2}\text{-}A^{u1})_{pu1}Sp^{u1}\text{-}Z^{u1}]\text{—}\end{array} \quad \text{[Chem. 8]}$$

$Z^{u1}$ in the general formula (U-1) is bonded to $G^2$ in the general formula (I). If $Z^{u1}$ denotes a single bond, $Sp^{u1}$ denotes a single bond, and pu1 is 0, then $G^2$ in the general formula (I) is bonded to W in the general formula (U-1). If $Z^{u1}$ denotes a single bond, $Sp^{u1}$ denotes a single bond, and pu1 denotes an integer in the range of 1 to 3, then G in the general formula (I) is bonded to $A^{u1}$ in the general formula (U-1). The general formula (U-1) does not include a —O—O—, —NH—O—, —O—NH—, —O—S—, or —S—O— group.

In the general formula (I), if n in the general formula (I) is 1, that is, if nu1 in the general formula (U-1) is 1, and W has a valence of 1, then W in the general formula (U-1) preferably denotes a hydrogen atom, a fluorine atom, a chlorine atom, a bromine atom, an iodine atom, a pentafluorosulfanyl group, a nitro group, an amino group, a hydroxy group, a mercapto group, or an alkyl group having 1 to 12 carbon atoms, and one —$CH_2$— or two or more nonadjacent —$CH_2$— groups in the alkyl group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—. From the perspective of manufacturability, W preferably denotes an alkyl group having 1 to 8 carbon atoms, and the alkyl group may be linear or branched, preferably linear.

More specifically, a compound in which n in the general formula (I) is 1 is preferably one of the compounds represented by the following formulae (I-1-1) to (I-1-109).

[Chem. 9]

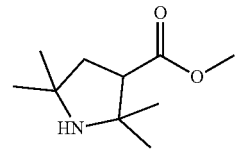

(I-1-1)

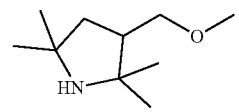

(I-1-2)

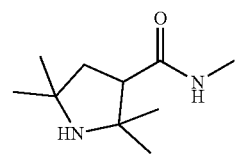

(I-1-3)

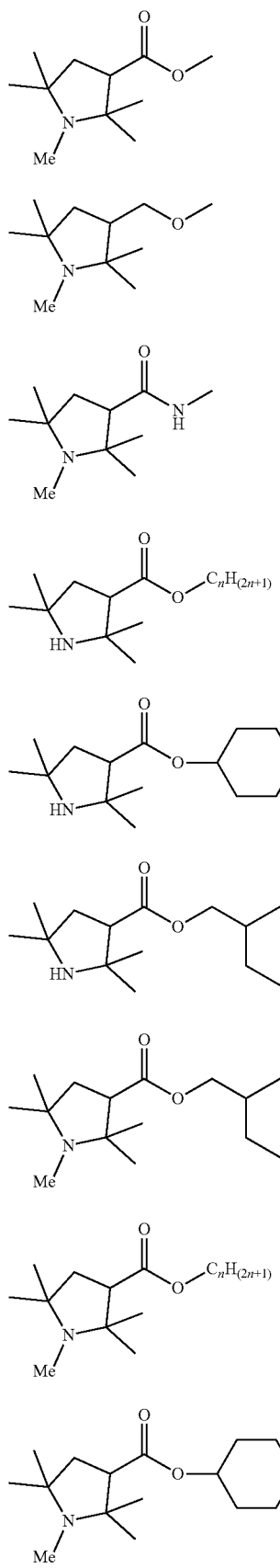
(I-1-4)
(I-1-5)
(I-1-6)
(I-1-7)
(I-1-8)
(I-1-9)
(I-1-10)
(I-1-11)
(I-1-12)
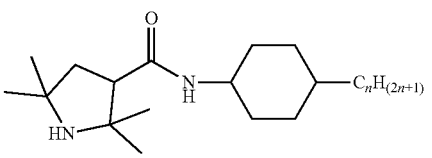
(I-1-13)
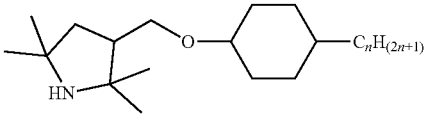
(I-1-14)
[Chem. 10]
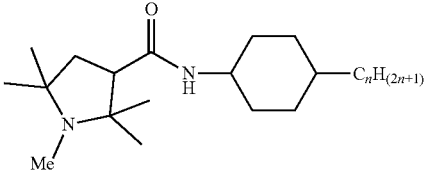
(I-1-15)
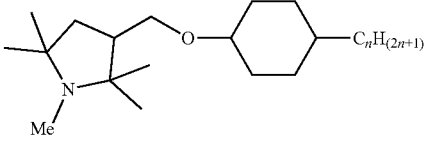
(I-1-16)
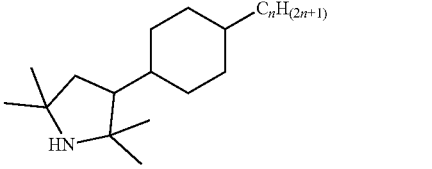
(I-1-17)
(I-1-18)
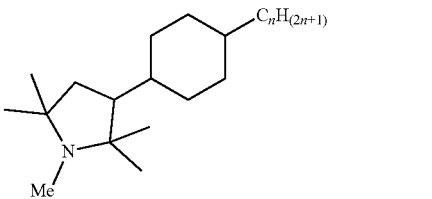
(I-1-19)
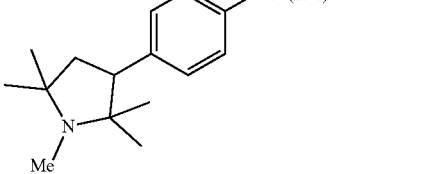
(I-1-20)

(I-1-21) 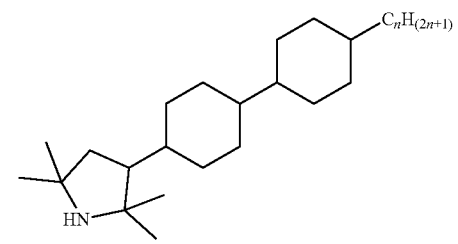
(I-1-22) 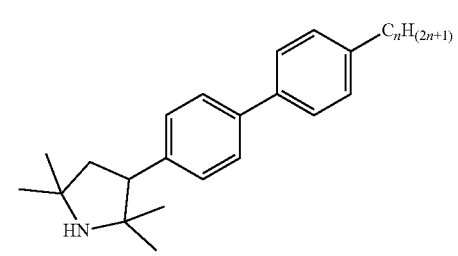
(I-1-23) 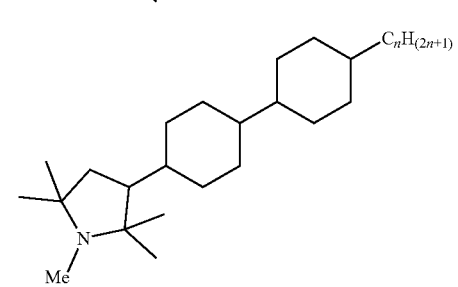
(I-1-24) 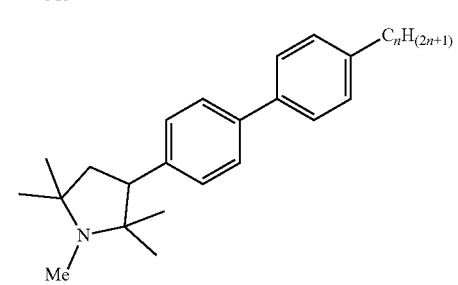
(I-1-25) 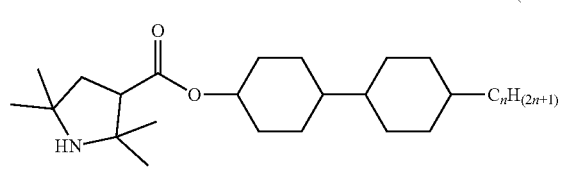
(I-1-26) 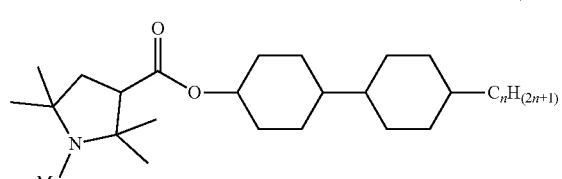
[Chem. 11]
(I-1-27) 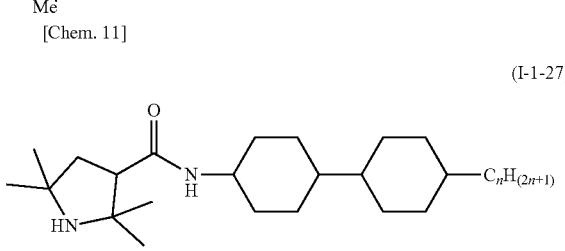
(I-1-28) 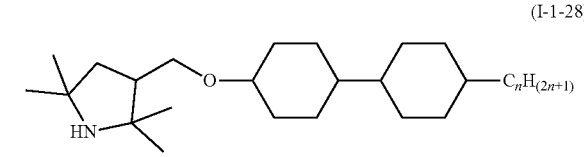
(I-1-29) 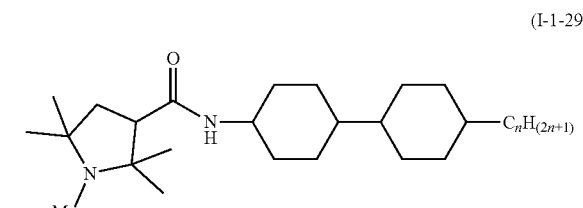
(I-1-30) 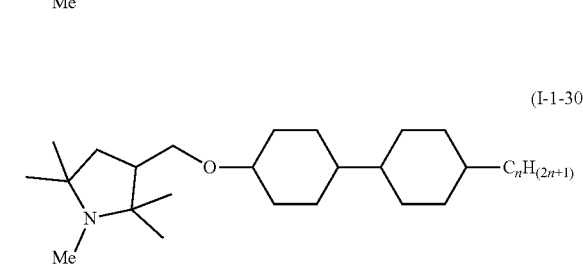
(I-1-31) 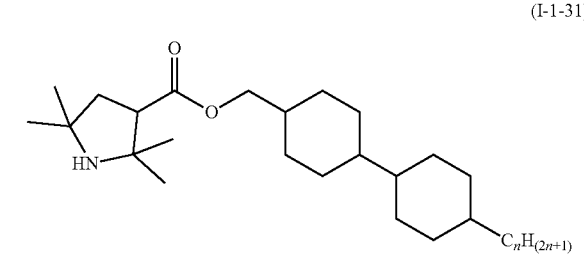
(I-1-32) 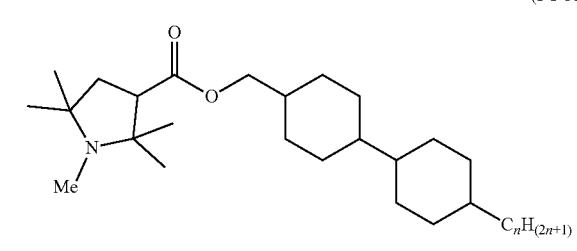
(I-1-33) 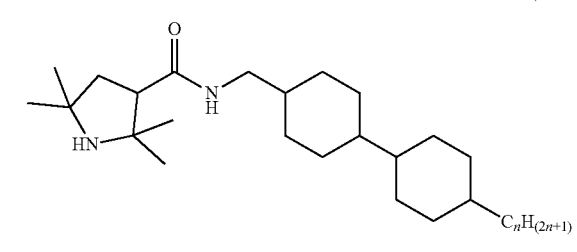
(I-1-34) 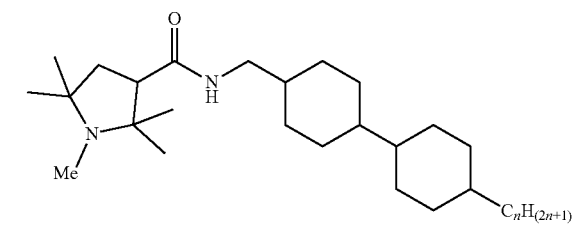

(I-1-35)
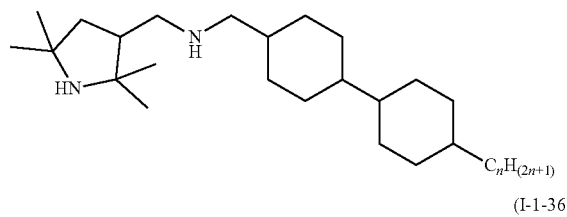
(I-1-36)
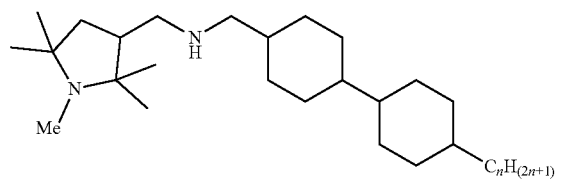
(I-1-37)
(I-1-38)
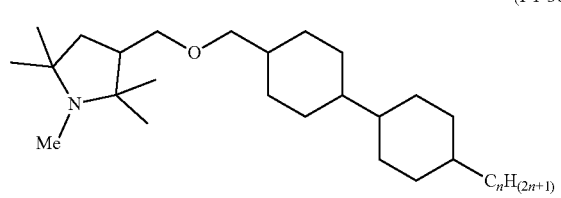
(I-1-39)
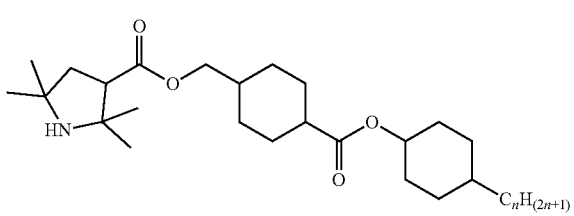
(I-1-40)
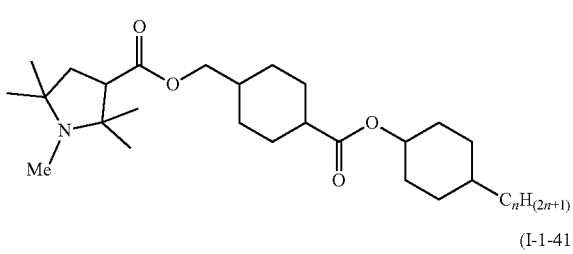
(I-1-41)
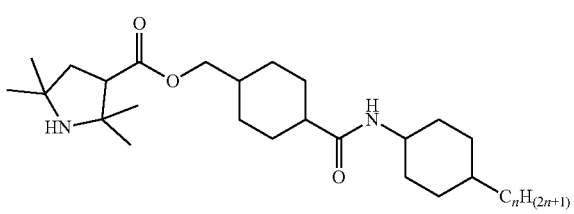
(I-1-42)
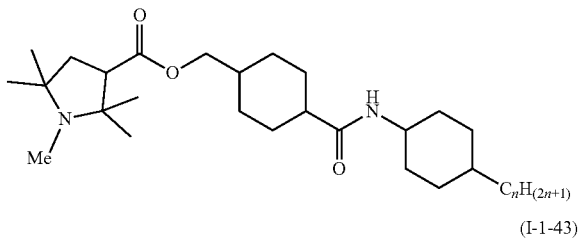
(I-1-43)
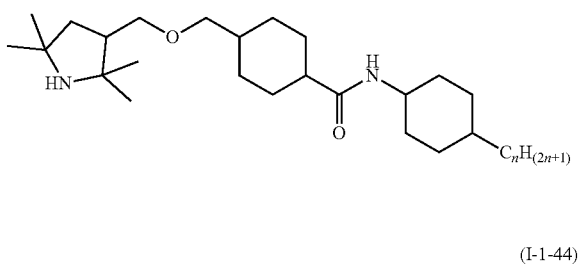
(I-1-44)
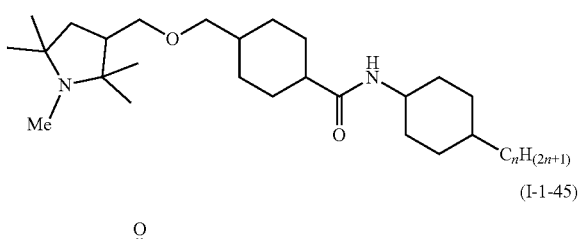
(I-1-45)
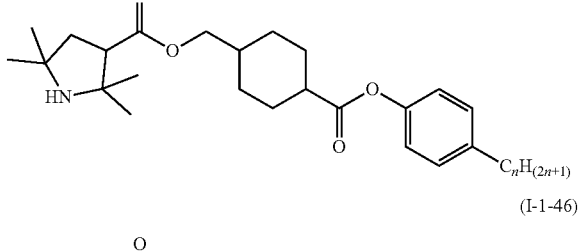
(I-1-46)
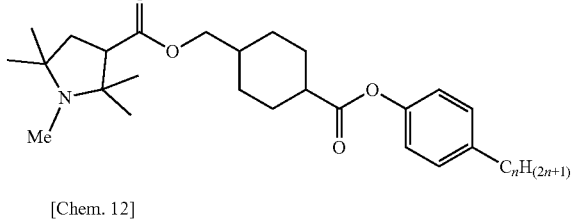
[Chem. 12]
(I-1-47)
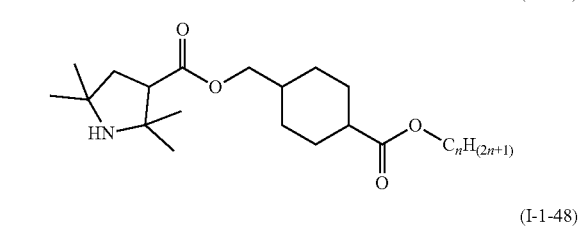
(I-1-48)
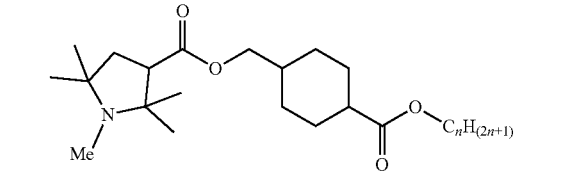

(I-1-49)
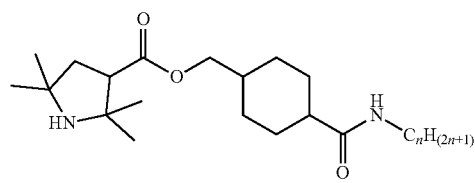
(I-1-50)
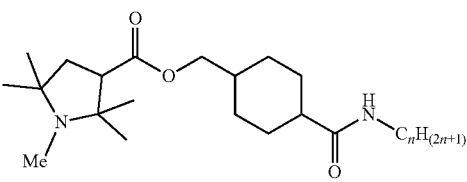
(I-1-51)
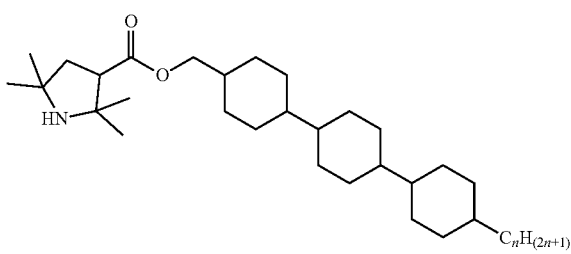
(I-1-52)
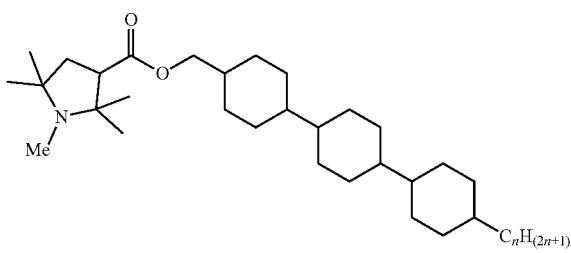
(I-1-53)
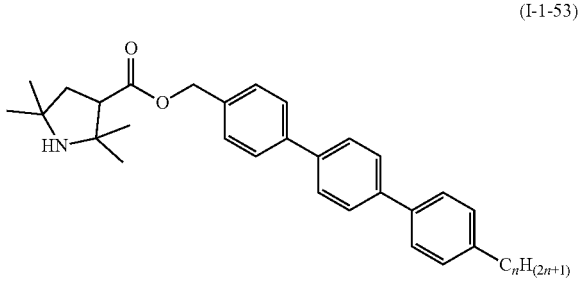
(I-1-54)
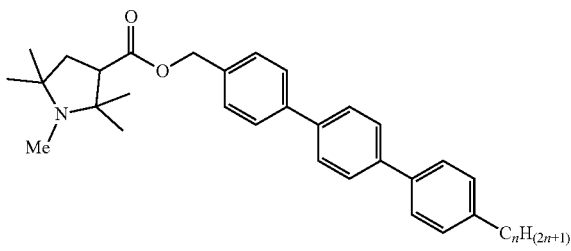
(I-1-55)
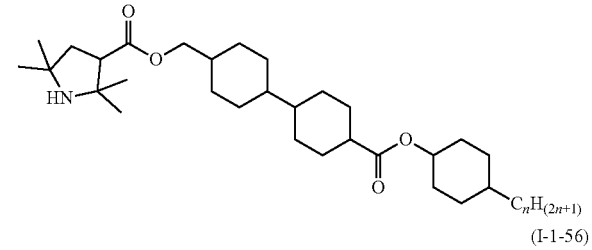
(I-1-56)
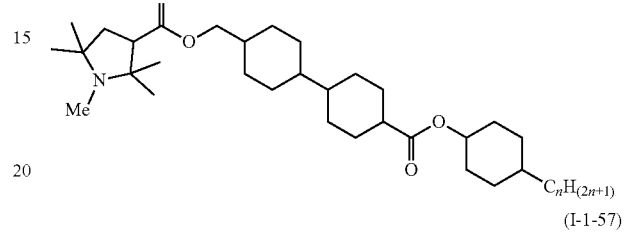
(I-1-57)
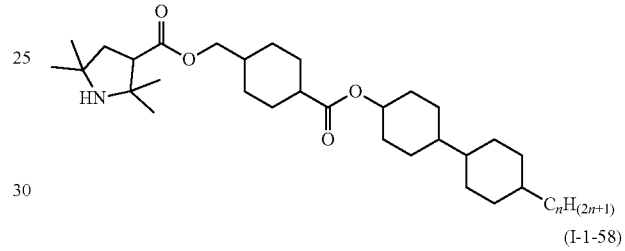
(I-1-58)
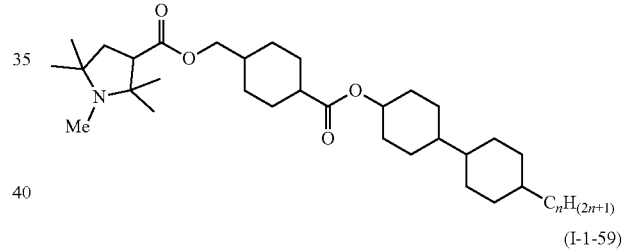
(I-1-59)
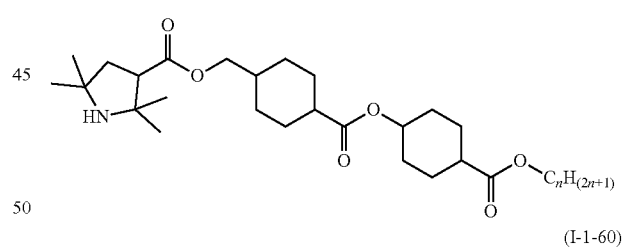
(I-1-60)
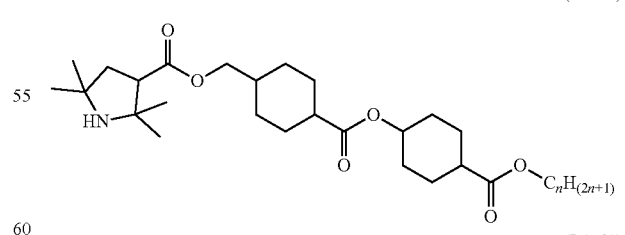
(I-1-61)
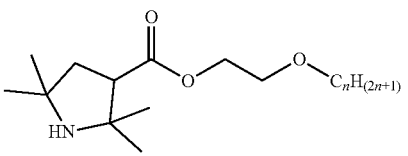

-continued
(I-1-62)
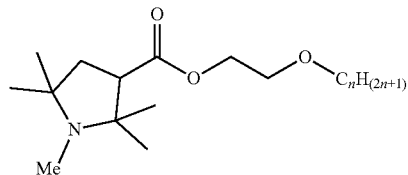
(I-1-63)
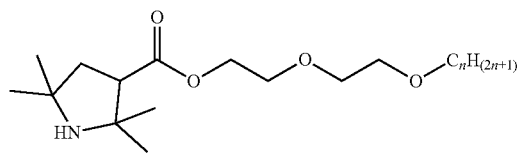
(I-1-64)
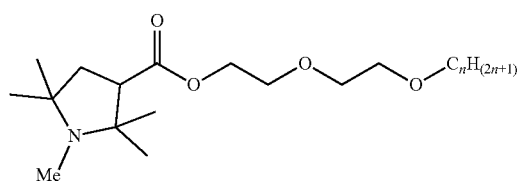
[Chem. 13]
(I-1-65)
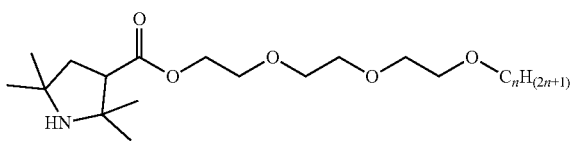
(I-1-66)
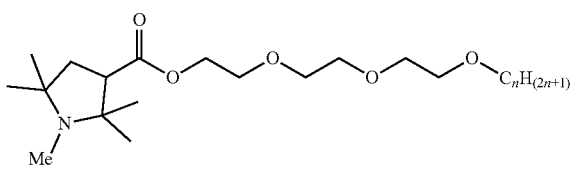
(I-1-67)
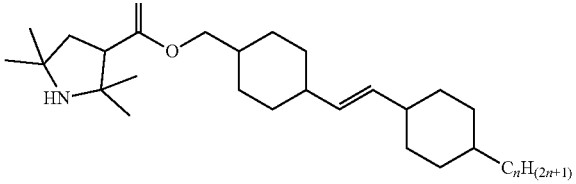
(I-1-68)
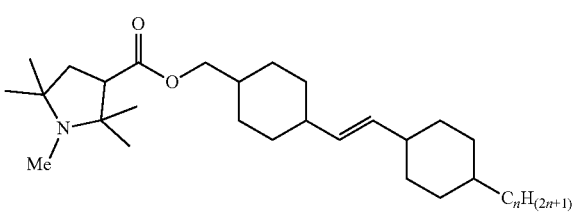
-continued
(I-1-69)
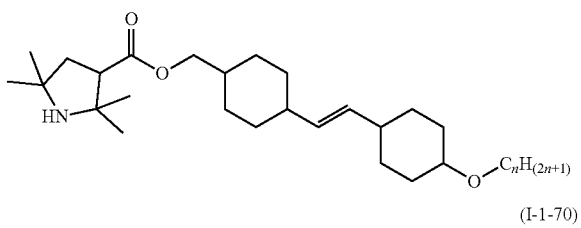
(I-1-70)
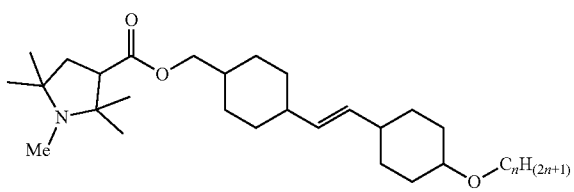
(I-1-71)
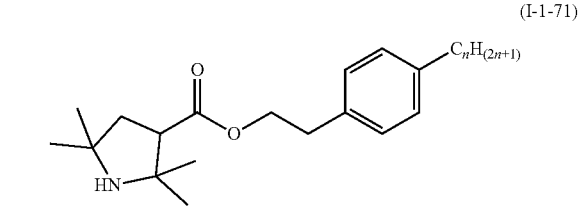
(I-1-72)
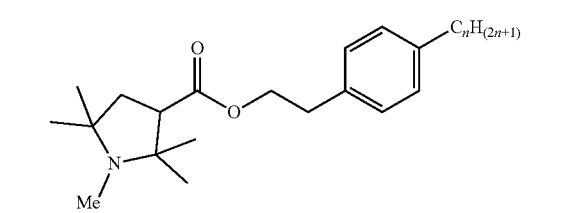
(I-1-73)
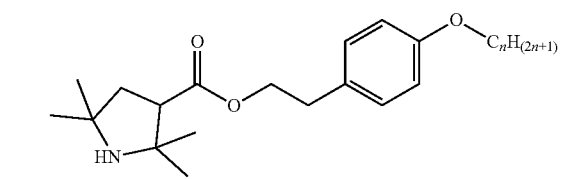
(I-1-74)
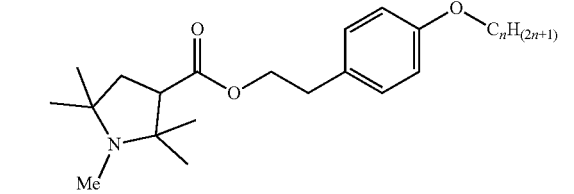
(I-1-75)
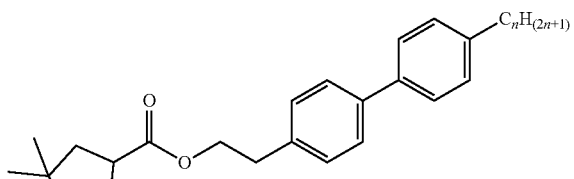

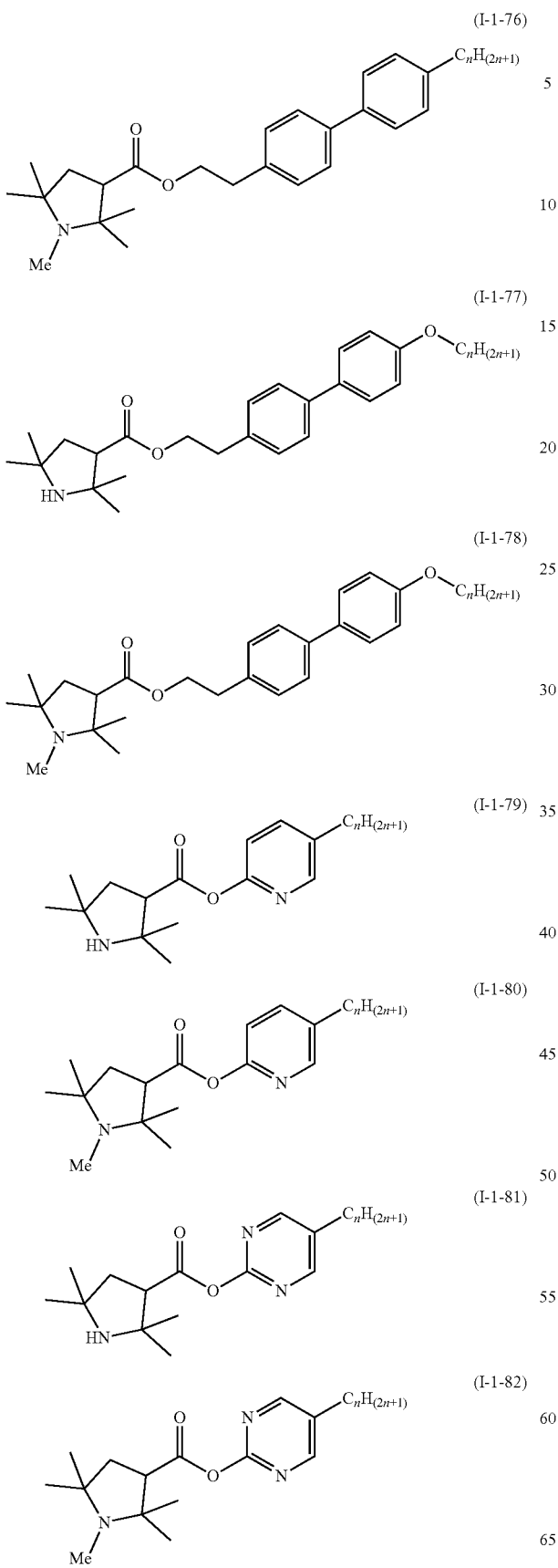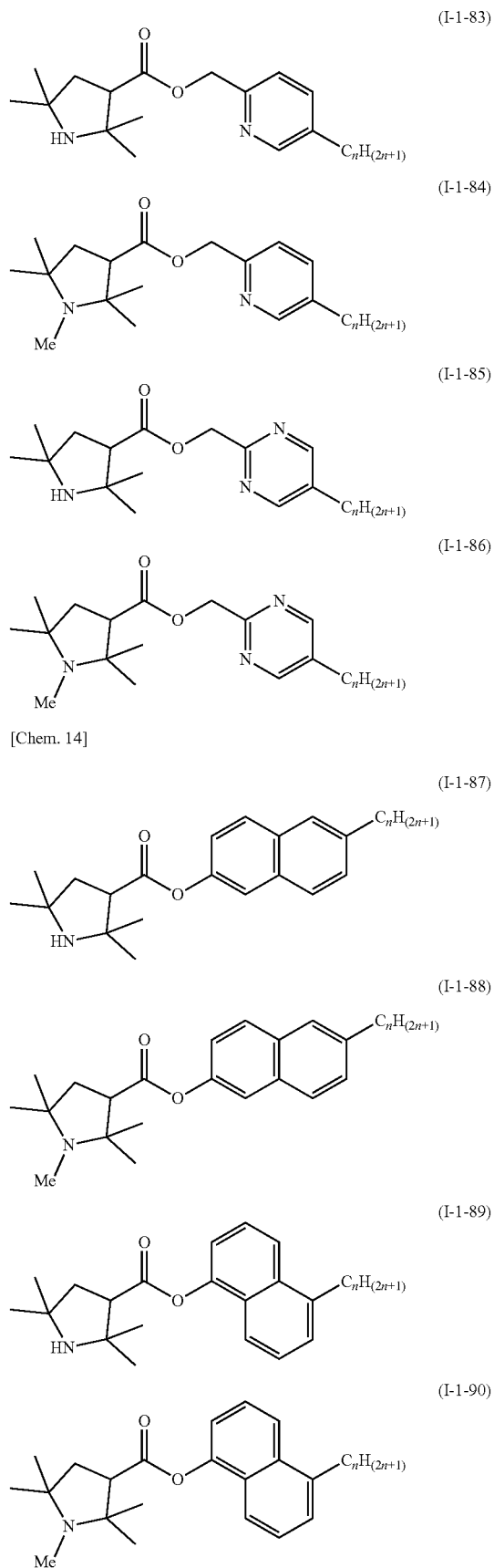

(I-1-91)
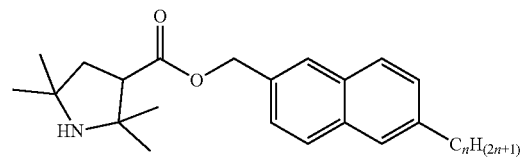
(I-1-92)
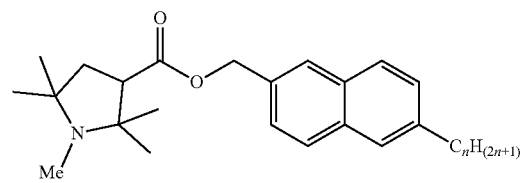
(I-1-93)
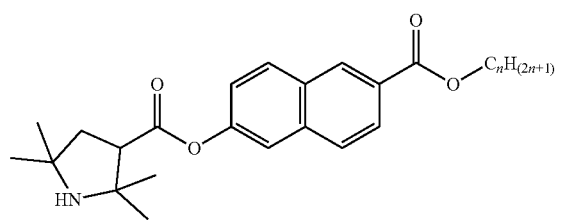
(I-1-94)
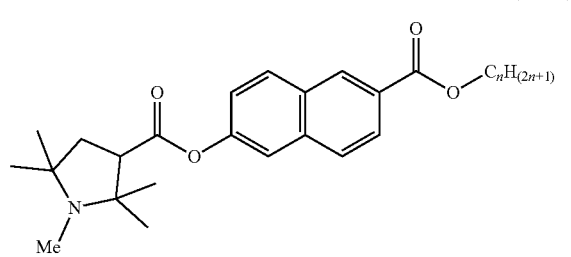
(I-1-95)
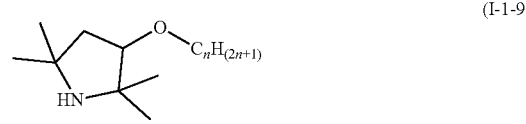
(I-1-96)
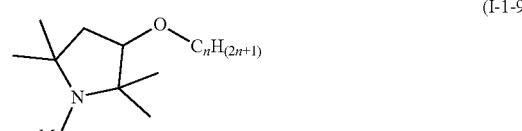
(I-1-97)
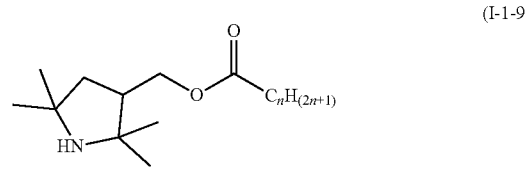
(I-1-98)
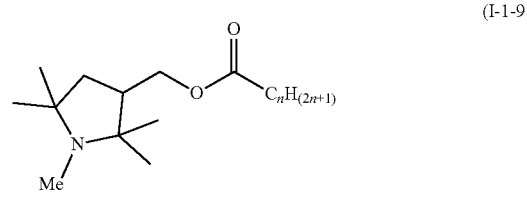
(I-1-99)
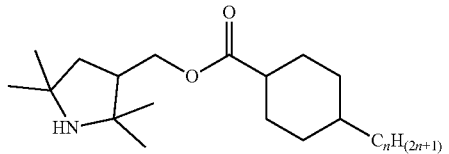
(I-1-100)
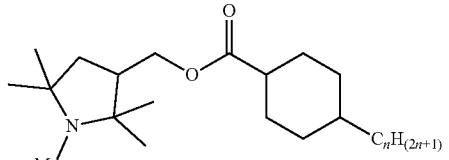
(I-1-101)
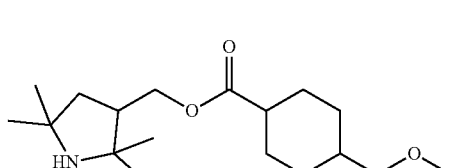
(I-1-102)
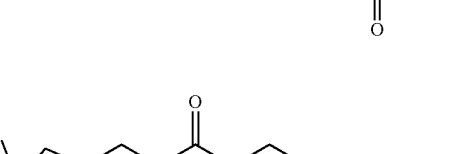
(I-1-103)
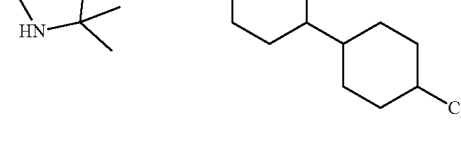
(I-1-104)
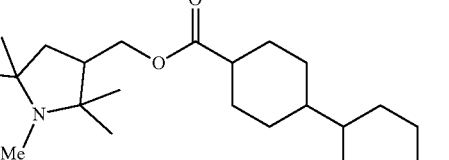
(I-1-105)
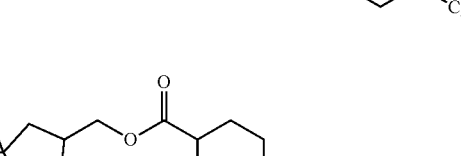

-continued

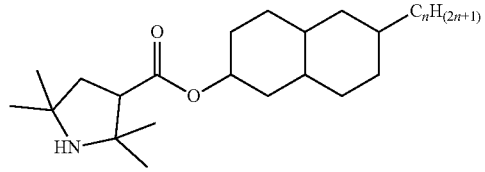
(I-1-106)

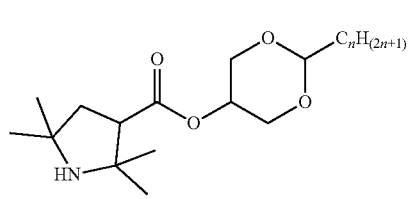
(I-1-107)

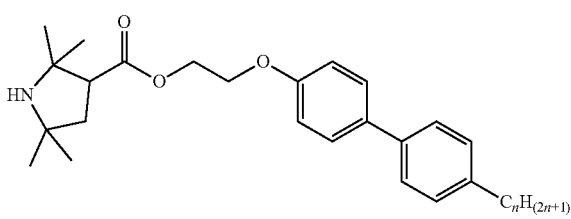
(I-1-108)

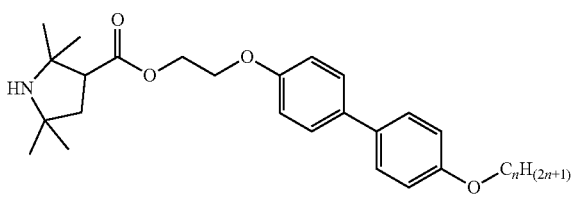
(I-1-109)

(In the formulae, Me denotes a methyl group, and n in $C_nH_{(2n+1)}$, denotes an integer in the range of 1 to 8.)

$C_nH_{(2n+1)}$ in the formulae may be linear or branched.

In the general formula (I), if n in the general formula (I) is 2, that is, if nu1 in the general formula (U-1) is 2, and W has a valence of 2, then W in the general formula (U-1) preferably denotes an alkylene group having 1 to 10 carbon atoms, and one —CH$_2$— or two or more nonadjacent —CH$_2$— groups in the alkylene group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—.

W preferably denotes a group selected from the group consisting of (a) a 1,4-cyclohexylene group (in which one —CH$_2$— or two or more nonadjacent —CH$_2$— groups may be substituted with —O—), (b) a 1,4-phenylene group (in which one —CH= or two or more nonadjacent —CH= groups may be substituted with —N=), and (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl group or the 1,2,3,4-tetrahydronaphthalene-2,6-diyl group may be substituted with —N=), and the groups (a), (b), and (c) may be independently substituted with a fluorine atom, a chlorine atom, a bromine atom, an iodine atom, a pentafluorosulfanyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —CH$_2$— or two or more nonadjacent —CH$_2$— groups in the alkyl group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—.

If W has a valence of 2, W in the general formula (U-1) preferably denotes an alkylene group having 1 to 8 carbon atoms, more preferably an alkylene group having 1 to 6 carbon atoms, and the alkylene group may be linear or branched, preferably linear. One —CH$_2$— or two or more nonadjacent —CH$_2$— groups in the alkylene group may be independently substituted with —O—, —COO—, —OCO—, —CH=CH—, or —C≡C—. W preferably denotes a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups are preferably independently unsubstituted or may be substituted with a cyano group, a fluorine atom, a chlorine atom, a methyl group, or a methoxy group.

A compound in which n in the general formula (I) is 2 is preferably a compound represented by the following general formula (I-2-a).

[Chem. 15]

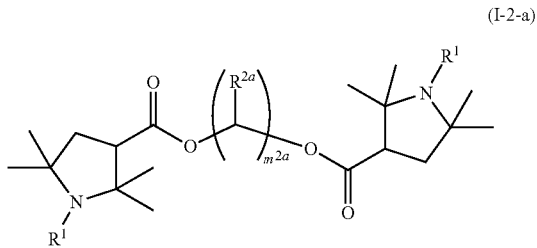

(I-2-a)

(In the formula, $R^1$ has the same meaning as R in the general formula (I), $R^{2a}$ denotes a hydrogen atom or an alkyl group having 1 to 10 carbon atoms, $m^{2a}$ denotes an integer in the range of 0 to 10, and if $m^{2a}$ ranges from 2 to 10, a plurality of $R^{2a}$s may be the same or different.)

In the general formula (I-2-a), $R^{2a}$ preferably denotes a hydrogen atom, a methyl group, or an ethyl group.

Preferably, $m^{2a}$ denotes an integer in the range of 1 to 7.

The general formula (I-2-a) preferably represents the following general formula (I-2-a1).

[Chem. 16]

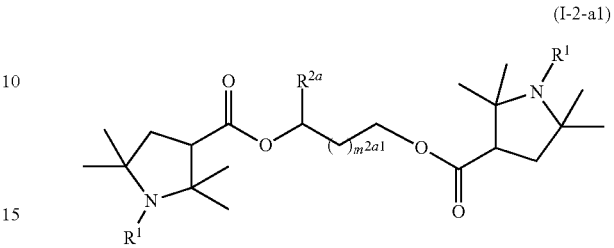

(I-2-a1)

(In the formula, $R^1$ has the same meaning as $R^1$ in the general formula (I), $R^{2a}$ has the same meaning as $R^{2a}$ in the general formula (I-2-a), and $m^{2a1}$ denotes an integer in the range of 0 to 9.) More specifically, a compound in which n in the general formula (I) is 2 is preferably one of the compounds represented by the following formulae (I-2-1) to (I-2-129).

[Chem. 17]

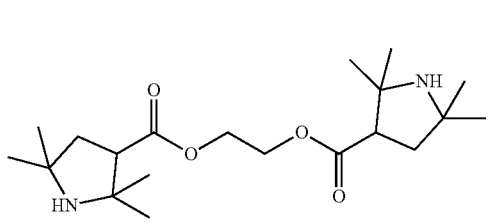

(I-2-1)

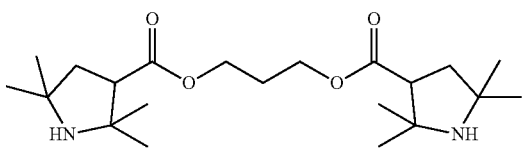

(I-2-2)

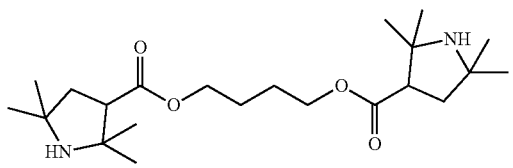

(I-2-3)

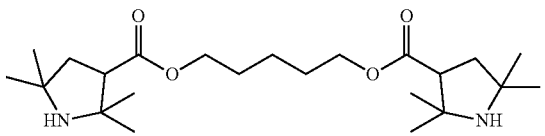

(I-2-4)

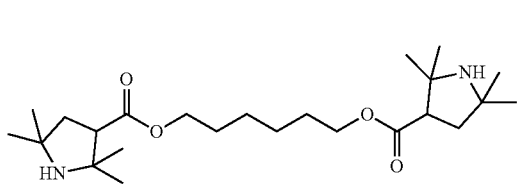

(I-2-5)

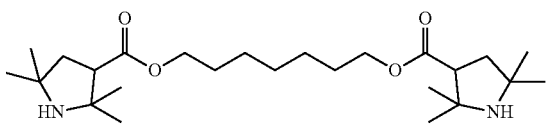

(I-2-6)

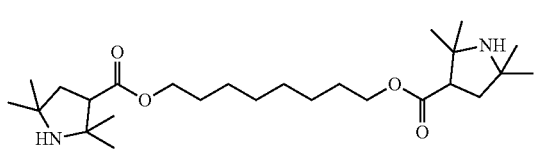

(I-2-7)

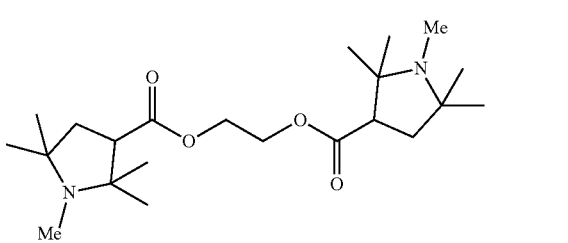

(I-2-8)

-continued
(I-2-9)
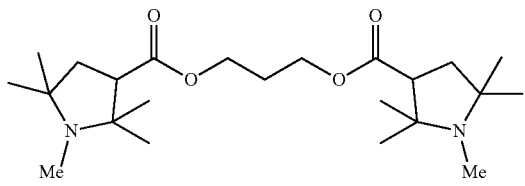
(I-2-10)
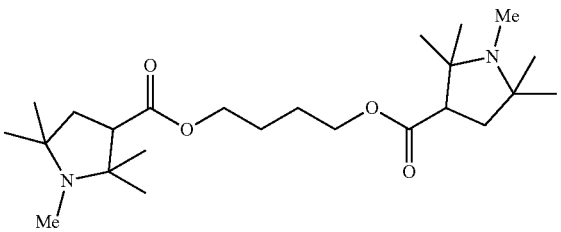
(I-2-11)
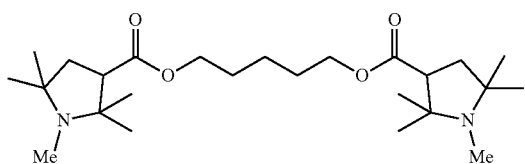
(I-2-13)
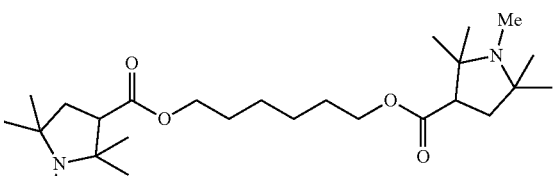
(I-2-14)
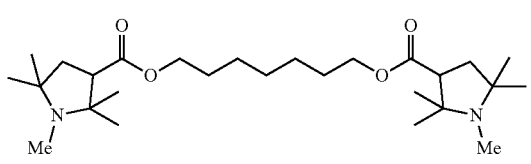
(I-2-15)
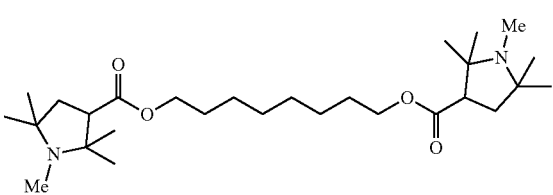
(I-2-16)
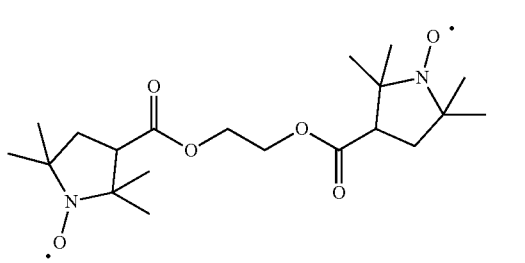
(I-2-17)
(I-2-18)
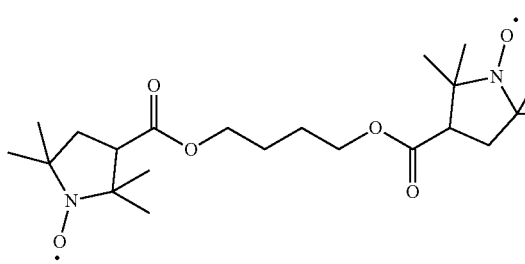
(I-2-19)
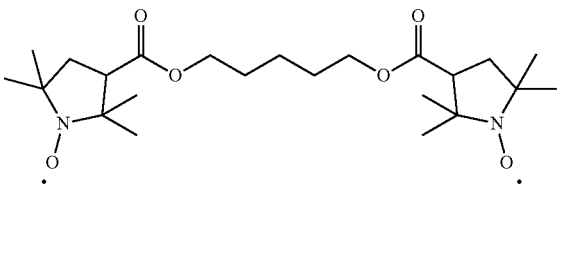
(I-2-20)
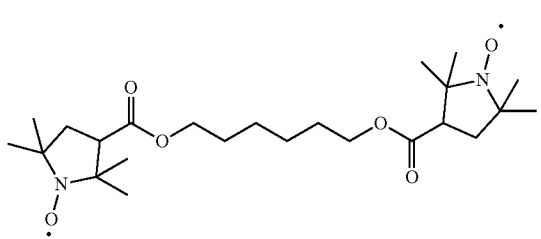
(I-2-21)
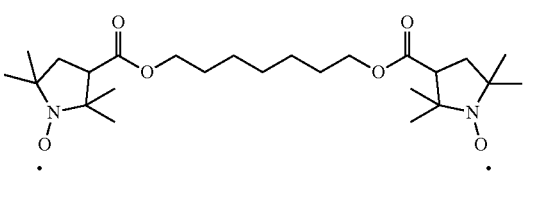

-continued
(I-2-22)
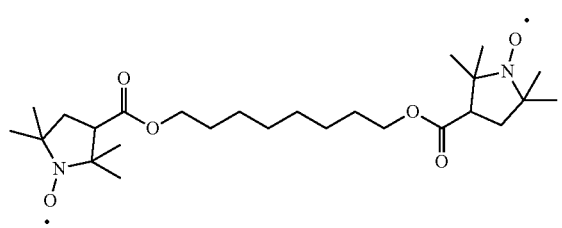
(I-2-23)
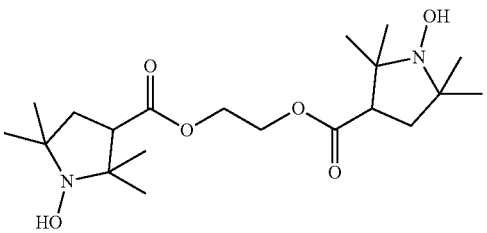
(I-2-24)
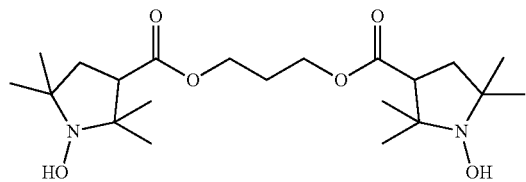
(I-2-25)
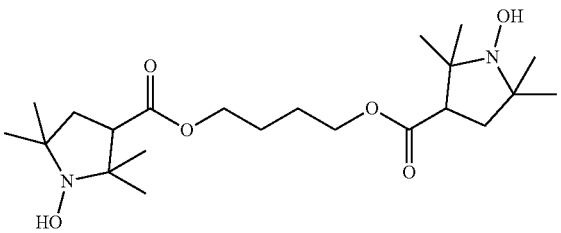
(I-2-26)
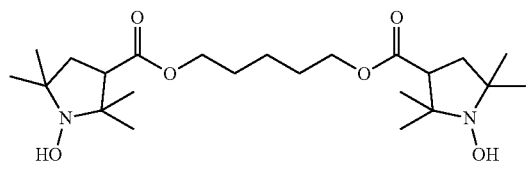
(I-2-27)
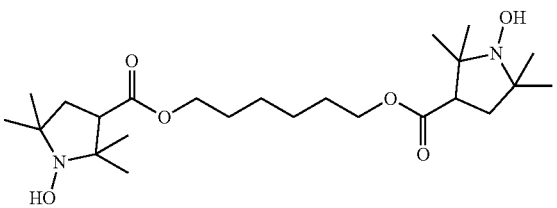
(I-2-28)
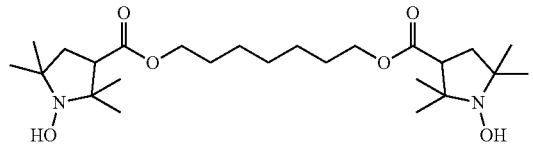
(I-2-29)
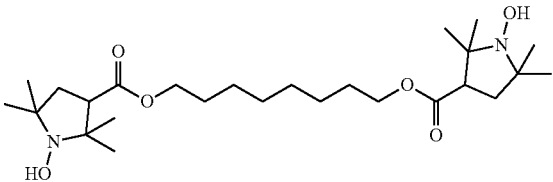
[Chem. 18]
(I-2-30)
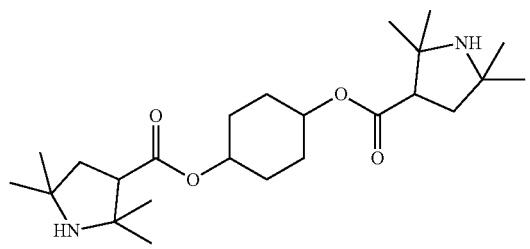
(I-2-31)
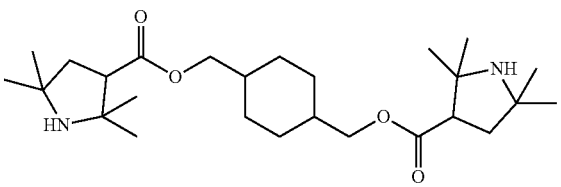
(I-2-32)
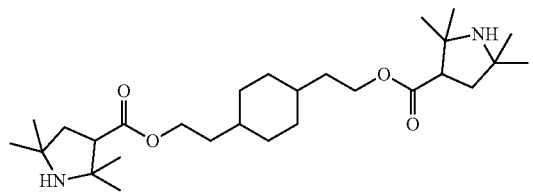
(I-2-33)
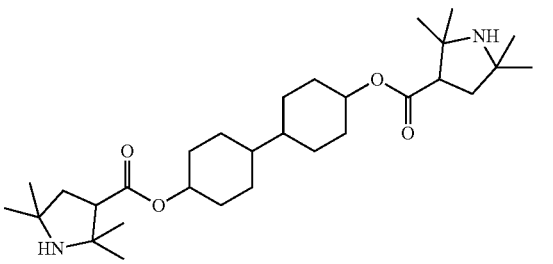

-continued
(I-2-34)
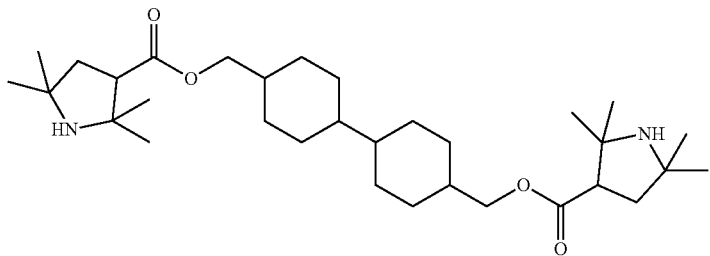
(I-2-35)
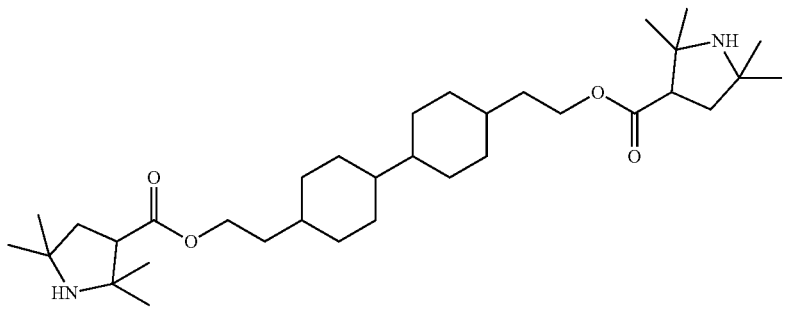
(I-2-36)
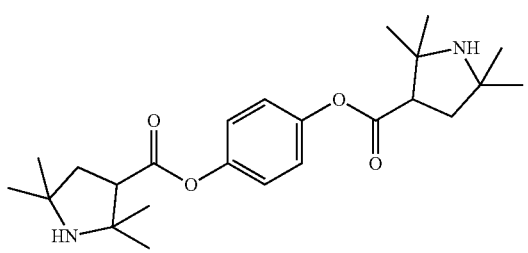
(I-2-37)
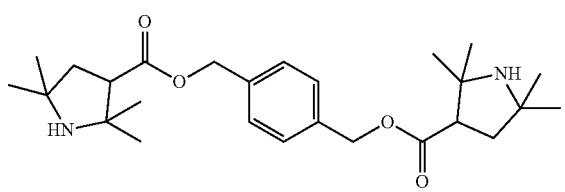
(I-2-38)
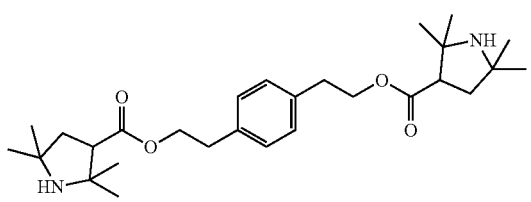
(I-2-39)
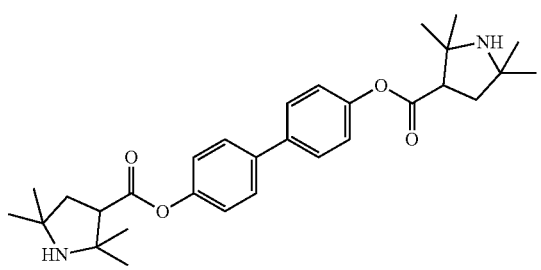
(I-2-40)
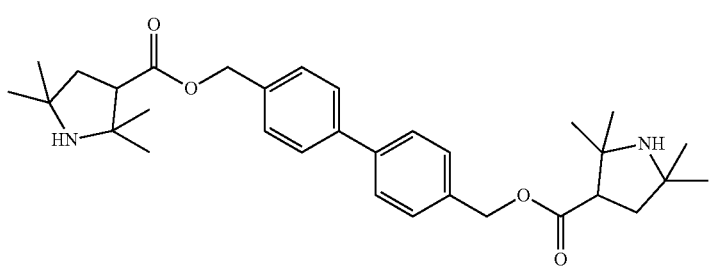

-continued
(I-2-41)
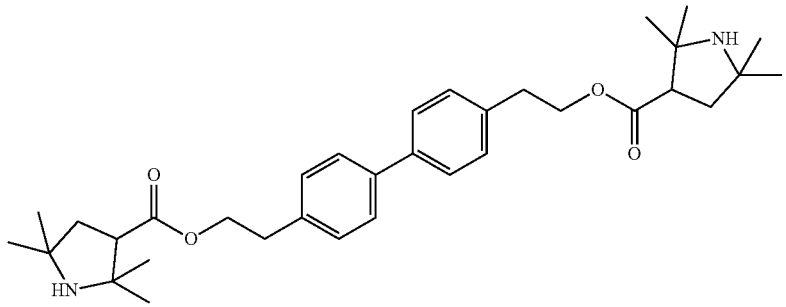
(I-2-42)
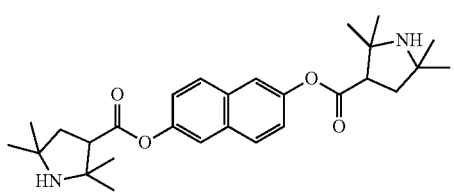
(I-2-43)
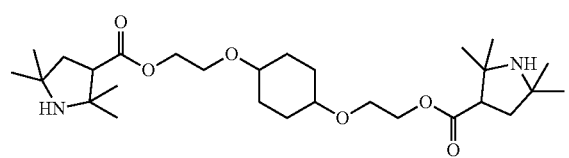
(I-2-44)
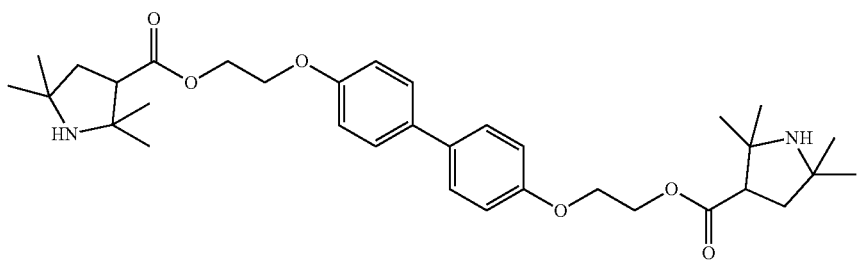
[Chem. 19]
(I-2-45)
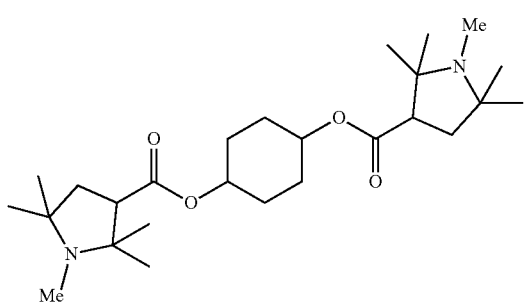
(I-2-46)
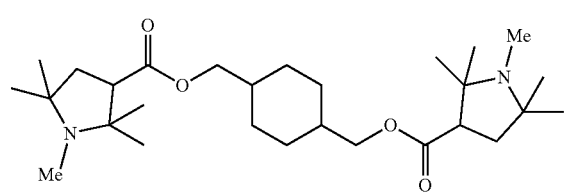
(I-2-47)
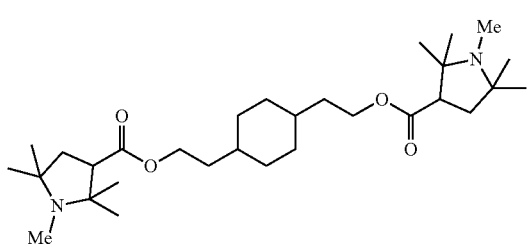
(I-2-48)
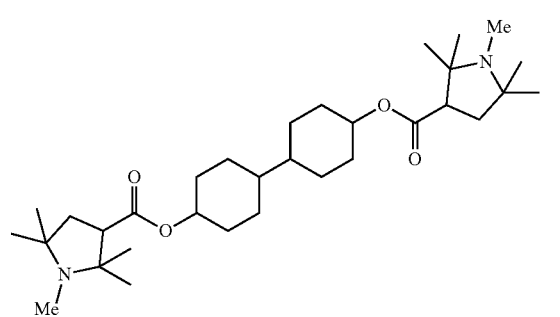

(I-2-49)
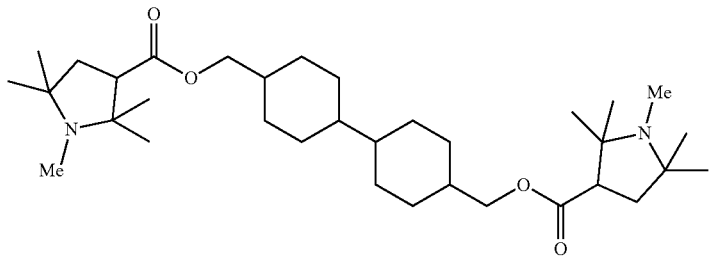
(I-2-50)
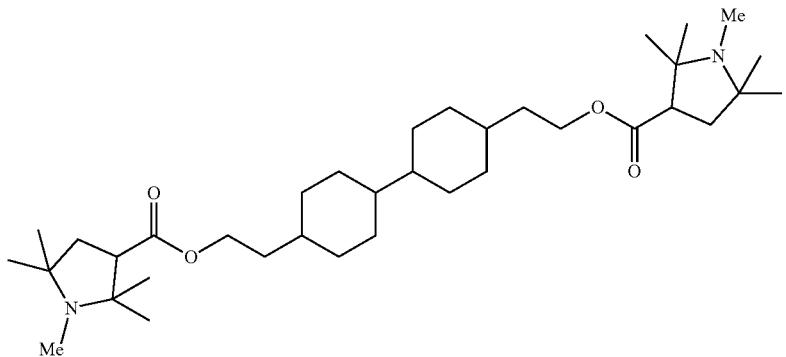
(I-2-51)
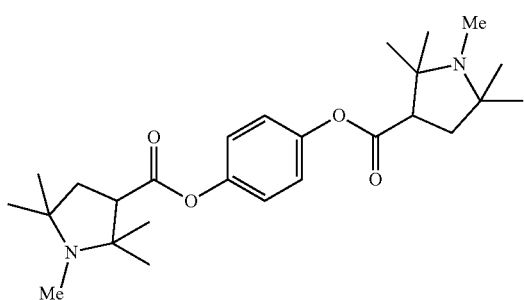
(I-2-52)
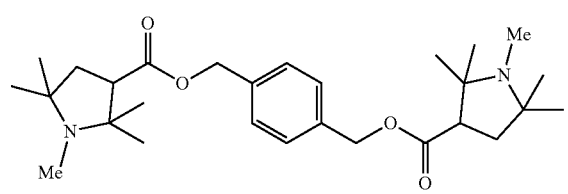
(I-2-53)
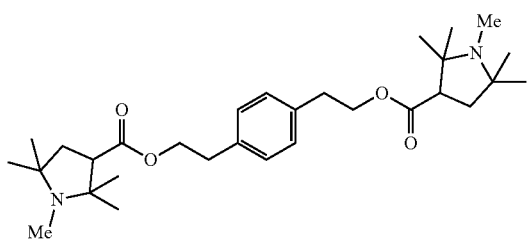
(I-2-54)
(I-2-55)
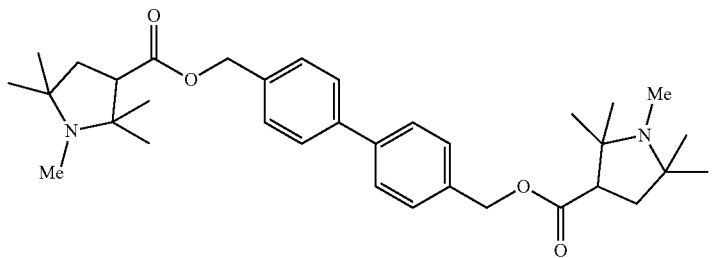

-continued
(I-2-56)
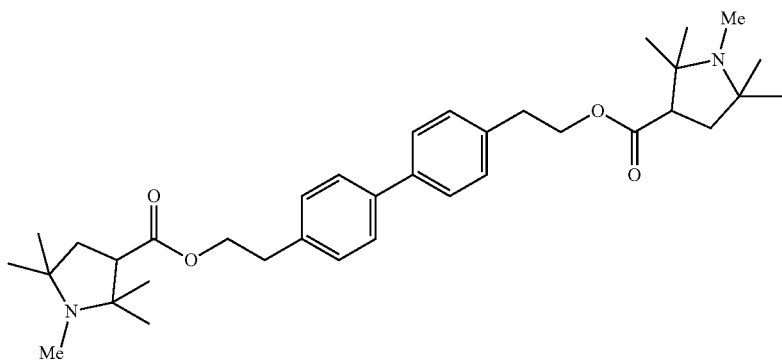
[Chem. 20]
(I-2-57)
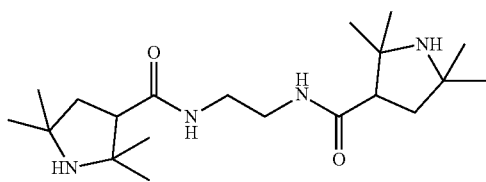
(I-2-58)
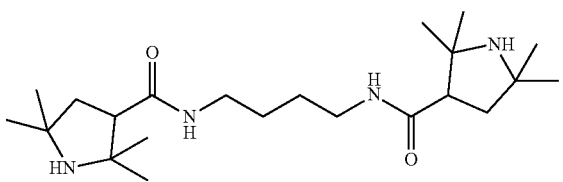
(I-2-59)
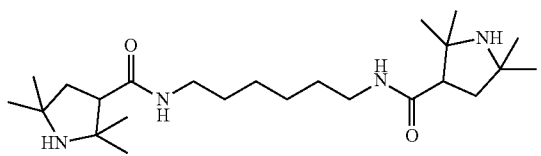
(I-2-60)
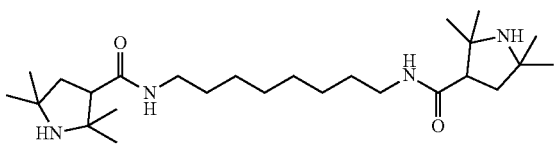
(I-2-61)
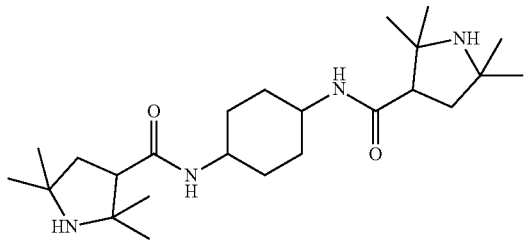
(I-2-62)
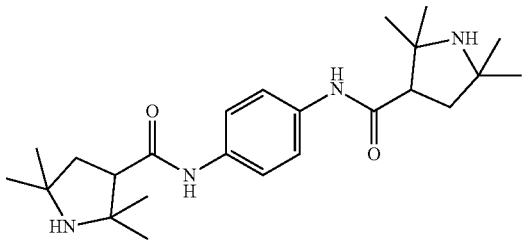
(I-2-63)
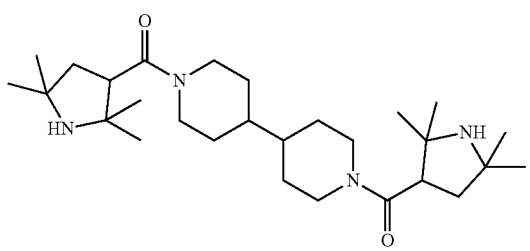
(I-2-64)
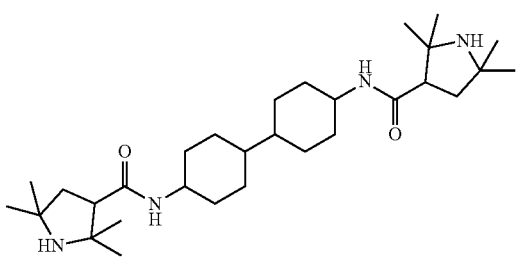
(I-2-65)
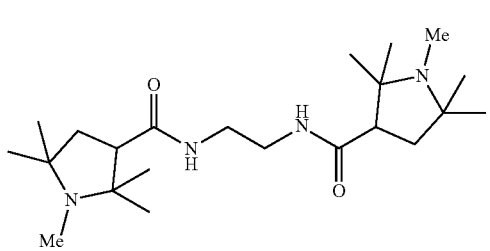
(I-2-66)
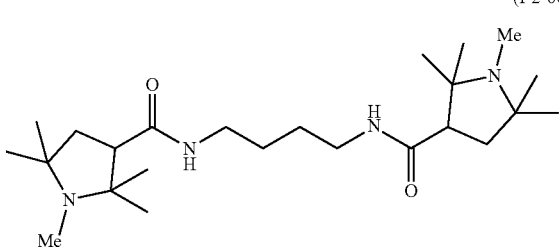

-continued
(I-2-67)
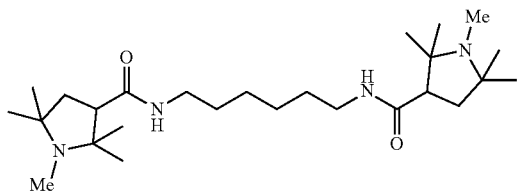
(I-2-68)
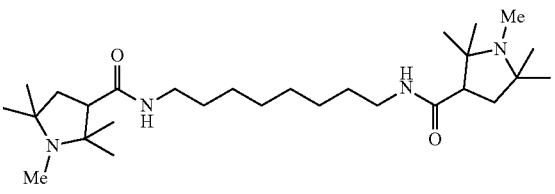
(I-2-69)
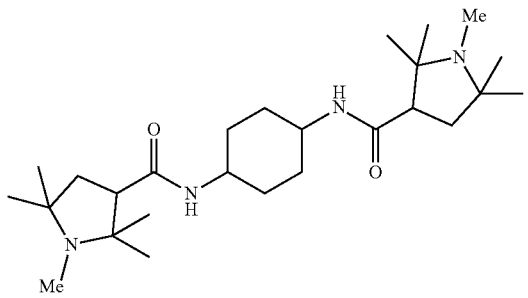
(I-2-70)
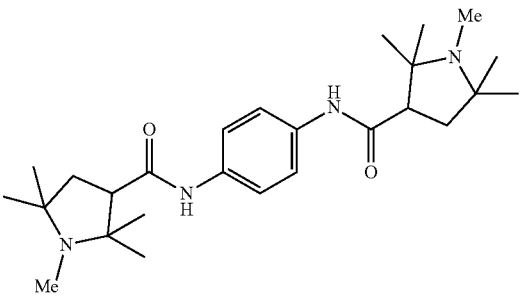
(I-2-71)
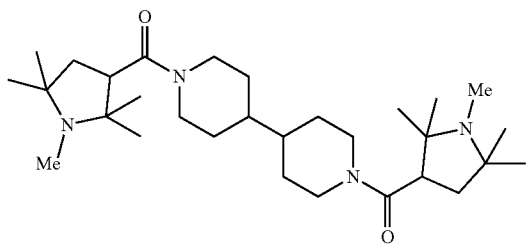
(I-2-72)
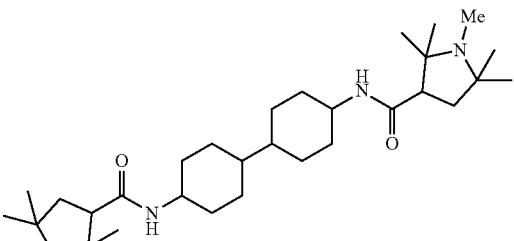
(I-2-73)
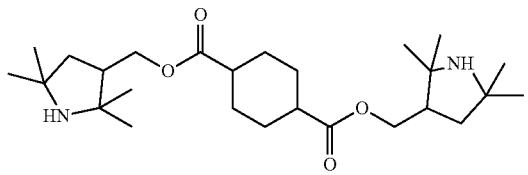
(I-2-74)
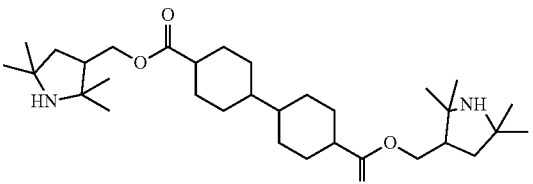
(I-2-75)
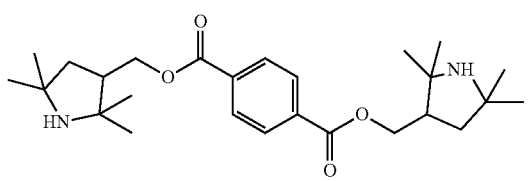
(I-2-76)
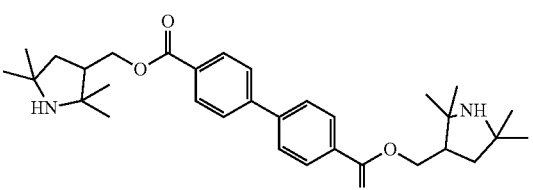
(I-2-77)
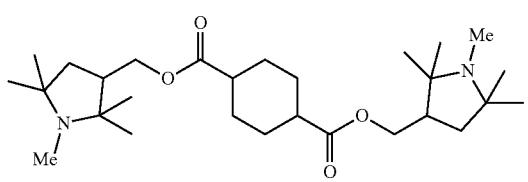
(I-2-78)
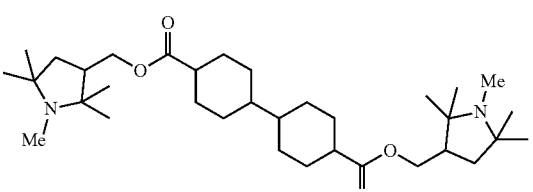

-continued
(I-2-79)
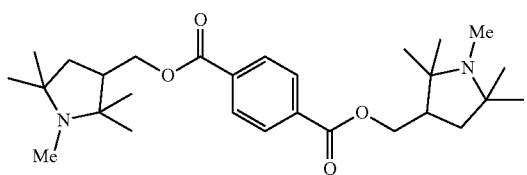
(I-2-80)
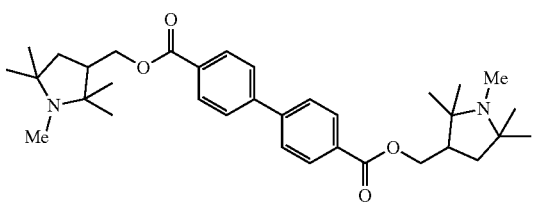
[Chem. 21]
(I-2-81)
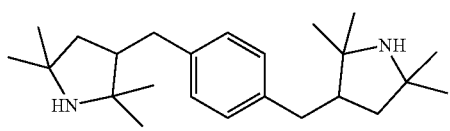
(I-2-82)
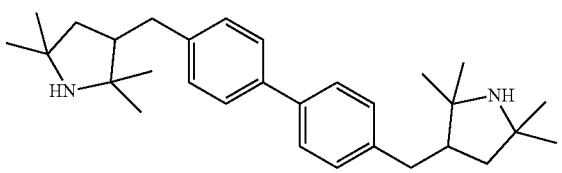
(I-2-83)
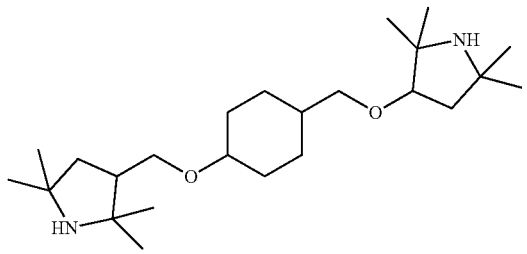
(I-2-84)
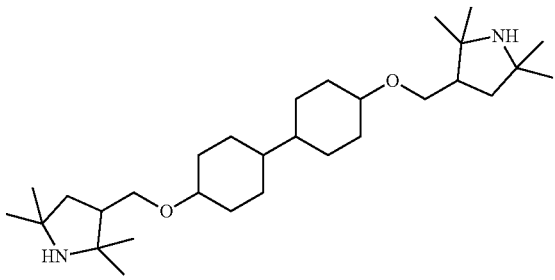
(I-2-85)
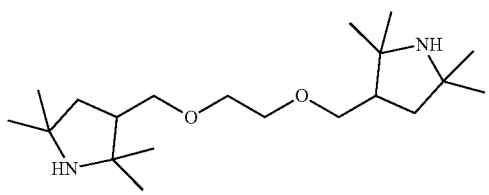
(I-2-86)
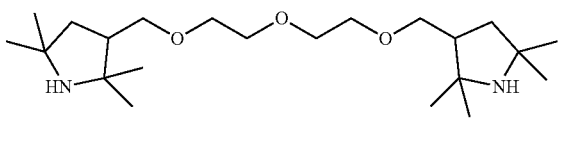
(I-2-87)
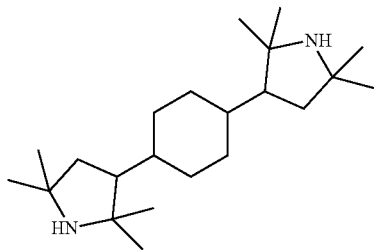
(I-2-88)
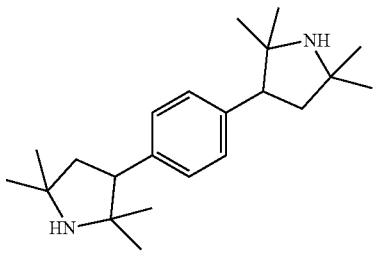
(I-2-89)
(I-2-90)
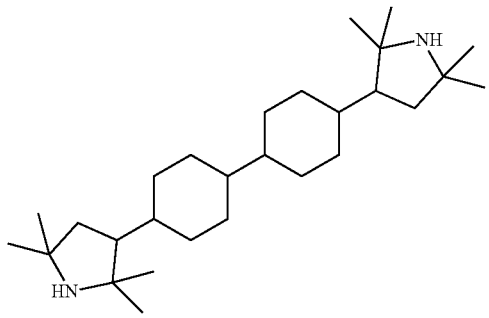

-continued
(I-2-91) 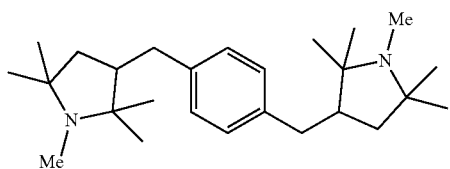
(I-2-92) 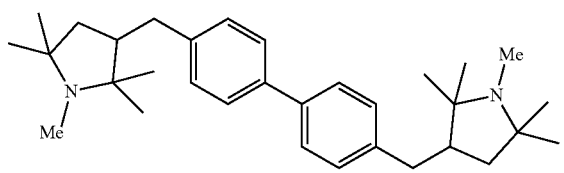
(I-2-93) 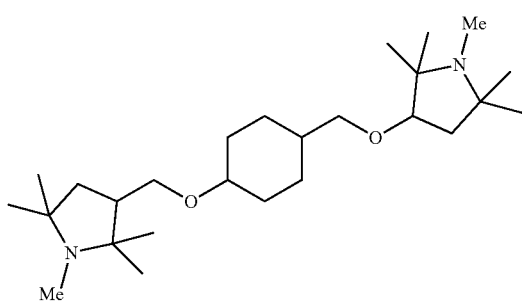
(I-2-94) 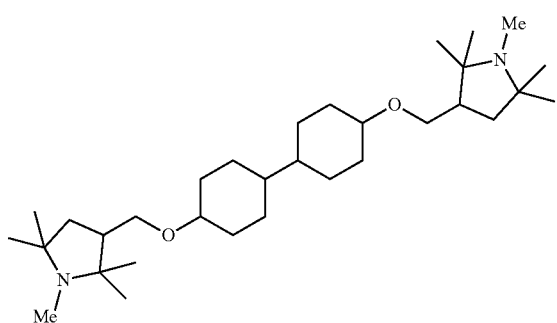
(I-2-95) 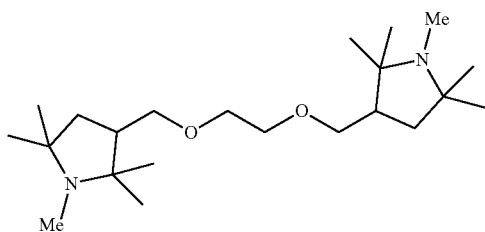
(I-2-96) 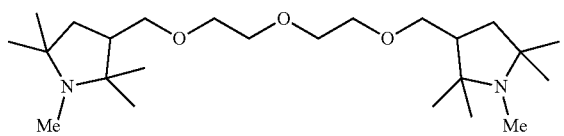
(I-2-97) 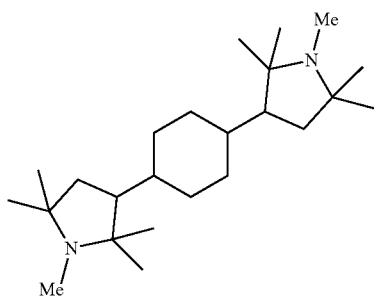
(I-2-98) 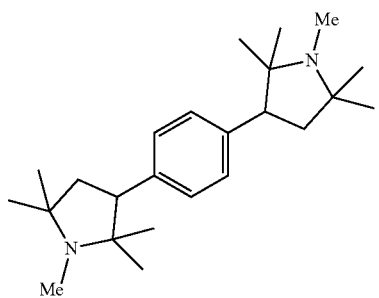

-continued
(I-2-99)
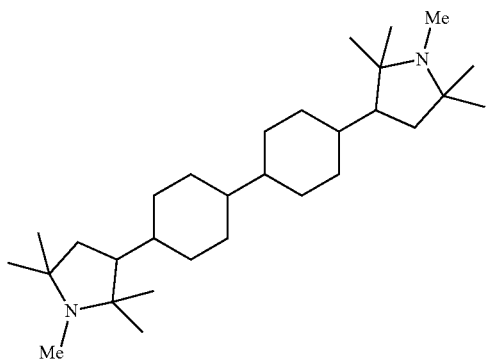
(I-2-100)
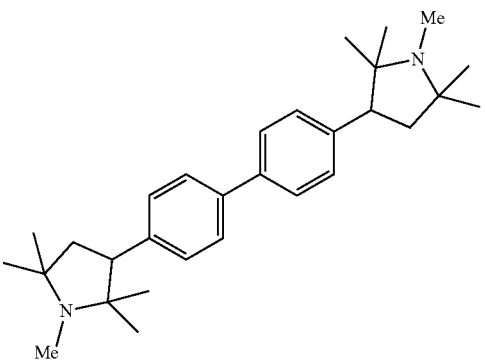
[Chem. 22]
(I-2-101)
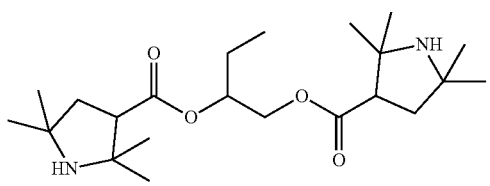
(I-2-102)
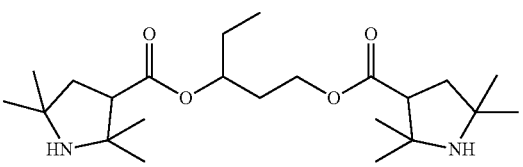
(I-2-103)
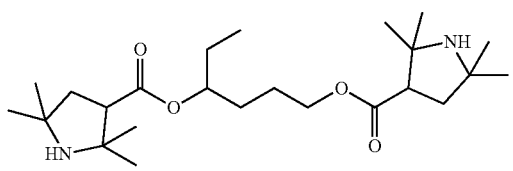
(I-2-104)
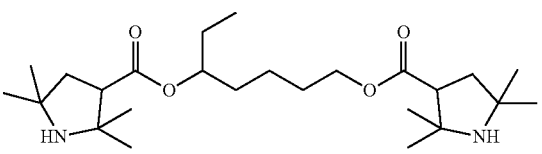
(I-2-105)
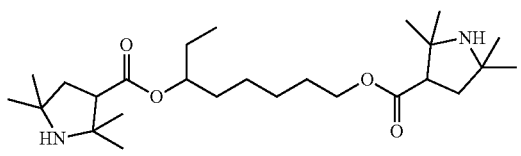
(I-2-106)
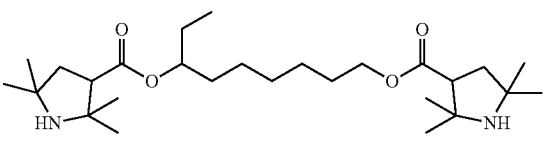
(I-2-107)
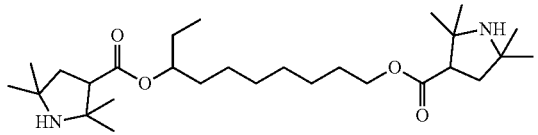
(I-2-108)
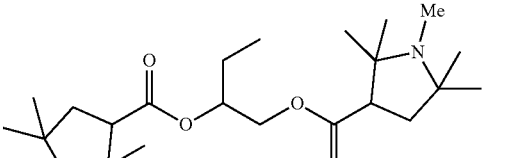
(I-2-109)
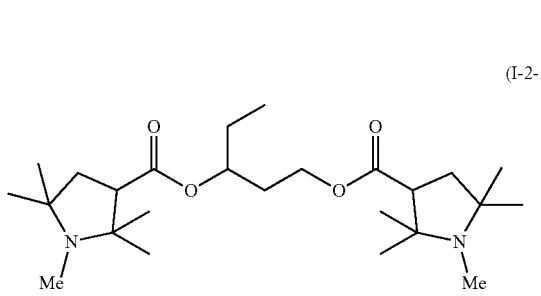
(I-2-110)
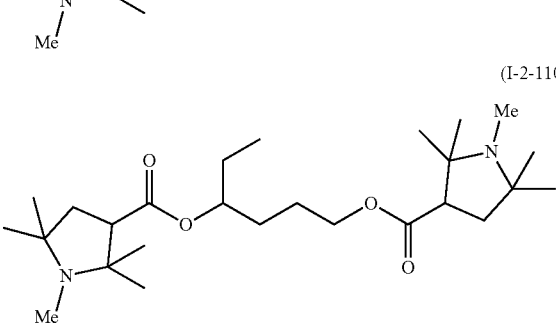

-continued
(I-2-111)
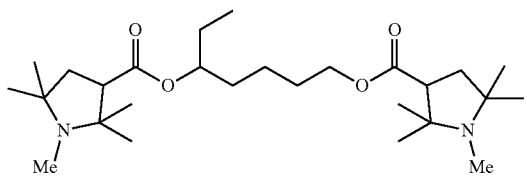
(I-2-113)
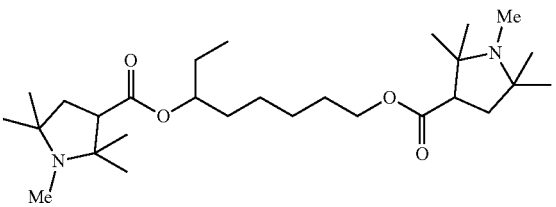
(I-2-114)
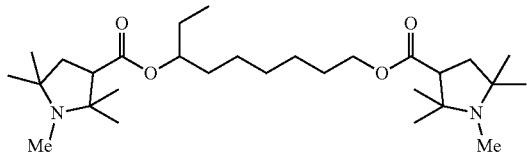
(I-2-115)
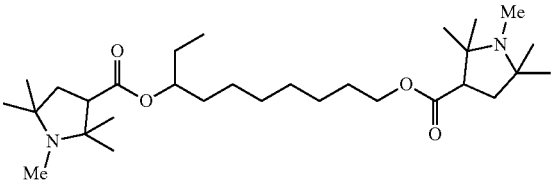
(I-2-116)
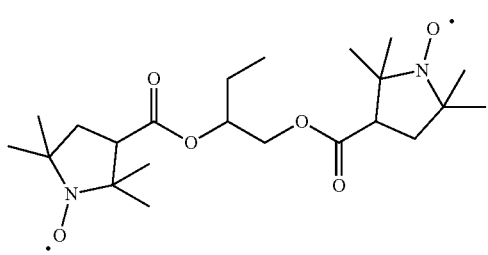
(I-2-117)
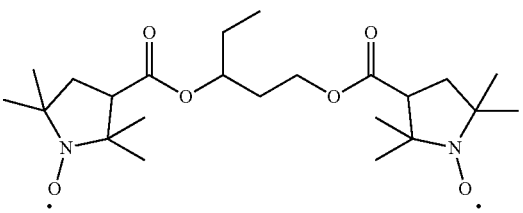
(I-2-118)
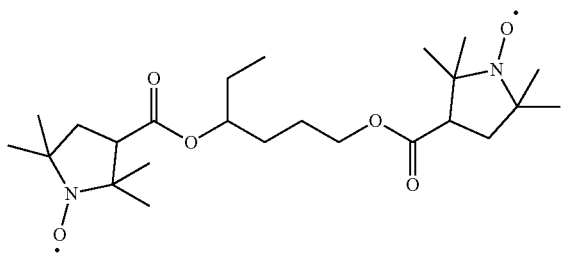
(I-2-119)
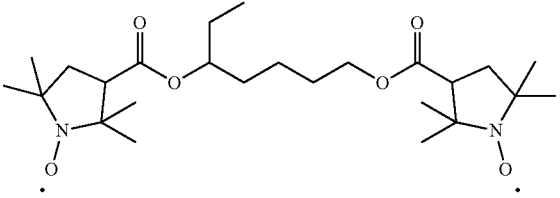
(I-2-120)
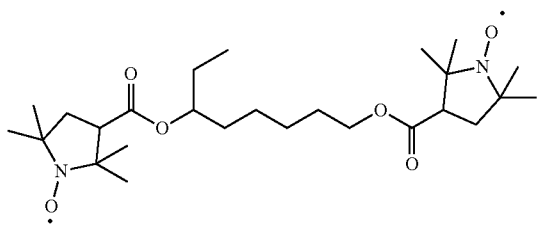
(I-2-121)
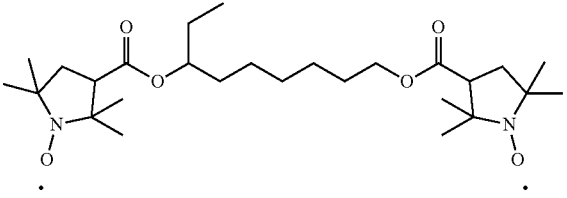
(I-2-122)
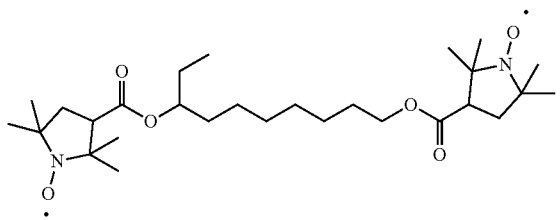
(I-2-123)
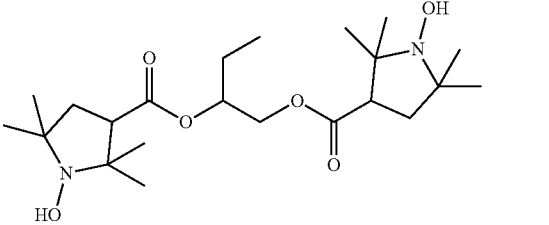

(I-2-124)
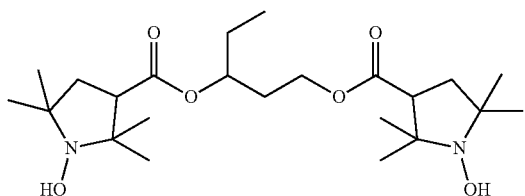

(I-2-125)
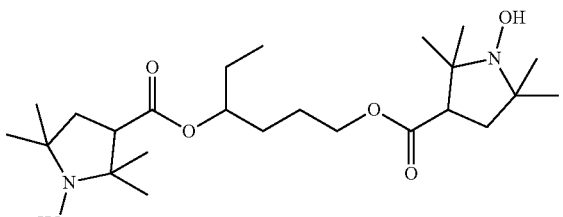

(I-2-126)
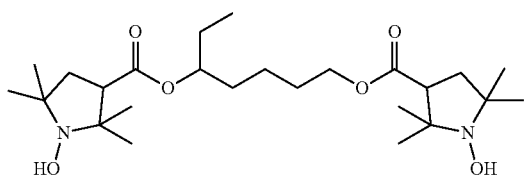

(I-2-127)
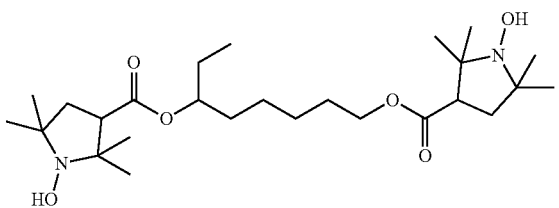

(I-2-128)
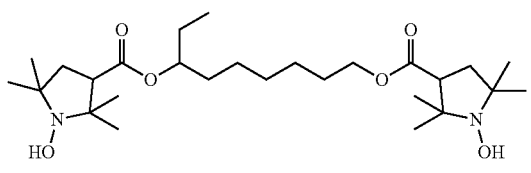

(I-2-129)
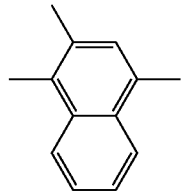

(In the fonrmulae, Me denotes a methyl group.)

In the general formula (I), if n in the general formula (I) is 3, that is, if nu1 in the general formula (U-1) is 3, and W has a valence of 3, then W in the general formula (U-1) preferably denotes a hydrocarbon group having 1 to 15 carbon atoms, one —CH$_2$— or two or more nonadjacent —CH$_2$— groups in the hydrocarbon group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—. W more preferably denotes a group selected from the groups represented by the formulae (W3-1) to (W3-12).

[Chem. 23]

(W3-1)
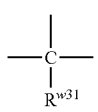

(W3-2)
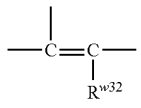

(W3-3)

(W3-4)
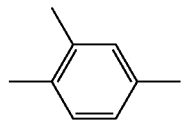

(W3-5)
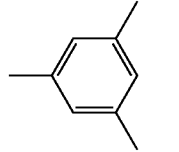

(W3-6)
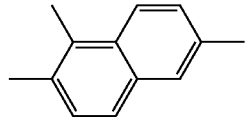

(W3-7)
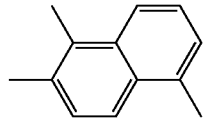

(W3-8)
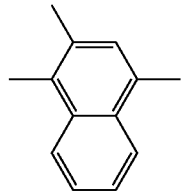

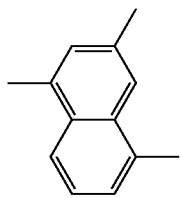 (W3-9)

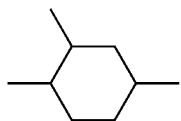 (W3-10)

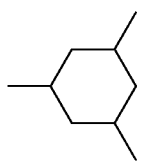 (W3-11)

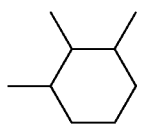 (W3-12)

(In the formulae, $R^{w31}$ and $R^{w32}$ denote a hydrogen atom, a hydroxy group, or an alkyl group having 1 to 10 carbon atoms, and one or two or more —$CH_2$— groups in the alkyl group may be independently substituted with —O—, —S—, —CH=CH—, —C≡C—, —CO—O—, or —O—CO—. A hydrogen atom in the ring structure may be substituted with a fluorine atom, a chlorine atom, a bromine atom, an iodine atom, a pentafluorosulfanyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —$CH_2$— or two or more nonadjacent —$CH_2$— groups in the alkyl group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —$OCF_2$—, —$CF_2O$—, or —C≡C—.)

$R^{w31}$ and $R^{w32}$ preferably denote a hydrogen atom, a hydroxy group, or an alkyl group having 1 to 8 carbon atoms and are preferably linear. The formulae (W3-4) to (W3-12) are preferably independently unsubstituted, and a hydrogen atom in the formulae (W3-4) to (W3-12) may be substituted with a cyano group, a fluorine atom, a chlorine atom, a methyl group, or a methoxy group.

From the perspective of the availability and manufacturability of raw materials, a group selected from the formula (W3-1), the formula (W3-2), and the unsubstituted formulae (W3-3) to (W3-12) is particularly preferred.

More specifically, a compound in which n in the general formula (I) is 3 is preferably one of the compounds represented by the following formulae (I-3-1) to (I-3-69).

[Chem. 24]

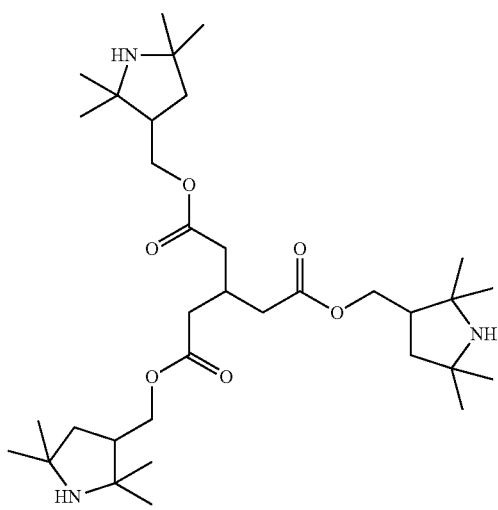

(I-3-1)

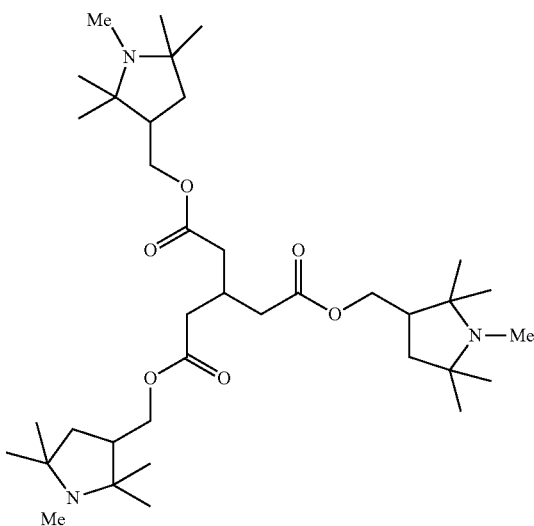

(I-3-2)

-continued
(I-3-3)
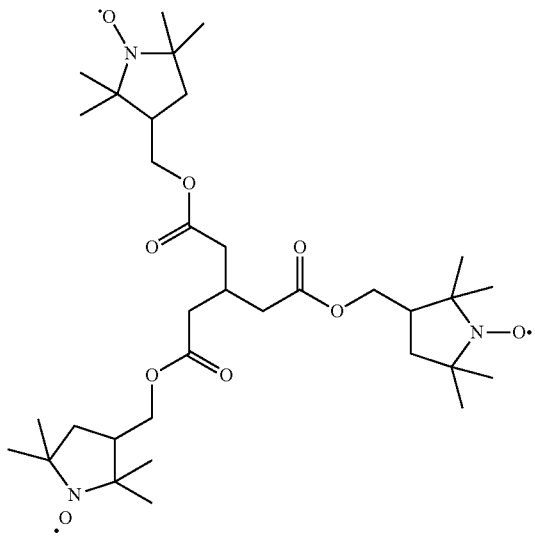
(I-3-4)
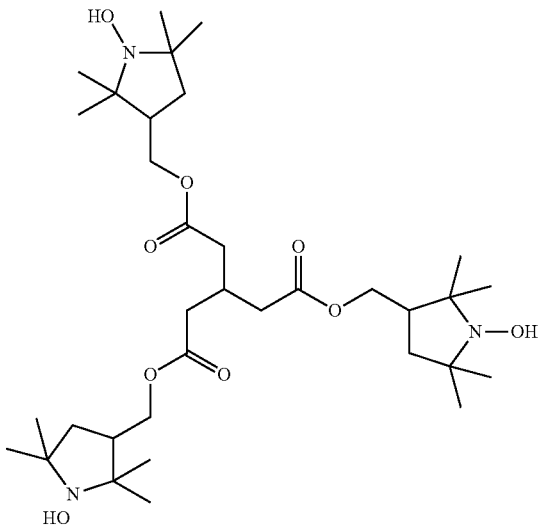
(I-3-5)
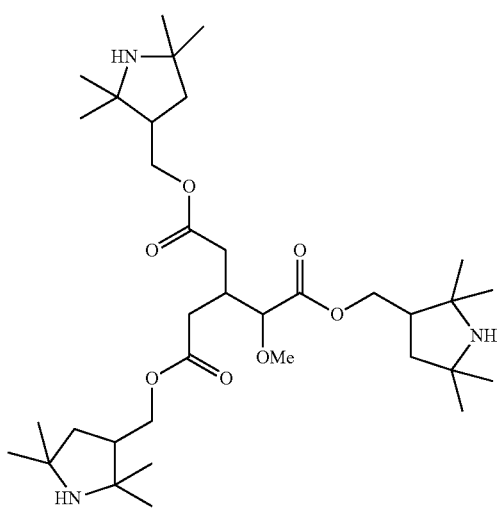
(I-3-6)
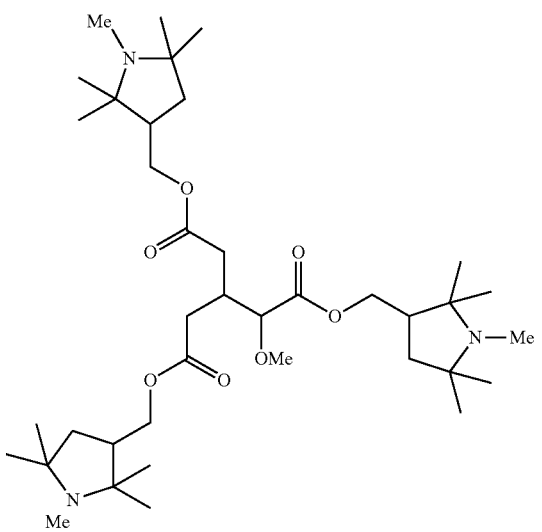
(I-3-7)
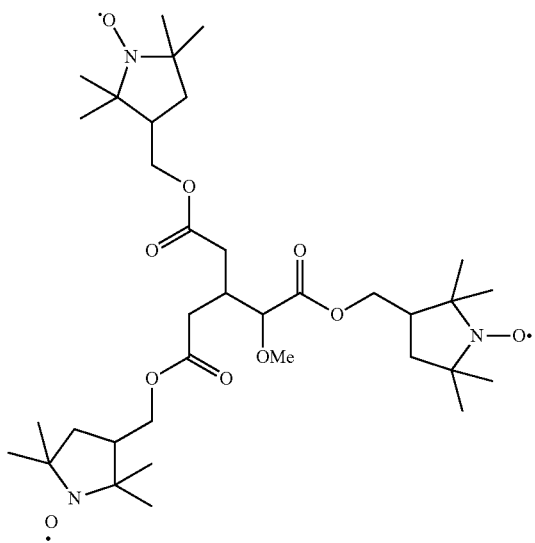
(I-3-8)
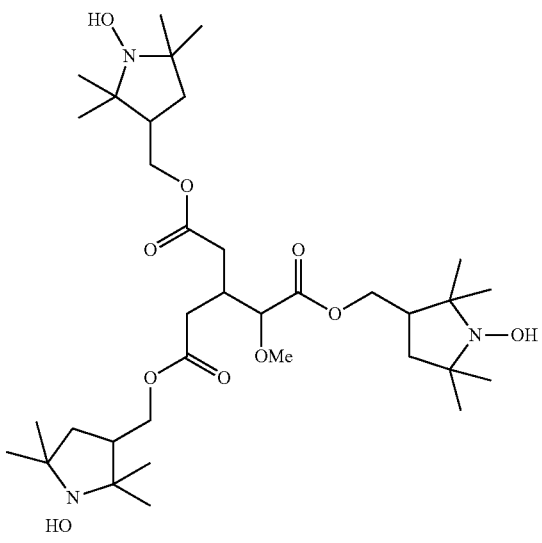

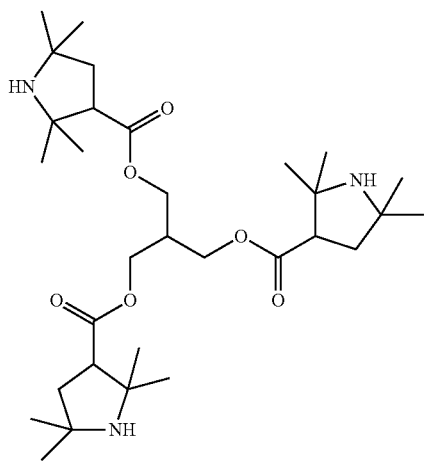 (I-3-9)
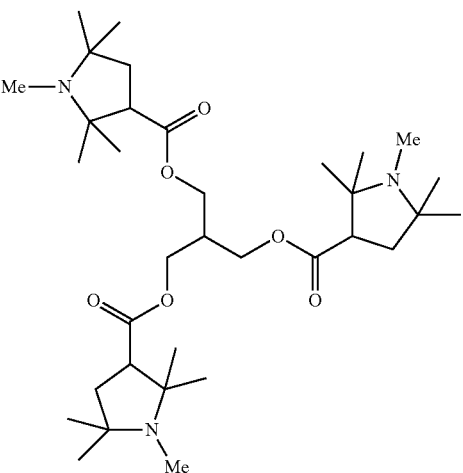 (I-3-10)
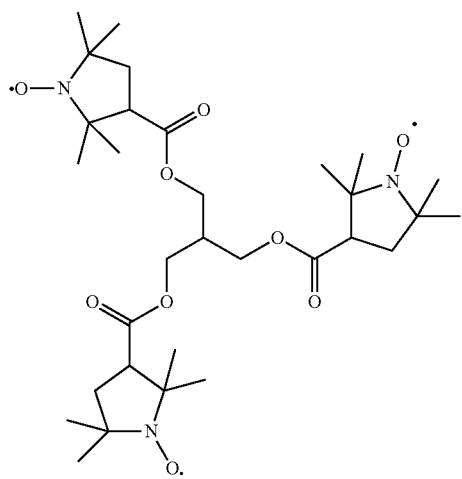 (I-3-11)
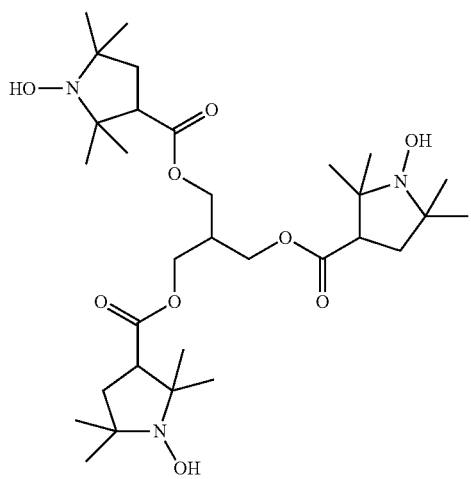 (I-3-12)
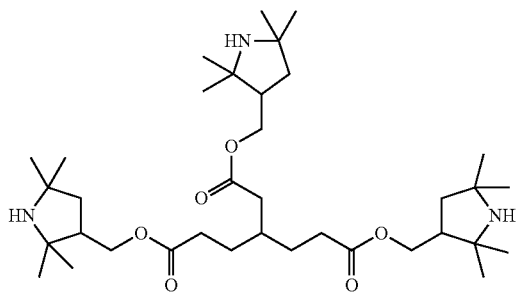 (I-3-13)
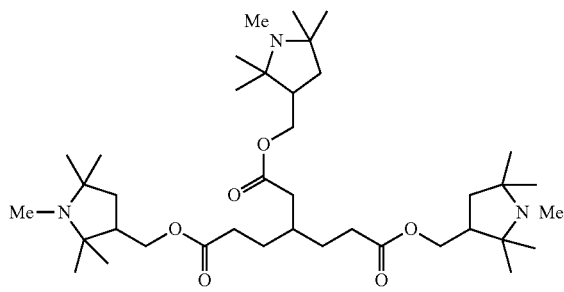 (I-3-14)

-continued
(I-3-15)
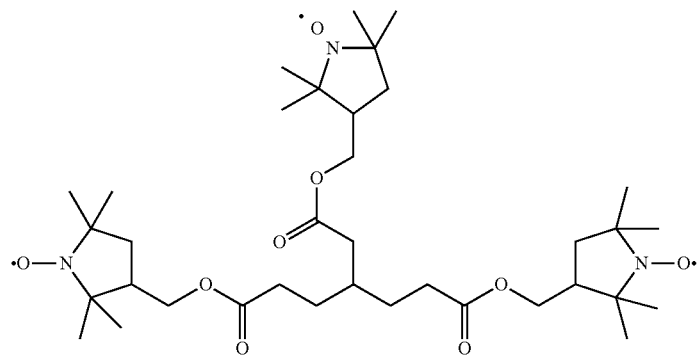
[Chem. 25]
(I-3-16)
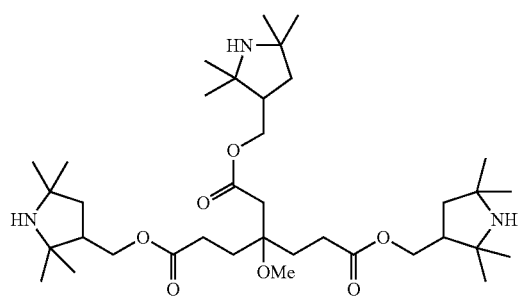
(I-3-17)
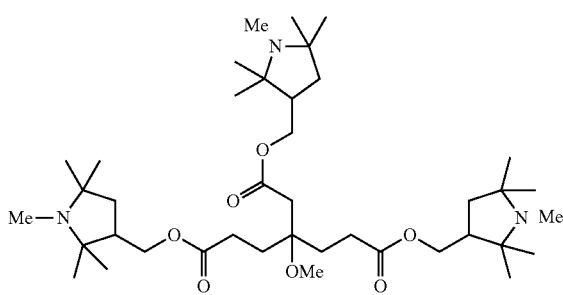
(I-3-18)
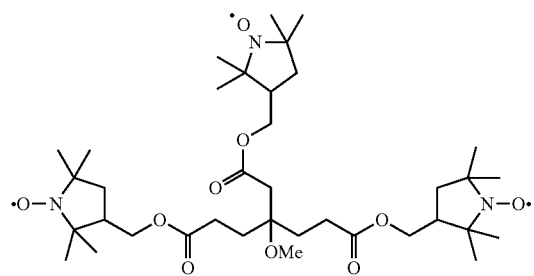
(I-3-19)
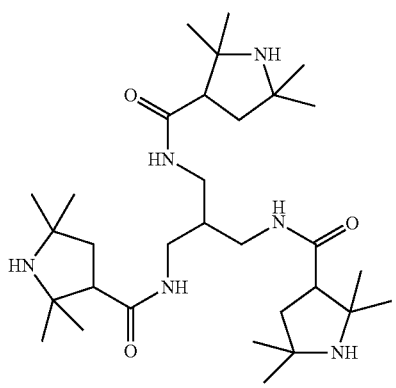
(I-3-20)
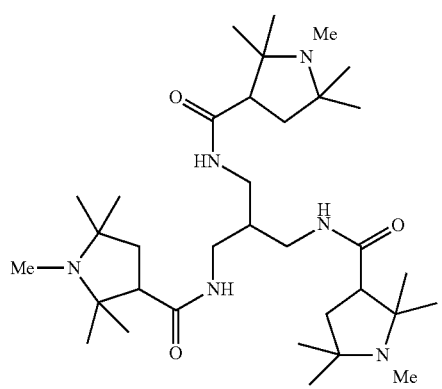
(I-3-21)
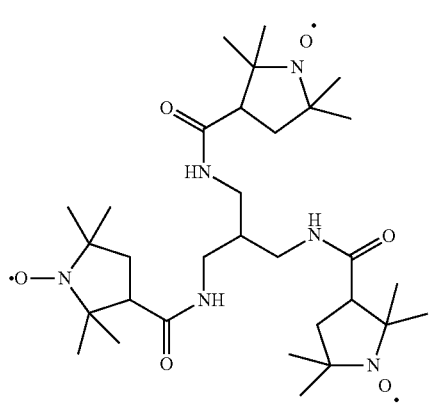

(I-3-22)
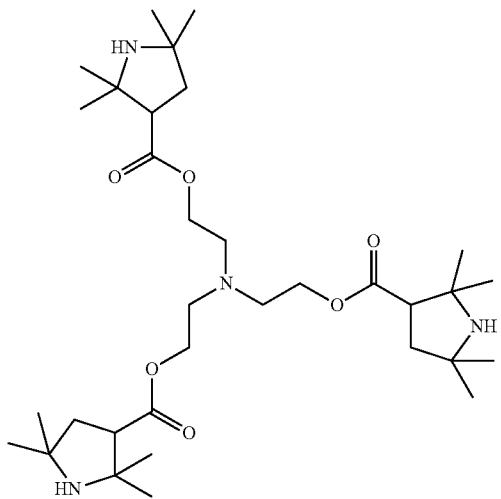
(I-3-23)
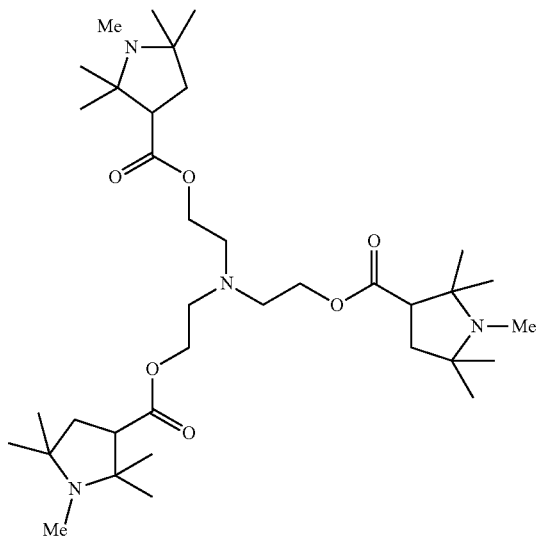
(I-3-24)
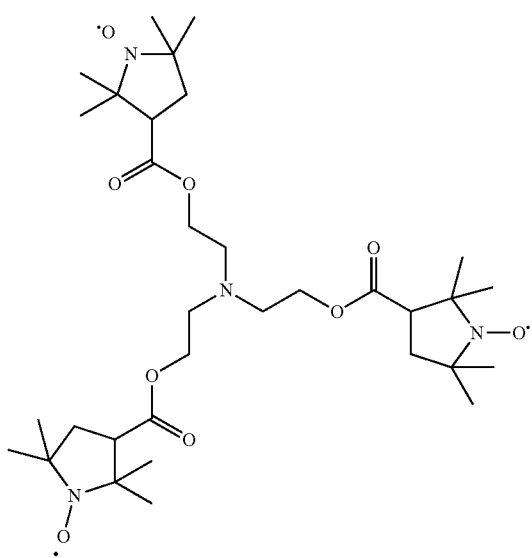
(I-3-25)
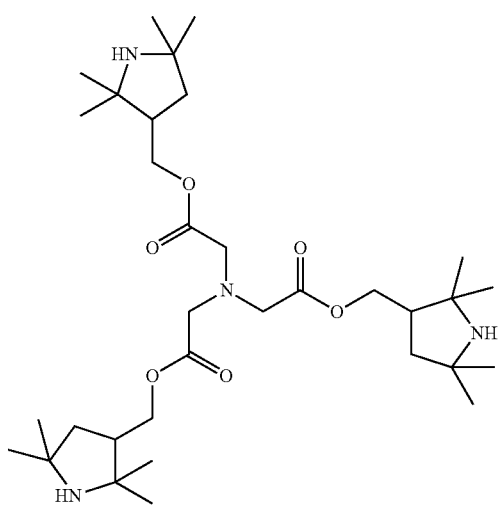

(I-3-26)
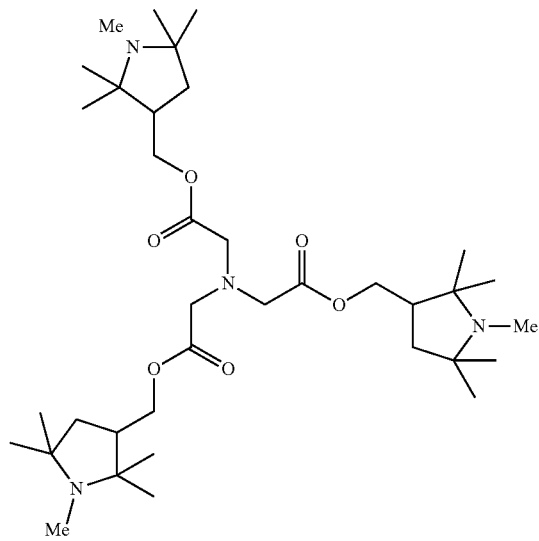
(I-3-27)
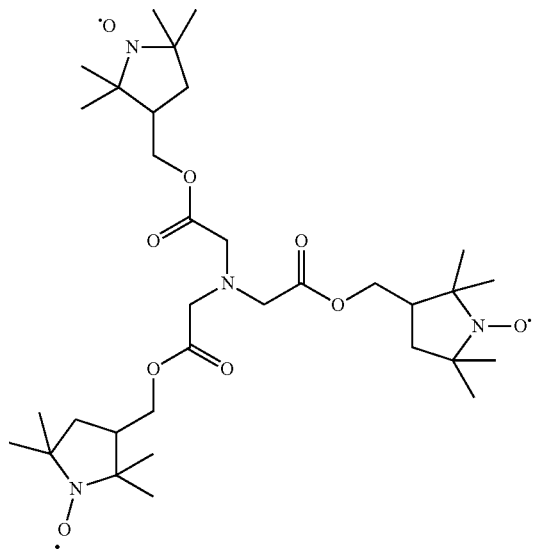
(I-3-28)
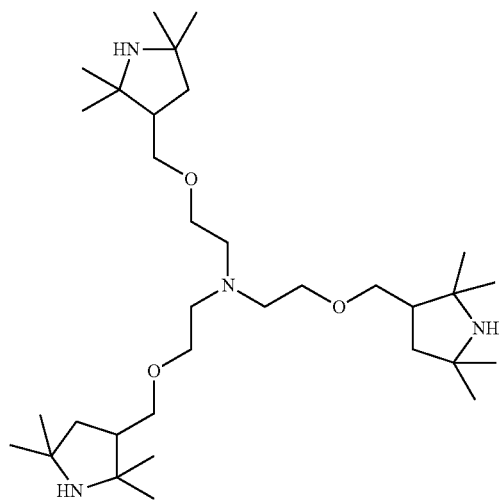
(I-3-29)
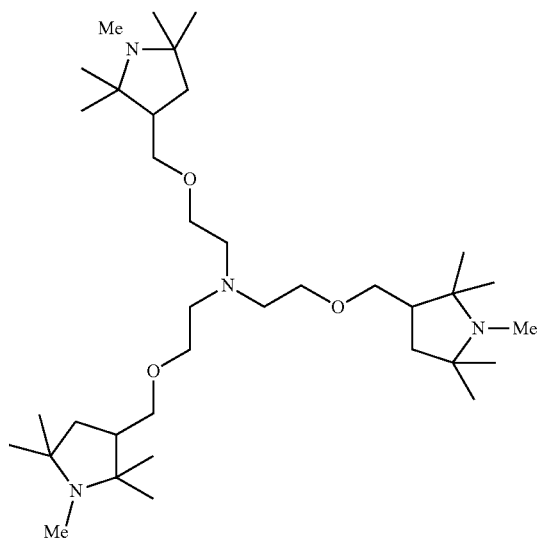

(I-3-30)
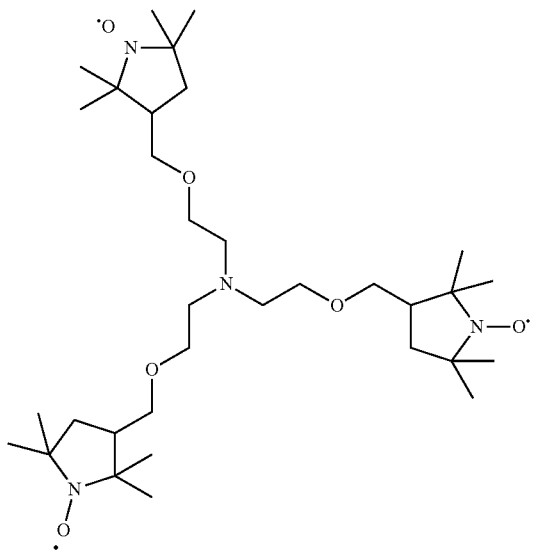
[Chem. 26]
(I-3-31)
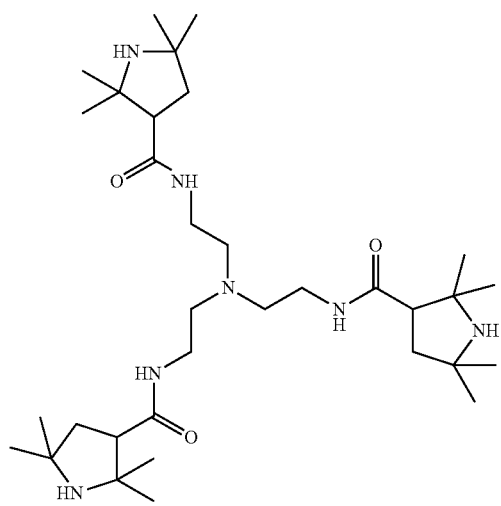
(I-3-32)
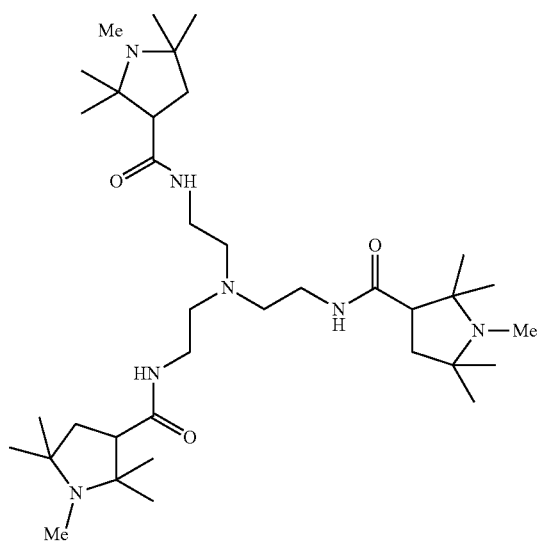

-continued
(I-3-33)
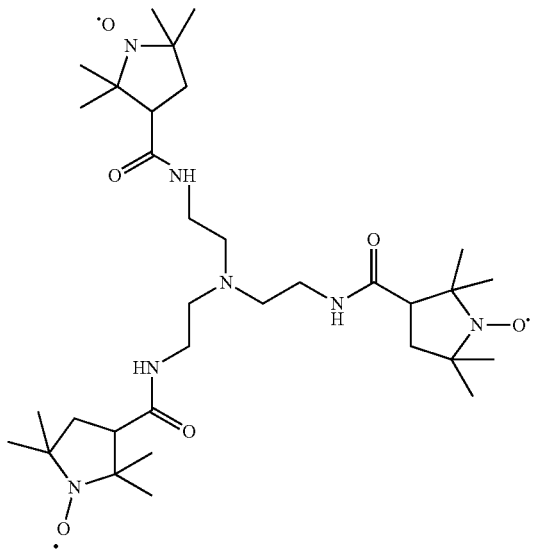
(I-3-34)
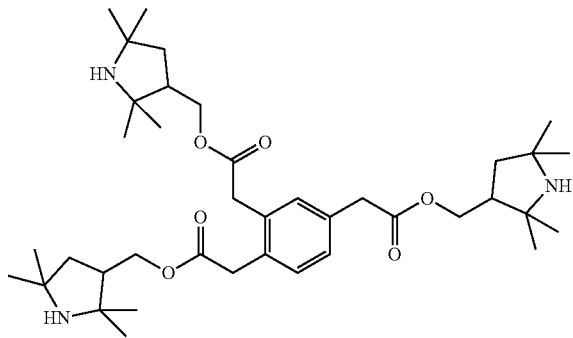
(I-3-35)
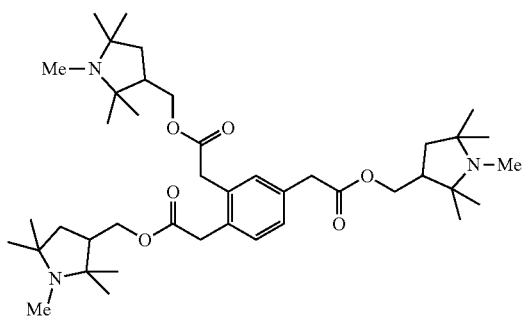
(I-3-36)
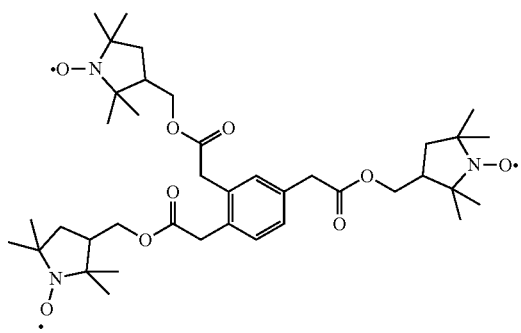
(I-3-37)
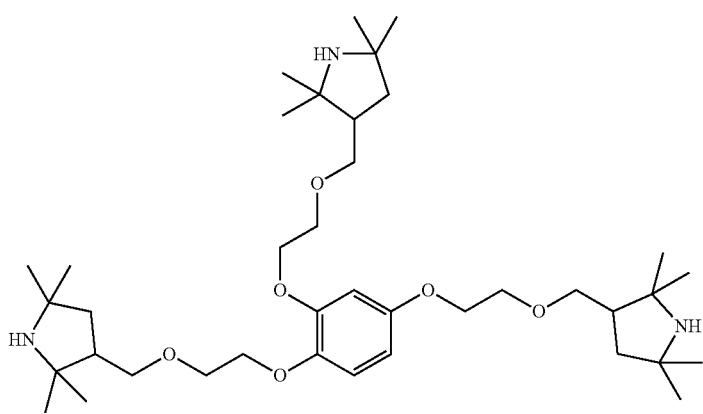

(I-3-38)
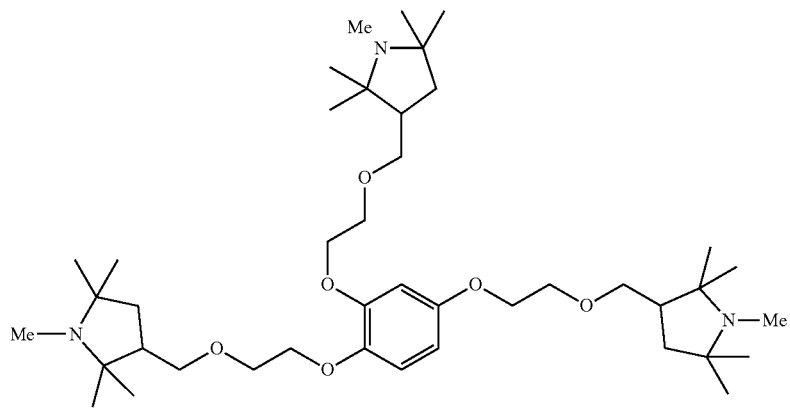
(I-3-39)
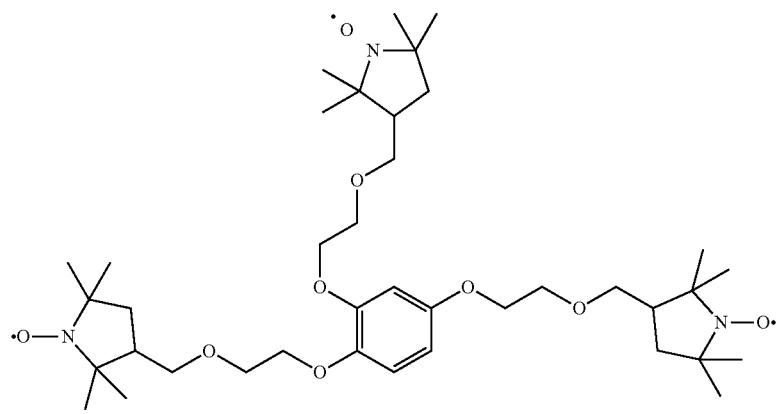
(I-3-40)
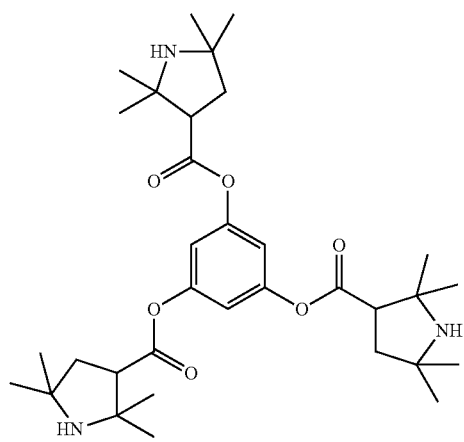
(I-3-41)
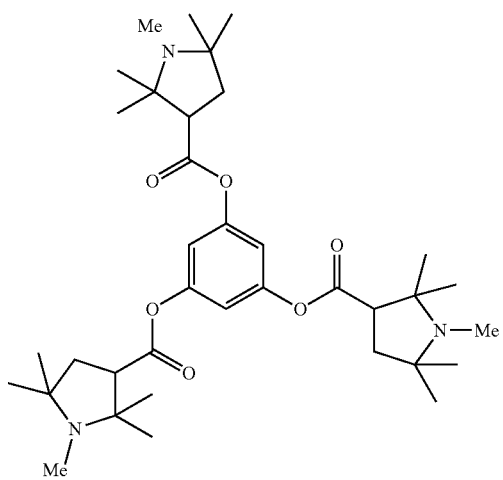

-continued
(I-3-42)
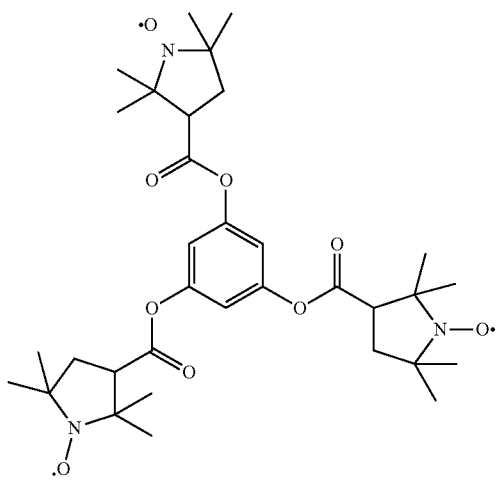
(I-3-43)
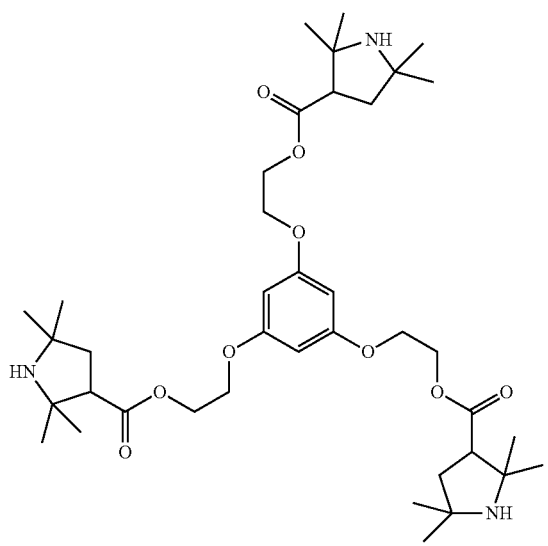
(I-3-44)
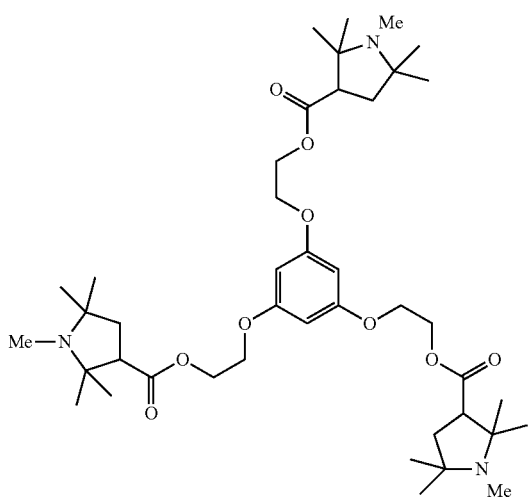
(I-3-45)
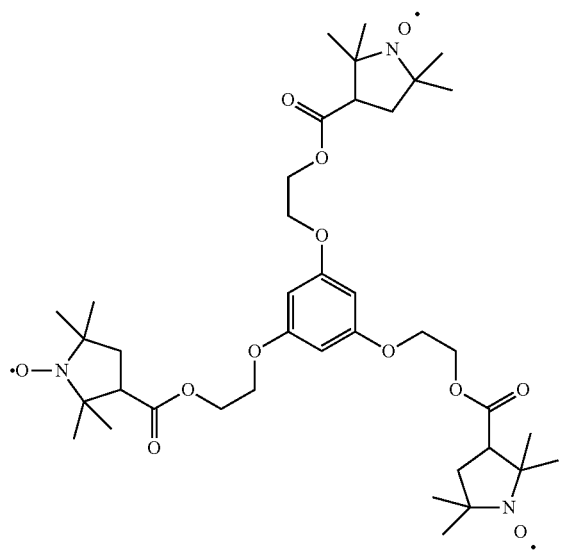
[Chem. 27]
(I-3-46)
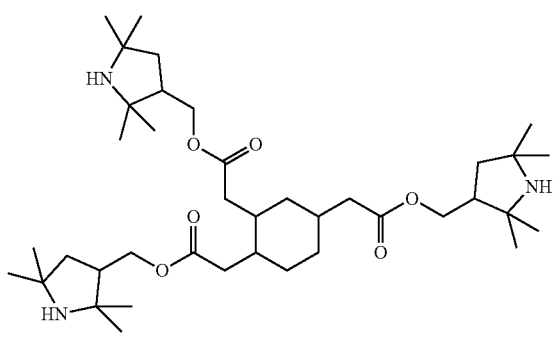
(I-3-47)
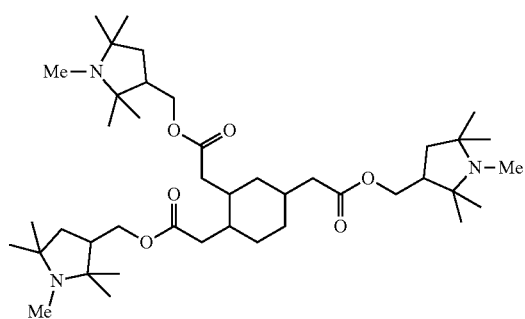

(I-3-48)
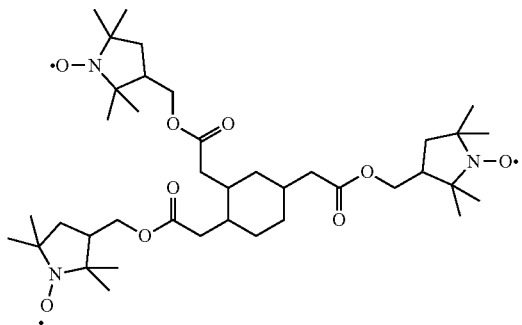
(I-3-49)
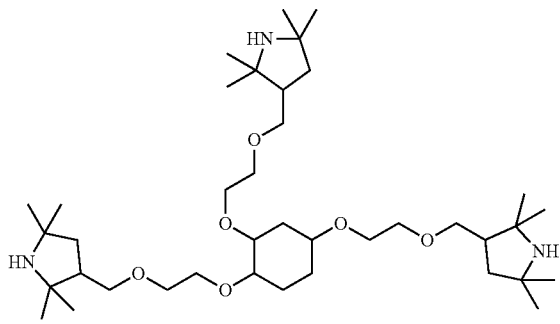
(I-3-50)
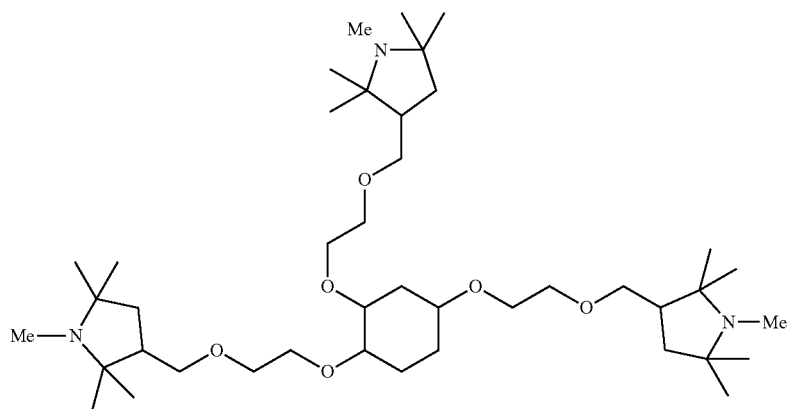
(I-3-51)
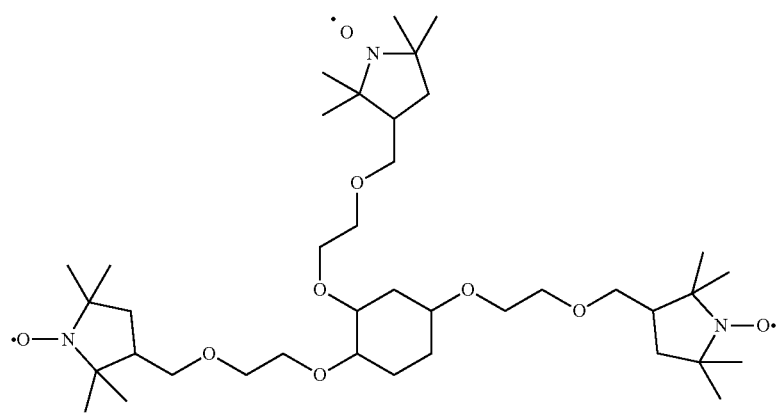

-continued
(I-3-52)
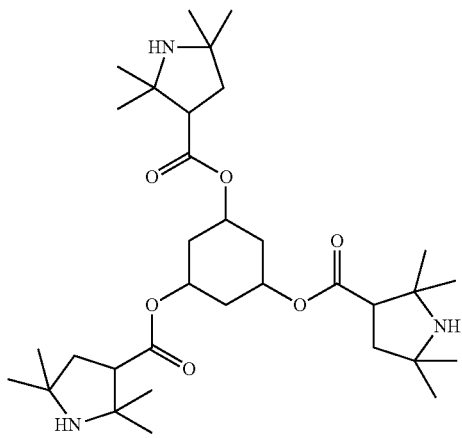
(I-3-53)
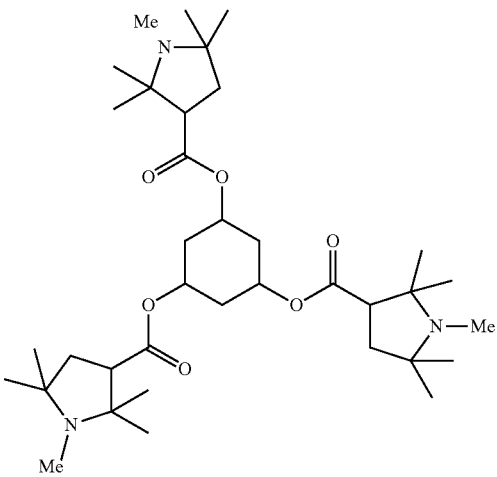
(I-3-54)
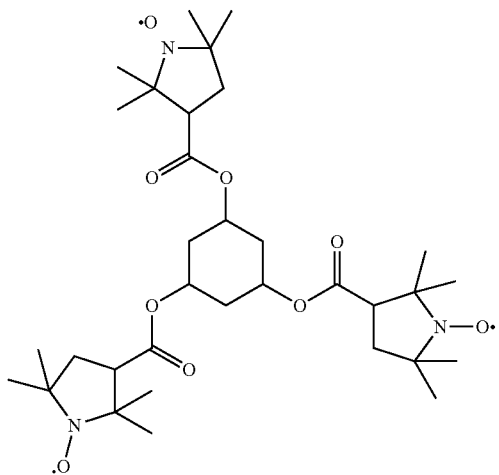
(I-3-55)
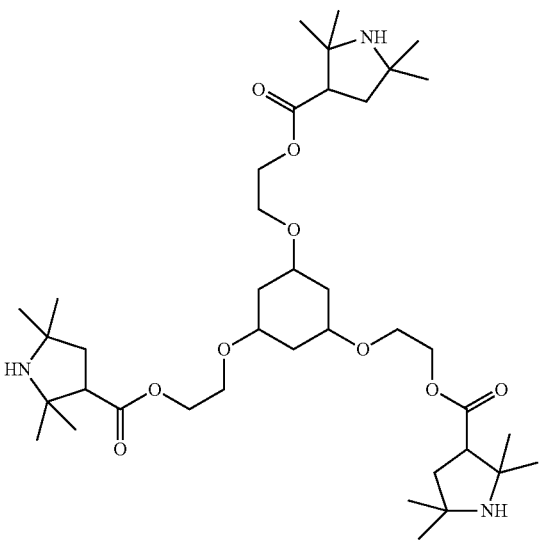
(I-3-56)
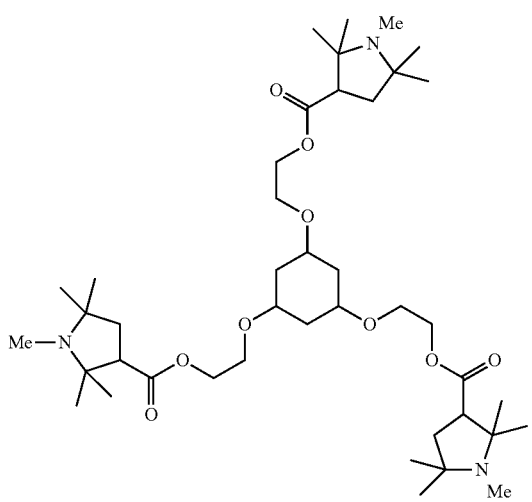
(I-3-57)
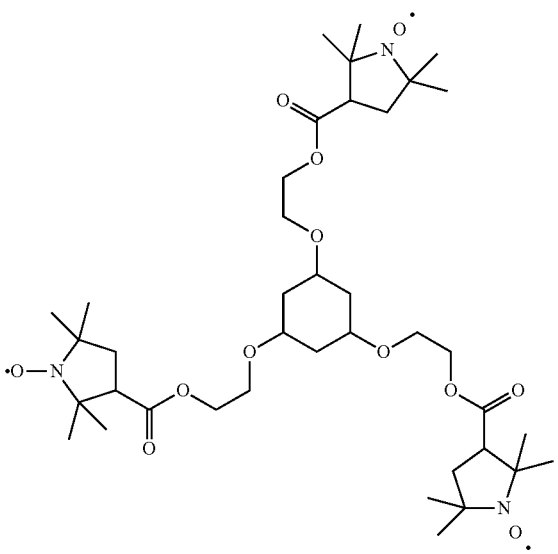

(I-3-58)
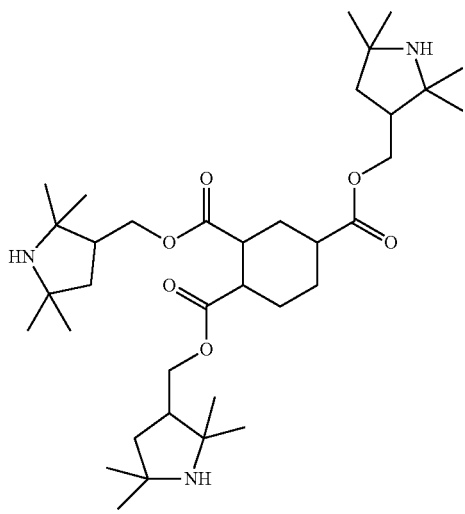
(I-3-59)
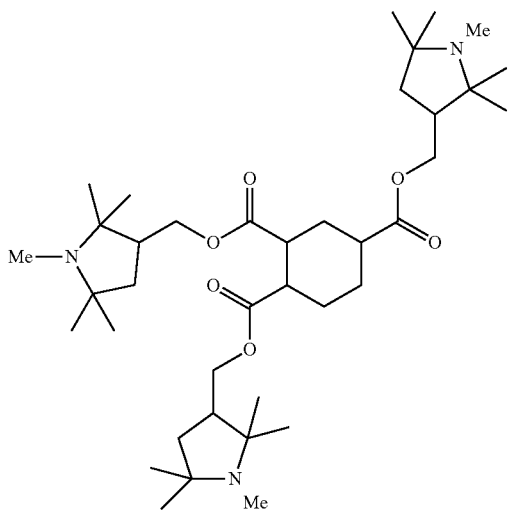
(I-3-60)
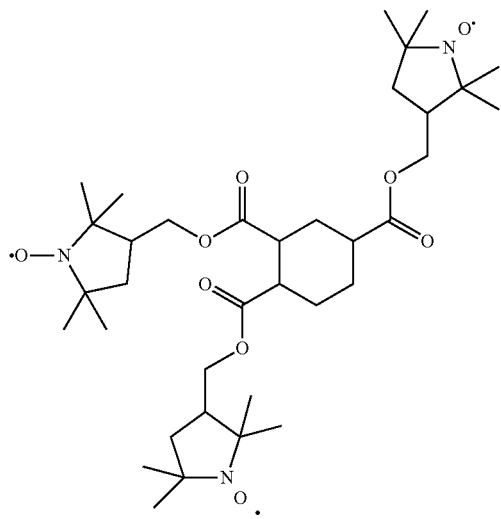
[Chem. 28]
(I-3-61)
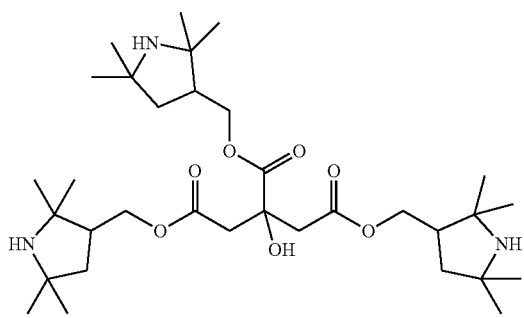
(I-3-62)
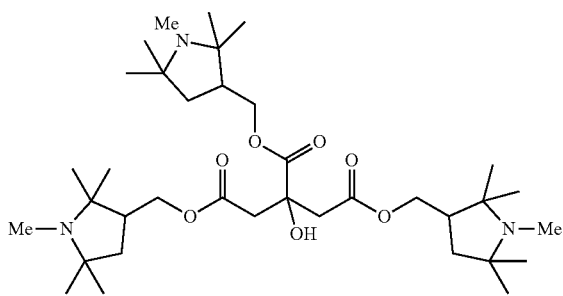

-continued (I-3-63)
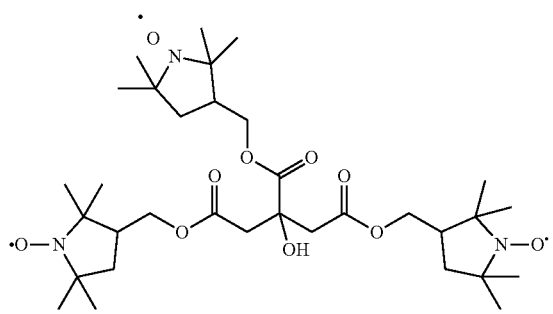

(I-3-64)
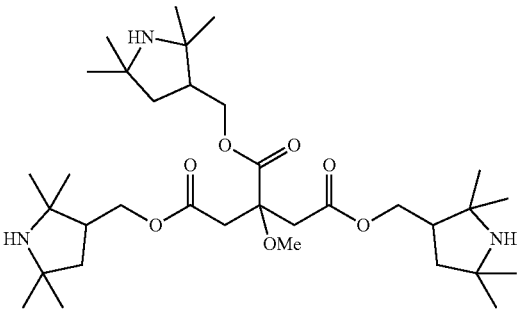

(I-3-65)
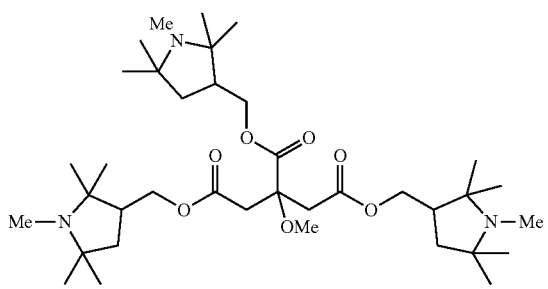

(I-3-66)
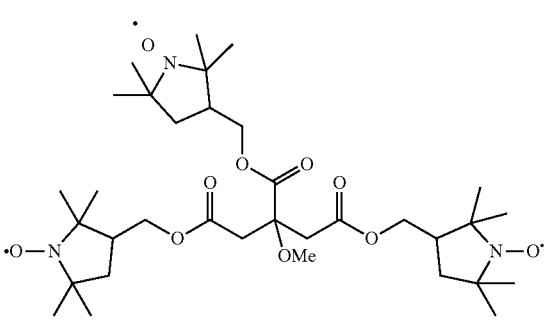

(I-3-67)
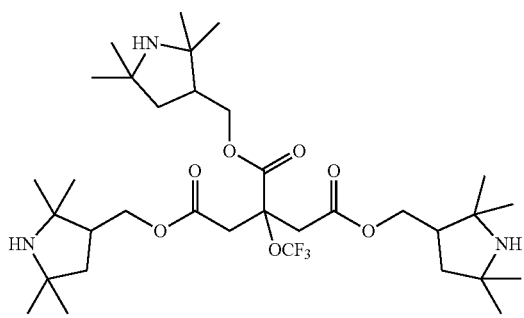

(I-3-68)

(I-3-69)
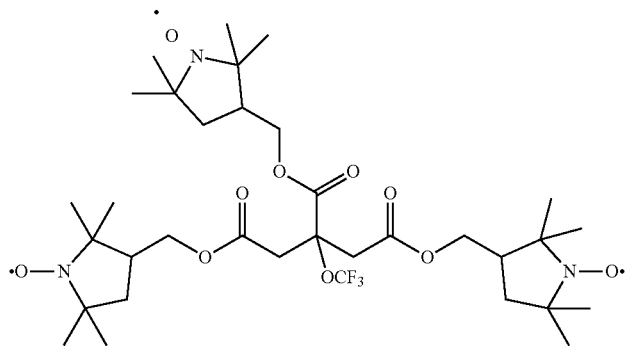

(In the formulae, Me denotes a methyl group.)

In the general formula (I), if n in the general formula (I) is 4, that is, if nu1 in the general formula (U-1) is 4, and W has a valence of 4, then W in the general formula (U-1) preferably denotes a hydrocarbon group having 1 to 15 carbon atoms, one —CH$_2$— or two or more nonadjacent —CH$_2$— groups in the hydrocarbon group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—. W more preferably denotes a group selected from the groups represented by the formulae (W4-1) to (W4-21).
[Chem. 29]
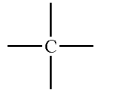
(W4-1)
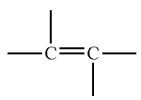
(W4-2)
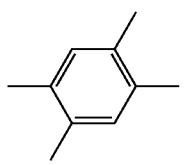
(W4-3)
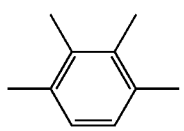
(W4-4)
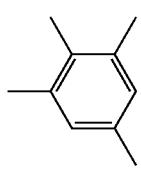
(W4-5)
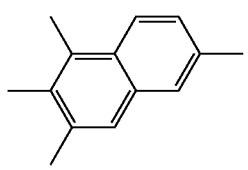
(W4-6)
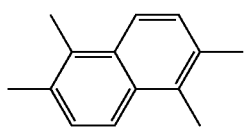
(W4-7)
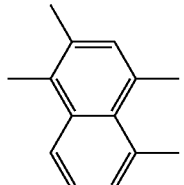
(W4-8)
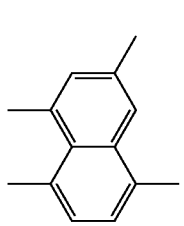
(W4-9)
-continued
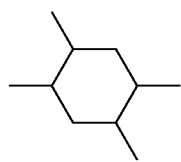
(W4-10)
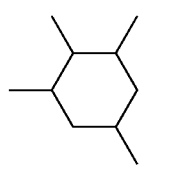
(W4-11)
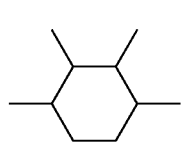
(W4-12)
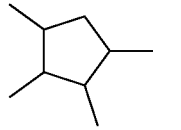
(W4-13)
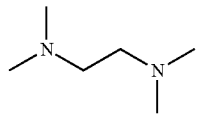
(W4-14)
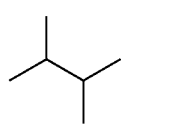
(W4-15)
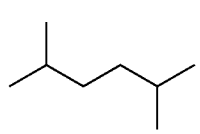
(W4-16)
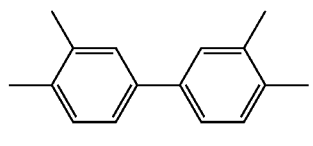
(W4-17)
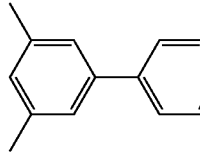
(W4-18)
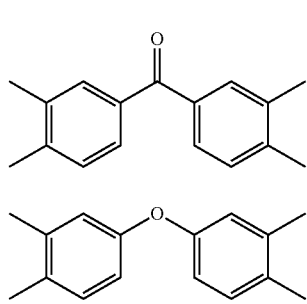
(W4-19)
(W4-20)

-continued (W4-21)

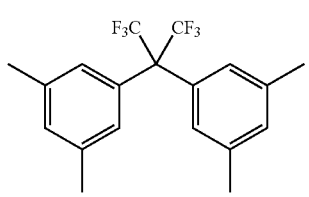

A hydrogen atom in the ring structure may be substituted with a fluorine atom, a chlorine atom, a bromine atom, an iodine atom, a pentafluorosulfanyl group, a nitro group, a cyano group, an isocyano group, an amino group, a hydroxy group, a mercapto group, a methylamino group, a dimethylamino group, a diethylamino group, a diisopropylamino group, a trimethylsilyl group, a dimethylsilyl group, a thioisocyano group, or an alkyl group having 1 to 12 carbon atoms, and one —CH$_2$— or two or more nonadjacent —CH$_2$— groups in the alkyl group may be independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—. The formulae (W4-3) to (W4-21) are preferably independently unsubstituted, and a hydrogen atom in the formulae (W4-3) to (W4-21) may be substituted with a cyano group, a fluorine atom, a chlorine atom, a methyl group, or a methoxy group.

From the perspective of the availability and manufacturability of raw materials, a group selected from the formula (W4-1), the formula (W4-2), and the unsubstituted formulae (W4-3) to (W4-21) is particularly preferred.

More specifically, a compound in which n in the general formula (I) is 4 is preferably one of the compounds represented by the following formulae (I-4-1) to (I-4-95).

[Chem. 30]

(I-4-1)

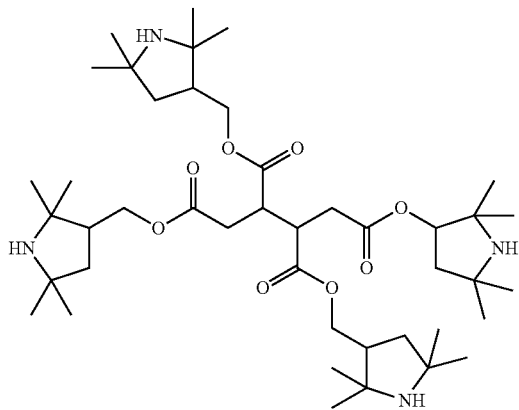

(I-4-2)

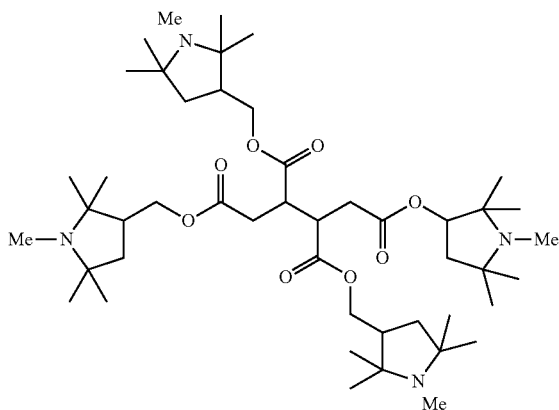

(I-4-3)

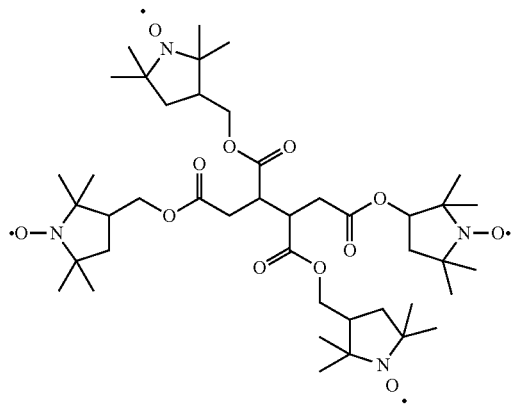

(I-4-4)

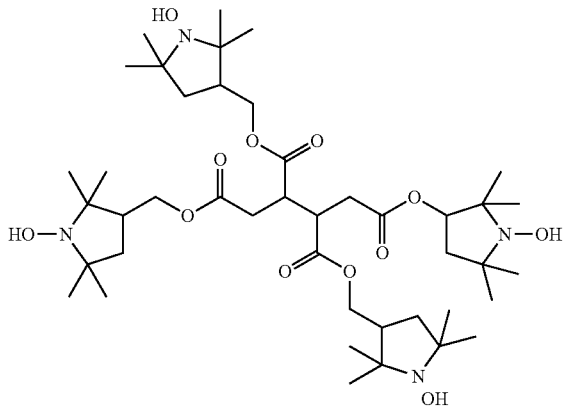

(I-4-5)
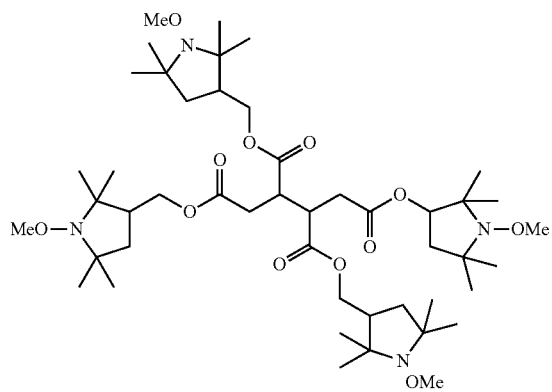
(I-4-6)
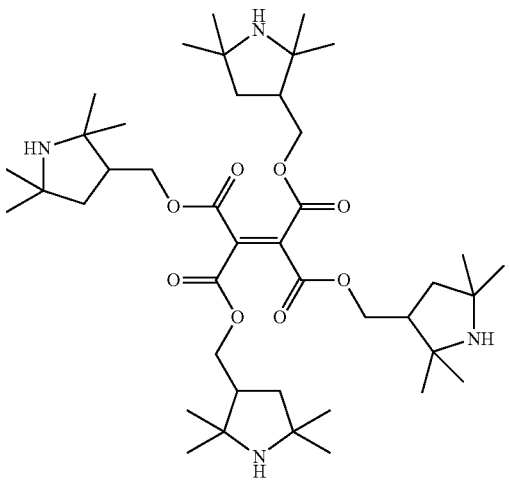
(I-4-7)
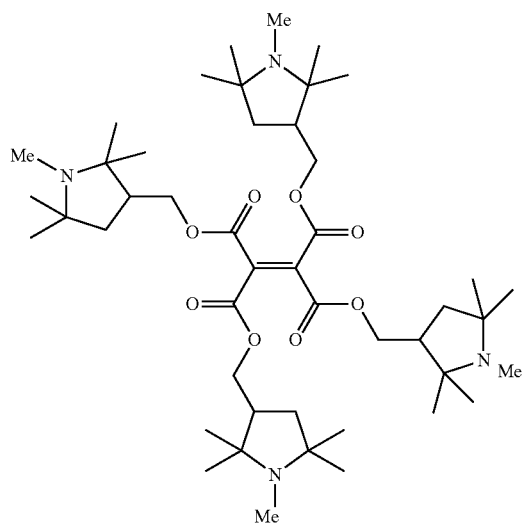
(I-4-8)
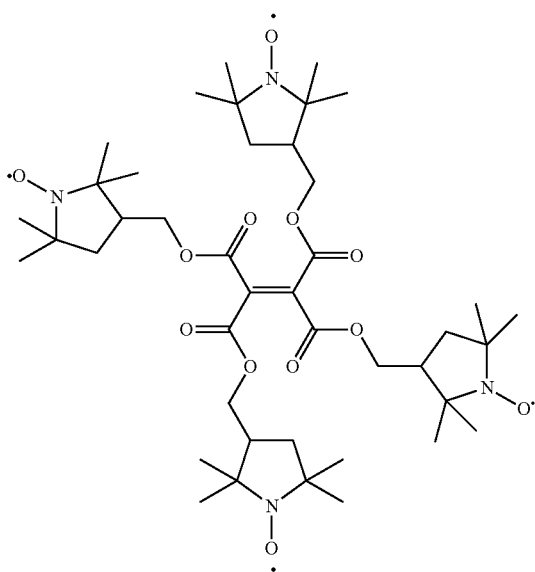
(I-4-9)
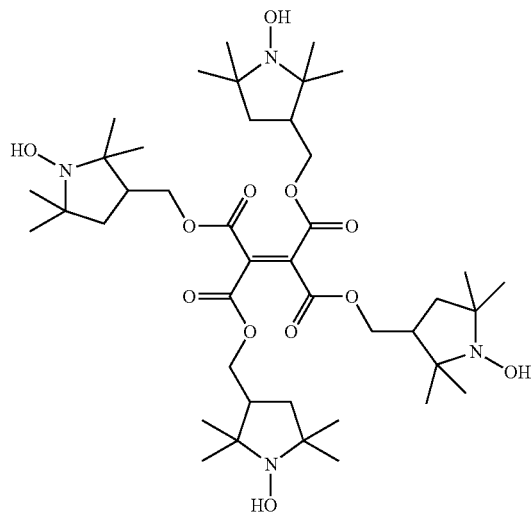
(I-4-10)
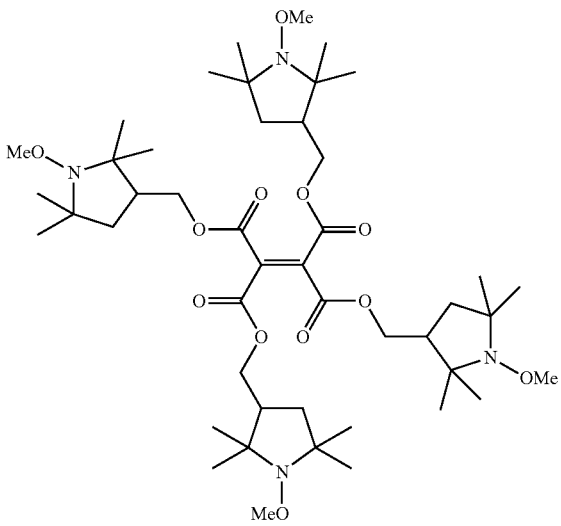

-continued
(I-4-11)
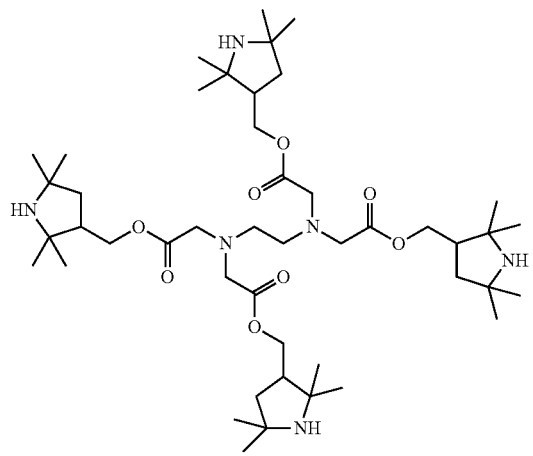
(I-4-12)
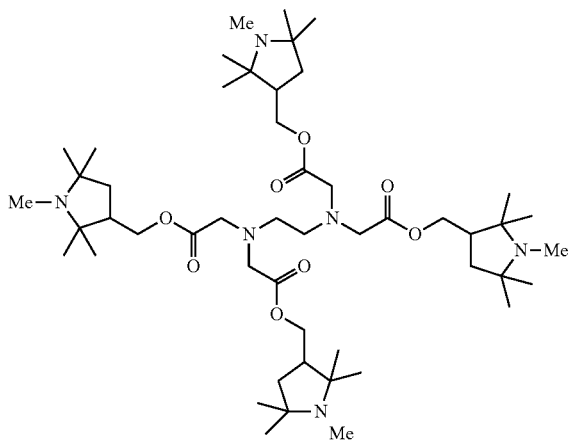
(I-4-13)
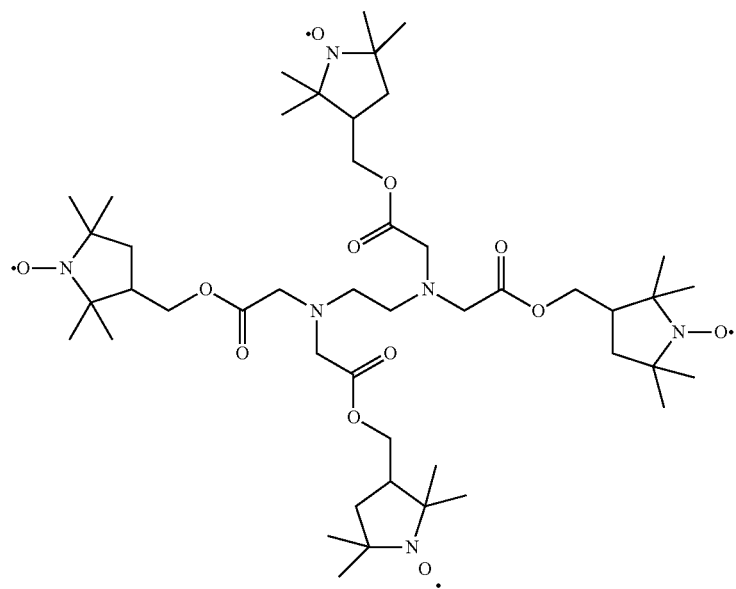
(I-4-14)
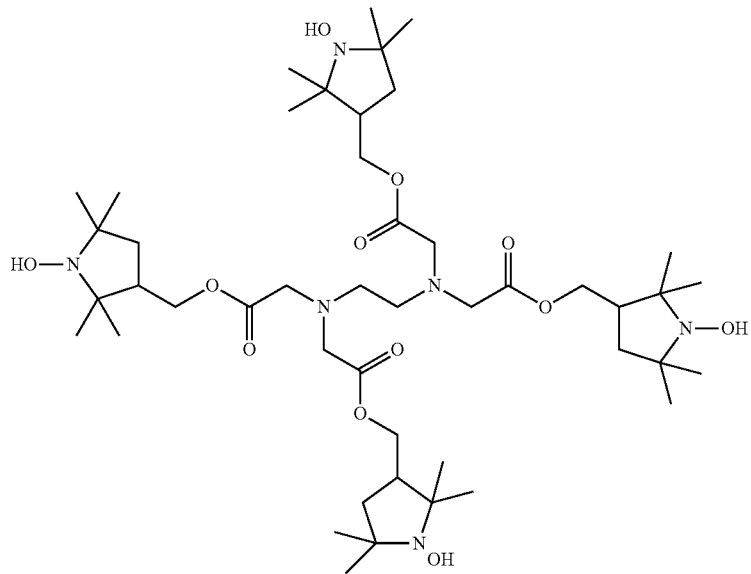

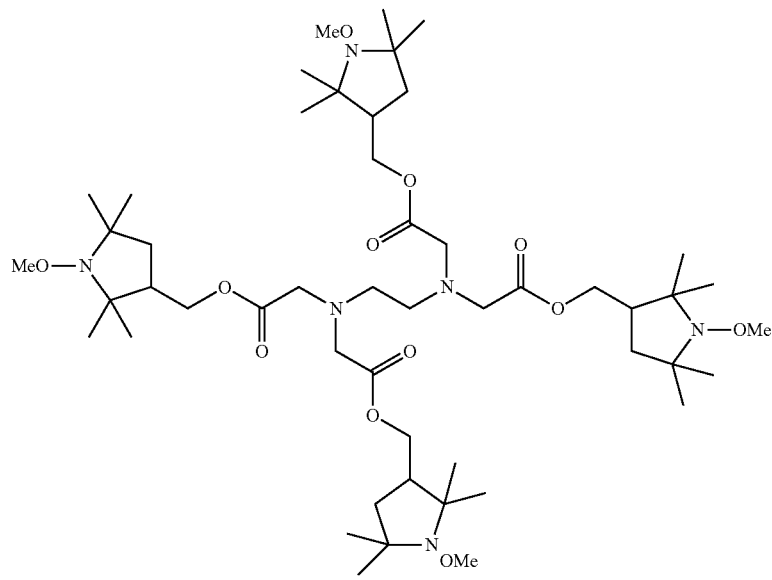
(I-4-15)
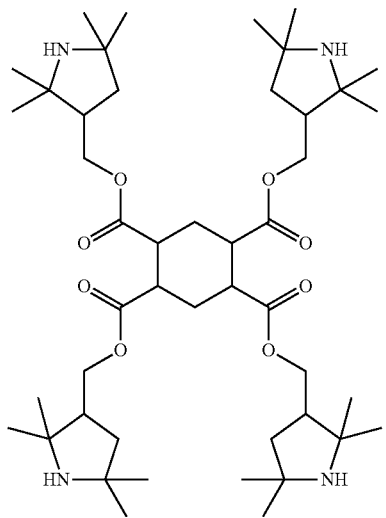
(I-4-16)
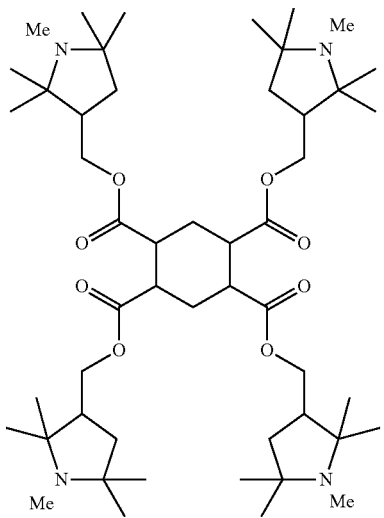
(I-4-17)
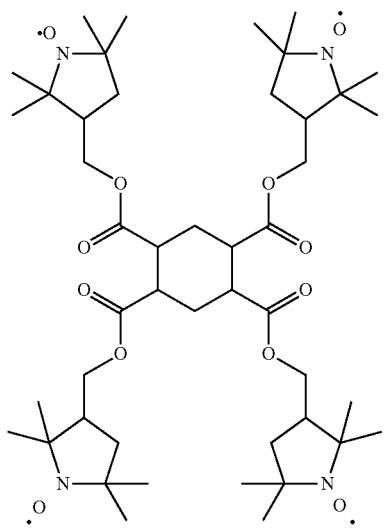
(I-4-18)
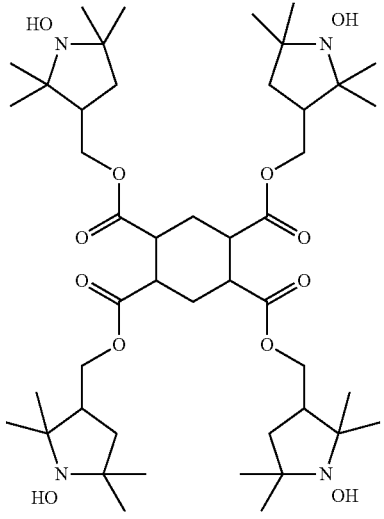
(I-4-19)

(I-4-20)
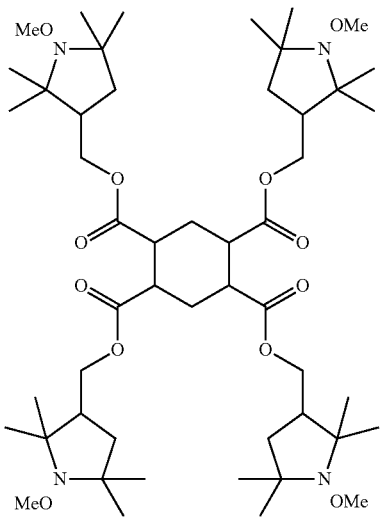
[Chem. 32]
(I-4-21)
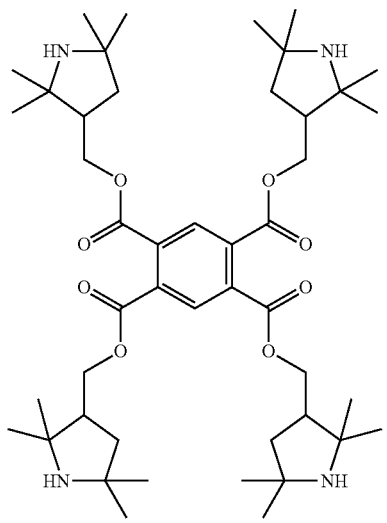
(I-4-22)
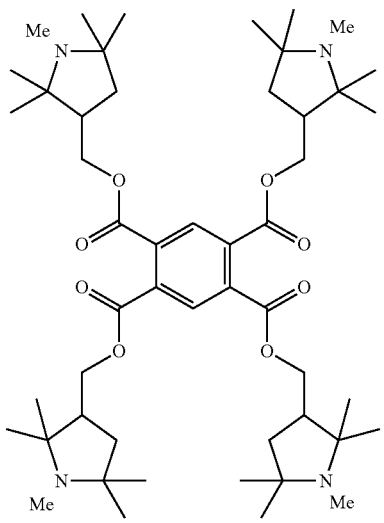
(I-4-23)
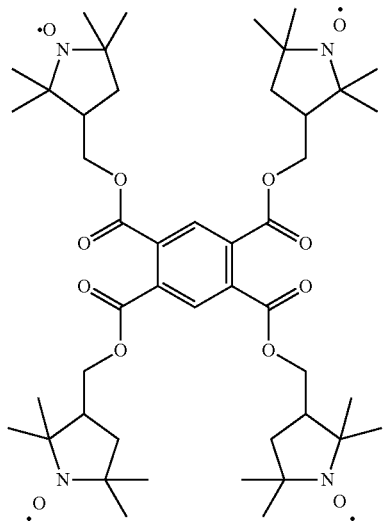
(I-4-24)
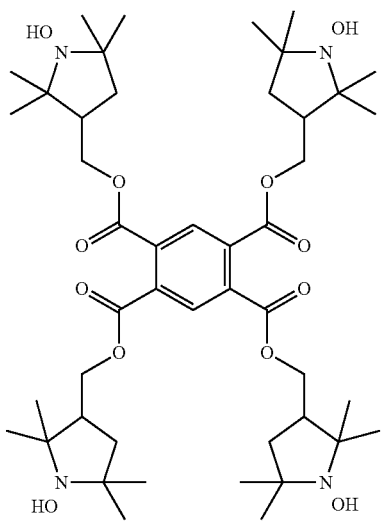

-continued
(I-4-25)
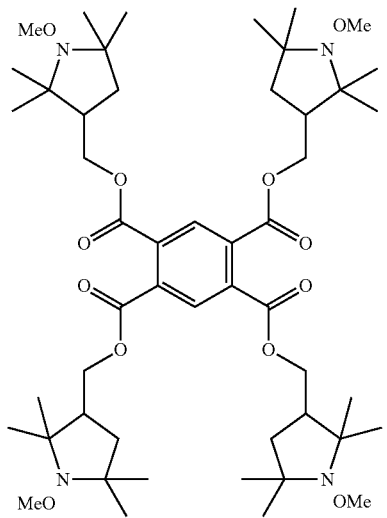
(I-4-26)
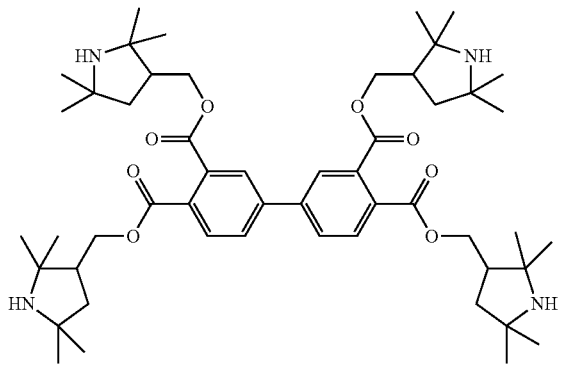
(I-4-27)
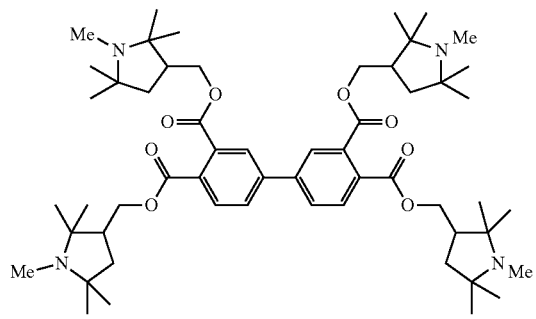
(I-4-28)
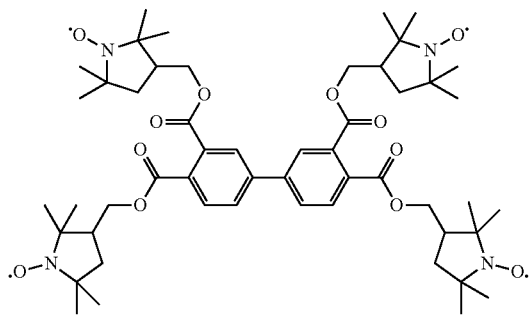
(I-4-29)
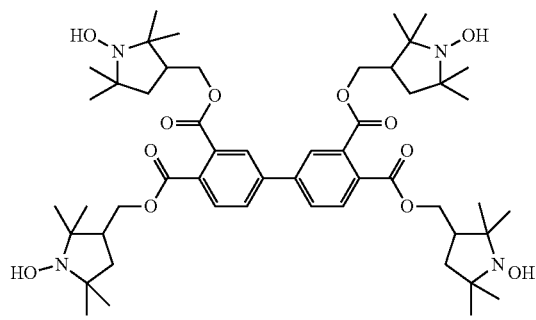
(I-4-30)
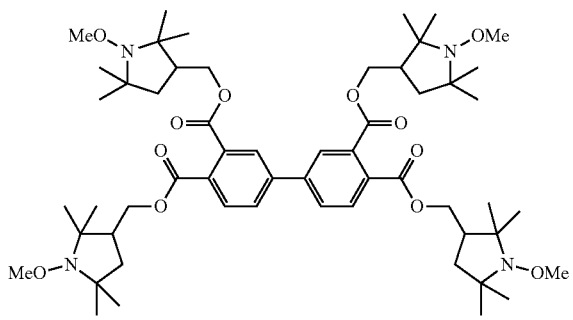

[Chem. 33]
(I-4-31)
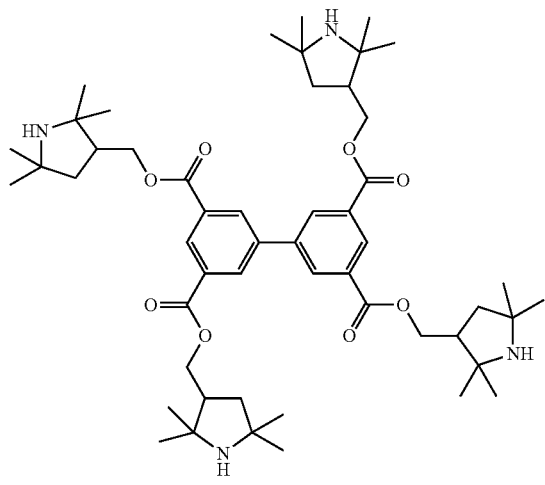
(I-4-32)
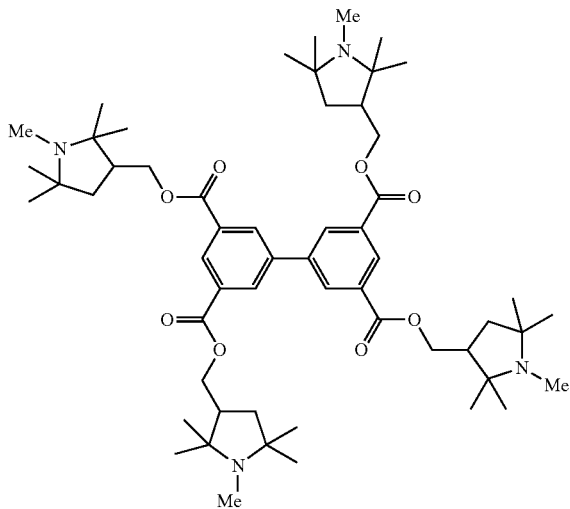
(I-4-33)
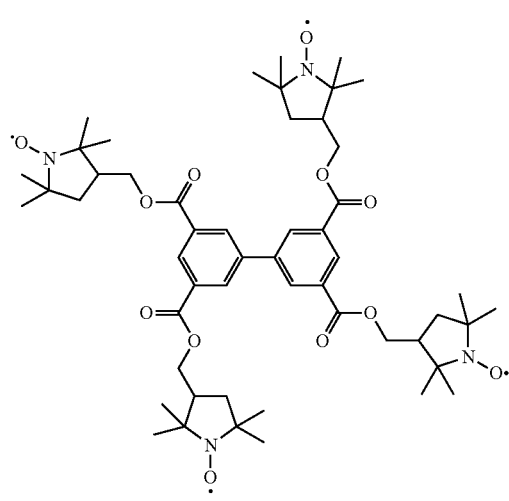
(I-4-34)
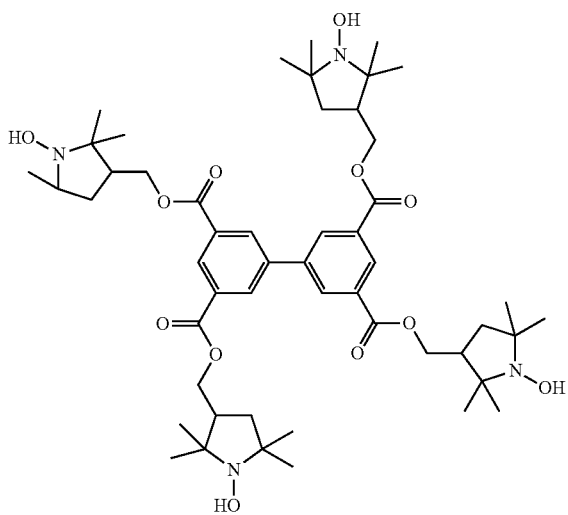
(I-4-35)
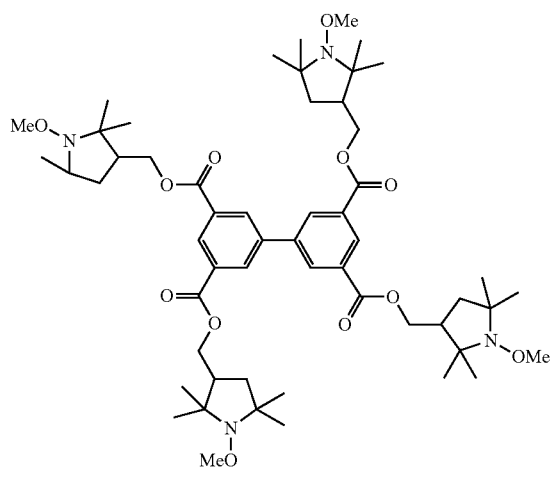
(I-4-36)
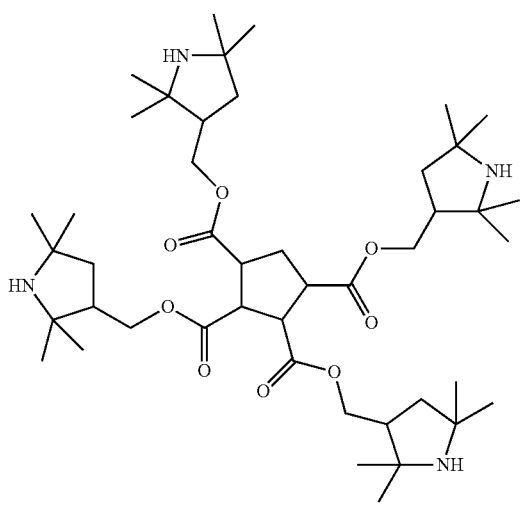

-continued
(I-4-37)
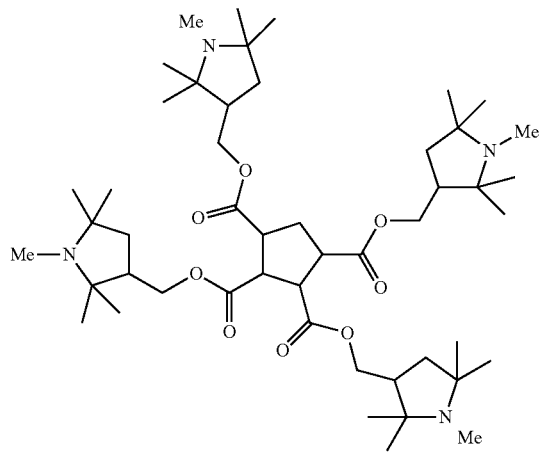
(I-4-38)
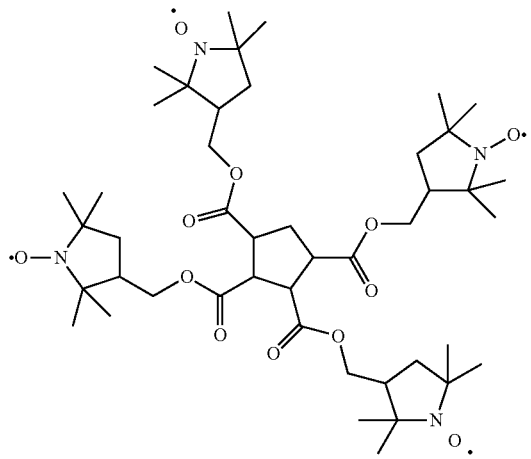
(I-4-39)
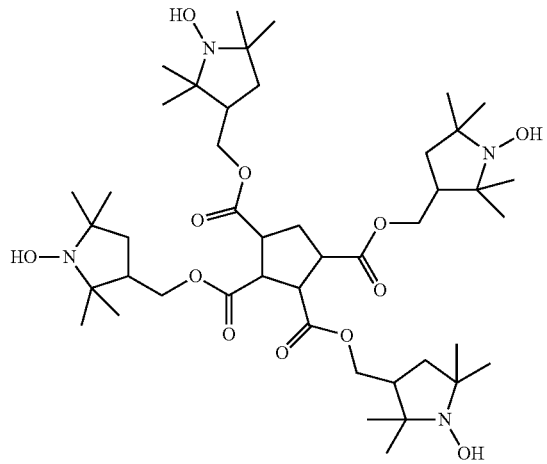
(I-4-40)
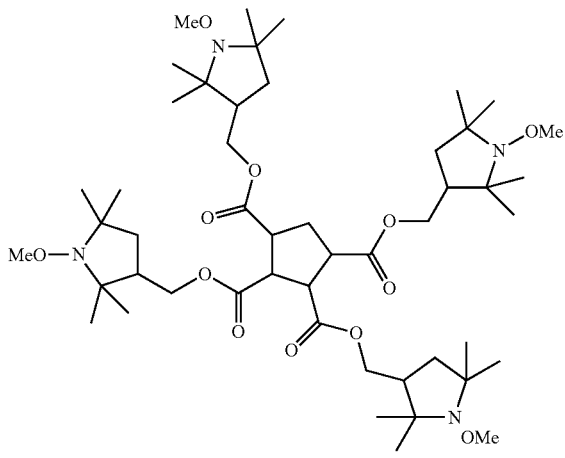
[Chem. 34]
(I-4-41)
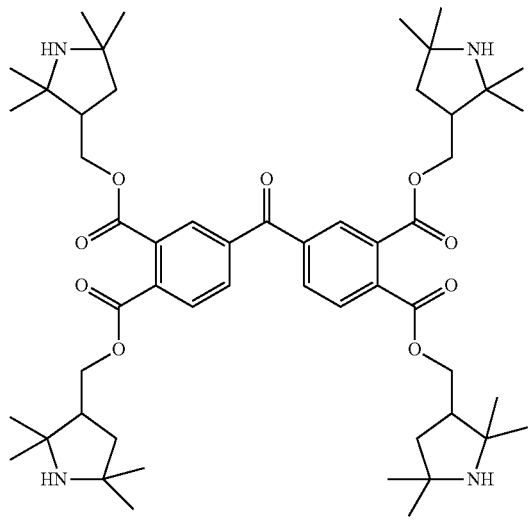
(I-4-42)
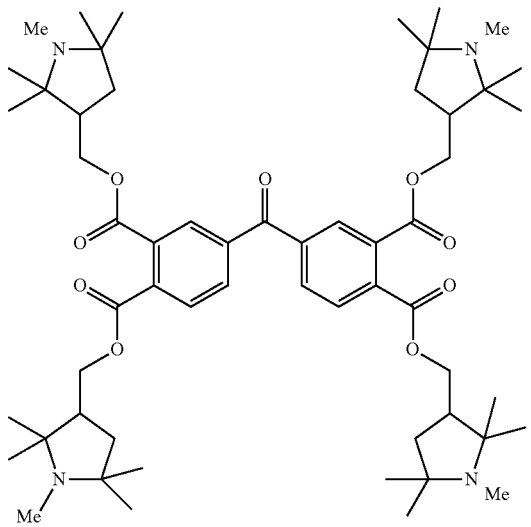

-continued
(I-4-43)
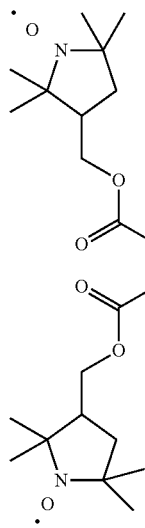
(I-4-44)
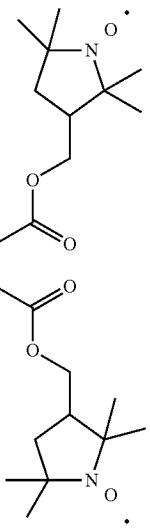
(I-4-45)
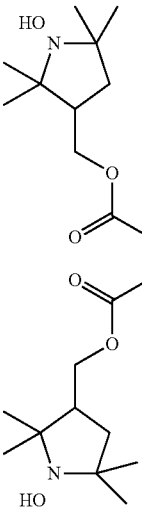
(I-4-46)
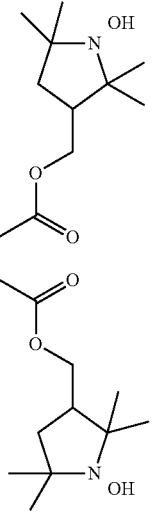
(I-4-47)
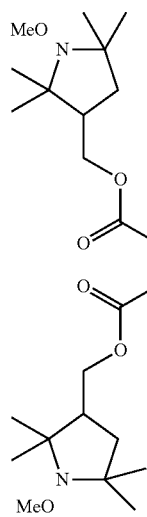
(I-4-48)
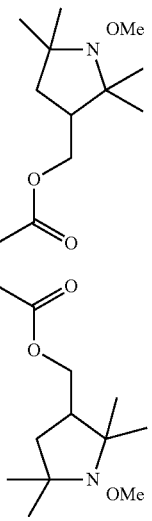
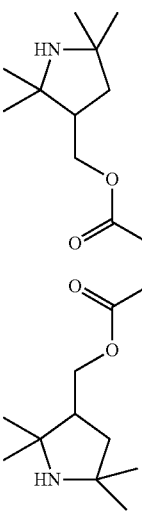
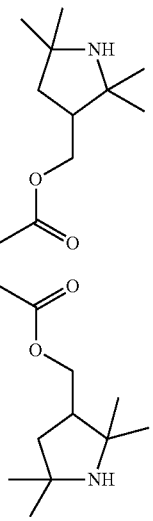

-continued
(I-4-49)
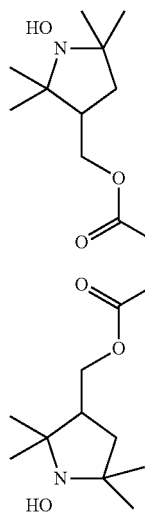
(I-4-50)
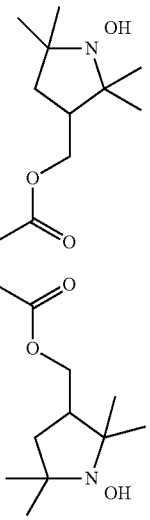
(I-4-50)
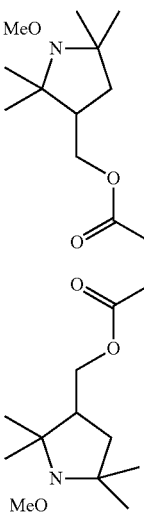
(I-4-50)
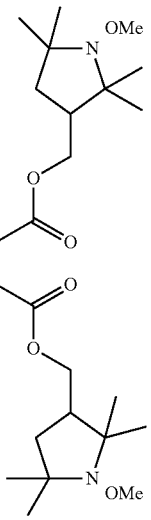
[Chem. 35]
(I-4-51)
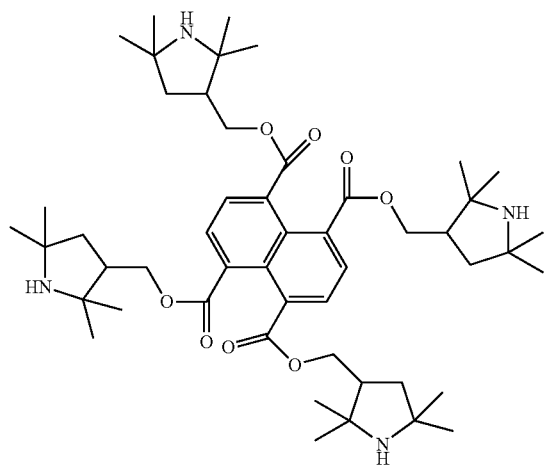
(I-4-52)
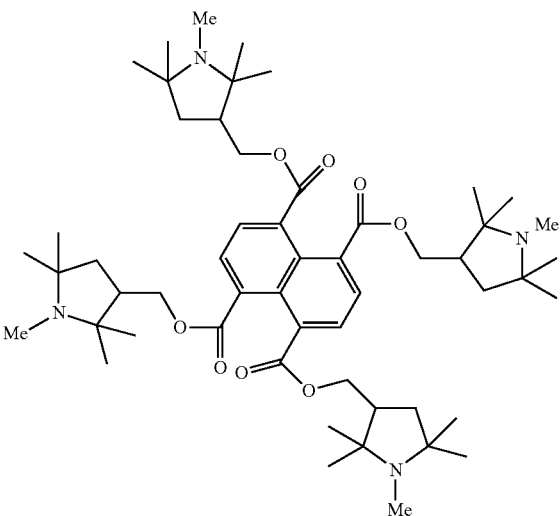
(I-4-53)
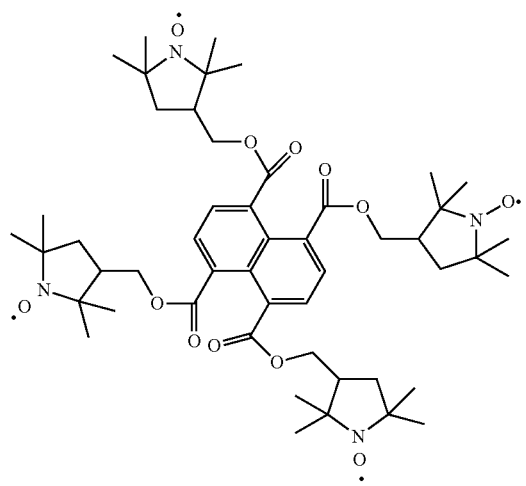
(I-4-54)
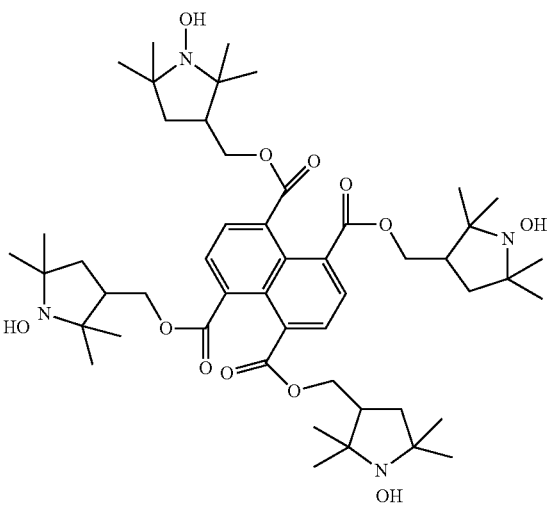

-continued
(I-4-55)
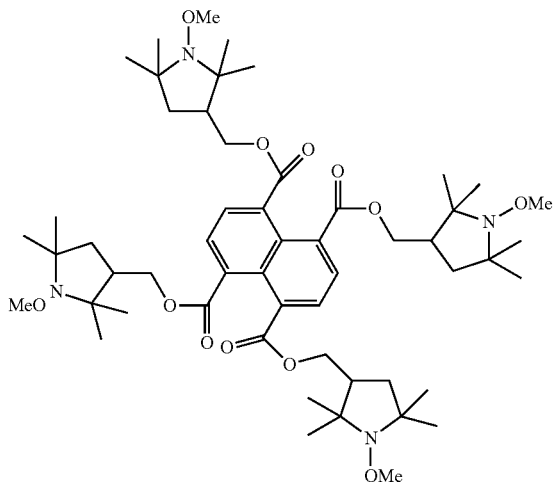
(I-4-56)
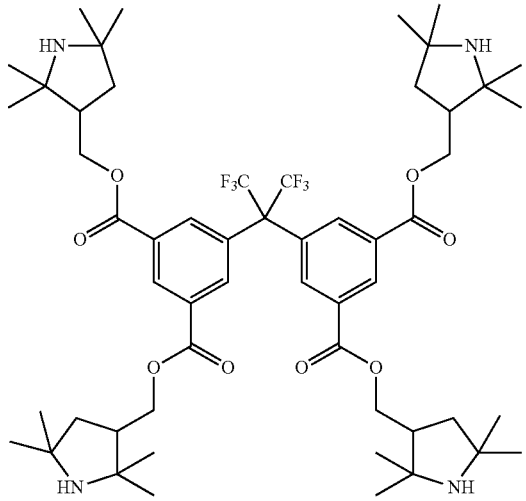
(I-4-57)
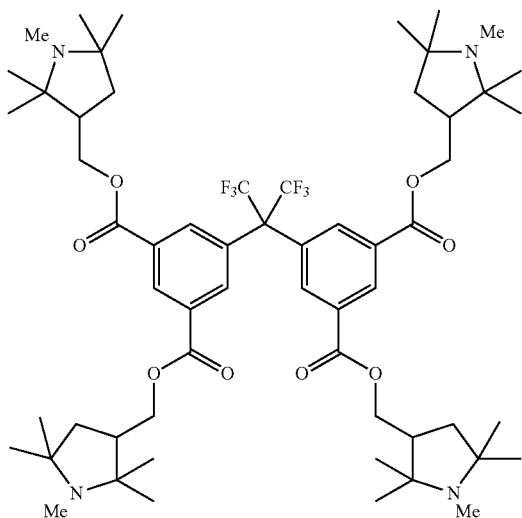
(I-4-58)
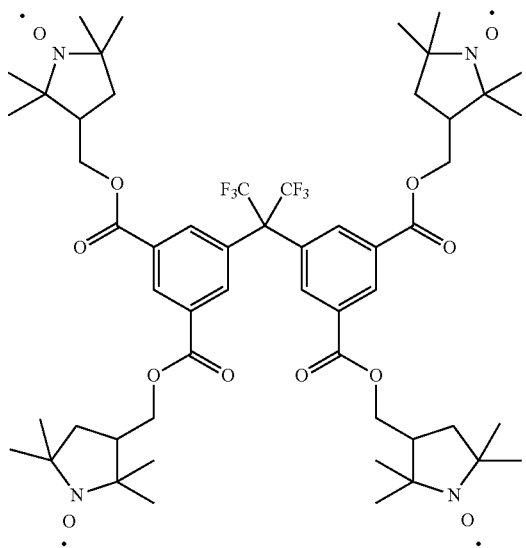
(I-4-59)
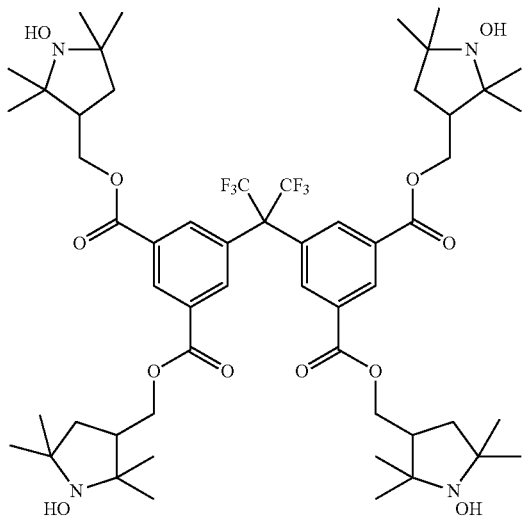
(I-4-60)
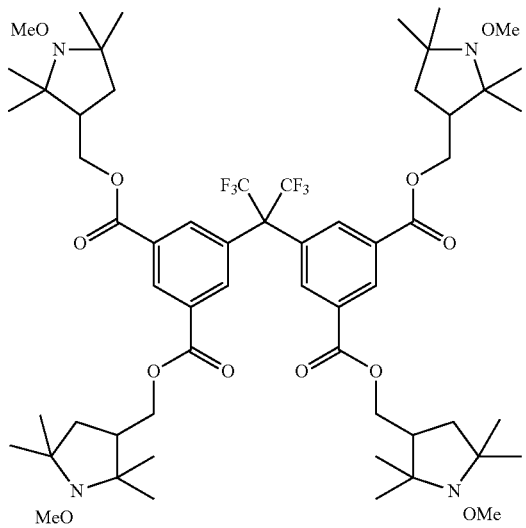

[Chem. 36]
(I-4-61)
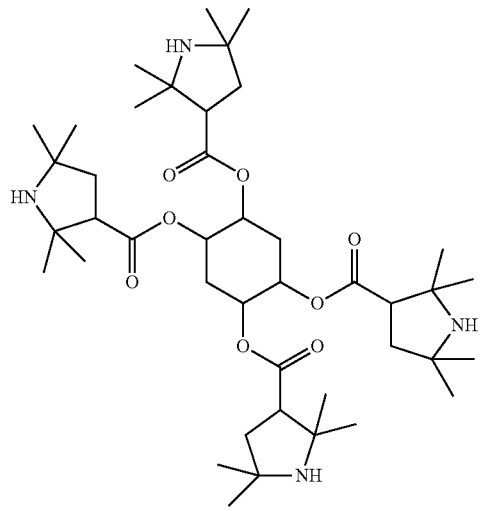
(I-4-62)
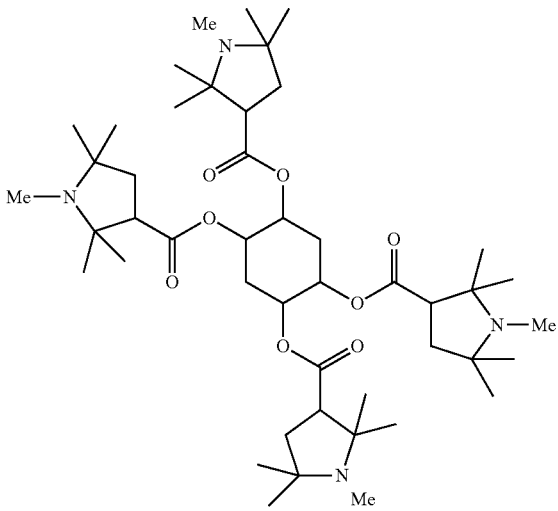
(I-4-63)
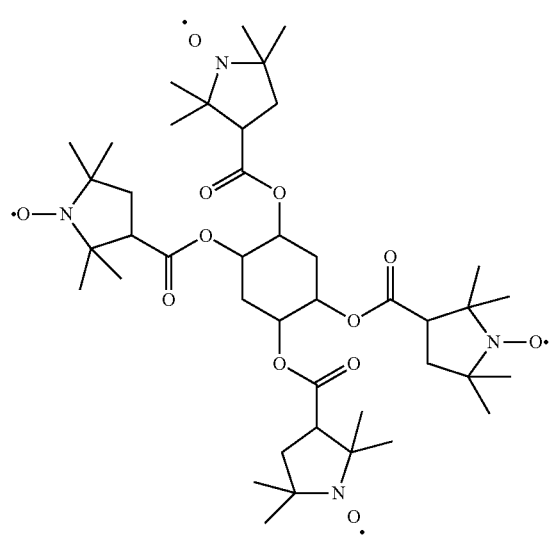
(I-4-64)
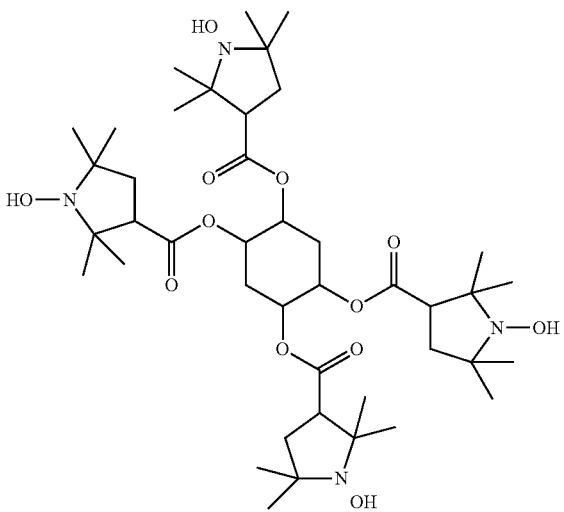
(I-4-65)
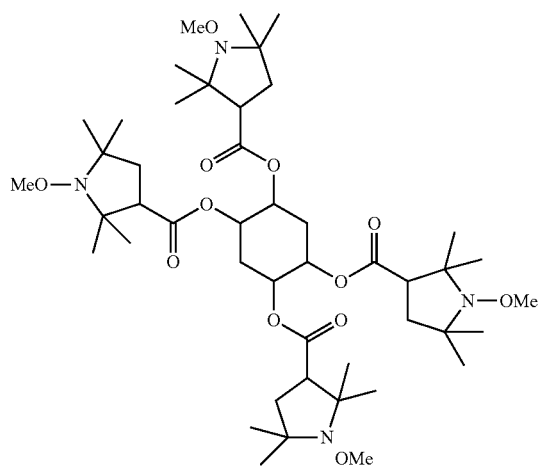
(I-4-66)
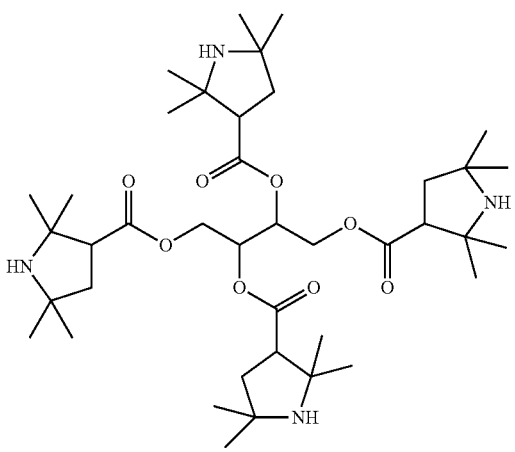

(I-4-67)
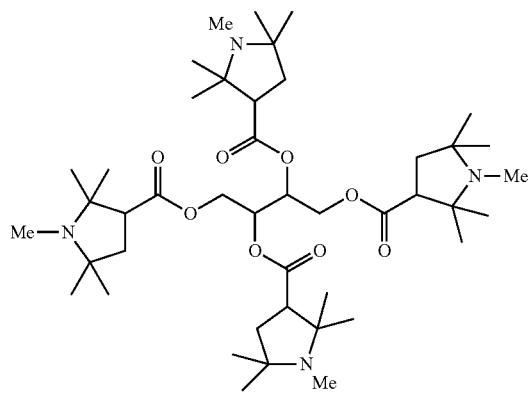
(I-6-68)
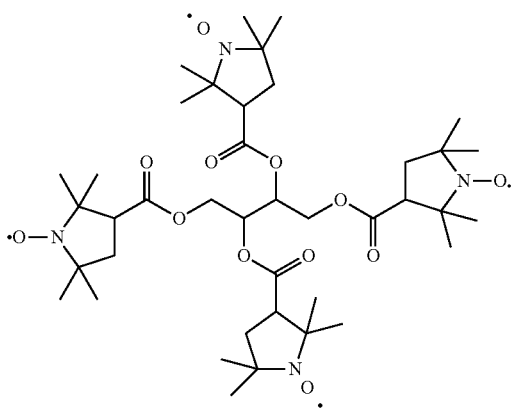
(I-4-69)
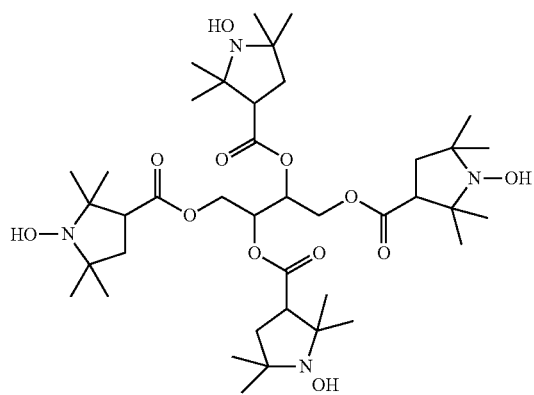
(I-4-70)
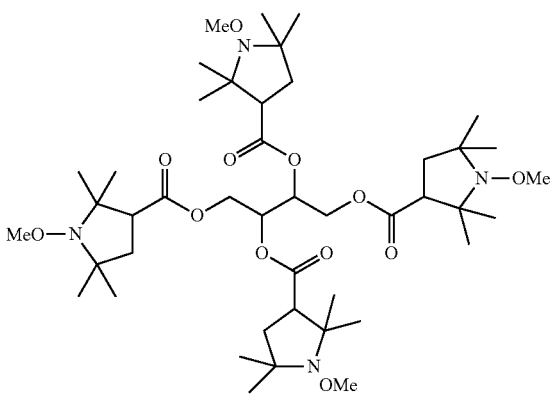
[Chem. 37]
(I-4-71)
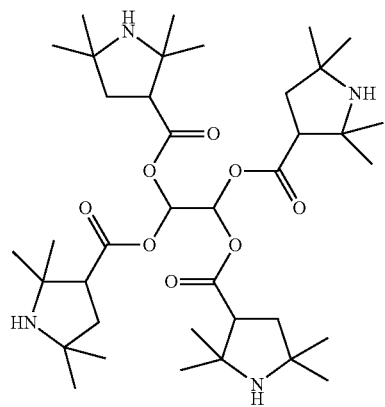
(I-4-72)
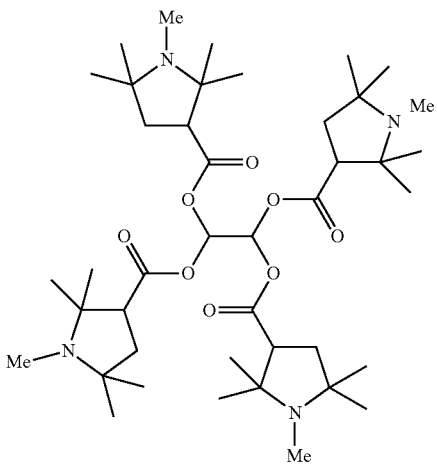

-continued
(I-4-73)
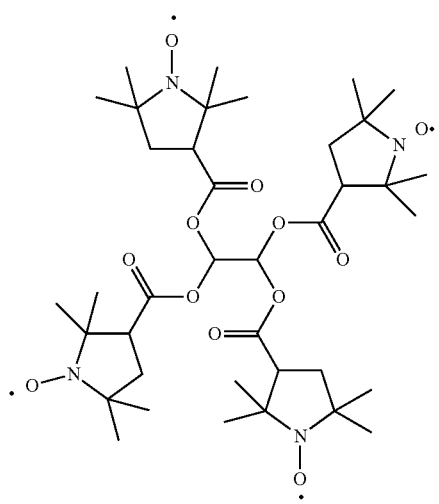
(I-4-74)
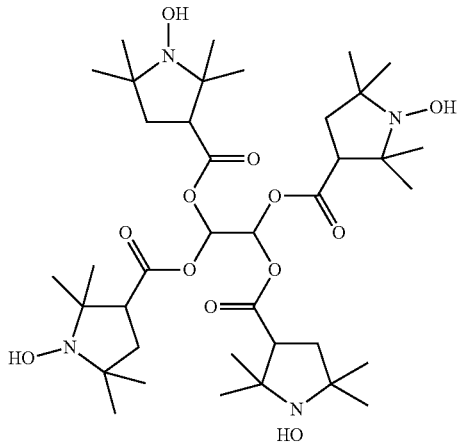
(I-4-75)
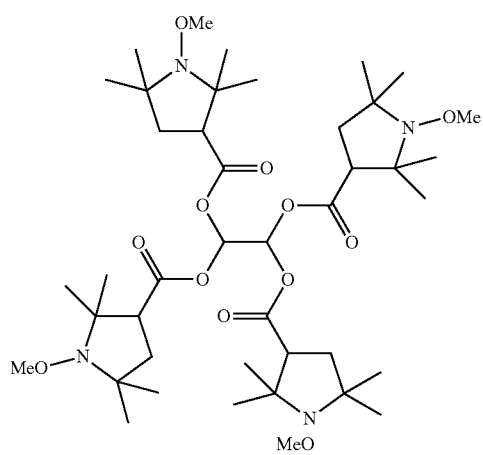
(I-4-76)
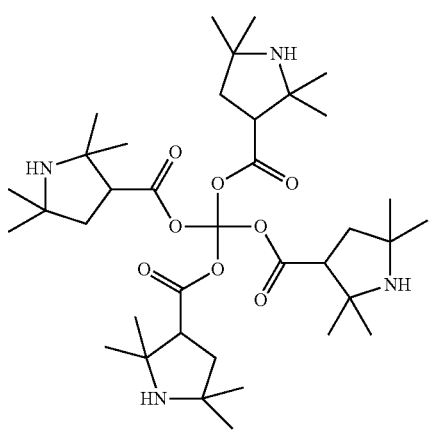
(I-4-77)
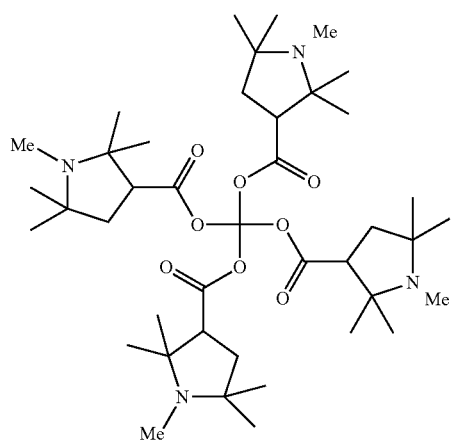
(I-4-78)
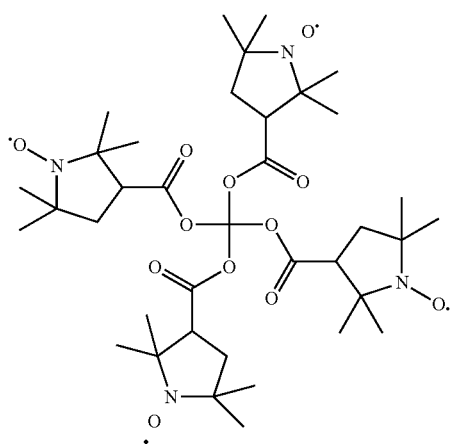

(I-4-79) 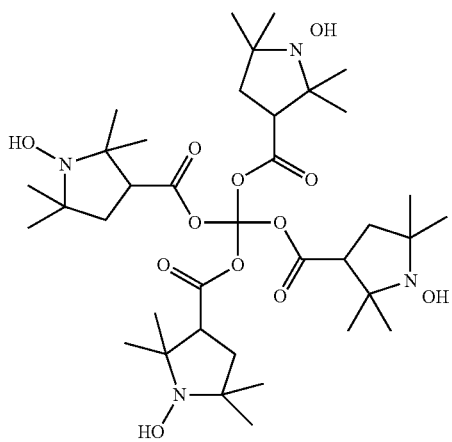
(I-4-80) 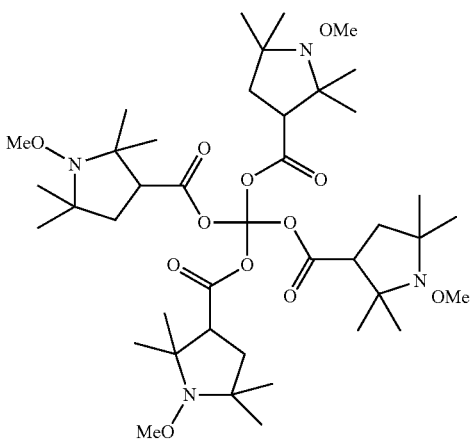
[Chem. 38]
(I-4-81) 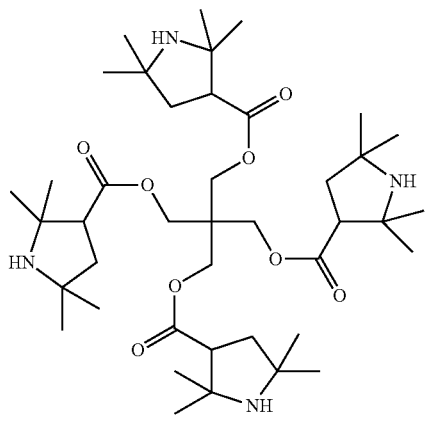
(I-4-82) 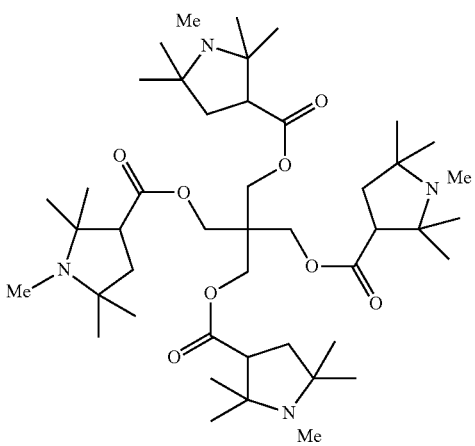
(I-4-83) 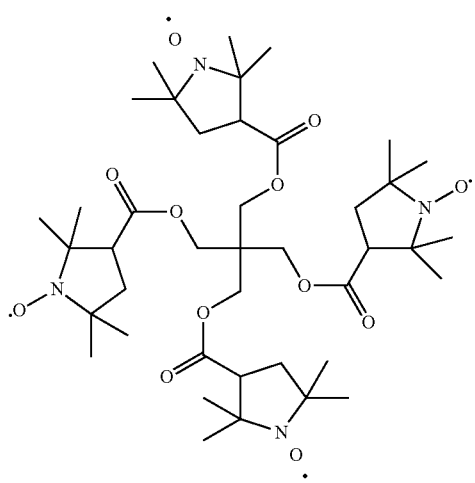
(I-04-84) 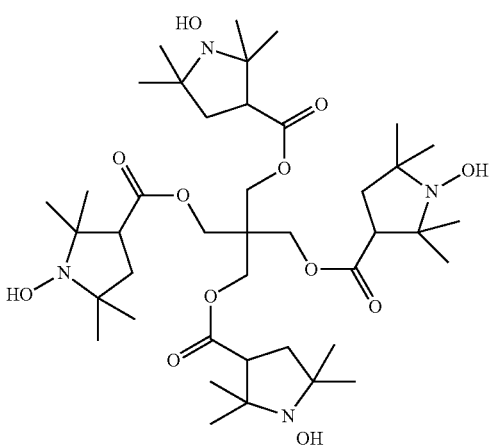

-continued
(I-4-85)
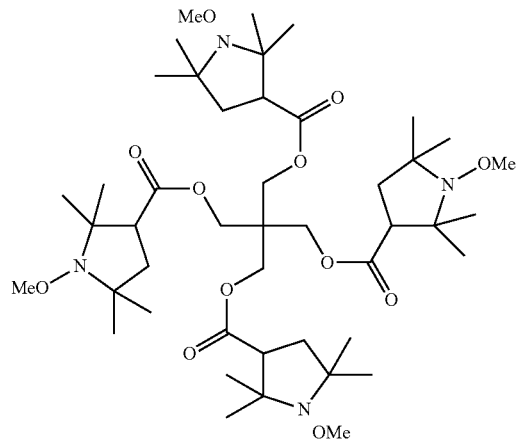
(I-4-86)
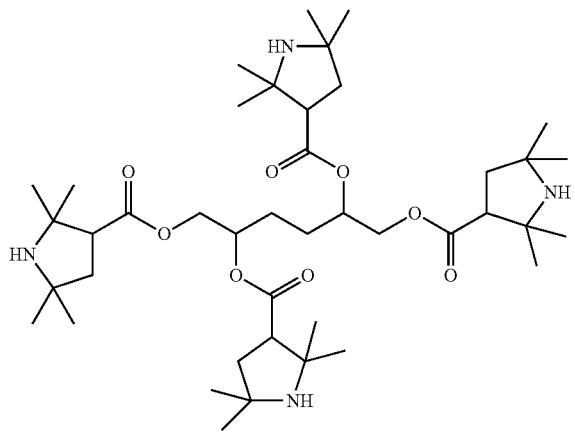
(I-4-87)
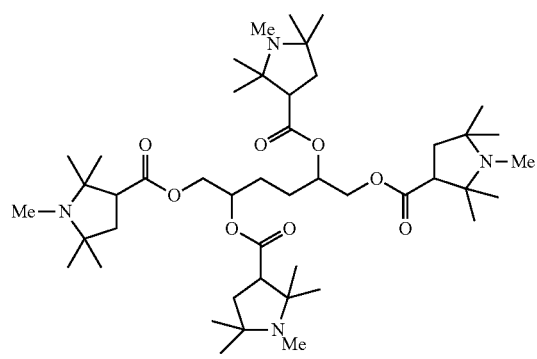
(I-4-88)
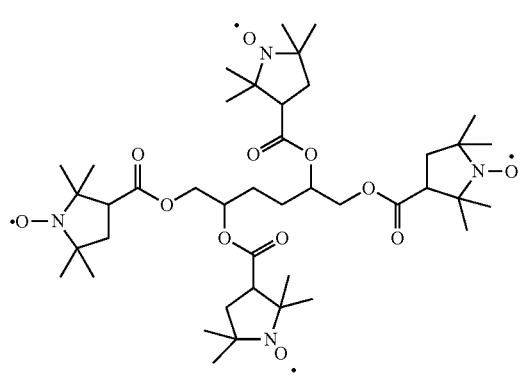
(i-4-89)
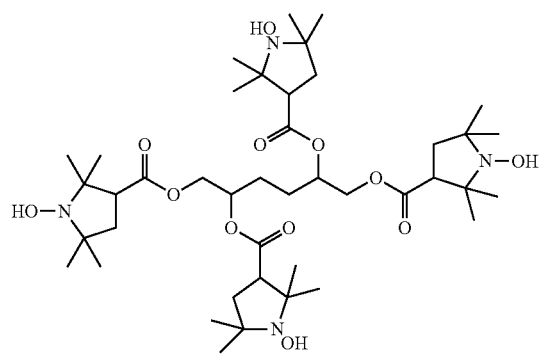
(i-4-90)
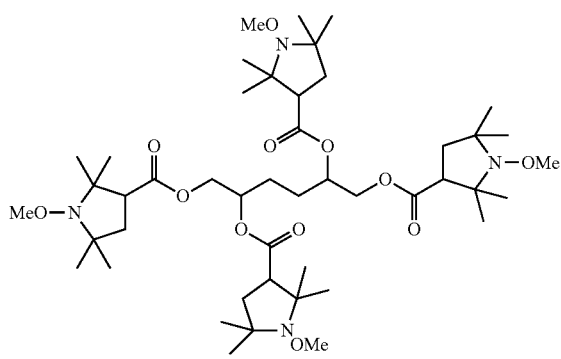

[Chem. 39]
(I-4-91)
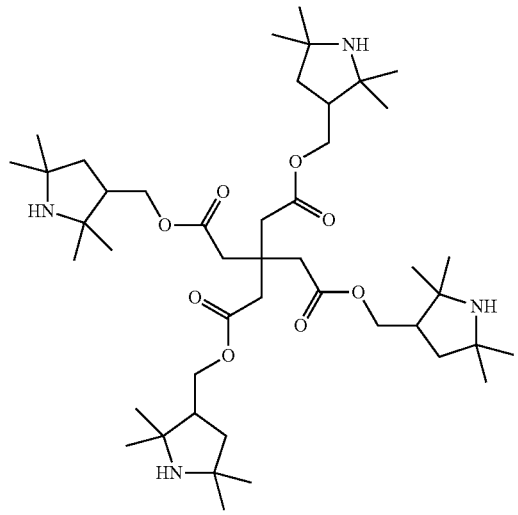
(I-4-92)
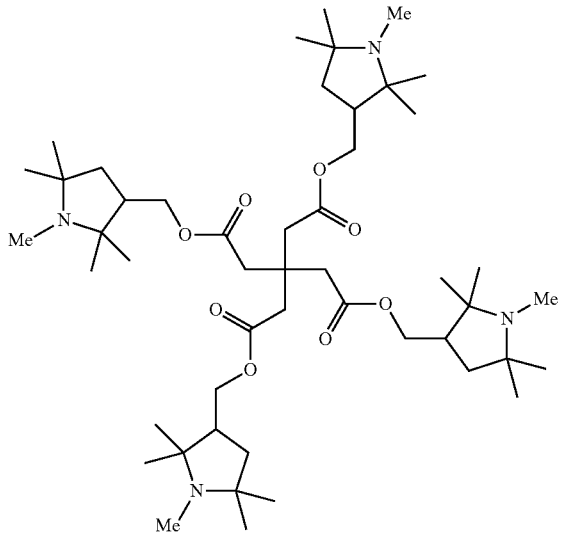
(I-4-93)
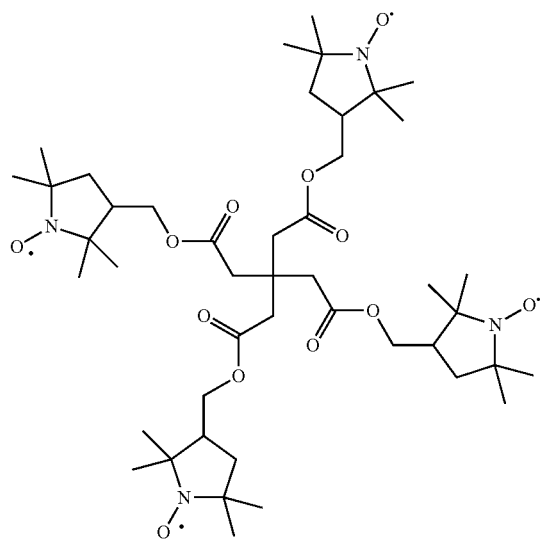
(I-4-94)
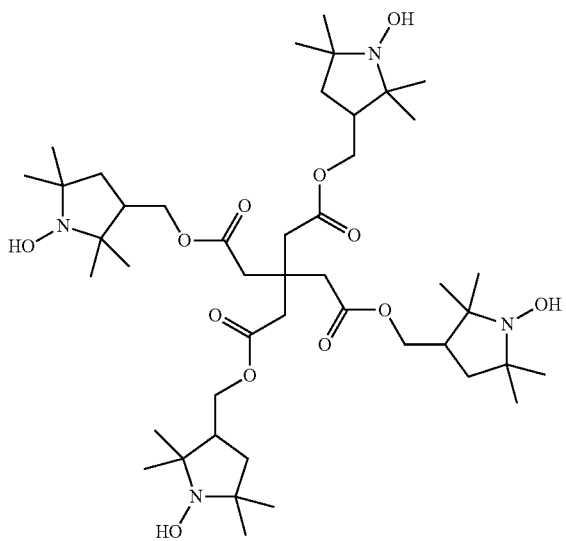

(I-4-95)

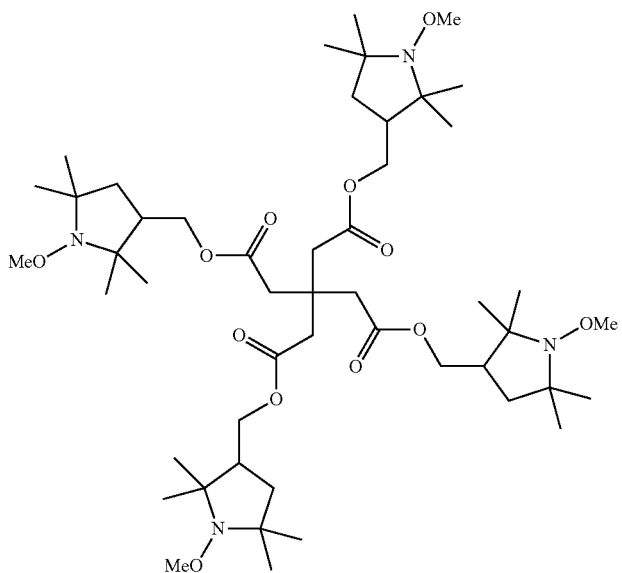

(In the formulae, Me denotes a methyl group.)

It is sufficient if a liquid crystal composition according to the present invention contains a compound represented by the general formula (I).

The lower limit of the total amount of compound(s) represented by the general formula (I) in a liquid crystal composition according to the present invention is preferably 0.001% or more, 0.002% or more, 0.003% or more, 0.004% or more, 0.005% or more, 0.006% or more, 0.007% or more, 0.008% or more, 0.009% or more, 0.01% or more, 0.02% or more, 0.03% or more, 0.04% or more, 0.05% or more, 0.06% or more, 0.07% or more, 0.08% or more, 0.09% or more, 0.10% or more, 0.11% or more, 0.12% or more, 0.13% or more, 0.14% or more, 0.15% or more, 0.20% or more, 0.25% or more, 0.30% or more, 0.35% or more, 0.40% or more, 0.50% or more, or 1% or more. The upper limit is preferably 5% or less, 3% or less, 2% or less, 1.5% or less, 1% or less, 0.9% or less, 0.8% or less, 0.7% or less, 0.6% or less, 0.5% or less, 0.45% or less, 0.4% or less, 0.35% or less, 0.3% or less, 0.25% or less, 0.2% or less, 0.15% or less, 0.1% or less, 0.07% or less, 0.05% or less, or 0.03% or less.

More specifically, 0.01% to 2% by mass is preferred, 0.01% to 1% by mass is preferred, 0.01% to 0.2% by mass is more preferred, or 0.01% to 0.15% by mass is particularly preferred. Still more specifically, when a reduction in precipitation at low temperatures is regarded as important, the content preferably ranges from 0.01% to 0.1% by mass. Furthermore, 0.01% to 1% by mass, 0.05% to 0.5% by mass, 0.10% to 0.3% by mass, and 0.15% to 0.25% are preferred in order to reduce nonuniformity in the device.

A liquid crystal composition according to the present invention preferably contains one or two or more compounds represented by the general formula (II).

[Chem. 40]

(In the formula, $R^{II1}$ denotes an alkyl group having 1 to 10 carbon atoms, and one —$CH_2$— or two or more nonadjacent —$CH_2$— groups in the alkyl group may be independently substituted with —CH=CH—, —C≡C—, —O—, —CO—, —COO—, or —OCO—, $A^{II1}$ and $A^{II2}$ independently denote a group selected from the group consisting of (a) a 1,4-cyclohexylene group (in which one —$CH_2$— or two or more nonadjacent —$CH_2$— groups may be substituted with —O—), (b) a 1,4-phenylene group (in which one —CH= or two or more nonadjacent —CH= groups may be substituted with —N=), and (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl group or the 1,2,3,4-tetrahydronaphthalene-2,6-diyl group may be substituted with —N=), the groups (a), (b), and (c) may be independently substituted with a cyano group, a fluorine atom, or a chlorine atom, $Z^{II1}$ denotes a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—, $Y^{II1}$ denotes a hydrogen atom, a fluorine atom, a chlorine atom, a cyano group, or an alkyl group having 1 to 10 carbon atoms, one —$CH_2$— or two or more nonadjacent —$CH_2$— groups in the alkyl group may be independently substituted with —CH=CH—, —C≡C—, —O—, —CO—, —COO—, or —OCO—, and one or two or more hydrogen atoms in the alkyl group may be substituted with a fluorine atom, and $m^{II1}$ is 1, 2, 3, or 4, and if $m^{II1}$ is 2, 3, or 4, pluralities of $A^{II1}$s and $Z^{II1}$s may be the same or different $A^{II1}$s and $Z^{II1}$s, respectively.)

<First Embodiment of Compound Represented by General Formula (II)>

A compound represented by the general formula (II) is a so-called p-type liquid crystal compound with positive dielectric constant anisotropy and may be a compound represented by the following general formula (J).

A compound represented by the general formula (II) preferably contains one or two or more compounds represented by the general formula (J). These compounds correspond to dielectrically positive compounds (with Δε of more than 2).

[Chem. 41]

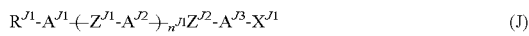

$$R^{J1}-A^{J1}-(-Z^{J1}-A^{J2}-)_{n^{J1}}Z^{J2}-A^{J3}-X^{J1} \quad (J)$$

(In the formula, $R^{J1}$ denotes an alkyl group having 1 to 8 carbon atoms, and one —$CH_2$— or two or more nonadjacent —$CH_2$— groups in the alkyl group may be independently substituted with —CH=CH—, —C≡C—, —O—, —CO—, —COO—, or —OCO—, $n^{J1}$ is 0, 1, 2, 3, or 4, $A^{J1}$, $A^{J2}$, and $A^{J3}$ independently denote a group selected from the group consisting of (a) a 1,4-cyclohexylene group (in which one —$CH_2$— or two or more nonadjacent —$CH_2$— groups may be substituted with —O—), (b) a 1,4-phenylene group (in which one —CH= or two or more nonadjacent —CH= groups may be substituted with —N=), and (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl group or the 1,2,3,4-tetrahydronaphthalene-2,6-diyl group may be substituted with —N=), the groups (a), (b), and (c) may be independently substituted with a cyano group, a fluorine atom, a chlorine atom, a methyl group, a trifluoromethyl group, or a trifluoromethoxy group, $Z^{J1}$ and $Z^{J2}$ independently denote a single bond, —$CH_2CH_2$—, —$(CH_2)_4$—, —$OCH_2$—, —$CH_2O$—, —$OCF_2$—, —$CF_2O$—, —COO—, —OCO—, or —C≡C—, if $n^{J1}$ is 2, 3, or 4, a plurality of $A^2$s may be the same or different, and if $n^{J1}$ is 2, 3, or 4, a plurality of $Z^{J1}$s may be the same or different, and $X^{J1}$ denotes a hydrogen atom, a fluorine atom, a chlorine atom, a cyano group, a trifluoromethyl group, a fluoromethoxy group, a difluoromethoxy group, a trifluoromethoxy group, or a 2,2,2-trifluoroethyl group.)

In the general formula (J), $R^{31}$ preferably denotes an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, still more preferably an alkyl group having 2 to 5 carbon atoms or an alkenyl group having 2 or 3 carbon atoms, particularly preferably an alkenyl group having 3 carbon atoms (a propenyl group).

$R^{J1}$ is preferably an alkyl group when reliability is regarded as important or an alkenyl group when reduced viscosity is regarded as important.

When the ring structure to which it is bonded is a phenyl group (aromatic), a linear alkyl group having 1 to 5 carbon atoms, a linear alkoxy group having 1 to 4 carbon atoms, or an alkenyl group having 4 or 5 carbon atoms is preferred. When the ring structure to which it is bonded is a saturated ring structure, such as cyclohexane, pyran, or dioxane, a linear alkyl group having 1 to 5 carbon atoms, a linear alkoxy group having 1 to 4 carbon atoms, or a linear alkenyl group having 2 to 5 carbon atoms is preferred. In order to stabilize the nematic phase, the total number of carbon atoms and, if present, oxygen atoms is preferably 5 or less, and a straight chain is preferred.

The alkenyl group is preferably selected, from the groups represented by the formulae (R1) to (R5). (The dark dot in each formula represents a carbon atom in the ring structure to which the alkenyl group is bonded.)

[Chem. 42]

 (R1)

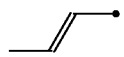 (R2)

 (R3)

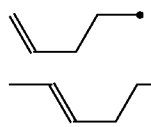 (R4)

 (R5)

$A^{J1}$, $A^{32}$, and $A^{33}$ preferably independently denote an aromatic when an increased Δn is required, denote an aliphatic to improve the response speed, or denote a trans-1,4-cyclohexylene group, a 1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, they optionally being substituted with a fluorine atom, more preferably independently denote the following structures,

[Chem. 43]

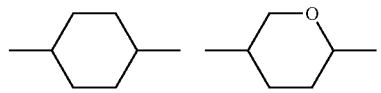

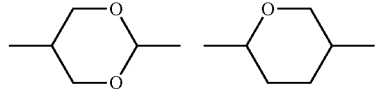

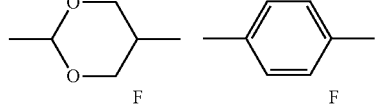

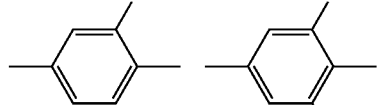

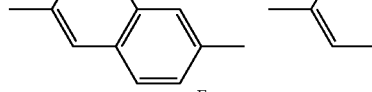

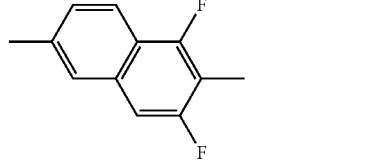

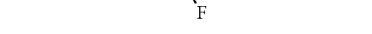

and more preferably independently denote the following structure.

[Chem. 44]

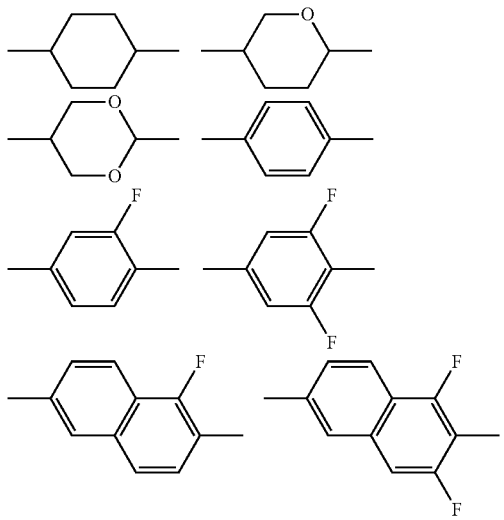

$Z^{J1}$ and $Z^{J2}$ preferably independently denote —CH$_2$O—, —OCH$_2$—, —CF$_2$O—, —CH$_2$CH$_2$—, —CF$_2$CF$_2$—, or a single bond, more preferably —OCH$_2$—, —CF$_2$O—, —CH$_2$CH$_2$—, or a single bond, particularly preferably —OCH$_2$—, —CF$_2$O—, or a single bond.

$X^{J1}$ preferably denotes a fluorine atom or a trifluoromethoxy group, preferably a fluorine atom.

$n^{J1}$ is preferably 0, 1, 2, or 3, preferably 0, 1, or 2, preferably 0 or 1 when improved Δε is regarded as important, preferably 1 or 2 when Tni is regarded as important.

Although compounds of any types may be combined, these compounds are combined in a manner that depends on the desired characteristics, such as solubility at low temperatures, transition temperature, electrical reliability, and birefringence index. For example, one, two, or three compounds are used in one embodiment of the present invention. Alternatively, four, five, six, or seven compounds are used in another embodiment of the present invention.

The amount of compound represented by the general formula (J) in a composition according to the present invention should be appropriately adjusted in a manner that depends on the desired characteristics, such as solubility at low temperatures, transition temperature, electrical reliability, birefringence index, process compatibility, drop marks, image sticking, and dielectric constant anisotropy.

The lower limit of the preferred amount of compound represented by the general formula (J) is 1%, 10%, 20%, 30%, 40%, 50%, 55%, 60%, 65%, 70%, 75%, or 80% of the total amount of composition according to the present invention. For example, in one embodiment of the present invention, the upper limit of the preferred amount is 95%, 85%, 75%, 65%, 55%, 45%, 35%, or 25% of the total amount of composition according to the present invention.

When a composition according to the present invention with a low viscosity and a high response speed is required, the lower limit is preferably decreased, and the upper limit is preferably decreased. When a composition according to the present invention with high Tni and temperature stability is required, the lower limit is preferably decreased, and the upper limit is preferably decreased. When the dielectric constant anisotropy is increased to maintain a low drive voltage, the lower limit is preferably increased, and the upper limit is preferably increased.

$R^{J1}$ is preferably an alkyl group when reliability is regarded as important or an alkenyl group when reduced viscosity is regarded as important.

A compound represented by the general formula (J) is preferably a compound represented by the general formula (M) or a compound represented by the general formula (K).

A composition according to the present invention preferably contains one or two or more compounds represented by the general formula (M). These compounds correspond to dielectrically positive compounds (with Δε of more than 2).

[Chem. 45]

(M)

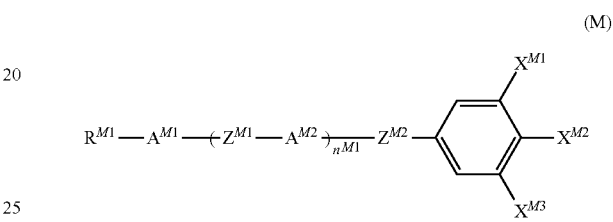

(In the formula, $R^{M1}$ denotes an alkyl group having 1 to 8 carbon atoms, and one —CH$_2$— or two or more nonadjacent —CH$_2$— groups in the alkyl group may be independently substituted with —CH=CH—, —C≡C—, —O—, —CO—, —COO—, or —OCO—, $n^{M1}$ is 0, 1, 2, 3, or 4, $A^{M1}$ and $A^{M2}$ independently denote a group selected from the group consisting of (a) a 1,4-cyclohexylene group (in which one —CH$_2$— or two or more nonadjacent —CH$_2$— groups may be substituted with —O— or —S—), and (b) a 1,4-phenylene group (in which one —CH= or two or more nonadjacent —CH= groups may be substituted with —N=), a hydrogen atom of the group (a) and the group (b) may be independently substituted with a cyano group, a fluorine atom, or a chlorine atom, $Z^{M1}$ and $Z^{M2}$ independently denote a single bond, —CH$_2$CH$_2$—, —(CH$_2$)$_4$—, —OCH$_2$—, —CH$_2$O—, —OCF$_2$—, —CF$_2$O—, —COO—, —OCO—, or —C≡C—, if $n^{M1}$ is 2, 3, or 4, a plurality of $A^{M2}$s may be the same or different, and if $n^{M1}$ is 2, 3, or 4, a plurality of Z's may be the same or different, $X^{M1}$ and $X^{M3}$ independently denote a hydrogen atom, a chlorine atom, or a fluorine atom, and $X^{M2}$ denotes a hydrogen atom, a fluorine atom, a chlorine atom, a cyano group, a trifluoromethyl group, a fluoromethoxy group, a difluoromethoxy group, a trifluoromethoxy group, or a 2,2,2-trifluoroethyl group.)

In the general formula (M), $R^{M1}$ preferably denotes an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, still more preferably an alkyl group having 2 to 5 carbon atoms or an alkenyl group having 2 or 3 carbon atoms, particularly preferably an alkenyl group having 3 carbon atoms (a propenyl group).

$R^{M1}$ is preferably an alkyl group when reliability is regarded as important or an alkenyl group when reduced viscosity is regarded as important.

When the ring structure to which it is bonded is a phenyl group (aromatic), a linear alkyl group having 1 to 5 carbon atoms, a linear alkoxy group having 1 to 4 carbon atoms, or an alkenyl group having 4 or 5 carbon atoms is preferred. When the ring structure to which it is bonded is a saturated ring structure, such as cyclohexane, pyran, or dioxane, a linear alkyl group having 1 to 5 carbon atoms, a linear alkoxy group having 1 to 4 carbon atoms, or a linear alkenyl group having 2 to 5 carbon atoms is preferred. In order to stabilize the nematic phase, the total number of carbon atoms and, if present, oxygen atoms is preferably 5 or less, and a straight chain is preferred.

The alkenyl group is preferably selected from the groups represented by the formulae (R1) to (R5). (The dark dot in each formula represents a carbon atom in the ring structure to which the alkenyl group is bonded.)

[Chem. 46]

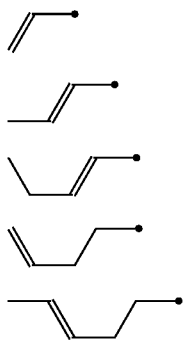

(R1)
(R2)
(R3)
(R4)
(R5)

$A^{M1}$ and $A^{M2}$ preferably independently denote an aromatic when an increased Δn is required, denote an aliphatic to improve the response speed, or denote a trans-1,4-cyclohexylene group, a 1,4-phenylene group, a 2-fluoro-1,4-phenylene group, a 3-fluoro-1,4-phenylene group, a 3,5-difluro-1,4-phenylene group, a 2,3-difluro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably independently denote the following structures,

[Chem. 47]

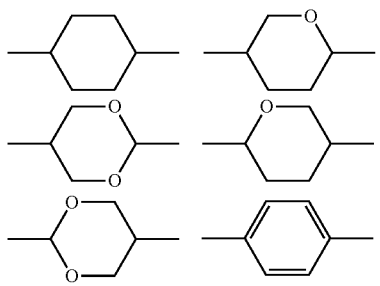

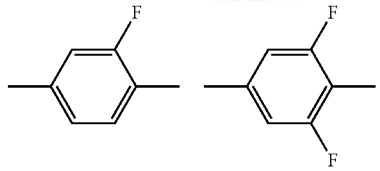

and more preferably independently denote the following structure.

[Chem. 48]

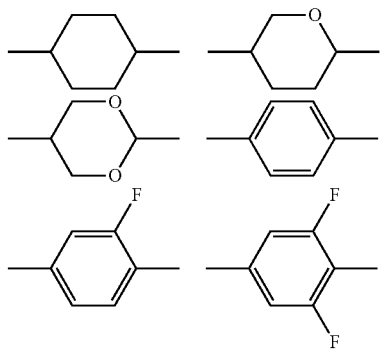

$Z^{M1}$ and $Z^{M2}$ preferably independently denote —$CH_2O$—, —$CF_2O$—, —$CH_2CH_2$—, —$CF_2CF_2$—, or a single bond, more preferably —$CF_2O$—, —$CH_2CH_2$—, or a single bond, particularly preferably —$CF_2O$— or a single bond.

$n^{M1}$ is preferably 0, 1, 2, or 3, preferably 0, 1, or 2, preferably 0 or 1 when improved Δε is regarded as important, preferably 1 or 2 when Tni is regarded as important.

Although compounds of any types may be combined, these compounds are combined in a manner that depends on the desired characteristics, such as solubility at low temperatures, transition temperature, electrical reliability, and birefringence index. For example, one, two, or three compounds are used in one embodiment of the present invention. Alternatively, four, five, six, or seven compounds are used in another embodiment of the present invention.

The amount of compound represented by the general formula (M) in a composition according to the present invention should be appropriately adjusted in a manner that depends on the desired characteristics, such as solubility at low temperatures, transition temperature, electrical reliability, birefringence index, process compatibility, drop marks, image sticking, and dielectric constant anisotropy.

The lower limit of the preferred amount of compound represented by the formula (M) is 0%, 1%, 10%, 20%, 30%, 40%, 50%, 55%, 60%, 65%, 70%, 75%, or 80% of the total amount of composition according to the present invention. For example, in one embodiment of the present invention, the upper limit of the preferred amount is 95%, 85%, 75%, 65%, 55%, 45%, 35%, or 25% of the total amount of composition according to the present invention.

When a composition according to the present invention with a low viscosity and a high response speed is required, the lower limit is preferably decreased, and the upper limit is preferably decreased. When a composition according to the present invention with high Tni and temperature stability is required, the lower limit is preferably decreased, and the upper limit is preferably decreased. When the dielectric constant anisotropy is increased to maintain a low drive voltage, the lower limit is preferably increased, and the upper limit is preferably increased.

More specifically, a liquid crystal compound represented by the general formula (M) is preferably represented by the following general formula (M-1) or (M-2).

[Chem. 49]

(M-1)

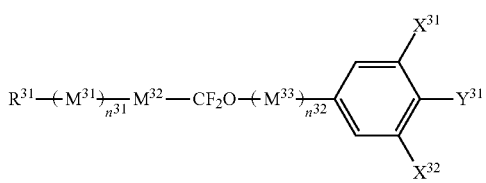

(M-2)

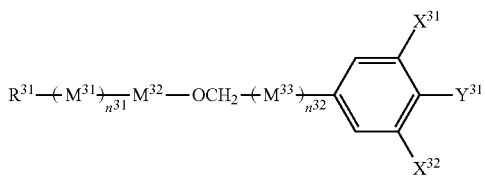

(In the formulae, $R^{31}$ denotes an alkyl group having 1 to 5 carbon atoms, an alkenyl group having 2 to 5 carbon atoms, or an alkoxy group having 1 to 4 carbon atoms, $X^{31}$ and $X^{32}$ independently denote a hydrogen atom or a fluorine atom, $Y^{31}$ denotes a fluorine atom or $OCF_3$, $M^{31}$ to $M^{33}$ independently denote a trans-1,4-cyclohexylene group or a 1,4-phenylene group, one or two —$CH_2$— groups in the trans-1,4-cyclohexylene group may be substituted with —O—, provided that oxygen atoms are not directly adjacent to each other, one or two hydrogen atoms in the phenylene group may be substituted with a fluorine atom, $n^{31}$ and $n^{32}$ are independently 0, 1, or 2, and $n^{41}+n^{42}$ is 1, 2, or 3.)

More specifically, a liquid crystal compound represented by the general formula (M-1) is preferably one of the compounds represented by the following general formulae (M-1-a) to (M-1-f).

[Chem. 50]

(M-1-a)

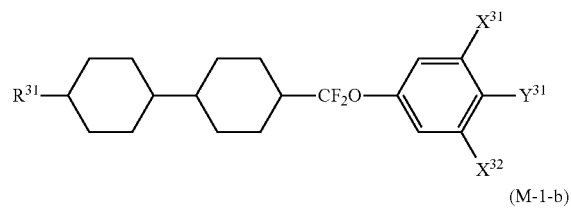

(M-1-b)

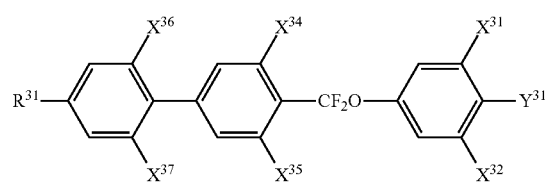

(M-1-c)

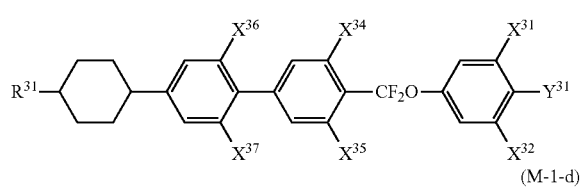

(M-1-d)

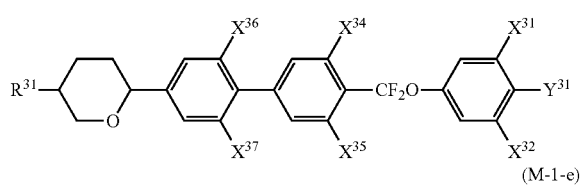

(M-1-e)

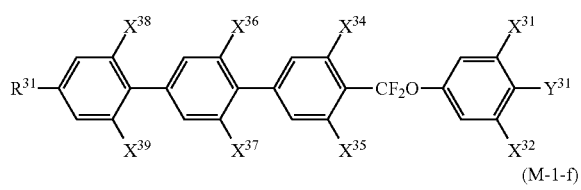

(M-1-f)

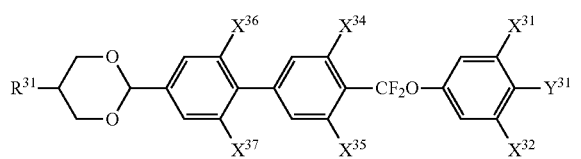

(In the formula, $R^{31}$, $X^{31}$, $X^{32}$, and $Y^{31}$ have the same meaning as $R^{31}$, $X^{31}$, $X^{32}$, and $Y^{31}$, respectively, in the general formula (M), and $X^{34}$ to $X^{34}$ independently denote a hydrogen atom or a fluorine atom.)

More specifically, a liquid crystal compound represented by the general formula (M-2) is preferably one of the compounds represented by the following general formulae (M-2-a) to (M-2-n).

[Chem. 51]

(M-2-a)

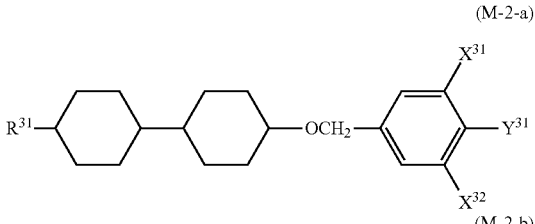

(M-2-b)

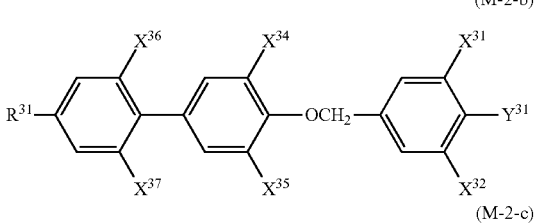

(M-2-c)

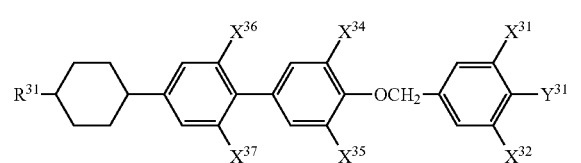

-continued (M-2-d)
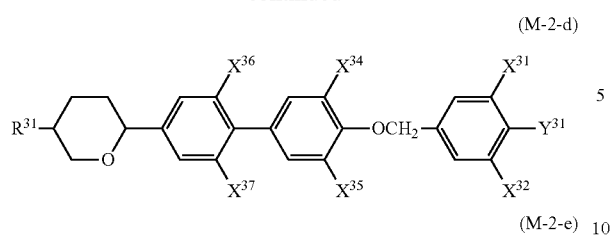

(M-2-e)
(M-2-f)

[Chem. 52]

(M-2-g)
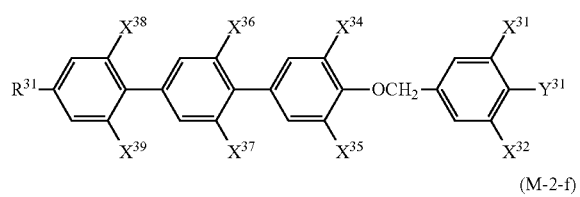

(M-2-h)
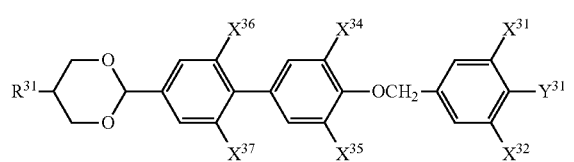

(M-2-i)
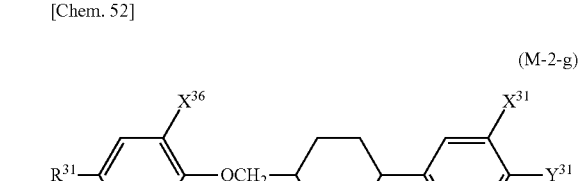

(M-2-j)
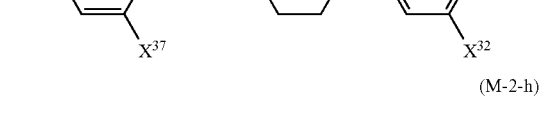

(M-2-k)
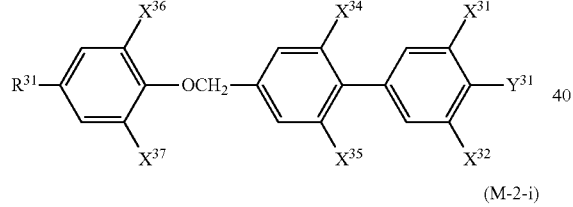

-continued (M-2-l)
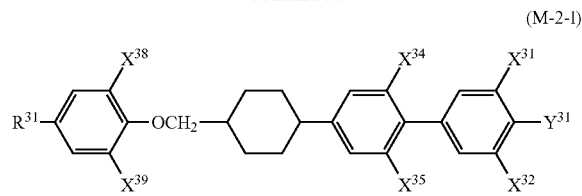

(M-2-m)
(M-2-n)

(In the formula, $R^{31}$, $X^{31}$, $X^{32}$, and $Y^{31}$, have the same meaning as $R^{31}$, $X^{31}$, $X^{32}$, and $Y^{31}$, respectively, in the general formula (M), and $X^{34}$ to $X^{39}$ independently denote a hydrogen atom or a fluorine atom.)

More specifically, a liquid crystal compound represented by the general formula (M) is preferably represented by one of the following general formulae (M-3) to (M-26).

[Chem. 53]

(M-3)
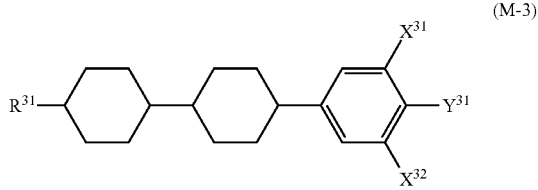

(M-4)
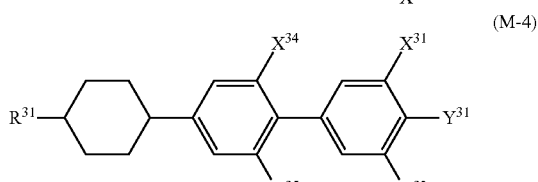

(M-5)
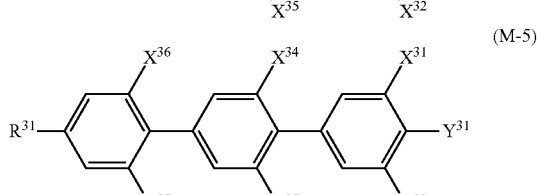

(M-6)
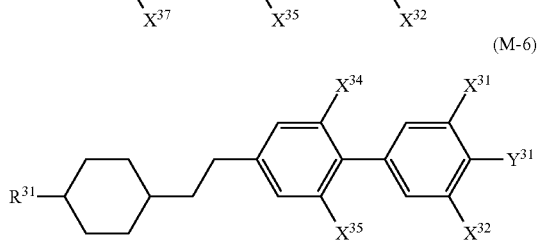

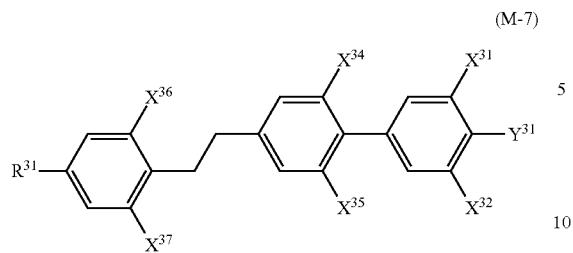
(M-7)
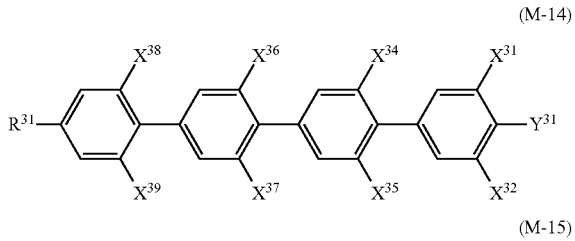
(M-14)
(M-8)
(M-15)
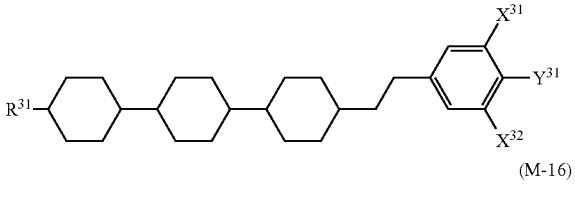
(M-9)
(M-16)
[Chem. 54]
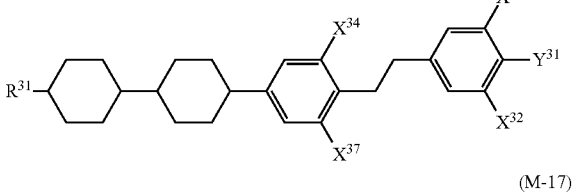
(M-10)
(M-17)
(M-18)
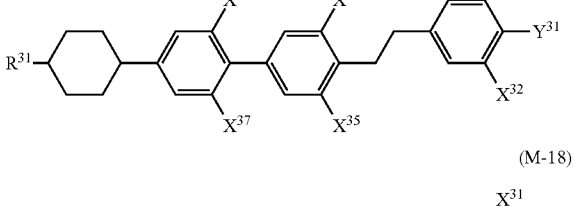
(M-11)
(M-19)
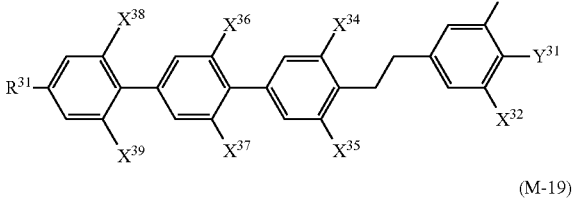
(M-12)
(M-20)
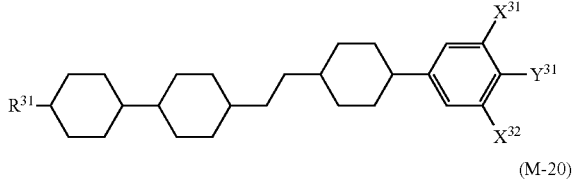
(M-13)
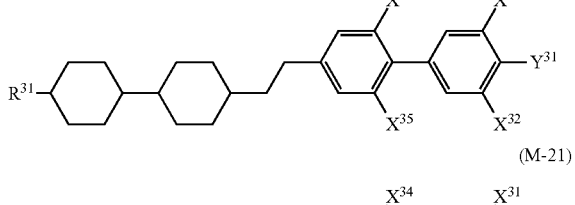
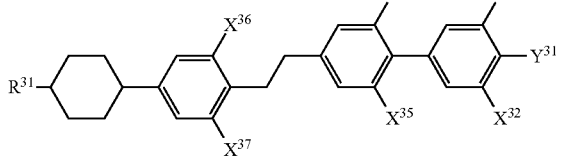
(M-21)

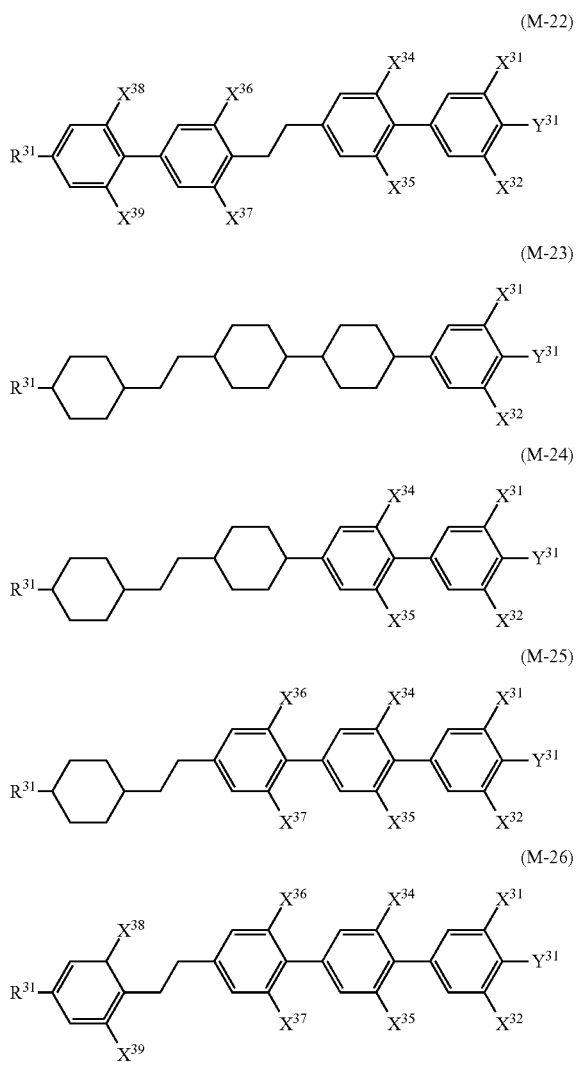

(In formula, $R^{31}$, $X^{31}$, $X^{32}$, and $Y^{31}$ have the same meaning as $R^{31}$, $X^{31}$ and $Y^{33}$, and $Y^{31}$, respectively, in the general formula (M), and $X^{34}$ to $X^{39}$ independently denote a hydrogen atom or a fluorine atom.)

A composition according to the present invention preferably contains one or two or more compounds represented by the general formula (K). These compounds correspond to dielectrically positive compounds (with Δε of more than 2).

[Chem. 55]

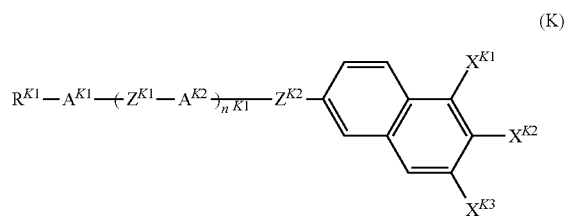

(In the formula, $R^{K1}$ denotes an alkyl group having 1 to 8 carbon atoms, and one —CH$_2$— or two or more nonadjacent —CH$_2$— groups in the alkyl group may be independently substituted with —CH=CH—, —C≡C—, —O—, —CO—, —COO—, or —OCO—, $n^{K1}$ is 0, 1, 2, 3, or 4, $A^{K1}$ and $A^{K2}$ independently denote a group selected from the group consisting of (a) a 1,4-cyclohexylene group (in which one —CH$_2$— or two or more nonadjacent —CH$_2$— groups may be substituted with —O— or —S—), and (b) a 1,4-phenylene group (in which one —CH= or two or more nonadjacent —CH= groups may be substituted with —N=), a hydrogen atom of the group (a) and the group (b) may be independently substituted with a cyano group, a fluorine atom, or a chlorine atom, $Z^{K1}$ and $Z^{K2}$ independently denote a single bond, —CH$_2$CH$_2$—, —(CH$_2$)$_4$—, —OCH$_2$—, —CH$_2$O—, —OCF$_2$—, —CF$_2$O—, —COO—, —OCO—, or —C≡C—, if $n^{K1}$ is 2, 3, or 4, a plurality of $A^{K2}$s may be the same or different, and if $n^{K1}$ is 2, 3, or 4, a plurality of $Z^{K1}$s may be the same or different, $X^{K1}$ and $X^{K3}$ independently denote a hydrogen atom, a chlorine atom, or a fluorine atom, and $X^{K2}$ denotes a hydrogen atom, a fluorine atom, a chlorine atom, a cyano group, a trifluoromethyl group, a fluoromethoxy group, a difluoromethoxy group, a trifluoromethoxy group, or a 2,2,2-trifluoroethyl group.)

In the general formula (K), $R^{K1}$ preferably denotes an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, still more preferably an alkyl group having 2 to 5 carbon atoms or an alkenyl group having 2 or 3 carbon atoms, particularly preferably an alkenyl group having 3 carbon atoms (a propenyl group).

$R^{K1}$ is preferably an alkyl group when reliability is regarded as important or an alkenyl group when reduced viscosity is regarded as important.

When the ring structure to which it is bonded is a phenyl group (aromatic), a linear alkyl group having 1 to 5 carbon atoms, a linear alkoxy group having 1 to 4 carbon atoms, or an alkenyl group having 4 or 5 carbon atoms is preferred. When the ring structure to which it is bonded is a saturated ring structure, such as cyclohexane, pyran, or dioxane, a linear alkyl group having 1 to 5 carbon atoms, a linear alkoxy group having 1 to 4 carbon atoms, or a linear alkenyl group having 2 to 5 carbon atoms is preferred. In order to stabilize the nematic phase, the total number of carbon atoms and, if present, oxygen atoms is preferably 5 or less, and a straight chain is preferred.

The alkenyl group is preferably selected from the groups represented by the formulae (R1) to (R5). (The dark dot in each formula represents a carbon atom in the ring structure to which the alkenyl group is bonded.)

[Chem. 56]

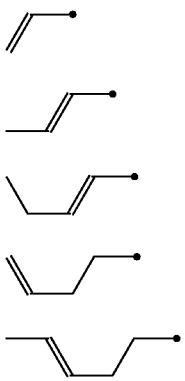

(R1)
(R2)
(R3)
(R4)
(R5)

$A^{K1}$ and $A^{K2}$ preferably independently denote an aromatic when an increased Δn is required, denote an aliphatic to improve the response speed, or denote a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably independently denote the following structures,

[Chem. 57]

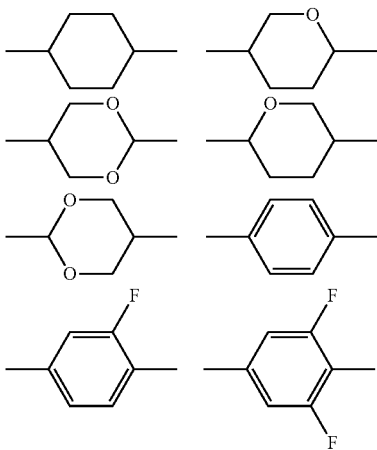

and more preferably independently denote the following structure.

[Chem. 58]

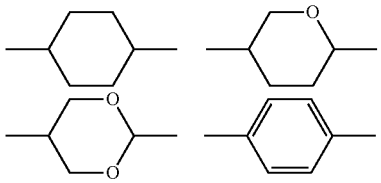

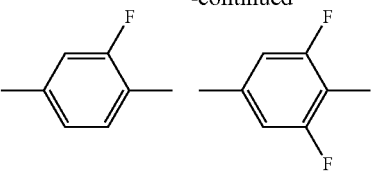

$Z^{K1}$ and $Z^{K2}$ preferably independently denote —CH$_2$O—, —CF$_2$O—, —CH$_2$CH$_2$—, —CF$_2$CF$_2$—, or a single bond, more preferably —CF$_2$O—, —CH$_2$CH$_2$—, or a single bond, particularly preferably —CF$_2$O— or a single bond.

$n^{K1}$ is preferably 0, 1, 2, or 3, preferably 0, 1, or 2, preferably 0 or 1 when improved Δε is regarded as important, preferably 1 or 2 when Tni is regarded as important.

Although compounds of any types may be combined, these compounds are combined in a manner that depends on the desired characteristics, such as solubility at low temperatures, transition temperature, electrical reliability, and birefringence index. For example, one, two, or three compounds are used in one embodiment of the present invention. Alternatively, four, five, six, or seven compounds are used in another embodiment of the present invention.

The amount of compound represented by the general formula (K) in a composition according to the present invention should be appropriately adjusted in a manner that depends on the desired characteristics, such as solubility at low temperatures, transition temperature, electrical reliability, birefringence index, process compatibility, drop marks, image sticking, and dielectric constant anisotropy.

The lower limit of the preferred amount of compound represented by the formula (K) is 1%, 10%, 20%, 30%, 40%, 50%, 55%, 60%, 65%, 70%, 75%, or 80% of the total amount of composition according to the present invention. For example, in one embodiment of the present invention, the upper limit of the preferred amount is 95%, 85%, 75%, 65%, 55%, 45%, 35%, or 25% of the total amount of composition according to the present invention.

When a composition according to the present invention with a low viscosity and a high response speed is required, the lower limit is preferably decreased, and the upper limit is preferably decreased. When a composition according to the present invention with high Tni and temperature stability is required, the lower limit is preferably decreased, and the upper limit is preferably decreased. When the dielectric constant anisotropy is increased to maintain a low drive voltage, the lower limit is preferably increased, and the upper limit is preferably increased.

More specifically, a liquid crystal compound represented by the general formula (K) is preferably represented by the following general formula (K-1) or (K-2).

[Chem. 59]

(K-1)

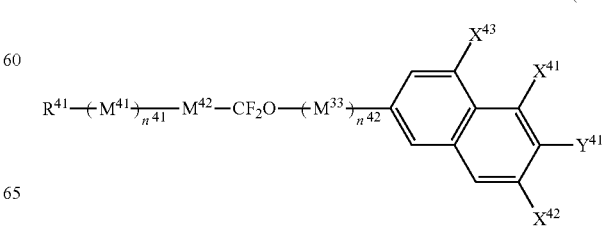

-continued (K-2)

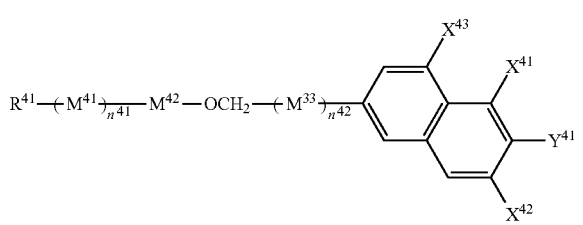

(In the formula, $R^{41}$ denotes an alkyl group having 1 to 5 carbon atoms, an alkenyl group having 2 to 5 carbon atoms, or an alkoxy group having 1 to 4 carbon atoms, $X^{41}$ and $X^{42}$ independently denote a hydrogen atom or a fluorine atom, $Y^{41}$ denotes a fluorine atom or $OCF_3$, $M^{41}$ to $M^{43}$ independently denote a trans-1,4-cyclohexylene group or a 1,4-phenylene group, one or two —$CH_2$— groups in the trans-1,4-cyclohexylene group may be substituted with —O—, provided that oxygen atoms are not directly adjacent to each other, one or two hydrogen atoms in the phenylene group may be substituted with a fluorine atom, $n^{41}$ and $n^{42}$ are independently 0, 1, or 2, and $n^{41}+n^{42}$ is 1, 2, or 3.)

More specifically, a liquid crystal compound represented by the general formula (K-1) is preferably one of the compounds represented by the following general formulae (K-1-a) to (K-1-d).

[Chem. 60]

(K-1-a)

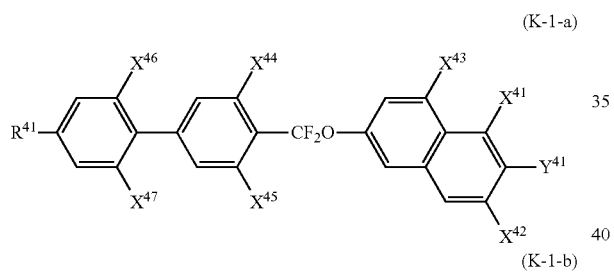

(K-1-b)

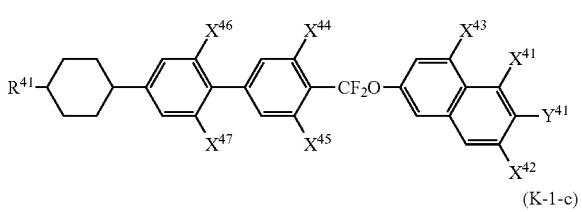

(K-1-c)

(K-1-d)

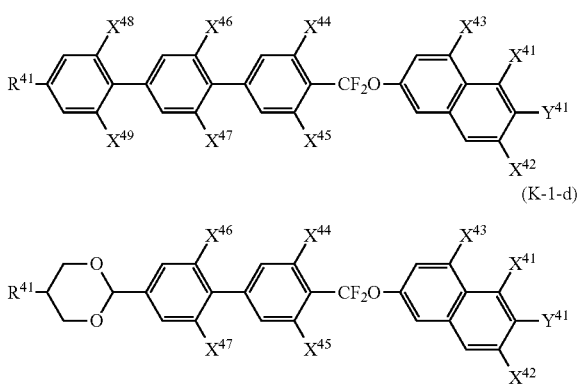

(In the formula, $R^{41}$, $X^{41}$, $X^{42}$, and $Y^{41}$ have the same meaning as $R^{41}$, $X^{41}$, $X^{42}$, and $Y^{41}$, respectively, in the general formula (K), and $X^{44}$ to $X^{49}$ independently denote a hydrogen atom or a fluorine atom.)

More specifically, a liquid crystal compound represented by the general formula (K-2) is preferably one of the compounds represented by the following general formulae (K-2-a) to (K-2-g).

[Chem. 61]

(K-2-a)

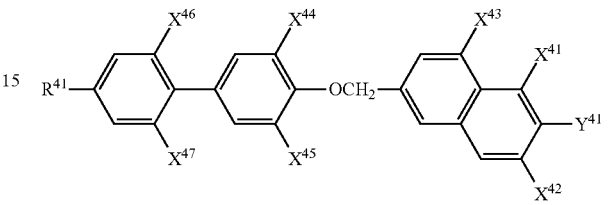

(K-2-b)

(K-2-c)

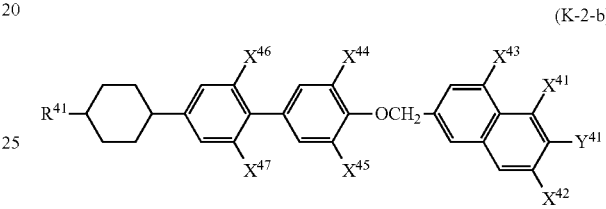

(K-2-d)

(K-2-e)

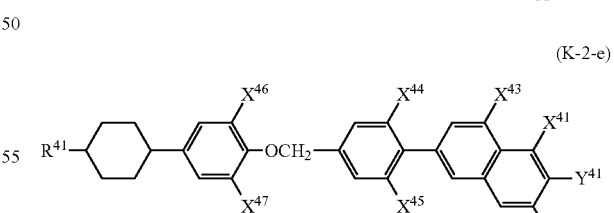

(K-2-f)

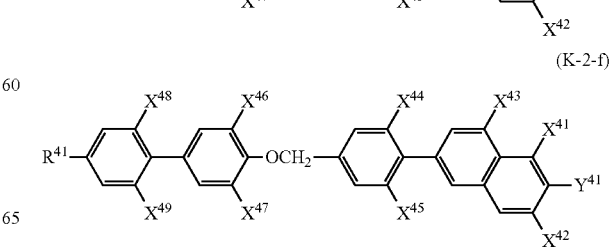

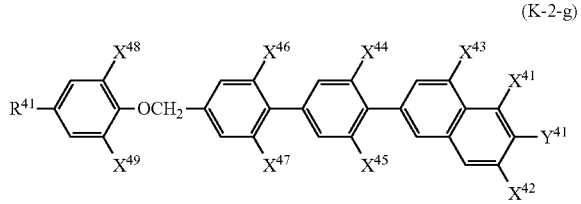

(In the formula, $R^{41}$, $X^4f$, $X^{42}$, and $Y^{41}$ have the same meaning as $R^{41}$, $X^{41}$, $X^{42}$, and $Y^{41}$, respectively, in the general formula (K), and $X^{44}$ to $X^{49}$ independently denote a hydrogen atom or a fluorine atom.)

More specifically, a liquid crystal compound represented by the general formula (K) is preferably represented by one of the following general formulae (K-3) to (K-5).

[Chem. 62]

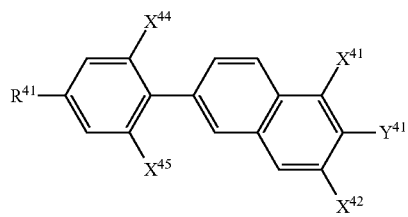

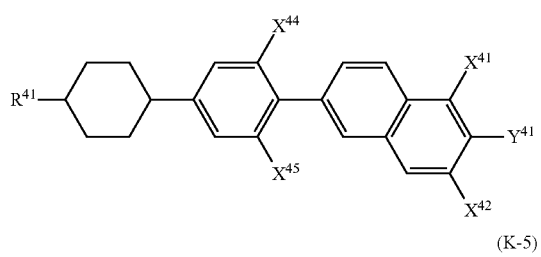

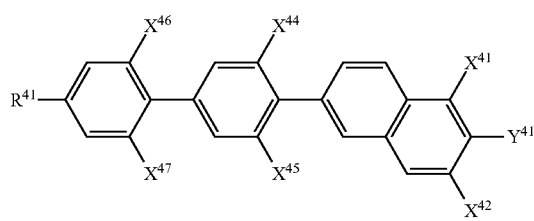

(In the formula, $R^{41}$, $X^{41}$, $X^{42}$, and $Y^{41}$ have the same meaning as $R^{41}$, $X^{41}$, $X^{42}$, and $Y^{41}$, respectively, in the general formula (K), and $X^{44}$ to $X^{49}$ independently denote a hydrogen atom or a fluorine atom.)

<Second Embodiment of Compound Represented by General Formula (II)>

A compound represented by the general formula (II) is a so-called n-type liquid crystal compound with negative dielectric constant anisotropy.

A compound represented by the general formula (II) preferably contains one or two or more compounds selected from the compound group represented by the general formulae (N-1) to (N-3).

[Chem. 63]

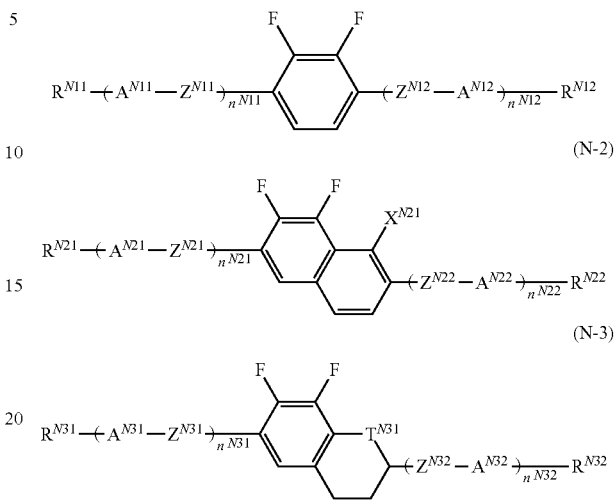

(In the formula, $R^{N11}$, $R^{N12}$, $R^{N21}$, $R^{N22}$, $R^{N31}$, and $R^{N32}$ independently denote an alkyl group having 1 to 8 carbon atoms, and one —$CH_2$— or two or more nonadjacent —$CH_2$— groups in the alkyl group may be independently substituted with —CH=CH—, —C≡C—, —O—, —CO—, —COO—, or —OCO—, $A^{N11}$, $A^{N12}$, $A^{N21}$, $A^{N22}$, $A^{N31}$, and $A^{N32}$ independently denote a group selected from the group consisting of (a) a 1,4-cyclohexylene group (in which one —$CH_2$— or two or more nonadjacent —$CH_2$— groups may be substituted with —O—), (b) a 1,4-phenylene group (in which one —CH= or two or more nonadjacent —CH= groups may be substituted with —N=), and (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl group or the 1,2,3,4-tetrahydronaphthalene-2,6-diyl group may be substituted with —N=), the groups (a), (b), and (c) may be independently substituted with a cyano group, a fluorine atom, or a chlorine atom, $Z^{N11}$, $Z^{N12}$, $Z^{N21}$, $Z^{N22}$, $Z^{N31}$, and $Z^{N32}$ independently denote a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—, $X^{N21}$ denotes a hydrogen atom or a fluorine atom, $T^{N31}$ denotes —$CH_2$— or an oxygen atom, and $n^{N11}$, $n^{N12}$, $n^{N21}$, $n^{N22}$, $n^{N31}$, and $n^{N32}$ independently denote an integer in the range of 0 to 3, $n^{N11}+n^{N12}$, $n^{N21}+n^{N22}$, and $n^{N31}+n^{N32}$ are independently 1, 2, or 3, and pluralities of $A^{N11}$s to $A^{N32}$s and $Z^{N11}$s to $Z^{N32}$s, if present, may be the same or different $A^{N11}$s to $A^{N32}$s and $Z^{N11}$s to $Z^{N32}$s, respectively, provided that the compounds represented by the general formula (N-1) are excluded from the compounds represented by the general formulae (N-2) and (N-3) and that the compounds represented by the general formula (N-2) are excluded from the compounds represented by the general formula (N-3).)

The compounds represented by the general formulae (N-1), (N-2), and (N-3) correspond to dielectrically negative compounds (with a negative Δε having an absolute value of more than 2), preferably compounds with a negative Δε having an absolute value of more than 3.

In the general formulae (N-1), (N-2), and (N-3), $R^{N11}$, $R^{N12}$, $R^{N21}$, $R^{N22}$, $R^{N31}$, and $R^{N32}$ independently denote an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, still more preferably an alkyl group having 2 to 5 carbon atoms or an alkenyl group having 2 or 3 carbon atoms, particularly preferably an alkenyl group having 3 carbon atoms (a propenyl group). In particular, a compound in which at least one of $R^{N11}$ and $R^{N12}$ denotes an alkenyl group and a compound represented by the general formula (I) can be used in combination to significantly reduce a decrease in voltage holding ratio (VHR). Likewise, a compound in which at least one of $R^{N21}$ and $R^{N22}$ denotes an alkenyl group and a compound represented by the general formula (I) can be used in combination to significantly reduce a decrease in voltage holding ratio (VHR), and a compound in which at least one of $R^{N31}$ and $R^{N32}$ denotes an alkenyl group and a compound represented by the general formula (I) can be used in combination to significantly reduce a decrease in voltage holding ratio (VHR).

When the ring structure to which it is bonded is a phenyl group (aromatic), a linear alkyl group having 1 to 5 carbon atoms, a linear alkoxy group having 1 to 4 carbon atoms, or an alkenyl group having 4 or 5 carbon atoms is preferred. When the ring structure to which it is bonded is a saturated ring structure, such as cyclohexane, pyran, or dioxane, a linear alkyl group having 1 to 5 carbon atoms, a linear alkoxy group having 1 to 4 carbon atoms, or a linear alkenyl group having 2 to 5 carbon atoms is preferred. In order to stabilize the nematic phase, the total number of carbon atoms and, if present, oxygen atoms is preferably 5 or less, and a straight chain is preferred.

The alkenyl group is preferably selected from the groups represented by the formulae (R1) to (R5). (The dark dot in each formula represents a carbon atom in the ring structure.)

[Chem. 64]

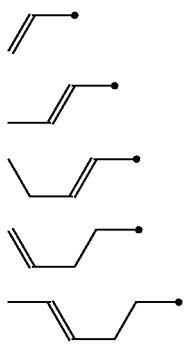

(R1)

(R2)

(R3)

(R4)

(R5)

$A^{N11}$, $A^{N12}$, $A^{N21}$, $A^{N22}$, $A^{N31}$, and $A^{N32}$ preferably independently denote an aromatic when an increased Δn is required, denote an aliphatic to improve the response speed, or denote a trans-1,4-cyclohexylene group, a 1,4-phenylene group, a 2-fluoro-1,4-phenylene group, a 3-fluoro-1,4-phenylene group, a 3,5-difluro-1,4-phenylene group, a 2,3-difluro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably independently denote the following structures,

[Chem. 65]

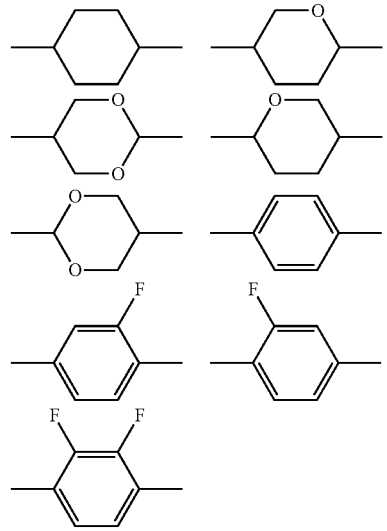

and more preferably independently denote a trans-1,4-cyclohexylene group or a 1,4-phenylene group.

$Z^{N11}$, $Z^{N12}$, $Z^{N21}$, $Z^{N22}$, $Z^{N31}$, and $Z^{N32}$ preferably independently denote —CH$_2$O—, —CF$_2$O—, —CH$_2$CH$_2$—, —CF$_2$CF$_2$—, or a single bond, more preferably —CH$_2$O—, —CH$_2$CH$_2$—, or a single bond, particularly preferably —CH$_2$O— or a single bond.

$X^{N21}$ preferably denotes a fluorine atom.

$T^{N31}$ preferably denotes an oxygen atom.

$n^{N11}+n^{N12}$, $n^{N21}+n^{N22}$, and $n^{N31}+n^{N32}$ are preferably 1 or 2, and a combination of $n^{N11}$ of 1 and $n^{N12}$ of 0, a combination of $n^{N11}$ of 2 and $n^{N12}$ of 0, a combination of $n^{N11}$ of 1 and $n^{N12}$ of 1, a combination of $n^{N11}$ of 2 and $n^{N12}$ of 1, a combination of $n^{N21}$ of 1 and $n^{N22}$ of 0, a combination of $n^{N21}$ of 2 and $n^{N22}$ of 0, a combination of $n^{N31}$ of 1 and $n^{N32}$ of 0, and a combination of $n^{N31}$ of 2 and $n^{N32}$ of 0 are preferred.

The lower limit of the preferred amount of compound represented by the formula (N-1) is 0%, 1%, 10%, 20%, 30%, 40%, 50%, 55%, 60%, 65%, 70%, 75%, or 80% of the total amount of composition according to the present invention. The upper limit of the preferred amount is 95%, 85%, 75%, 65%, 55%, 45%, 35%, 25%, or 20%.

The lower limit of the preferred amount of compound represented by the formula (N-2) is 0%, 1%, 10%, 20%, 30%, 40%, 50%, 55%, 60%, 65%, 70%, 75%, or 80% of the total amount of composition according to the present invention. The upper limit of the preferred amount is 95%, 85%, 75%, 65%, 55%, 45%, 35%, 25%, or 20%.

The lower limit of the preferred amount of compound represented by the formula (N-3) is 0%, 1%, 10%, 20%, 30%, 40%, 50%, 55%, 60%, 65%, 70%, 75%, or 80% of the total amount of composition according to the present invention. The upper limit of the preferred amount is 95%, 85%, 75%, 65%, 55%, 45%, 35%, 25%, or 20%.

When a composition according to the present invention with a low viscosity and a high response speed is required, the lower limit is preferably low, and the upper limit is preferably low. When a composition according to the present invention with a high Tni and high temperature stability is required, the lower limit is preferably low, and the upper limit is preferably low. When dielectric constant anisotropy is increased to maintain a low driving voltage, the lower limit is preferably high, and the upper limit is preferably high.

A liquid crystal composition according to the present invention preferably contains as the general formula (N-1) one or two or more compounds represented by the general formula (i-1).

[Chem. 66]

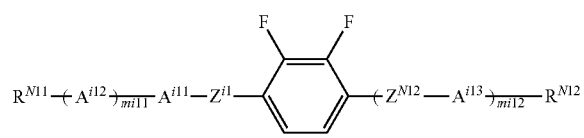
(i-1)

(In the formula, $A^{i11}$, $A^{i12}$, and $A^{i13}$ independently denote a 1,4-cyclohexylene group or a 1,4-phenylene group, one —$CH_2$— or two or more nonadjacent —$CH_2$— groups in the 1,4-cyclohexylene group may be substituted with —O— or —S—, one hydrogen atom in the 1,4-phenylene group may be independently substituted with a fluorine atom or a chlorine atom, $Z^{i1}$ denotes —$OCH_2$—, —$CH_2O$—, —$CF_2O$—, —$OCF_2$—, —$CH_2CH_2$—, or —$CF_2CF_2$—, $m^{i11}$ and $m^{i12}$ are independently 0 or 1, and $R^{N11}$, $R^{N12}$, and $Z^{N12}$ have the same meaning as $R^{N11}$, $R^{N12}$, and $Z^{N12}$, respectively, in the general formula (N-1).)

A compound represented by the general formula (i-1) is preferably a compound represented by the general formula (i-1A), (i-1B), or (i-1C).

[Chem. 67]

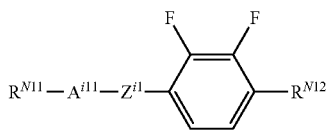
(i-1A)

(In the formula, $R^{N11}$, $R^{N12}$, $A^{i11}$, and $Z^{i1}$ have the same meaning as $R^{N11}$, $R^{N12}$, $A^{i11}$, and $Z^{i1}$, respectively, in the general formula (i-1).)

[Chem. 68]

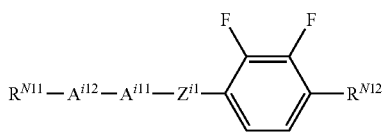
(i-1B)

(In the formula, $R^{N11}$, $R^{N12}$, $A^{i11}$, $A^{i12}$, and $Z^{i1}$ have the same meaning as $R^{N11}$, $R^{N12}$, $A^{i11}$, $A^{i12}$, and $Z^{i1}$, respectively, in the general formula (i-1).)

[Chem. 69]

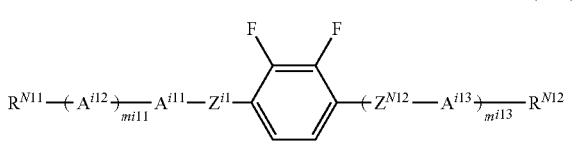
(i-1C)

(In the formula, $m^{i13}$ is 1, $R^{N11}$, $R^{N12}$, $A^{i11}$, $A^{i12}$, $A^{i13}$, $Z^{i1}$, Zi2, and $m^{i11}$ have the same meaning as $R^{N11}$, $R^{N12}$, $A^{i11}$, $A^{i12}$, $A^{i13}$, $Z^{i1}$, Zi2, and $m^{i11}$, respectively, in the general formula (i-1).)

A compound represented by the general formula (i-1A) is preferably one of the compounds represented by the following general formulae (i-1A-1) to (i-1A-4).

[Chem. 70]

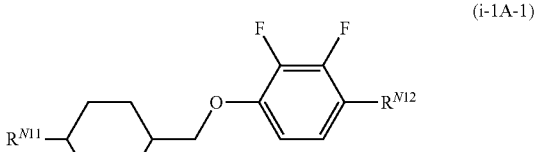
(i-1A-1)

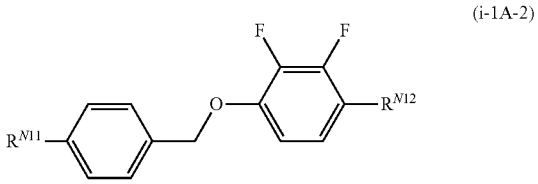
(i-1A-2)

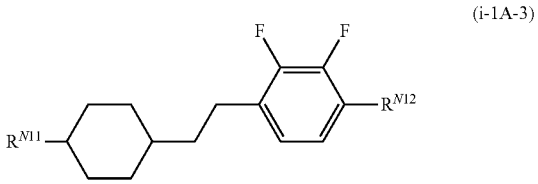
(i-1A-3)

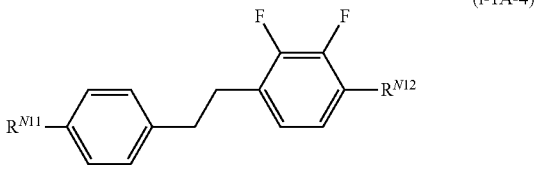
(i-1A-4)

(In the formula, $R^{N11}$ and $R^{N12}$ have the same meaning as $R^{N11}$ and $R^{N12}$, respectively, in the general formula (i-1).)

A compound represented by the general formula (i-1B) is preferably one of the compounds represented by the following general formulae (i-1B-1) to (i-1B-7).

[Chem .71]

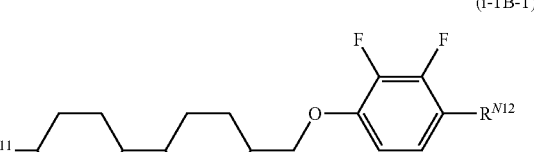
(i-1B-1)

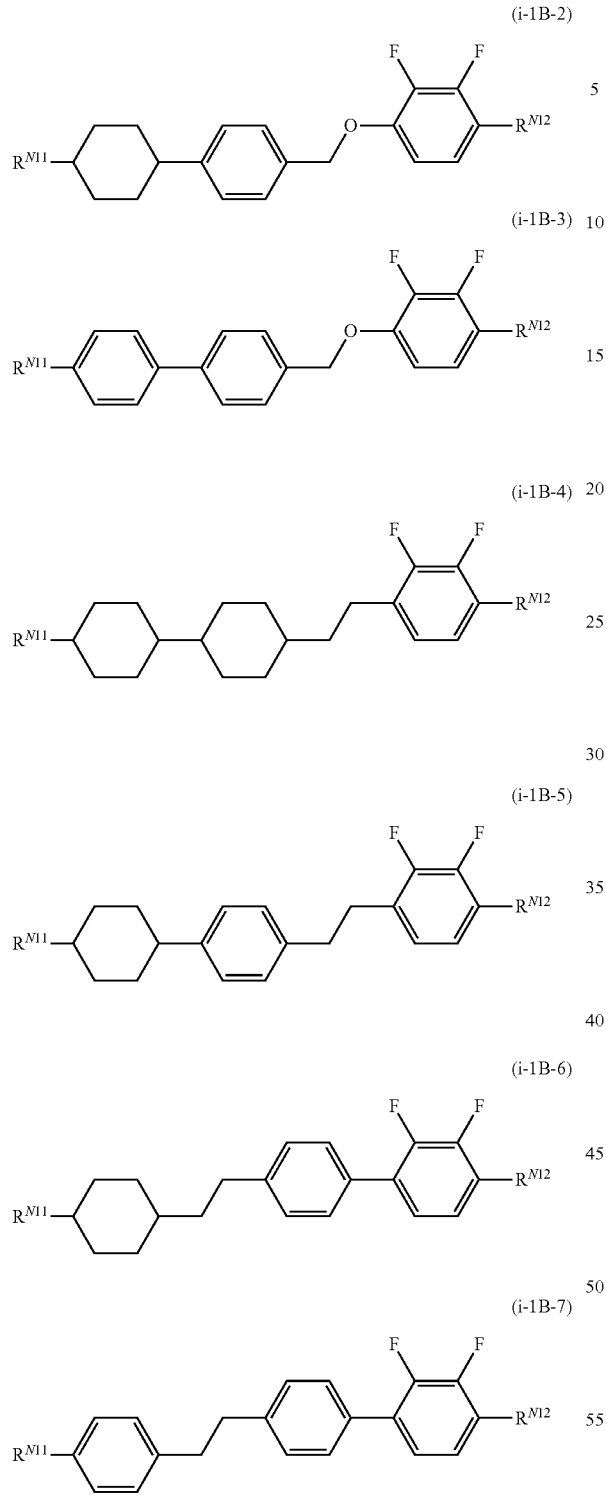

(i-1B-2)
(i-1B-3)
(i-1B-4)
(i-1B-5)
(i-1B-6)
(i-1B-7)

(In the formula, $R^{N11}$ and $R^{N12}$ have the same meaning as $R^{N11}$ and $R^{N12}$, respectively, in the general formula (i-1).)

A compound represented by the general formula (i-1C) is preferably a compound represented by one of the following general formulae (i-1C-1) to (i-1C-2), more preferably a compound represented by the general formulae (i-1C-1) or (i-1C-2).

[Chem. 72]

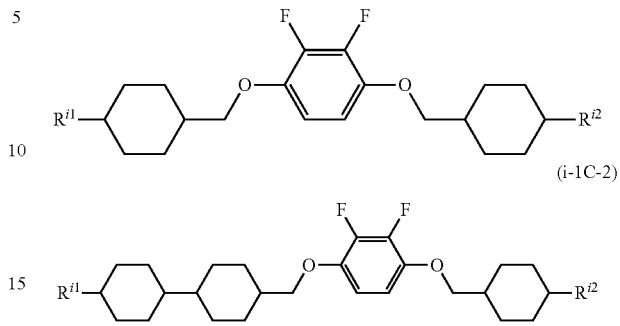

(i-1C-1)
(i-1C-2)

(In the formula, $R^{i1}$ and $R^{i2}$ have the same meaning as $R^{i1}$ and $R^{i2}$, respectively, in the general formula (i-1).)

A liquid crystal composition according to the present invention preferably contains one or two or more compounds represented by the general formula (i) and may contain one or two or more compounds selected from the compound group represented by the general formula (i-1A), (i-1B), or (i-1C) or one or more compounds represented by each of the general formulae (i-1A), (i-1B), and (i-1C). One or two or more, more preferably two to ten, compounds represented by the general formula (i-1A) and/or the general formula (i-1B) are preferably contained.

More specifically, the general formulae (i-1A), (i-1B), and (i-1C) preferably include one or two or more compounds selected from the compound group represented by the general formulae (i-1A-1), (i-1B-1), and (i-1C-1) and are more preferably a combination of a compound represented by the general formula (i-1A-1) and a compound represented by the general formula (i-1B-1).

A liquid crystal composition according to the present invention preferably contains one or two or more compounds represented by the general formula (ii).

[Chem. 73]

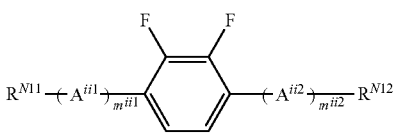

(ii)

(In the formula, $A^{ii1}$ and $A^{ii2}$ independently denote a 1,4-cyclohexylene group or a 1,4-phenylene group, one —CH$_2$— or two or more nonadjacent —CH$_2$— groups in the 1,4-cyclohexylene group may be substituted with —O— or —S—, one hydrogen atom in the 1,4-phenylene group may be independently substituted with a fluorine atom or a chlorine atom, $m^{ii1}$ and $m^{ii2}$ are independently 1 or 2, and $R^{N11}$ and $R^{N12}$ have the same meaning as $R^{N11}$ and $R^{N12}$, respectively, in the general formula (N-1).)

One or two or more compounds represented by the general formula (ii-1) are preferably contained as the general formula (ii).

[Chem. 74]

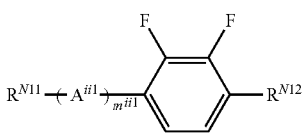
(ii-1)

(In the formula, $R^{N11}$, $R^{N12}$, $A^{ii1}$, and $m^{ii1}$ have the same meaning as $R^{N11}$, $R^{N12}$, $A^{ii1}$, and $m^{ii1}$, respectively, in the general formula (ii).)

A compound represented by the general formula (ii-1) is preferably a compound represented by the general formula (ii-1A) or (ii-1B).

[Chem. 75]

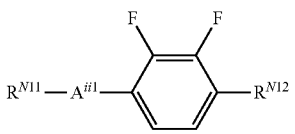
(ii-1A)

(In the formula, $R^{N11}$, $R^{N12}$, and $A^{ii1}$ have the same meaning as $R^{N11}$, $R^{N12}$, and $A^{ii1}$, respectively, in the general formula (ii).)

[Chem. 76]

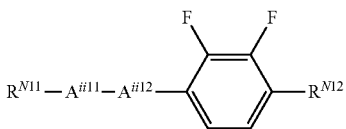
(ii-1B)

(In the formula, $A^{ii11}$ and $A^{ii12}$ independently denote a 1,4-cyclohexylene group or a 1,4-phenylene group, one —CH$_2$— or two or more nonadjacent —CH$_2$— groups in the 1,4-cyclohexylene group may be substituted with —O— or —S—, one hydrogen atom in the 1,4-phenylene group may be independently substituted with a fluorine atom or a chlorine atom, and $R^{N11}$ and $R^{N12}$ have the same meaning as $R^{N11}$ and $R^{N12}$, respectively, in the general formula (ii).)

A compound represented by the general formula (ii-1A) is preferably a compound represented by the following general formula (ii-1A-1) or (ii-1A-2).

[Chem. 77]

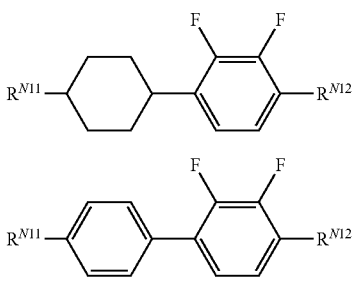
(ii-1A-1)
(ii-1A-2)

(In the formula, $R^{N11}$ and $R^{N12}$ have the same meaning as $R^{N11}$ and $R^{N12}$ in the general formula (ii).)

A compound represented by the general formula (ii-1B) is preferably a compound represented by one of the following general formulae (ii-1B-1) to (ii-1B-3).

[Chem. 78]

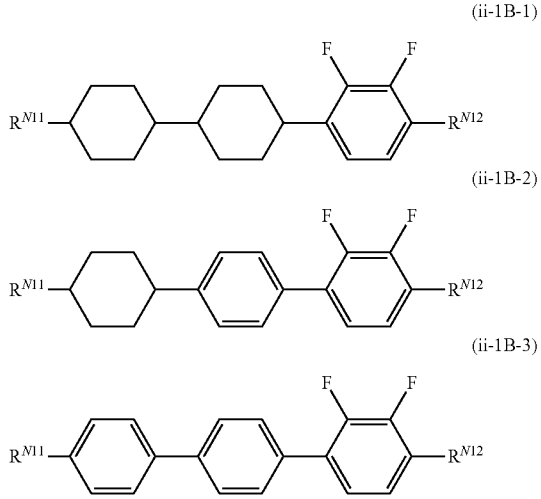
(ii-1B-1)
(ii-1B-2)
(ii-1B-3)

(In the formula, $R^{N11}$ and $R^{N12}$ have the same meaning as $R^{N11}$ and $R^{N12}$ in the general formula (ii).)

A liquid crystal composition according to the present invention preferably contains one or two or more compounds represented by the general formula (ii) and may contain one or two or more compounds selected from the compound group represented by the general formulae (ii-1A) and (ii-1B) or one or more compounds represented by each of the general formulae (ii-1A) and (ii-1B). Two to ten compounds represented by the general formulae (ii-1A) and (ii-1B) are preferably contained.

More specifically, the general formula (ii-1A) preferably includes one or two or more compounds selected from the compound group represented by the general formula (ii-1A-1), and the general formula (ii-1B) preferably includes one or two or more compounds selected from the compound group represented by the general formulae (ii-1B-1) and (ii-1B-2), and a combination of compounds represented by the general formulae (ii-1A-1) and (ii-1B-1) is more preferred.

One or two or more compounds represented by the following general formula (LC3-b) are preferably contained as the general formula (N-1).

[Chem. 79]

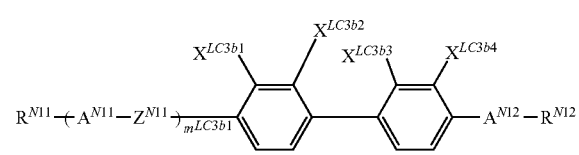
(LC3-b)

(In the formula, $R^{N11}$, $R^{N12}$, $A^{N11}$, $A^{N12}$, and $Z^{N11}$ have the same meaning as $R^{N11}$, $R^{N12}$, $A^{N11}$, $A^{N12}$, and $Z^{N11}$, respectively, in the general formula (N-1), and $X^{LC3b1}$ to $X^{LC3b4}$ denote a hydrogen atom or a fluorine atom. $X^{LC3b1}$ and $X^{LC3b2}$ independently denote a fluorine atom, or $X^{LC3b3}$ and $X^{LC3b4}$ independently denote a fluorine atom, or $X^{LC3b1}$ to $X^{LC3b4}$ independently denote a fluorine atom, and $m^{LC3b1}$ is 0 or 1. The compounds represented by the general formulae (i-1) and (ii) are excluded from the compounds represented by the general formula (LC3-b).)

The general formula (LC3-b) preferably represents the following general formulae (LC3-b1) to (LC3-b10).

[Chem. 80]

(LC3-b1)
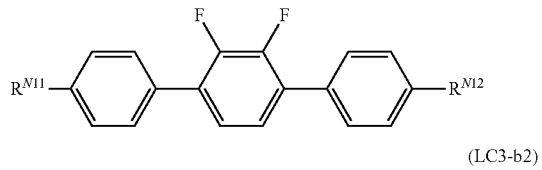

(LC3-b2)
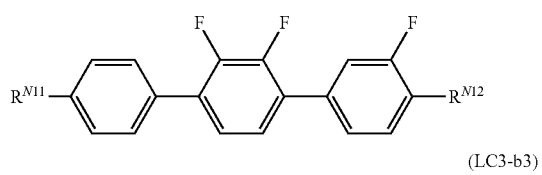

(LC3-b3)
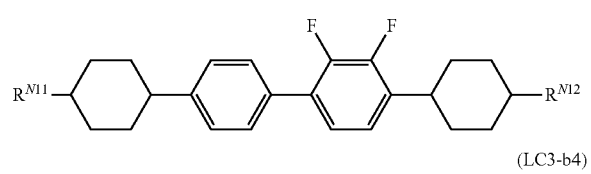

(LC3-b4)
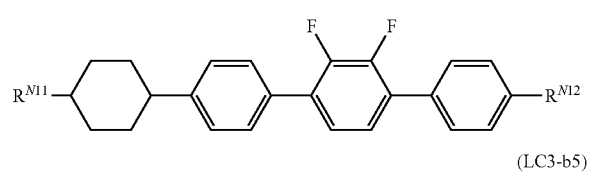

(LC3-b5)
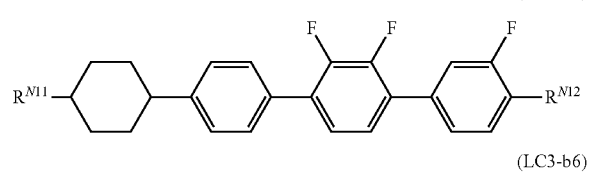

(LC3-b6)
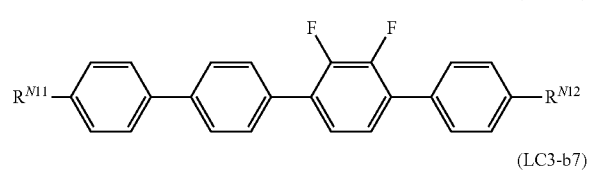

(LC3-b7)
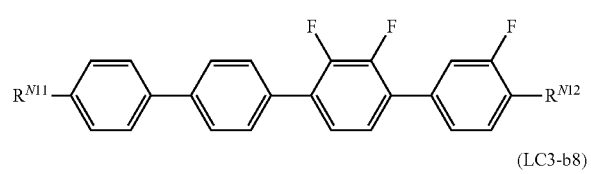

(LC3-b8)
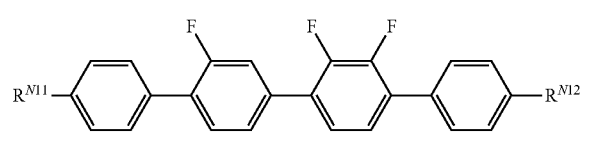

(LC3-b9)
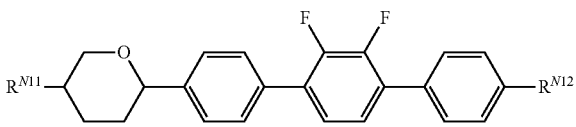

(LC3-b10)
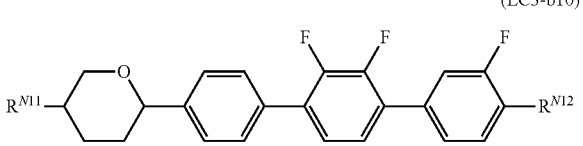

(In the formula, $R^{N11}$ and $R^{N12}$ have the same meaning as $R^{N11}$ and $R^{N12}$, respectively, in the general formula (N-1).)

A combination of $R^{N11}$ and $R^{N12}$ is not particularly limited. Preferably, both $R^{N11}$ and $R^{N12}$ denote an alkyl group; both $R^{N11}$ and $R^{N12}$ denote an alkenyl group; one of $R^{N11}$ and $R^{N12}$ denotes an alkyl group, and the other denotes an alkenyl group; one of $R^{N11}$ and $R^{N12}$ denotes an alkyl group, and the other denotes an alkoxy; or one of $R^{N11}$ and $R^{N12}$ denotes an alkyl group, and the other denotes an alkenyloxy group. More preferably, both $R^{N11}$ and $R^{N12}$ denote an alkyl group, or both $R^{N11}$ and $R^{N12}$ denote an alkenyl group.

The general formula (LC3-b) preferably represents the following general formula (LC3-c).

[Chem. 81]

(LC3-c)
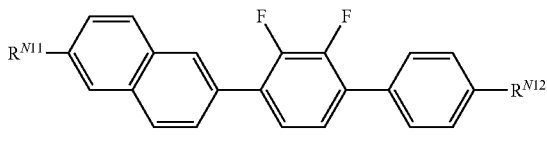

(In the formula, $R^{N11}$ and $R^{N12}$ have the same meaning as $R^{N11}$ and $R^{N12}$, respectively, in the general formula (N-1).)

A compound represented by the general formula (N-2) is preferably a compound selected from the compound group represented by the general formulae (N-2-1) to (N-2-3).

[Chem. 82]

(N-2-1)
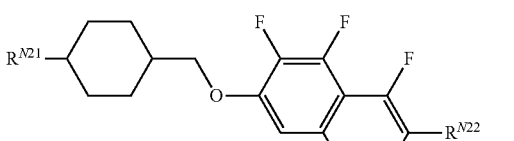

(N-2-2)
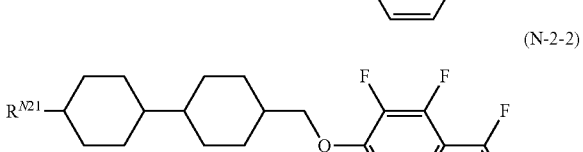

-continued (N-2-3)

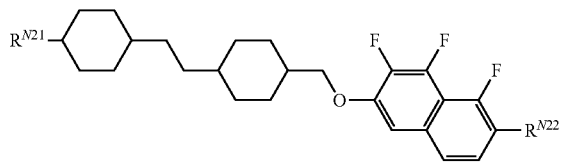

(In the formula, $R^{N21}$ and $R^{N22}$ have the same meaning as $N^{N211}$ and $R^{N22}$, respectively, in the general formula (N-2).)

A compound represented by the general formula (N-3) is preferably a compound selected from the compound group represented by the general formulae (N-3-1) and (N-3-2).

A compound represented by the general formula (N-3-1) is the following compound.

[Chem. 83]

(N-3-1)

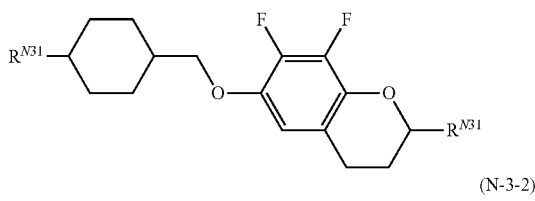

(N-3-2)

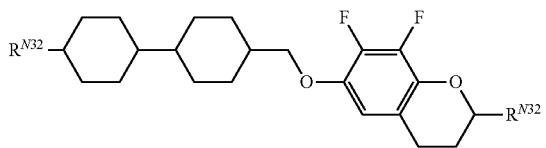

(In the formula, $R^{n31}$ and $R^{N32}$ have the same meaning as $R^{N31}$ and $R^{N32}$, respectively, in the general formula (N-3).)

<Third Embodiment of Compound Represented by General Formula (II)>

A fourth component is a so-called nonpolar liquid crystal compound, which has a dielectric constant anisotropy of approximately 0, and may be a compound represented by the following general formula (L).

A composition according to the present invention preferably contains one or two or more compounds represented by the general formula (L). A compound represented by the general formula (L) corresponds to a dielectrically nearly neutral compound (with Δε in the range of −2 to 2).

[Chem. 84]

$$R^{L1}\text{-}A^{L1}\text{-}Z^{L1}\text{-}(A^{L2}\text{-}Z^{L2})_{n^{L1}}A^{L3}\text{-}R^{L2} \quad (L)$$

(In the formula, $R^{L1}$ and $R^{L2}$ independently denote an alkyl group having 1 to 8 carbon atoms, and one —CH$_2$— or two or more nonadjacent —CH$_2$— groups in the alkyl group may be independently substituted with —CH=CH—, —C≡C—, —O—, —CO—, —COO—, or —OCO—, $n^{L1}$ is 0, 1, 2, or 3, $A^{L1}$, $A^{L2}$, and $A^{L3}$ independently denote a group selected from the group consisting of (a) a 1,4-cyclohexylene group (in which one —CH$_2$— or two or more nonadjacent —CH$_2$— groups may be substituted with —O—), (b) a 1,4-phenylene group (in which one —CH= or two or more nonadjacent —CH= groups may be substituted with —N=), and (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl group or the 1,2,3,4-tetrahydronaphthalene-2,6-diyl group may be substituted with —N=), the groups (a), (b), and (c) may be independently substituted with a cyano group, a fluorine atom, or a chlorine atom.

$Z^{L1}$ and $Z^{L2}$ independently denote a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—, and if $n^{L1}$ is 2 or 3, a plurality of $A^{L2}$s may be the same or different, and if $n^{L1}$ is 2 or 3, a plurality of $Z^{L2}$s may be the same or different. The compounds represented by the general formulae (J), (N-1), (N-2), and (N-3) are excluded.)

The compounds represented by the general formula (L) may be used alone or in combination. Although compounds of any types may be combined, these compounds are appropriately combined in a manner that depends on the desired characteristics, such as solubility at low temperatures, transition temperature, electrical reliability, and birefringence index. For example, one compound is used in one embodiment of the present invention. Two, three, four, five, six, seven, eight, nine, ten, or more compounds are used in another embodiment of the present invention.

The amount of compound represented by the general formula (L) in a composition according to the present invention should be appropriately adjusted in a manner that depends on the desired characteristics, such as solubility at low temperatures, transition temperature, electrical reliability, birefringence index, process compatibility, drop marks, image sticking, and dielectric constant anisotropy.

The lower limit of the preferred amount of compound represented by the formula (L) is 0%, 1%, 10%, 20%, 30%, 40%, 50%, 55%, 60%, 65%, 70%, 75%, or 80% of the total amount of composition according to the present invention. The upper limit of the preferred amount is 95%, 85%, 75%, 65%, 55%, 45%, 35%, or 25%.

When a composition according to the present invention with a low viscosity and a high response speed is required, the lower limit is preferably high, and the upper limit is preferably high. When a composition according to the present invention with a high Tni and high temperature stability is required, the lower limit is preferably high, and the upper limit is preferably high. When dielectric constant anisotropy is increased to maintain a low driving voltage, the lower limit is preferably low, and the upper limit is preferably low.

When reliability is regarded as important, both $R^{L1}$ and $R^{L2}$ preferably denote an alkyl group. When reduced volatility of the compound is regarded as important, both $R^{L1}$ and $R^{L2}$ preferably denote an alkoxy group. When reduced viscosity is regarded as important, at least one of $R^{L1}$ and $R^{L2}$ preferably denotes an alkenyl group.

When the ring structure to which $R^{L1}$ and $R^{L2}$ are bonded is a phenyl group (aromatic), $R^{L1}$ and $R^{L2}$ preferably denote a linear alkyl group having 1 to 5 carbon atoms, a linear alkoxy group having 1 to 4 carbon atoms, or an alkenyl group having 4 or 5 carbon atoms. When the ring structure to which $R^{L1}$ and $R^{L2}$ are bonded is a saturated ring structure, such as cyclohexane, pyran, or dioxane, $R^{L1}$ and $R^{L2}$ preferably denote a linear alkyl group having 1 to 5 carbon atoms, a linear alkoxy group having 1 to 4 carbon atoms, or a linear alkenyl group having 2 to 5 carbon atoms. In order to stabilize the nematic phase, the total number of carbon atoms and, if present, oxygen atoms is preferably 5 or less, and a straight chain is preferred.

The alkenyl group is preferably selected from the groups represented by the formulae (R1) to (R5). (The dark dot in each formula represents a carbon atom in the ring structure.)

[Chem. 85]

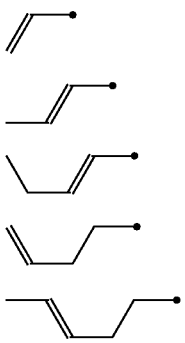

In particular, a compound in which at least one of $R^{L1}$ and $R^{L2}$ denotes an alkenyl group and a compound represented by the general formula (I) can be used in combination to significantly reduce a decrease in voltage holding ratio (VHR).

When the response speed is regarded as important, $n^{L1}$ is preferably 0. In order to improve the upper limit temperature of the nematic phase, $n^{L1}$ is preferably 2 or 3. In order to achieve the balance therebetween, $n^{L1}$ is preferably 1. In order to satisfy the characteristics required for the composition, compounds with different $n^{L1}$s are preferably combined.

$A^{L1}$, $A^{L2}$, and $A^{L3}$ preferably independently denote an aromatic when an increased Δn is required, denote an aliphatic to improve the response speed, or denote a trans-1,4-cyclohexylene group, a 1,4-phenylene group, a 2-fluoro-1,4-phenylene group, a 3-fluoro-1,4-phenylene group, a 3,5-difluro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably the following structures,

[Chem. 86]

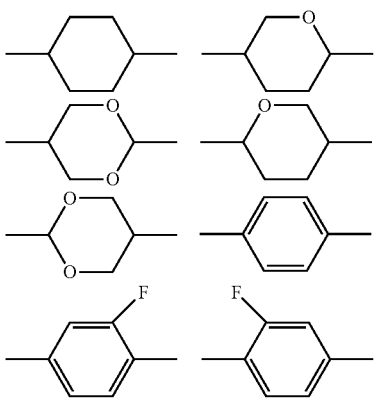

and more preferably independently denote a trans-1,4-cyclohexylene group or a 1,4-phenylene group.

When the response speed is regarded as important, $Z^{L1}$ and $Z^{L2}$ preferably denote a single bond.

The number of halogen atoms in the molecule is preferably 0 or 1.

A compound represented by the general formula (L) is preferably a compound selected from the compounds represented by the general formula (L-1).

[Chem. 87]

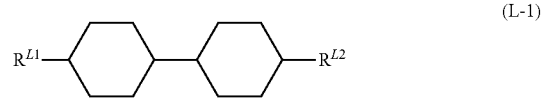

(L-1)

(In the formula, $R^{L1}$ and $R^{L2}$ have the same meaning as RU and $R^{L2}$, respectively, in the general formula (L).)

$R^{L11}$ and $R^{L12}$ preferably denote a linear alkyl group having 1 to 5 carbon atoms, a linear alkoxy group having 1 to 4 carbon atoms, or a linear alkenyl group having 2 to 5 carbon atoms. The compounds represented by the general formula (L-1) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The lower limit of the preferred amount is 1%, 2%, 3%, 5%, 7%, 10%, 15%, 20%, 25%, 30%, 35%, 40%, 45%, 50%, or 55% of the total amount of composition according to the present invention. The upper limit of the preferred amount is 95%, 90%, 85%, 80%, 75%, 70%, 65%, 60%, 55%, 50%, 45%, 40%, 35%, 30%, or 25% of the total amount of composition according to the present invention.

When a composition according to the present invention with a low viscosity and a high response speed is required, the lower limit is preferably high, and the upper limit is preferably high. When a composition according to the present invention with a high Tni and high temperature stability is required, the lower limit is preferably medium, and the upper limit is preferably medium. When dielectric constant anisotropy is increased to maintain a low driving voltage, the lower limit is preferably low, and the upper limit is preferably low.

A compound represented by the general formula (L-1) is preferably a compound represented by the general formula (L-1-1).

[Chem. 88]

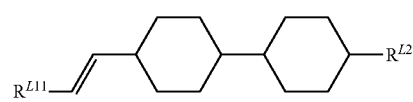

(L-1-1)

(In the formula, $R^{L11}$ denotes a hydrogen atom or a methyl group, and $R^{L2}$ has the same meaning as R in the general formula (L).)

A compound represented by the general formula (L-1-1) is preferably a compound selected from the compound group represented by the formulae (L-1-1.11) to (L-1-1.13), preferably a compound represented by the formula (L-1-1.12) or (L-1-1.13), particularly preferably the compound represented by the formula (L-1-1.13).

[Chem. 89]

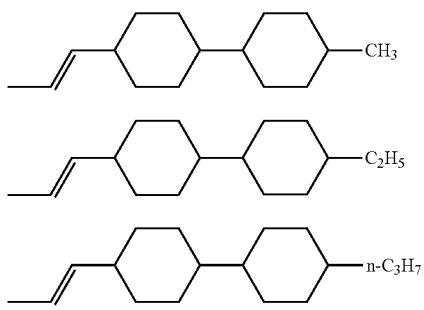

(L-1-1.11)
(L-1-1.12)
(L-1-1.13)

A compound represented by the general formula (L-1-1) is preferably a compound selected from the compound group represented by the formulae (L-1-1.21) to (L-1-1.24), preferably a compound represented by one of the formulae (L-1-1.22) to (L-1-1.24). In particular, the compound represented by the formula (L-1-1.22) is preferred in order to particularly improve the response speed of a composition according to the present invention. The compound represented by the formula (L-1-1.23) or (L-1-1.24) is preferably used to increase Tni rather than the response speed.

[Chem. 90]

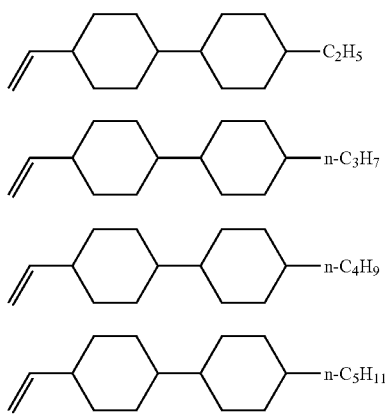

(L-1-1.21)
(L-1-1.22)
(L-1-1.23)
(L-1-1.24)

A compound represented by the general formula (L-1-1) is preferably a compound selected from the compound group represented by the formulae (L-1-1.31) and (L-1-1.41).

[Chem. 91]

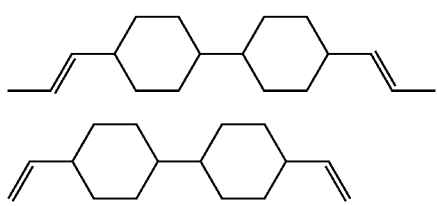

(L-1-1.31)
(L-1-1.41)

A compound represented by the general formula (L-1) is preferably a compound represented by the general formula (L-1-2).

[Chem. 92]

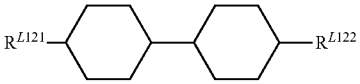

(L-1-2)

(In the formula, $R^{L121}$ and $R^{L122}$ independently denote an alkyl group having 1 to 8 carbon atoms or an alkoxy group having 1 to 8 carbon atoms.)

A compound represented by the general formula (L-1-2) is preferably a compound selected from the compound group represented by the formulae (L-1-2.1) to (L-1-2.12), preferably a compound represented by the formula (L-1-2.1), (L-1-2.3), or (L-1-2.4). In particular, the compound represented by the formula (L-1-2.1) is preferred in order to particularly improve the response speed of a composition according to the present invention. The compounds represented by the formulae (L-1-2.3), (L-1-2.4), (L-1-2.11), and (L-1-2.12) are preferably used to increase Tni rather than the response speed. In order to improve solubility at low temperatures, it is undesirable that the total amount of compounds represented by the formulae (L-1-2.3), (L-1-2.4), (L-1-2.11), and (L-1-2.12) be 20% or more.

[Chem. 93]

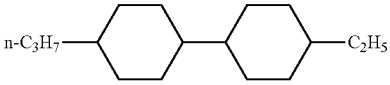

(L-1-2.1)

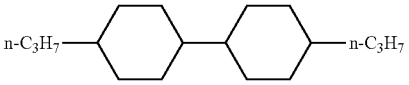

(L-1-2.2)

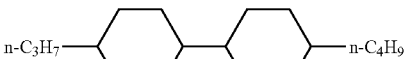

(L-1-2.3)

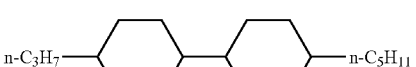

(L-1-2.4)

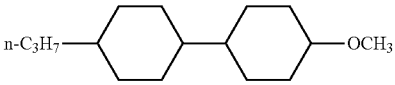

(L-1-2.11)

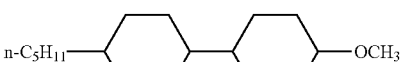

(L-1-2.12)

A compound represented by the general formula (L-1) is preferably a compound selected from the compound group represented by the general formulae (L-1-3) and/or (L-1-4).

[Chem. 94]

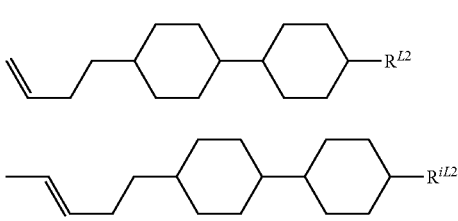

(L-1-3)

(L-1-4)

(In the formula, $R^{ii31}$ and $R^{ii41}$ independently have the same meaning as $R^{ii2}$ in the general formula (L).)

A compound represented by the general formula (L) is preferably a compound represented by one of the following general formulae (L-2) to (L-11). A liquid crystal composition according to the present invention preferably contains one or two or more compounds represented by the general formulae (L-2) to (L-11) as a compound or compounds represented by the general formula (L).

[Chem. 95]

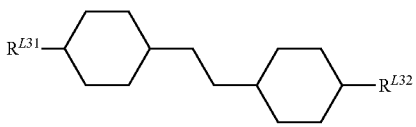

(L-2)

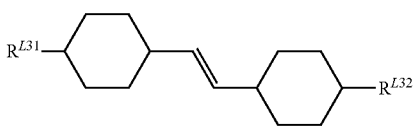

(L-3)

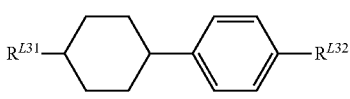

(L-4)

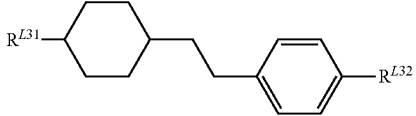

(L-5)

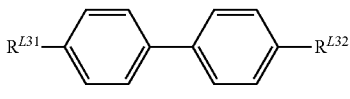

(L-6)

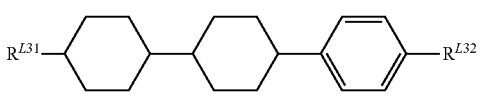

(L-7)

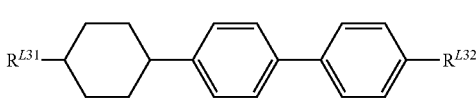

(L-8)

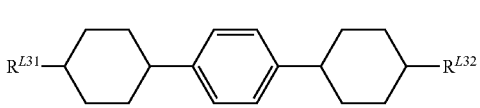

(L-9)

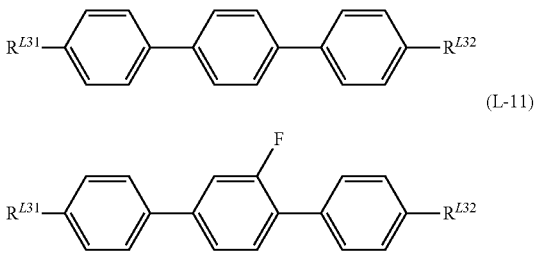

(L-10)

(L-11)

(In the formula, $R^{L31}$ and $R^{L32}$ denotes an alkyl group having 1 to 5 carbon atoms or an alkenyl group having 2 to 5 carbon atoms, and $R^{L3}$ denotes an alkyl group having 1 to 5 carbon atoms, an alkoxy group having 1 to 5 carbon atoms, an alkenyl group having 2 to 5 carbon atoms, or an alkenyloxy group having 2 to 5 carbon atoms.)

A compound represented by the general formula (L) is preferably a compound selected from the general formulae (L-4), (L-6), (L-7), and (L-8), more preferably a compound selected from the general formulae (L-6), (L-7), and (L-8), still more preferably a compound selected from the general formulae (L-7) and (L-8), and a compound selected from the general formulae (L-6) and (L-8) is also preferred. More specifically, when a high Δn is required, a compound selected from the general formulae (L-6), (L-8), and (L-11) is preferred.

In a compound represented by the general formula (L-4), (L-7), or (L-8), $R^{L31}$ preferably denotes an alkyl group having 1 to 5 carbon atoms or an alkenyl group having 2 to 5 carbon atoms, $R^{L32}$ preferably denotes an alkyl group having 1 to 5 carbon atoms or an alkoxy group having 1 to 5 carbon atoms, $R^{L32}$ more preferably denotes an alkenyl group having 2 to 5 carbon atoms, still more preferably an alkenyl group having 2 or 3 carbon atoms. In a compound represented by the general formula (L-6), $R^{L31}$ and $R^{L32}$ preferably independently denote an alkyl group having 1 to 5 carbon atoms or an alkenyl group having 2 to 5 carbon atoms.

One or two or more compounds represented by the general formula (L-12), (L-13), or (L-14) are preferably contained as a compound or compounds represented by the general formula (L).

[Chem. 96]

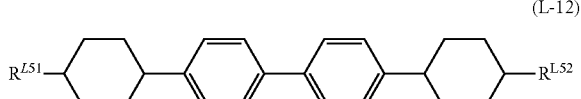

(L-12)

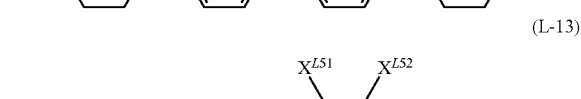

(L-13)

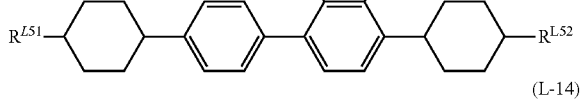

(L-14)

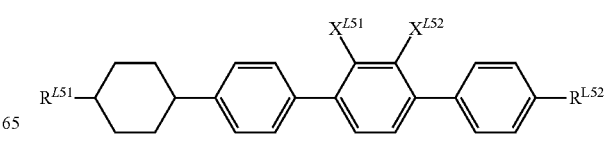

(In the formulae, $R^{L51}$ and $R^{L52}$ independently denote an alkyl group having 1 to 5 carbon atoms, an alkenyl group having 2 to 5 carbon atoms, or an alkoxy group having 1 to 4 carbon atoms, $X^{L51}$ and $X^{L52}$ independently denote a fluorine atom or a hydrogen atom, and one of $X^{L51}$ and $X^{L52}$ denotes a fluorine atom, and the other denotes a hydrogen atom.)

One or two or more compounds represented by the general formulae (L-16.1) to (L-16.3) may be contained as a compound or compounds represented by the general formula (L).

[Chem. 97]

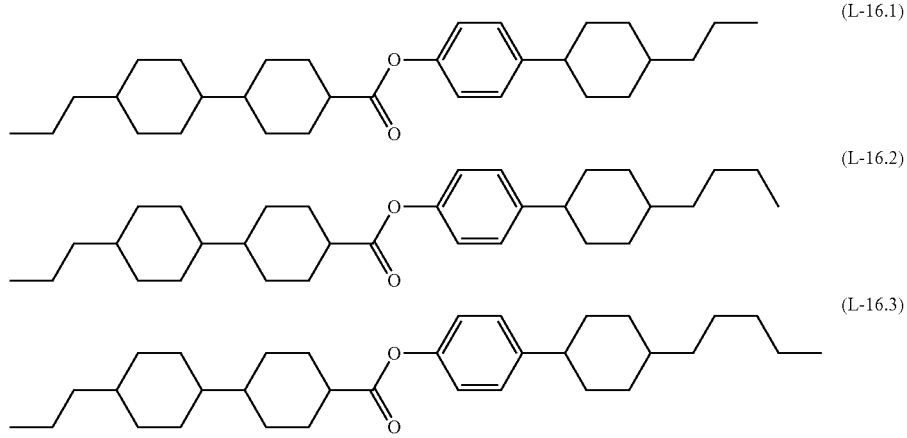

One or two or more compounds represented by the general formula (N-001) may be contained as a compound or compounds represented by the general formula (L).

[Chem. 98]

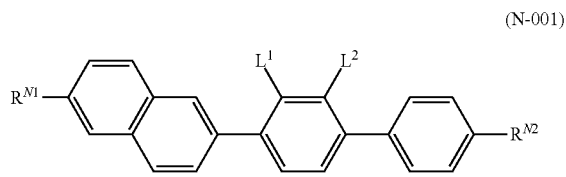

(In the formula, $R^{N1}$ and $R^{N2}$ independently denote an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, and $L^1$ and $L^2$ independently denote a hydrogen atom, a fluorine atom, $CH_3$, or $CF_3$, provided that either $L^1$ or $L^2$ is not a fluorine atom.)

$R^{N1}$ and $R^{N2}$ preferably denote an alkyl group having 1 to 5 carbon atoms.

A liquid crystal composition according to the present invention preferably has a positive dielectric constant anisotropy (Δε) at 25° C. and preferably has a dielectric constant anisotropy (Δε) in the range of 1.5 to 20.0, more preferably 1.5 to 18.0, still more preferably 1.5 to 15.0, still more preferably 1.5 to 11, particularly preferably 1.5 to 8, at 25° C.

A liquid crystal composition with a positive dielectric constant anisotropy (Δε) preferably contains a compound represented by the general formula (J) and a compound represented by the general formula (L). More specifically, such a liquid crystal composition preferably contains a compound represented by the general formula (M) and a compound represented by the general formula (L-1), preferably a compound represented by the general formula (M-1) and/or the general formula (M-2) and a compound represented by the general formula (L-1-1).

The lower limit of the total amount of compound(s) represented by the general formula (I), compound(s) represented by the general formula (J), and compound(s) represented by the general formula (L) in a liquid crystal composition according to the present invention is preferably 5% or more, 80% or more, 85% or more, 88% or more, 90% or more, 92% or more, 95% or more, 97% or more, 98% or more, 99% or more. Preferably, a liquid crystal composition according to the present invention is substantially free from the other compounds. The upper limit is preferably 90% or less, preferably 95% or less, preferably 98% or less, preferably 99% or less. Preferably, a liquid crystal composition according to the present invention is substantially free from the other compounds. The term "substantially", as used herein, refers to excluding unintentional compounds, such as incidental impurities, during production.

The lower limit of the total amount of compound(s) represented by the general formula (I), compound(s) represented by the general formula (M), and compound(s) represented by the general formula (L) in a liquid crystal composition according to the present invention is preferably 5% or more, 80% or more, 85% or more, 88% or more, 90% or more, 92% or more, 95% or more, 97% or more, 98% or more, 99% or more. Preferably, a liquid crystal composition according to the present invention is substantially free from the other compounds. The upper limit is preferably 90% or less, preferably 95% or less, preferably 98% or less, preferably 99% or less. Preferably, a liquid crystal composition according to the present invention is substantially free from the other compounds.

The lower limit of the total amount of compound(s) represented by the general formula (I), compound(s) represented by the general formula (J), and compound(s) represented by the general formula (L-1) in a liquid crystal composition according to the present invention is preferably 5% or more, 10% or more, 13% or more, 15% or more, 18% or more, 20% or more, 23% or more, 25% or more, 28% or more, 30% or more, 33% or more, 35% or more, 38% or more, 40% or more. The upper limit is preferably 95% or less, preferably 90% or less, preferably 88% or less, preferably 85% or less, preferably 83% or less, preferably 80% or less, preferably 78% or less, preferably 75% or less, preferably 73% or less, preferably 70% or less, preferably 68% or less, preferably 65% or less, preferably 63% or less, preferably 60% or less, preferably 55% or less, preferably 50% or less, preferably 40% or less.

A liquid crystal composition according to the present invention preferably has a negative dielectric constant anisotropy ($\Delta\varepsilon$) at 25° C. and preferably has a dielectric constant anisotropy ($\Delta\varepsilon$) in the range of −2.0 to −8.0, preferably −2.0 to −6.0, more preferably −2.0 to −5.0, particularly preferably −2.5 to −4.0, at 25° C.

A liquid crystal composition with a negative dielectric constant anisotropy ($\Delta\varepsilon$) preferably contains a compound represented by the general formulae (N-1) to (N-3) and a compound represented by the general formula (L). More specifically, a compound represented by the general formula (N-1) and a compound represented by the general formula (L-1) are preferably contained, and a compound represented by the general formula (N-1) and a compound represented by the general formula (L-1-1) are preferably contained.

The lower limit of the total amount of compound(s) represented by the general formula (I), compounds represented by the general formulae (N-1) to (N-3), and compound(s) represented by the general formula (L) in a liquid crystal composition according to the present invention is preferably 5% or more, 80% or more, 85% or more, 88% or more, 90% or more, 92% or more, 95% or more, 97% or more, 98% or more, 99% or more. Preferably, a liquid crystal composition according to the present invention is substantially free from the other compounds. The upper limit is preferably 90% or less, preferably 95% or less, preferably 98% or less, preferably 99% or less. Preferably, a liquid crystal composition according to the present invention is substantially free from the other compounds.

The lower limit of the total amount of compound(s) represented by the general formula (I), compound(s) represented by the general formula (N-1), and compound(s) represented by the general formula (L) in a liquid crystal composition according to the present invention is preferably 5% or more, 80% or more, 85% or more, 88% or more, 90% or more, 92% or more, 95% or more, 97% or more, 98% or more, 99% or more. Preferably, a liquid crystal composition according to the present invention is substantially free from the other compounds. The upper limit is preferably 90% or less, preferably 95% or less, preferably 98% or less, preferably 99% or less. Preferably, a liquid crystal composition according to the present invention is substantially free from the other compounds.

The lower limit of the total amount of compound(s) represented by the general formula (I), compound(s) represented by the general formula (J), and compound(s) represented by the general formula (L-1) in a liquid crystal composition according to the present invention is preferably 5% or more, 10% or more, 13% or more, 15% or more, 18% or more, 20% or more, 23% or more, 25% or more, 28% or more, 30% or more, 33% or more, 35% or more, 38% or more, 40% or more. The upper limit is preferably 95% or less, preferably 90% or less, preferably 88% or less, preferably 85% or less, preferably 83% or less, preferably 80% or less, preferably 78% or less, preferably 75% or less, preferably 73% or less, preferably 70% or less, preferably 68% or less, preferably 65% or less, preferably 63% or less, preferably 60% or less, preferably 55% or less, preferably 50% or less, preferably 40% or less.

A liquid crystal composition according to the present invention has a refractive index anisotropy ($\Delta n$) in the range of 0.08 to 0.14, preferably 0.09 to 0.13, particularly preferably 0.09 to 0.12, at 25° C. More specifically, the refractive index anisotropy ($\Delta n$) preferably ranges from 0.10 to 0.13 for a small cell gap and 0.08 to 0.10 for a large cell gap.

A liquid crystal composition according to the present invention has a viscosity ($\eta$) in the range of 10 to 50 mPa·s, preferably 10 to 40 mPa·s, particularly preferably 10 to 35 mPa·s, at 25° C.

A liquid crystal composition according to the present invention has a rotational viscosity ($\gamma_1$) in the range of 60 to 130 mPa·s, preferably 60 to 110 mPa·s, particularly preferably 60 to 100 mPa·s, at 25° C.

A liquid crystal composition according to the present invention has a nematic phase-isotropic liquid phase transition temperature ($T_{ni}$) in the range of 60° C. to 120° C., preferably 70° C. to 100° C., particularly preferably 70° C. to 85° C.

A liquid crystal composition according to the present invention may contain an ordinary nematic liquid crystal, smectic liquid crystal, cholesteric liquid crystal, antioxidant, ultraviolet absorber, infrared absorber, polymerizable monomer, or light stabilizer (HALS) except the present invention, in addition to the compounds described above.

For example, a liquid crystal composition according to the present invention may contain a liquid crystal compound with a dielectric constant anisotropy ($\Delta\varepsilon$) in the range of +2.0 to +50.0 at 25° C. as an ordinary nematic liquid crystal or smectic liquid crystal, and the amount of the liquid crystal compound ranges from 0% to 50% by mass, preferably 1% to 30% by mass, preferably 3% to 30% by mass, preferably 5% to 20% by mass.

For example, a liquid crystal composition may contain 0.01% to 2% by mass polymerizable compound, such as a biphenyl derivative or a terphenyl derivative, as a polymerizable monomer.

One or two or more monofunctional polymerizable compounds with one reactive group and polyfunctional polymerizable compounds with two or more reactive groups, such as bifunctional or trifunctional, may be contained as a polymerizable monomer or polymerizable monomers. A polymerizable compound with a reactive group may or may not include a mesogenic moiety.

In a polymerizable compound with a reactive group, the reactive group is preferably a photopolymerizable substituent.

Among polymerizable compounds with a reactive group, a specific monofunctional polymerizable compound with a reactive group is preferably a polymerizable compound represented by the following general formula (VI).

[Chem. 99]

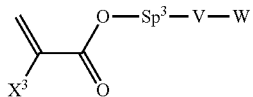

(VI)

(In the formula, $X^3$ denotes a hydrogen atom or a methyl group, $Sp^3$ denotes a single bond, an alkylene group having 1 to 8 carbon atoms, or —O—$(CH_2)_t$— (wherein t denotes an integer in the range of 2 to 7, and the oxygen atom is bonded to an aromatic ring), V denotes a linear or branched polyvalent alkylene group having 2 to 20 carbon atoms or a polyvalent cyclic substituent having 5 to 30 carbon atoms, an alkylene group in the polyvalent alkylene group may be substituted with an oxygen atom, provided that oxygen atoms are not adjacent to each other, or may be substituted with an alkyl group having 5 to 20 carbon atoms (an alkylene group in the group may be substituted with an oxygen atom, provided that oxygen atoms are not adjacent to each other) or a cyclic substituent, and W denotes a hydrogen atom, a halogen atom, or an alkylene group having 1 to 8 carbon atoms.)

In the general formula (VI), $X^3$ denotes a hydrogen atom or a methyl group, preferably a hydrogen atom when the reaction rate is regarded as important, preferably a methyl group when a decreased residual amount after the reaction is regarded as important.

In the general formula (VI), $Sp^3$ denotes a single bond, an alkylene group having 1 to 8 carbon atoms, or —O—$(CH_2)_t$— (wherein t denotes an integer in the range of 2 to 7, and the oxygen atom is bonded to an aromatic ring). The carbon chain is preferably not too long. Thus, a single bond or an alkylene group having 1 to 5 carbon atoms is preferred, and a single bond or an alkylene group having 1 to 3 carbon atoms is more preferred. When $Sp^3$ denotes —O—$(CH_2)_t$—, t preferably ranges from 1 to 5, more preferably 1 to 3.

In the general formula (VI), V denotes a linear or branched polyvalent alkylene group having 2 to 20 carbon atoms or a polyvalent cyclic substituent having 5 to 30 carbon atoms. An alkylene group in the polyvalent alkylene group may be substituted with an oxygen atom, provided that oxygen atoms are not adjacent to each other, or may be substituted with an alkyl group having 5 to 20 carbon atoms (an alkylene group in the group may be substituted with an oxygen atom, provided that oxygen atoms are not adjacent to each other) or a cyclic substituent, and is preferably substituted with two or more cyclic substituents.

More specifically, a polymerizable compound represented by the general formula (VI) may be a compound represented by the general formula (X1a).

[Chem. 100]

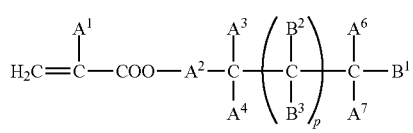

(XIa)

(In the formula, $A^1$ denotes a hydrogen atom or a methyl group, $A^2$ denotes a single bond or an alkylene group having 1 to 8 carbon atoms (one or two or more methylene groups in the alkylene group may be independently substituted with an oxygen atom, —CO—, —COO—, or —OCO—, provided that oxygen atoms are not directly bonded to each other, and one or two or more hydrogen atoms in the alkylene group may be independently substituted with a fluorine atom, a methyl group, or an ethyl group), $A^3$ and $A^6$ independently denote a hydrogen atom, a halogen atom, or an alkyl group having 1 to 10 carbon atoms (one or two or more methylene groups in the alkyl group may be independently substituted with an oxygen atom, —CO—, —COO—, or —OCO—, provided that oxygen atoms are not directly bonded to each other, and one or two or more hydrogen atoms in the alkyl group may be independently substituted with a halogen atom or an alkyl group having 1 to 17 carbon atoms), $A^4$ and $A^7$ independently denote a hydrogen atom, a halogen atom, or an alkyl group having 1 to 10 carbon atoms (one or two or more methylene groups in the alkyl group may be independently substituted with an oxygen atom, —CO—, —COO—, or —OCO—, provided that oxygen atoms are not directly bonded to each other, and one or two or more hydrogen atoms in the alkyl group may be independently substituted with a halogen atom or an alkyl group having 1 to 9 carbon atoms), p ranges from 1 to 10, $B^1$, $B^2$, and $B^3$ independently denote a hydrogen atom or a linear or branched alkyl group having 1 to 10 carbon atoms (one or two or more methylene groups in the alkyl group may be independently substituted with an oxygen atom, —CO—, —COO—, or —OCO—, provided that oxygen atoms are not directly bonded to each other, and one or two or more hydrogen atoms in the alkyl group may be independently substituted with a halogen atom or a trialkoxysilyl group having 3 to 6 carbon atoms.)

More specifically, a polymerizable compound represented by the general formula (VI) may also be a compound represented by the general formula (X1b).

[Chem. 101]

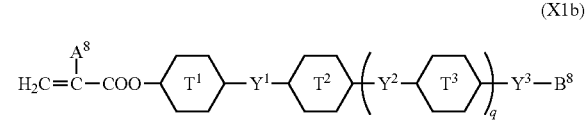

(X1b)

(In the formula, $A^8$ denotes a hydrogen atom or a methyl group, 6-membered rings $T^1$, $T^2$, and $T^3$ independently denote any one of

[Chem. 102]

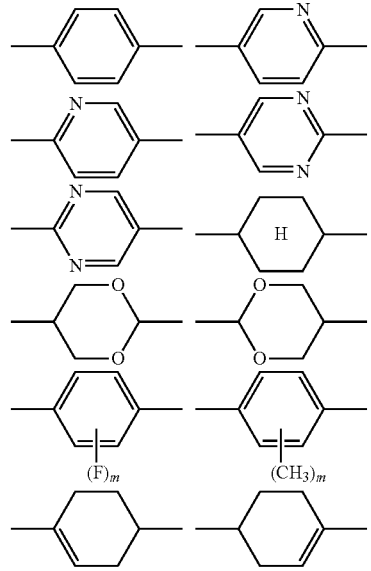

m denotes an integer in the range of 1 to 4)

q is 0 or 1, $Y^1$ and $Y^2$ independently denote a single bond, —$CH_2CH_2$—, —$CH_2O$—, —$OCH_2$—, —COO—, —OCO—, —C≡C—, —CH=CH—, —CF=CF—, —$(CH_2)_4$—, —$CH_2CH_2CH_2O$—, —$OCH_2CH_2CH_2$—, —CH=CHCH$_2$CH—, or —CH$_2$CH$_2$CH=CH—, $Y^3$ denotes a single bond, —COO—, or —OCO—, and $B^8$ denotes a hydrocarbon group having 1 to 18 carbon atoms.)

More specifically, a polymerizable compound represented by the general formula (VI) may also be a compound represented by the general formula (X1c).

[Chem. 103]

(X1c)

(In the formula, $R^{70}$ denotes a hydrogen atom or a methyl group, and $R^{71}$ denotes a hydrocarbon group with a fused ring.)

Among polymerizable compounds with a reactive group, a polyfunctional polymerizable compound with a reactive group is preferably a polymerizable compound represented by the following general formula (VII).

[Chem. 104]

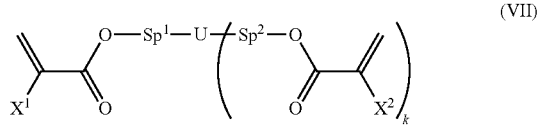

(VII)

(In the formula, $X^1$ and $X^2$ independently denote a hydrogen atom or a methyl group, $Sp^1$ and $Sp^2$ independently denote a single bond, an alkylene group having 1 to 8 carbon atoms, or —O—$(CH_2)_s$— (wherein s denotes an integer in the range of 2 to 7, and the oxygen atom is bonded to an aromatic ring), U denotes a linear or branched polyvalent alkylene group having 2 to 20 carbon atoms or a polyvalent cyclic substituent having 5 to 30 carbon atoms, an alkylene group in the polyvalent alkylene group may be substituted with an oxygen atom, provided that oxygen atoms are not adjacent to each other, or may be substituted with an alkyl group having 5 to 20 carbon atoms (an alkylene group in the group may be substituted with an oxygen atom, provided that oxygen atoms are not adjacent to each other) or a cyclic substituent, and k denotes an integer in the range of 1 to 5.)

In the general formula (VII), $X^1$ and $X^2$ independently denote a hydrogen atom or a methyl group, preferably a hydrogen atom when the reaction rate is regarded as important, preferably a methyl group when a decreased residual amount after the reaction is regarded as important.

In the general formula (VII), $Sp^1$ and $Sp^2$ independently denote a single bond, an alkylene group having 1 to 8 carbon atoms, or —O—$(CH_2)_s$— (wherein s denotes an integer in the range of 2 to 7, and the oxygen atom is bonded to an aromatic ring). The carbon chain is preferably not too long. Thus, a single bond or an alkylene group having 1 to 5 carbon atoms is preferred, and a single bond or an alkylene group having 1 to 3 carbon atoms is more preferred. When $Sp^1$ and $Sp^2$ denote —O—$(CH_2)_s$—, s preferably ranges from 1 to 5, more preferably 1 to 3, and at least one of $Sp^1$ and $Sp^2$ more preferably denotes a single bond, and particularly preferably both $Sp^1$ and $Sp^2$ denote a single bond.

In the general formula (VII), U denotes a linear or branched polyvalent alkylene group having 2 to 20 carbon atoms or a polyvalent cyclic substituent having 5 to 30 carbon atoms. An alkylene group in the polyvalent alkylene group may be substituted with an oxygen atom, provided that oxygen atoms are not adjacent to each other, or may be substituted with an alkyl group having 5 to 20 carbon atoms (an alkylene group in the group may be substituted with an oxygen atom, provided that oxygen atoms are not adjacent to each other) or a cyclic substituent, and is preferably substituted with two or more cyclic substituents.

In the general formula (VII), more specifically, U preferably denotes the following formulae (VII-1) to (VII-5), more preferably the formulae (VII-1) to (VII-3), particularly preferably the formula (VII-1).

[Chem. 105]

(VII-1)

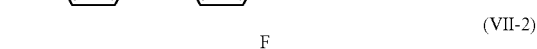

(VII-2)

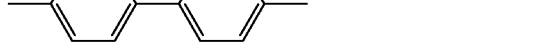

(VII-3)

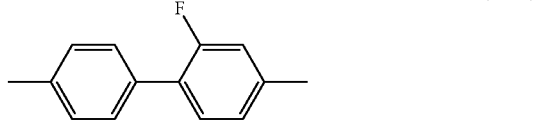

(VII-4)

(VII-5)

(In the formula, each end is bonded to $Sp^1$ or $Sp^2$.)

When U has a ring structure, at least one of $Sp^1$ and $Sp^2$ preferably denotes a single bond, and both $Sp^1$ and $Sp^2$ also preferably denote a single bond.

In the general formula (VII), k denotes an integer in the range of 1 to 5, a bifunctional compound with k being 1 or a trifunctional compound with k being 2 is preferred, and a bifunctional compound is more preferred.

More specifically, one or two or more polymerizable compounds represented by the general formula (P) are preferably contained.

[Chem. 106]

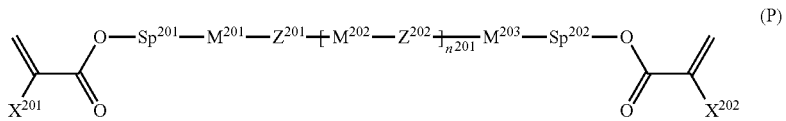

In the general formula (P), $X^{201}$ and $X^{202}$ independently denote a hydrogen atom, a methyl group, or a —$CF_3$ group. A diacrylate derivative with $X^{201}$ and $X^{202}$ being a hydrogen atom or a dimethacrylate derivative with $X^{201}$ and $X^{202}$ being a methyl group is preferred. In another preferred compound, one of $X^{201}$ and $X^{202}$ denotes a hydrogen atom, and the other denotes a methyl group. A compound suitable for each application can be used. In PSA display devices, a polymerizable compound represented by the general formula (P) preferably includes at least one methacrylate derivative or two methacrylate derivatives.

In the general formula (P), $Sp^{201}$ and $Sp^{202}$ independently denote a single bond, an alkylene group having 1 to 8 carbon atoms, or —O—$(CH_2)_s$— (wherein s denotes an integer in the range of 2 to 7, and the oxygen atom is bonded to a ring). In PSA liquid crystal display devices, at least one of $Sp^{201}$ and $Sp^{202}$ preferably denotes a single bond. A compound with both $Sp^{201}$ and $Sp^{202}$ being a single bond is preferred. Alternatively, preferably, one of $Sp^{201}$ and $Sp^{202}$ denotes a single bond, and the other denotes an alkylene group having 1 to 8 carbon atoms or —O—$(CH_2)_s$—, wherein an alkylene group having 1 to 4 carbon atoms is preferred, and s preferably ranges from 1 to 4.

In the general formula (P), $M^{201}$, $M^{202}$, and $M^{203}$ independently denote a trans-1,4-cyclohexylene group (one —$CH_2$— or two or more nonadjacent —$CH_2$— groups in the group may be substituted with —O— or —S—), a 1,4-phenylene group (one —CH= or two or more nonadjacent —CH= groups in the group may be substituted with —N=), a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, and a hydrogen atom in the groups may be substituted with a fluorine atom, a —$CF_3$ group, an alkyl group having 1 to 10 carbon atoms, an alkoxy group having 1 to 10 carbon atoms, or any of the formulae (R-1) to (R-15).

[Chem. 107]

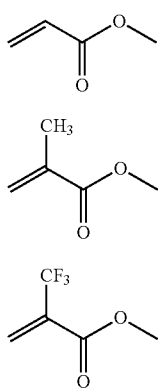

(R-1)

(R-2)

(R-3)

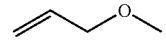 (R-4)

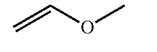 (R-5)

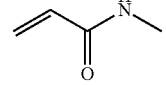 (R-6)

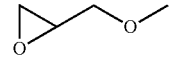 (R-7)

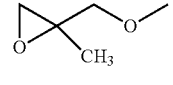 (R-8)

 (R-9)

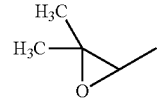 (R-10)

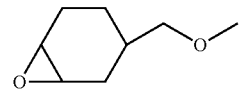 (R-11)

 (R-12)

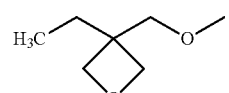 (R-13)

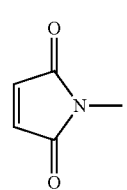 (R-14)

HS— (R-15)

In the general formula (P), $Z^{201}$ and $Z^{202}$ independently denote —$OCH_2$—, —$CH_2O$—, —COO—, —OCO—, —$CF_2O$—, —$OCF_2$—, —$CH_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —$CY^1$=$CY^2$— (wherein $Y^1$ and $Y^2$ independently denote a fluorine atom or a hydrogen atom), —C≡C—, or a single bond, preferably —COO—, —OCO—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —C≡C—, or a single bond, more preferably —COO—, —OCO—, —CH═CH—COO—, —CH═CH—OCO—, —COO—CH═CH—, —OCO—CH═CH—, —COO—CH═CH$_2$—, —OCO—CH$_2$CH$_2$—, —CH$_2$CH$_2$—COO—, —CH$_2$CH$_2$—OCO—, or a single bond.

In the general formula (P), $n^{201}$ is 0, 1, or 2, preferably 0 or 1. Pluralities of $M^{202}$s and $Z^{202}$s, if present, may be different or the same $M^{202}$s and $Z^{202}$s, respectively.

At least one, preferably 1 to 5, more preferably 1 to 3, polymerizable compound represented by the general formula (P) may be contained.

The general formula (P) content preferably ranges from 0.01% to 2.00% by mass, more preferably 0.05% to 1.00% by mass, particularly preferably 0.10% to 0.50% by mass.

More specifically, when $n^{201}$ in the general formula (P) is 0, a ring structure between $Sp^{201}$ and $Sp^{202}$ is preferably represented by the formulae (XXa-1) to (XXa-5), more preferably the formulae (XXa-1) to (XXa-3), particularly preferably the formula (XXa-1) or (XXa-2). Each end of the formulae is bonded to $Sp^{201}$ or $Sp^{202}$.

[Chem. 108]

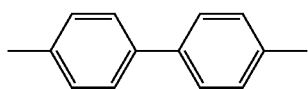

(XXa-1)

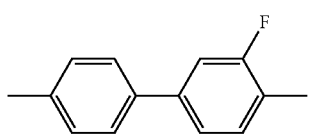

(XXa-2)

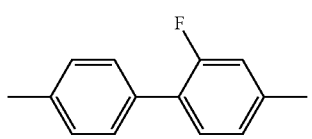

(XXa-3)

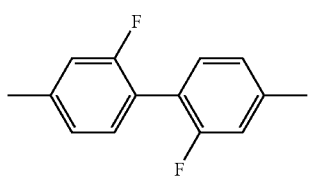

(XXa-4)

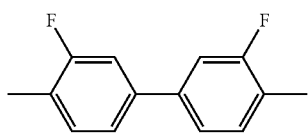

(XXa-5)

Polymerizable compounds represented by the general formula (P) having such a skeleton are most suitable for PSA liquid crystal display devices with respect to alignment regulating force after polymerization and can provide a satisfactory alignment state, thus causing little or no variation in display.

Thus, the compounds represented by the formulae (XX-1) to the general formula (XX-10), more preferably the formulae (XX-1) to (XX-4), are preferred as polymerizable monomers.

[Chem. 109]

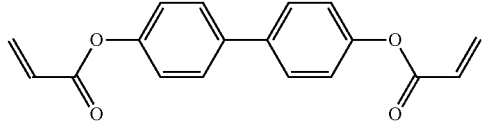

(XX-1)

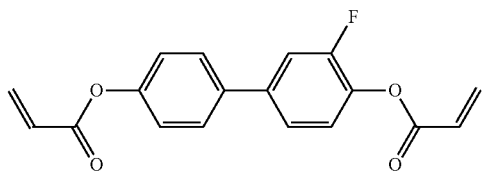

(XX-3)

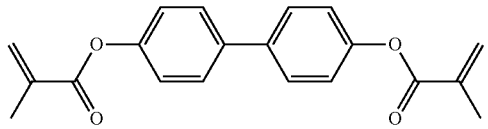

(XX-2)

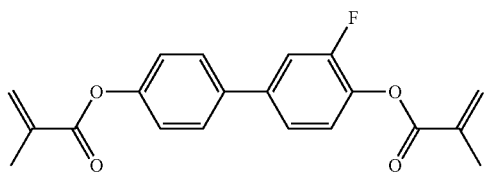

(XX-4)

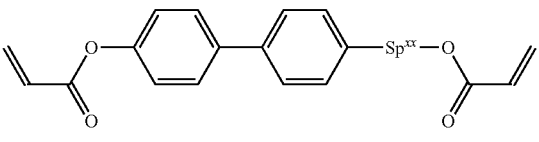

(XX-5)

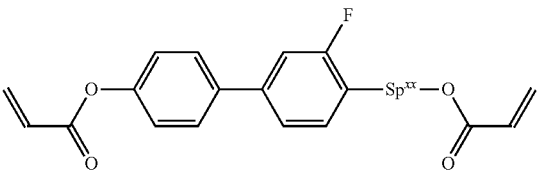

(XX-7)

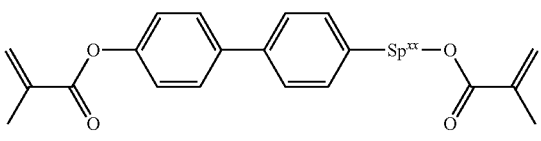

(XX-6)

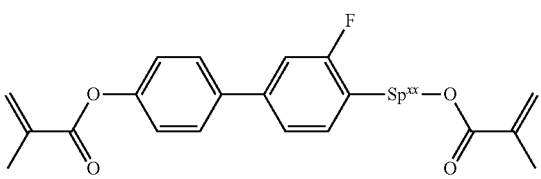

(XX-8)

In the formula (XX-5) to the general formula (XX-10), $Sp^{xx}$ denotes an alkylene group having 1 to 8 carbon atoms or —O—$(CH_2)_s$— (wherein s denotes an integer in the range of 2 to 7, and the oxygen atom is bonded to a ring).

In the formula (XX-1) to the general formula (XX-10), a hydrogen atom in the 1,4-phenylene groups may be further substituted with —F, —Cl, —$CF_3$, —$CH_3$, or any of the formulae (R-1) to (R-15).

When $n^{201}$ in the general formula (P) is 1, for example, the polymerizable compounds represented by the formulae (P31) to (P48) are preferred.

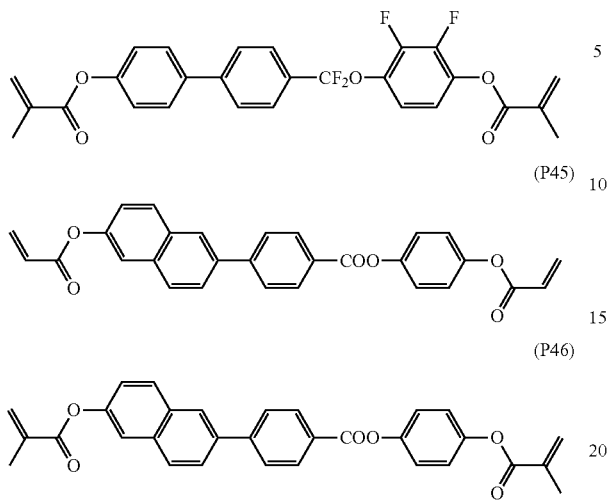

A hydrogen atom of the 1,4-phenylene groups and naphthalene groups in the formulae (P31) to (P48) may be further substituted with —F, —Cl, —CF$_3$, —CH$_3$, or any of the formulae (R-1) to (R-15).

Polymerizable compounds represented by the general formula (P) having such a skeleton are most suitable for PSA liquid crystal display devices with respect to alignment regulating force after polymerization and can provide a satisfactory alignment state, thus causing little or no variation in display.

When n$^{201}$ in the general formula (P) is 1, and the general formula (P) includes a plurality of groups represented by the formula (R-1) or (R-2), for example, the polymerizable compounds represented by the formulae (P301) to (P316) are preferred.

[Chem. 111]

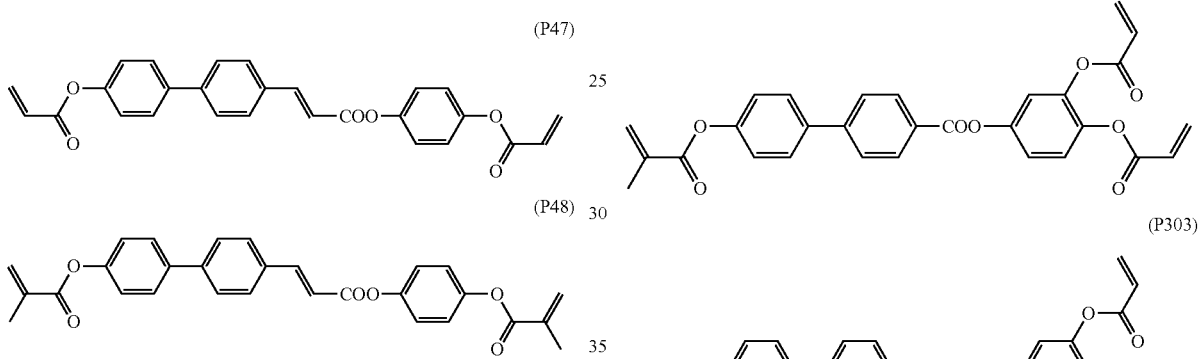

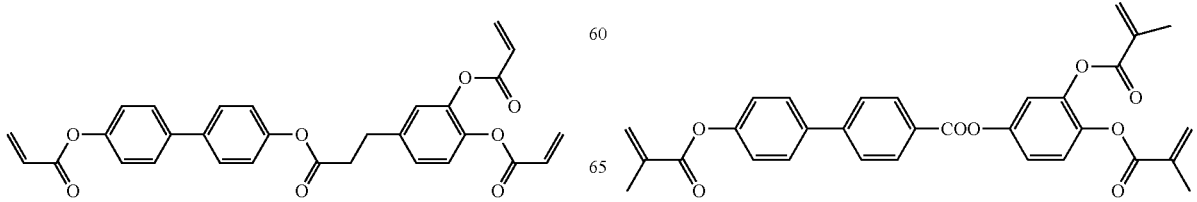

-continued
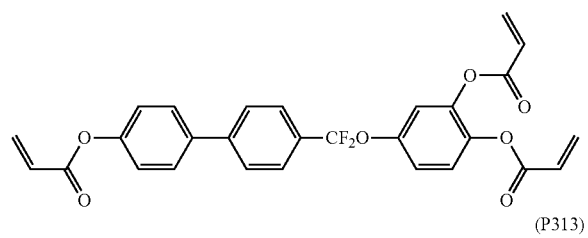
(P305)
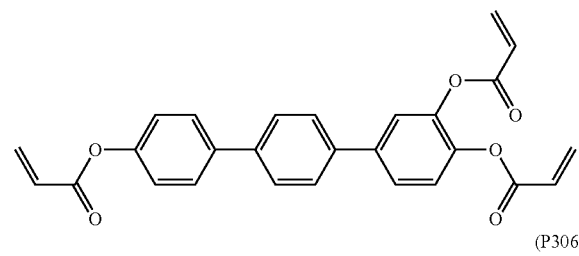
(P306)
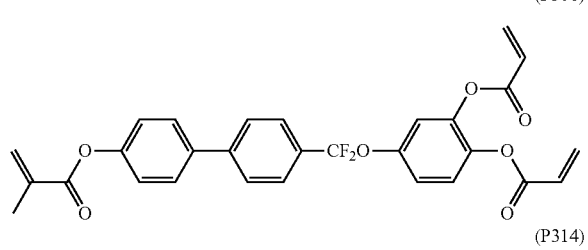
(P314)
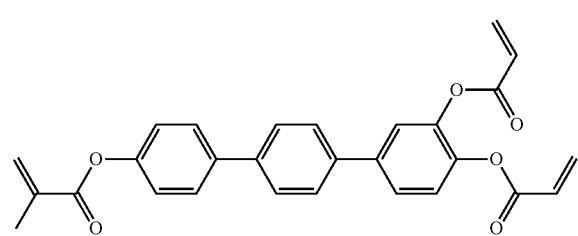
(P307)
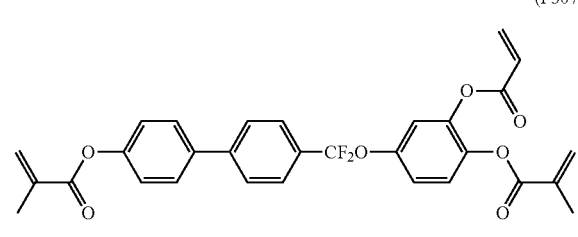
(P313)
-continued
(P315)
(P308)
(P316)
A hydrogen atom of the 1,4-phenylene groups and naphthalene groups in the formulae (P301) to (P316) may be further substituted with —F, —Cl, —CF₃, or —CH₃.
For example, a polymerizable compound represented by the general formula (P) is also preferably a polymerizable compound represented by one of the formulae (Ia-1) to (Ia-31).
[Chem. 112]
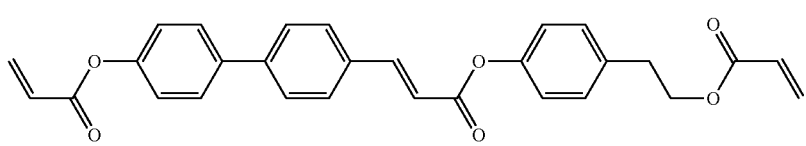
(Ia-1)
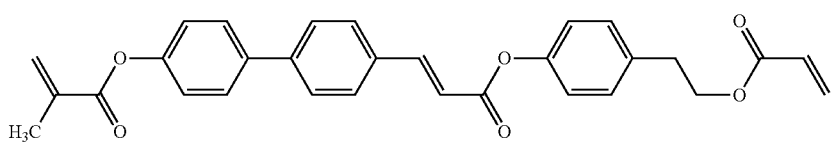
(Ia-2)

-continued
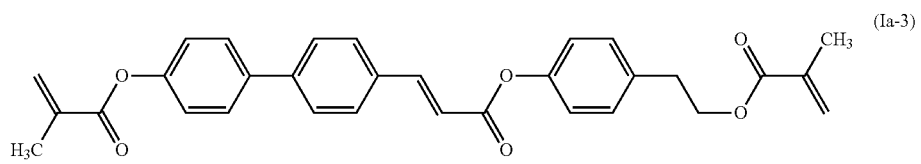
(Ia-3)
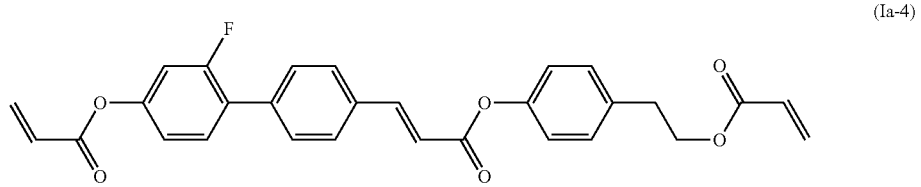
(Ia-4)
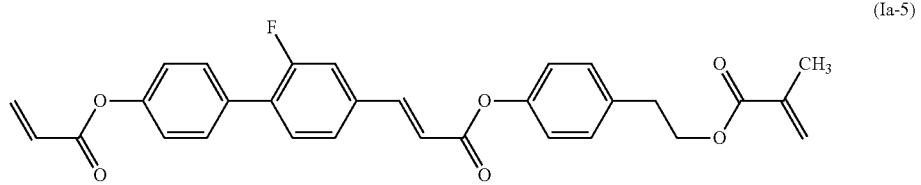
(Ia-5)
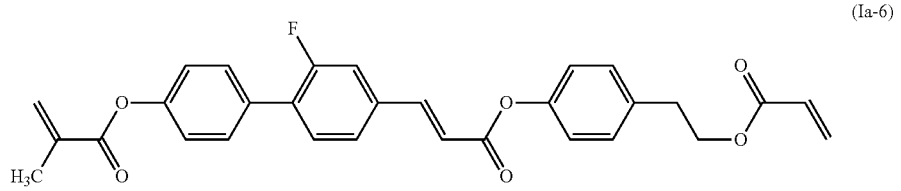
(Ia-6)
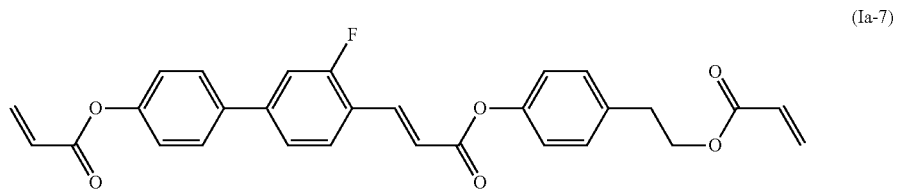
(Ia-7)
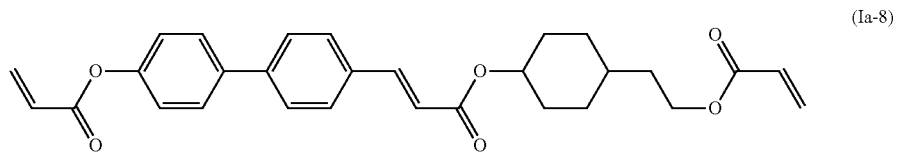
(Ia-8)
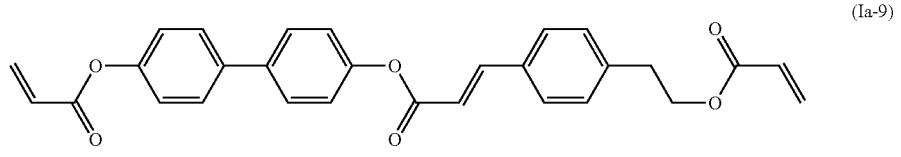
(Ia-9)
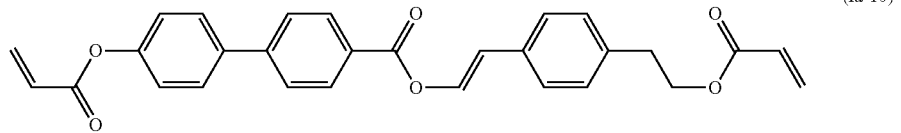
(Ia-10)
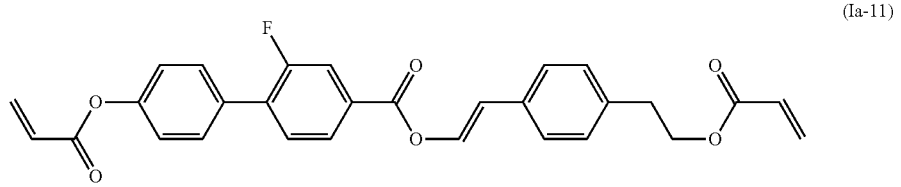
(Ia-11)

(Ia-12)
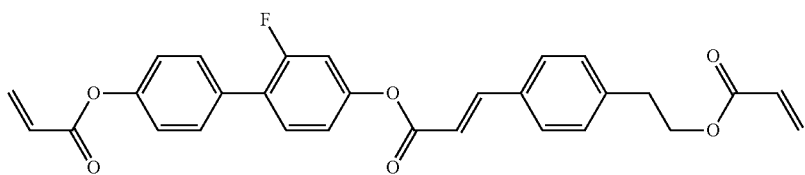
(Ia-13)
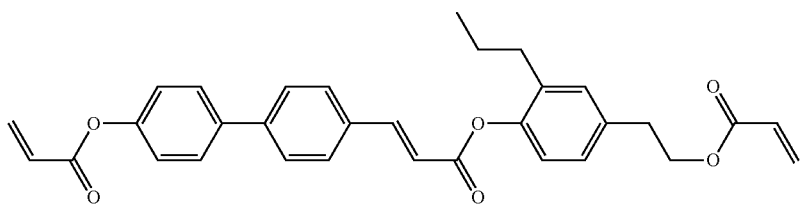
[Chem. 113]
(Ia-14)
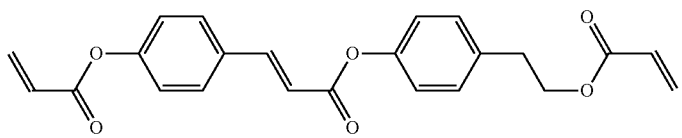
(Ia-15)
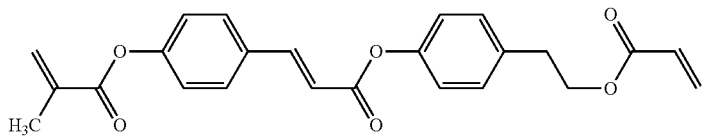
(Ia-16)
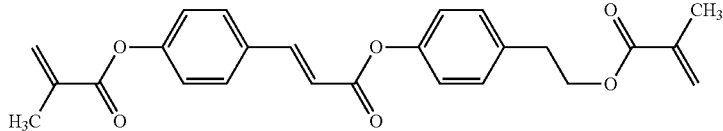
(Ia-17)
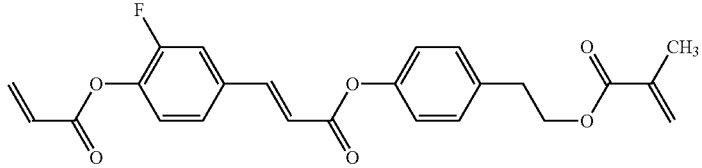
(Ia-18)
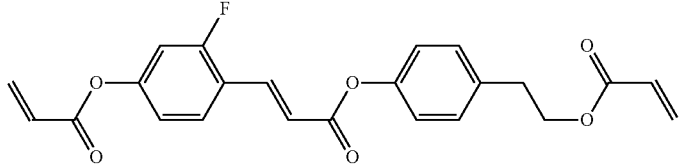
[Chem. 114]
(Ia-19)
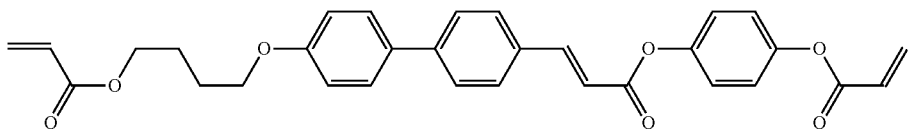
(Ia-20)
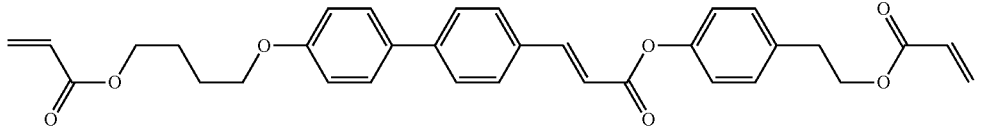

-continued
(Ia-21)
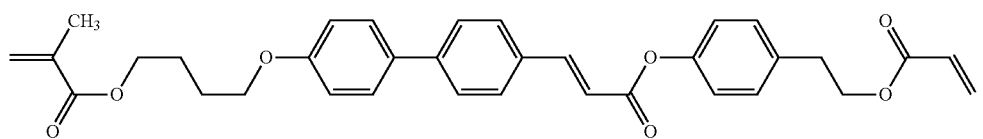
(Ia-22)
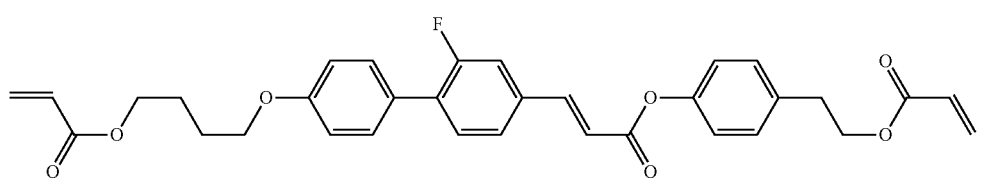
(Ia-23)
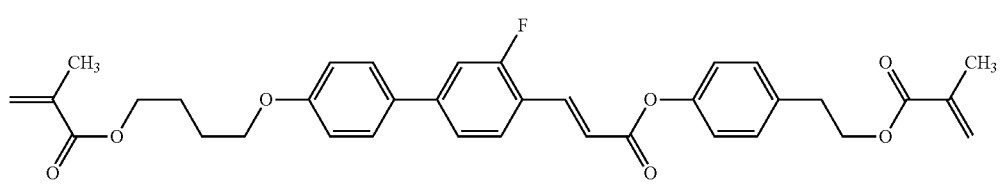
(Ia-24)
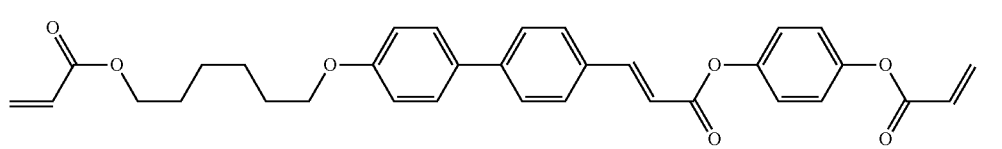
(Ia-25)
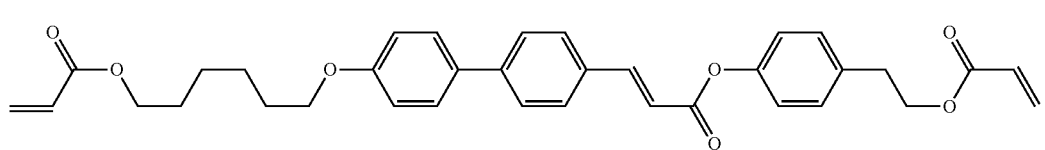
(Ia-26)
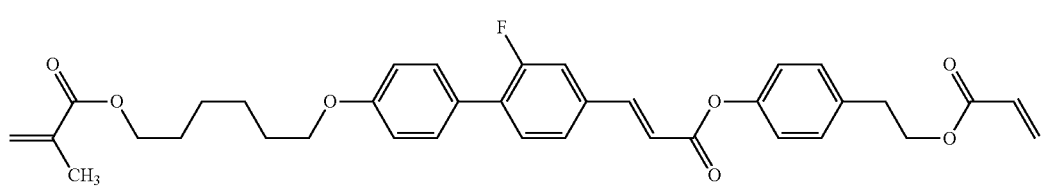
(Ia-27)
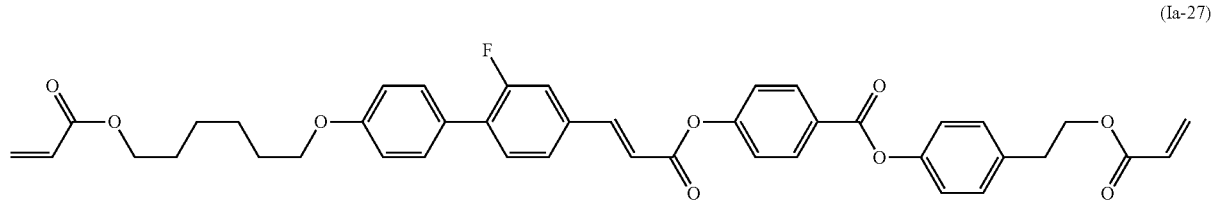
(Ia-28)
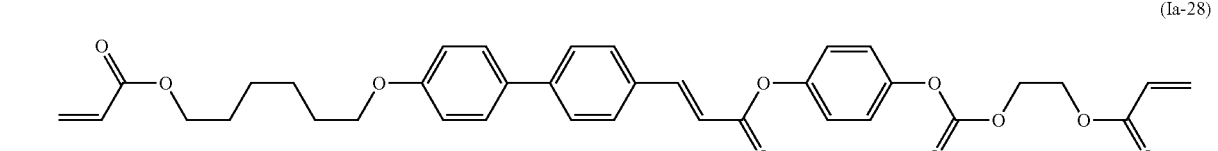
(Ia-29)
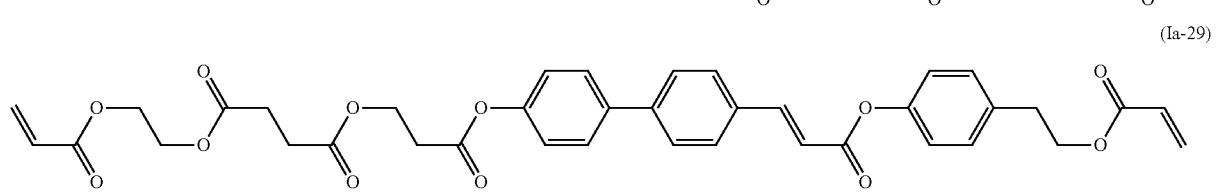

(Ia-30)

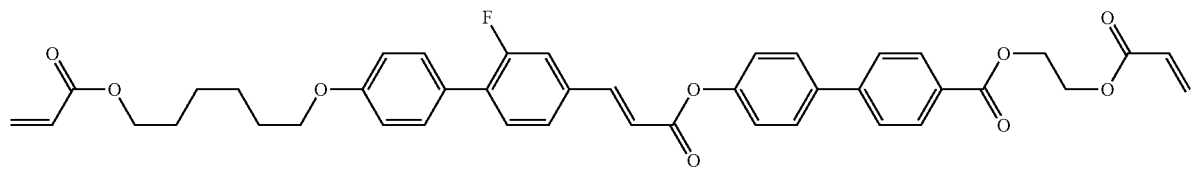

[Chem. 115]

(Ia-31)

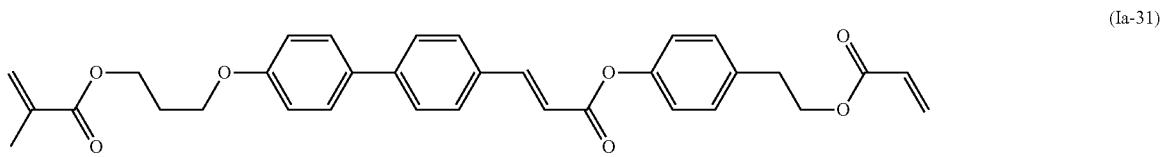

Preferred antioxidants are hindered phenols represented by the general formulae (H-1) to (H-4).

[Chem. 116]

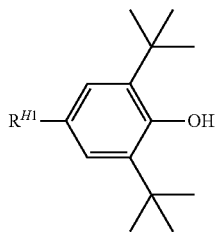

(H-1)

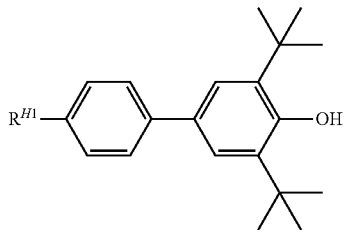

(H-2)

(H-3)

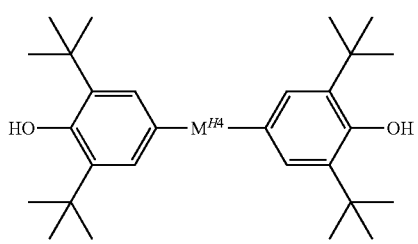

(H-4)

In the general formulae (H-1) to (H-4), $R^{H1}$ denotes an alkyl group having 1 to 10 carbon atoms, an alkoxy group having 1 to 10 carbon atoms, an alkenyl group having 2 to 10 carbon atoms, or an alkenyloxy group having 2 to 10 carbon atoms, one —$CH_2$— or two or more nonadjacent —$CH_2$— groups in the groups may be independently substituted with —O— or —S—, and one or two or more hydrogen atoms in the groups may be independently substituted with a fluorine atom or a chlorine atom. More specifically, an alkyl group having 2 to 7 carbon atoms, an alkoxy group having 2 to 7 carbon atoms, an alkenyl group having 2 to 7 carbon atoms, or an alkenyloxy group having 2 to 7 carbon atoms is preferred, and an alkyl group having 3 to 7 carbon atoms or an alkenyl group having 2 to 7 carbon atoms is more preferred.

In the general formula (H-4), $M^{H4}$ denotes an alkylene group having 1 to 15 carbon atoms (one or two or more —$CH_2$— groups in the alkylene group may be substituted with —O—, —CO—, —COO—, or —OCO—, provided that oxygen atoms are not directly adjacent to each other), —$OCH_2$—, —CH=O—, —COO—, —OCO—, —$CF_2$O—, —$OCF_2$—, —$CF_2CF_2$—, —CH=CH—COO—, —CH=CH—OCO—, —COO—CH=CH—, —OCO—CH=CH—, —CH=CH—, —C≡C—, a single bond, a 1,4-phenylene group (a hydrogen atom in the 1,4-phenylene group may be substituted with a fluorine atom), or a trans-1,4-cyclohexylene group, preferably an alkylene group having 1 to 14 carbon atoms. The number of carbon atoms is preferably large in terms of volatility but is preferably not too large in terms of viscosity. Thus, the number of carbon atoms more preferably ranges from 2 to 12, still more preferably 3 to 10, still more preferably 4 to 10, still more preferably 5 to 10, still more preferably 6 to 10.

In the general formulae (H-1) to (H-4), one —CH= or two or more nonadjacent —CH= groups in the 1,4-phenylene groups may be substituted with —N=. A hydrogen atom in the 1,4-phenylene groups may be independently substituted with a fluorine atom or a chlorine atom.

In the general formulae (H-1) to (H-4), one —$CH_2$— or two or more nonadjacent —$CH_2$— groups in the 1,4-cyclohexylene groups may be substituted with —O— or —S—. A hydrogen atom in the 1,4-cyclohexylene groups may be independently substituted with a fluorine atom or a chlorine atom.

Additional specific examples include the formulae (H-11) to (H-15).

[Chem. 117]

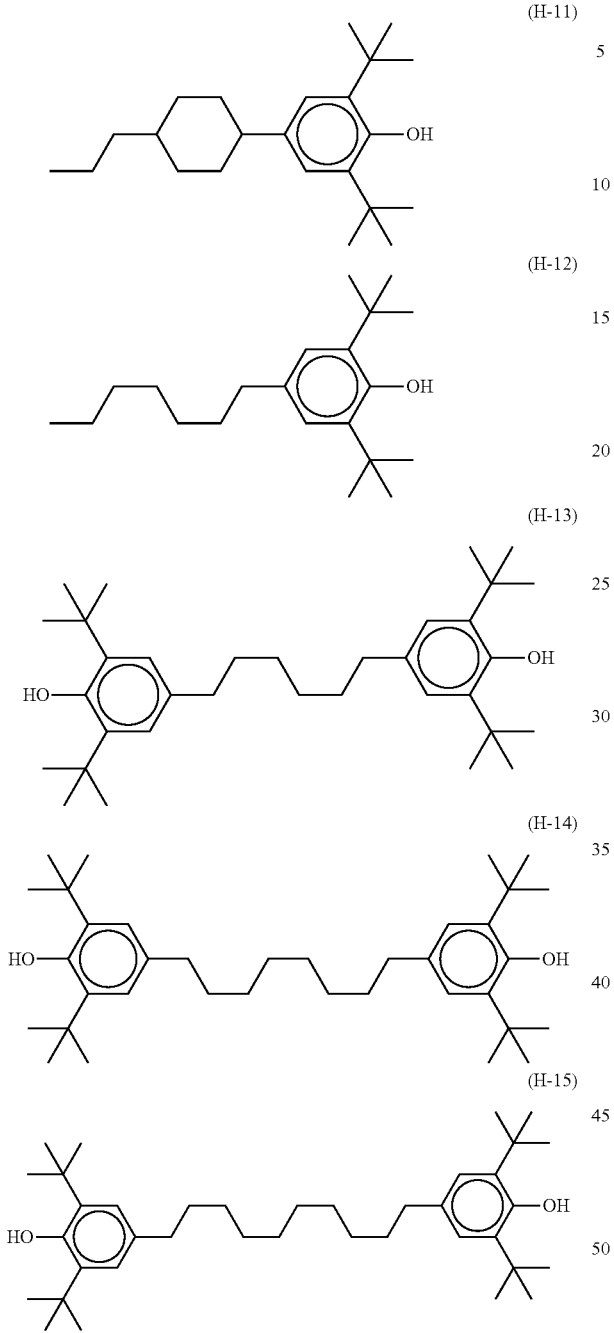

A liquid crystal composition according to the present invention may contain 1 ppm by mass or more, preferably 10 ppm by mass or more, preferably 20 ppm by mass or more, preferably 50 ppm by mass or more, antioxidant. The upper limit of the antioxidant content is 10000 ppm by mass, preferably 1000 ppm by mass, preferably 500 ppm by mass, preferably 100 ppm by mass.

A liquid crystal display device including a liquid crystal composition according to the present invention has no or few display defects, high display quality, and a high response speed, and can be particularly applied as an active-matrix liquid crystal display device to the TN, OCB, VA, VA-IPS, PSVA, PSA, FFS, IPS, or ECB mode, for example. The PSVA mode and the PSA mode are substantially synonymous.

Furthermore, a liquid crystal composition according to the present invention containing a polymerizable compound can provide a polymer-stabilized liquid crystal display device of the VA, PSA, TN, OCB, ECB, IPS, FFS, or VA-IPS mode manufactured by polymerizing the polymerizable compound in the liquid crystal composition under voltage application or under no voltage application.

EXAMPLES

Although the present invention will be further described in the following examples, the present invention is not limited to these examples. The unit "%" with respect to compositions in the following examples and comparative examples refers to "% by mass".

The following abbreviations are used to describe compounds in the examples.
(Side Chain)
-n —$C_nH_{2n+1}$ a linear alkyl group having n carbon atoms
n- $C_nH_{2n+1}$— a linear alkyl group having n carbon atoms
-On —$OC_nH_{2n+1}$ a linear alkoxy group having n carbon atoms
nO— $C_nH_{2n+1}O$— a linear alkoxy group having n carbon atoms
—V —CH=$CH_2$
V— $CH_2$=CH—
—V1 —CH=CH—$CH_3$
1V— $CH_3$—CH=CH—
-2V —$CH_2$—$CH_2$—CH=$CH_2$
V2- $CH_2$=CH—$CH_2$—$CH_2$—
-2V1 —$CH_2$—$CH_2$—CH=CH—$CH_3$
1V2- $CH_3$—CH=CH—$CH_2$—$CH_2$—
(Linking Group)
—CFFO— —$CF_2$—O—
—OCFF— —O—$CF_2$—
-1O— —$CH_2$—O—
—O1- —O—$CH_2$—
—COO— —COO—
—OCO— —OCO—
(Ring Structure)

[Chem. 118]

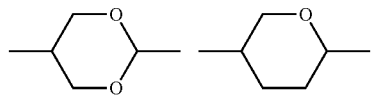

Oc      Py

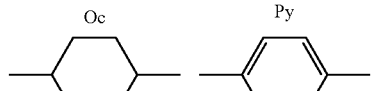

Cy      Ph

Ph1      Ph2

183
-continued
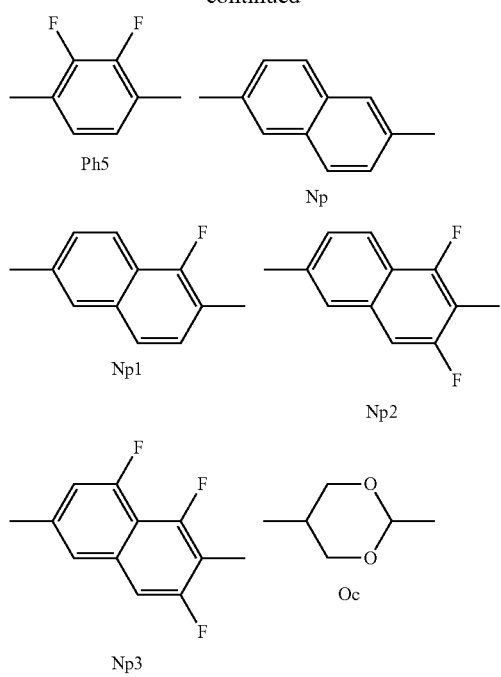
The compounds represented by the following formulae were used as compounds represented by the general formula (I).
[Chem. 119]
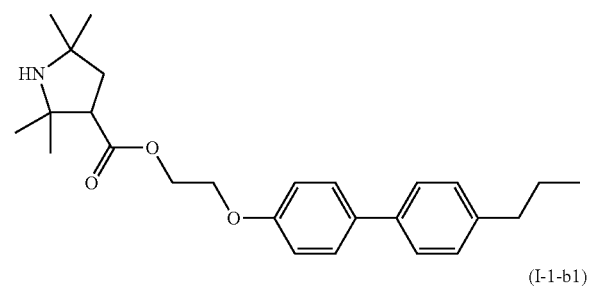
(I-1-a1)
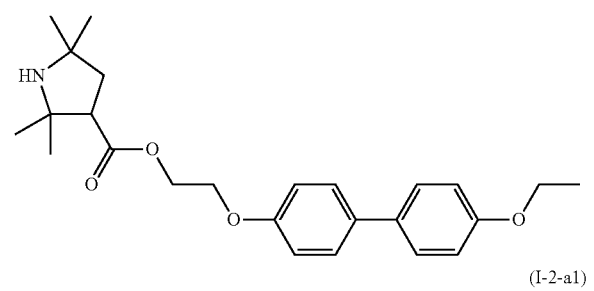
(I-1-b1)
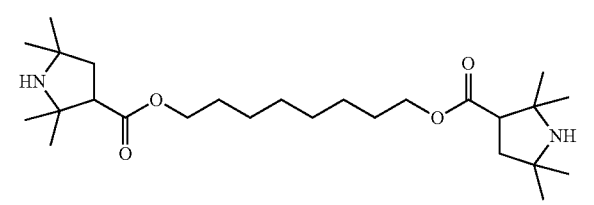
(I-2-a1)
184
-continued
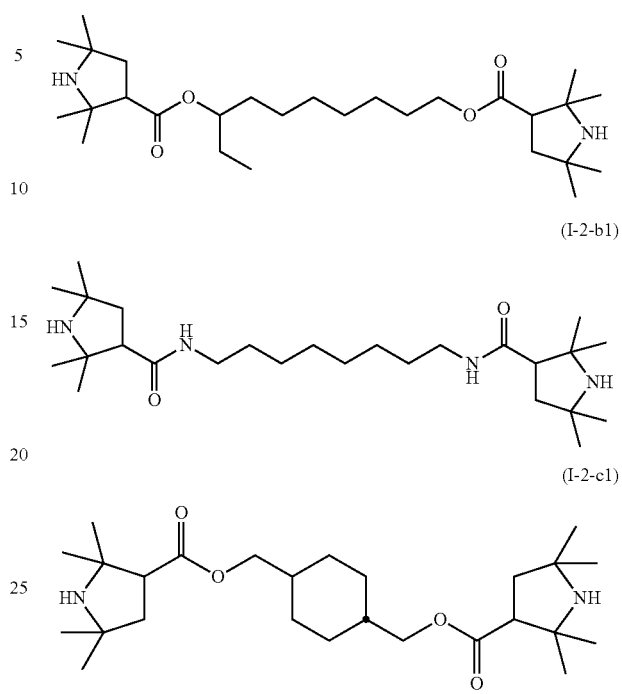
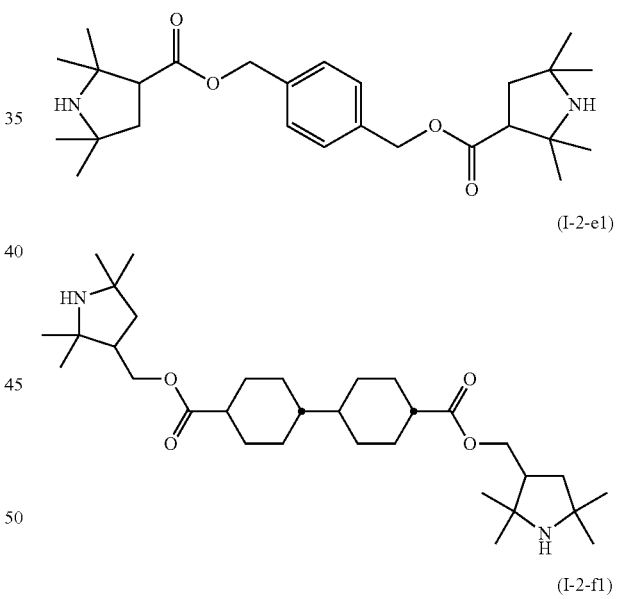
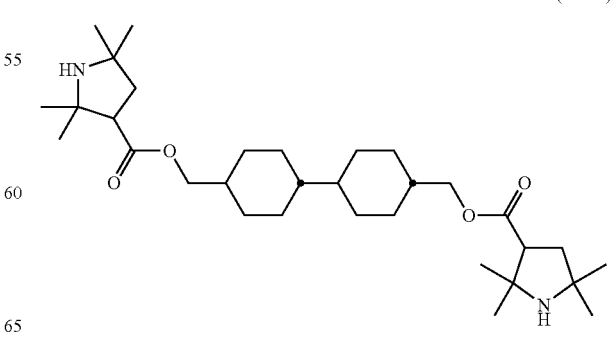

(I-3-a1)
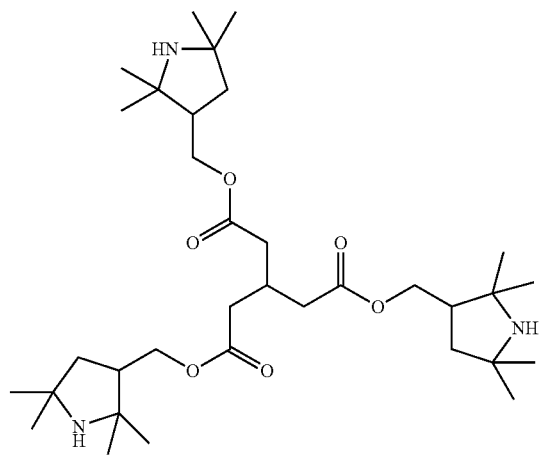
(I-4-a1)
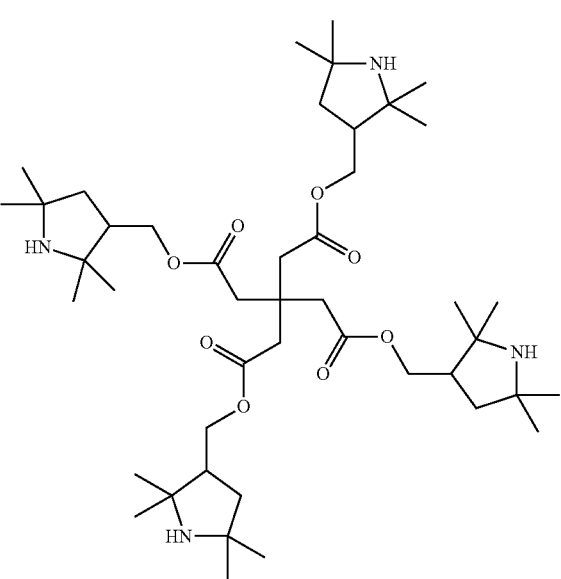
[Chem. 120]
(I-1-a2)
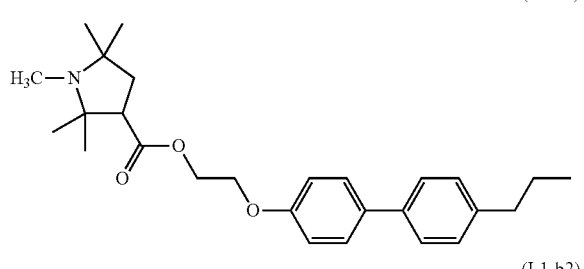
(I-1-b2)
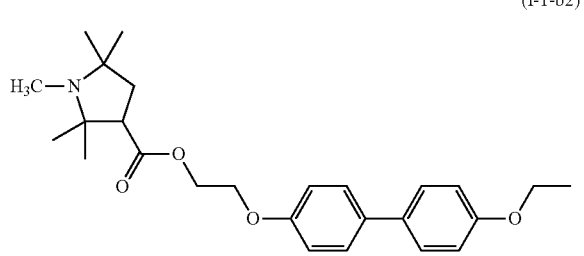
(I-2-a2)
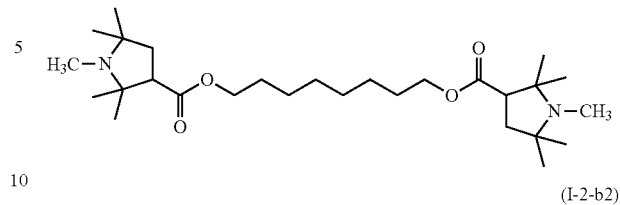
(I-2-b2)
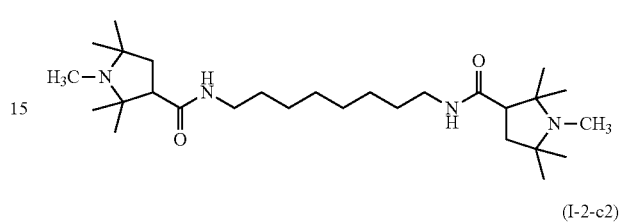
(I-2-c2)
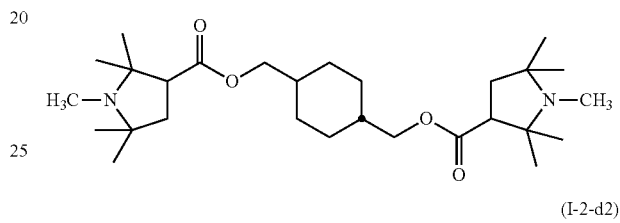
(I-2-d2)
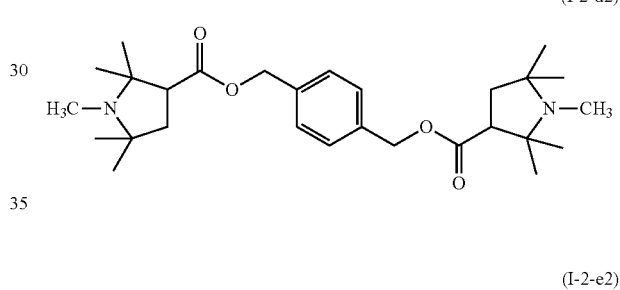
(I-2-e2)
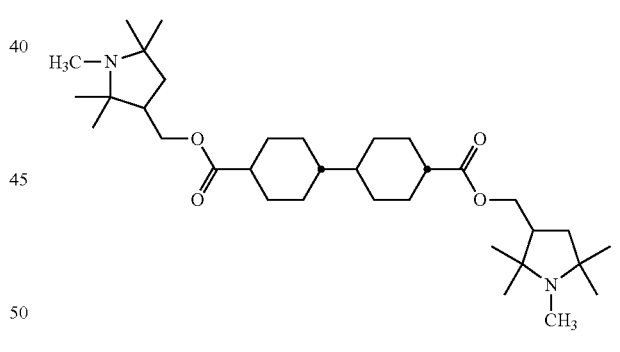
(I-2-f2)

(I-3-a2)
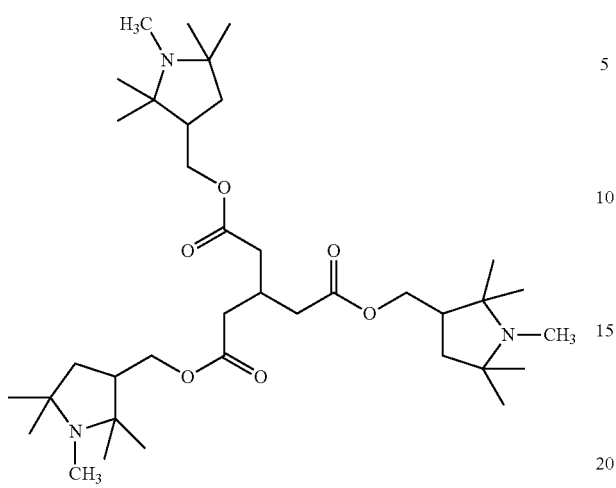
(I-2-f3)
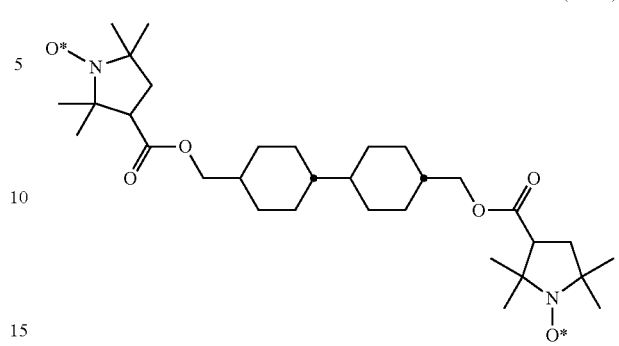
(I-4-a2)
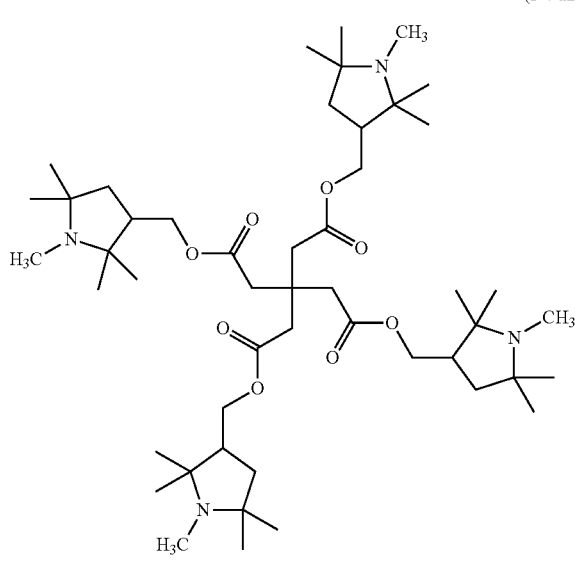
[Chem. 122]
(I-1-a4)
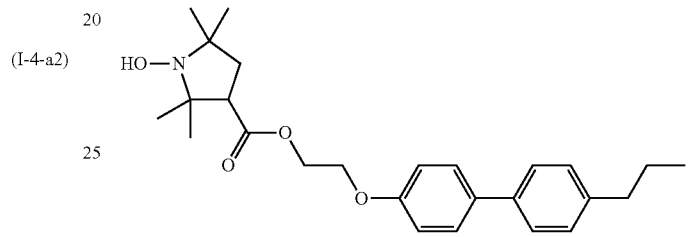
[Chem. 121]
(I-2-c3)
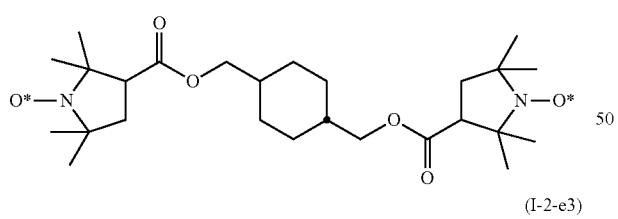
(I-1-b4)
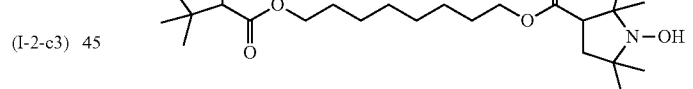
(I-2-a4)
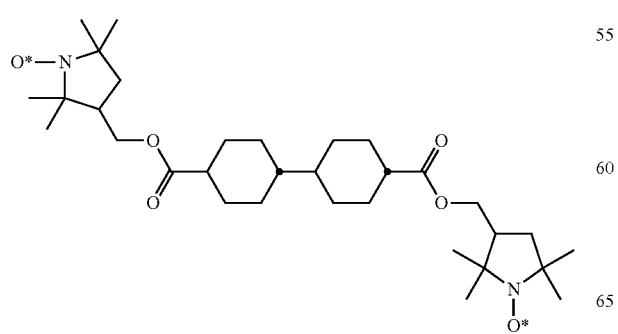
(I-2-e3)
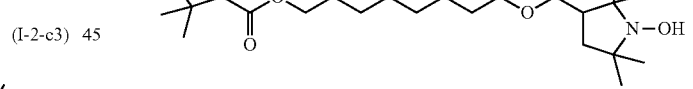
(I-2-b4)
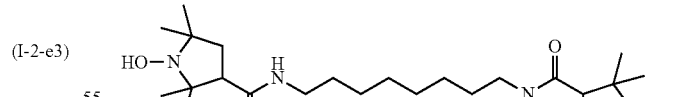
(I-2-c4)
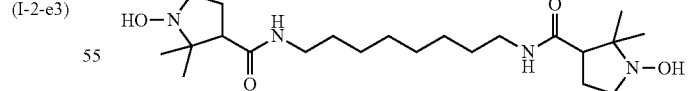

-continued (I-2-d4)

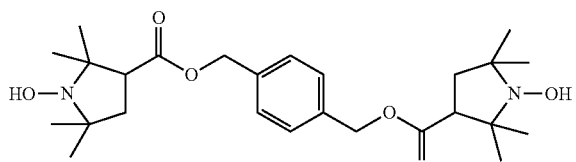

[Chem. 123]

(I-2-a5)

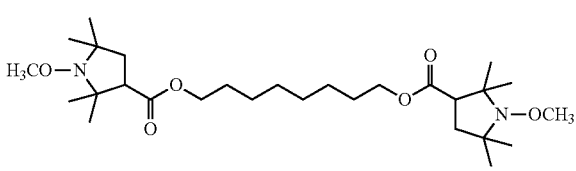

(I-2-b5)

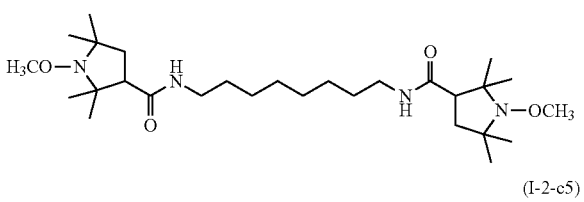

(I-2-c5)

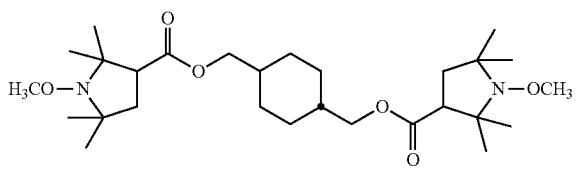

In the examples, the following characteristics were measured in composition examples.

$T_{ni}$: nematic phase-isotropic liquid phase transition temperature (° C.)

Δn: refractive index anisotropy at 25° C.

Δε: dielectric constant anisotropy at 25° C.

$γ_1$: rotational viscosity (mPa·s) at 25° C.

VHR (UV): Voltage holding ratio (%) based on the initial applied voltage after 150 (J) UV irradiation with a high-pressure mercury lamp. The measurement conditions include 1 V, 60 Hz, 60° C., an illuminance of 100 mW/cm² at 365 nm, and a cell thickness of 3.5 μm in a test panel. The alignment film for vertical alignment is JALS2096, and the alignment film for horizontal alignment is AL1051.

VHR (HEAT): Voltage holding ratio (%) based on the initial applied voltage after heating at 100° C. for 26 hours. The measurement conditions include 1 V, 60 Hz, 60° C., and a cell thickness of 3.5 μm in a test panel. The alignment film for vertical alignment is JALS2096, and the alignment film for horizontal alignment is AL1051.

Comparative Example 1, Examples 1 to 3

The following LC-A liquid crystal composition was prepared and measured for the physical properties. The components and physical properties of the liquid crystal composition are listed in the table.

TABLE 1

| | LC-A |
|---|---|
| 3-Ph-Ph-1 | 8 |
| 3-Cy-Cy-V | 29 |
| 3-Cy-Cy-2 | 4 |
| 3-Cy-1O-Ph5-O1 | 3 |
| 3-Cy-1O-Ph5-O2 | 7 |
| 2-Cy-Cy-1O-Ph5-O2 | 13 |
| 3-Cy-Cy-1O-Ph5-O2 | 13 |
| 4-Cy-Cy-1O-Ph5-O2 | 7 |
| V-Cy-Cy-1O-Ph5-O2 | 6 |
| 3-Ph-Ph5-Ph-1 | 4 |
| 3-Ph-Ph5-Ph-2 | 6 |
| Total (%) | 100 |
| $T_{NI}$ [° C.] | 76 |
| Δn | 0.098 |
| $γ_1$ [mPa · s] | 89 |
| Δε | −3.7 |

In Example 1, 0.10 parts by weight of the compound represented by the formula (I-2-c1) was added to 100 parts by weight of the liquid crystal composition LC-A to prepare a liquid crystal composition LC-1. In Example 2, 0.05 parts by weight of the compound represented by the formula (I-2-c1) was added to 100 parts by weight of the liquid crystal composition LC-A to prepare a liquid crystal composition LC-2. In Example 3, 0.02 parts by weight of the compound represented by the formula (I-2-c1) was added to 100 parts by weight of the liquid crystal composition LC-A to prepare a liquid crystal composition LC-3. A liquid crystal composition composed of 100 parts by weight of LC-A was used as Comparative Example 1. The VHR (UV) and VHR (HEAT) results are listed in the table.

TABLE 2

| | Comparative example 1 LC-A | Example 1 LC-1 | Example 2 LC-2 | Example 3 LC-3 |
|---|---|---|---|---|
| Compound of formula (I-2-c1) (parts by mass) | — | 0.10 | 0.05 | 0.02 |
| Liquid crystal composition LC-A (parts by mass) | 100 | 100 | 100 | 100 |
| VHR (UV) | 71 | 97 | 96 | 96 |
| VHR (HEAT) | 65 | 87 | 86 | 86 |

Examples 1 to 3 had a sufficiently higher VHR (UV) and VHR (HEAT) than Comparative Example 1. Examples 1 to 3 had no variation in display. The liquid crystal compositions LC-1, LC-2, and LC-3 had the same $T_{ni}$, Δn, Δε, and $γ_1$ as the liquid crystal composition LC-A.

Liquid crystal compositions were prepared from the compound represented by the formula (I-2-c2) instead of the compound represented by the formula (I-2-c1) in Examples 1 to 3 and were measured for VHR. Compounds in which $R^1$ in the general formula (I) were substituted with —$CH_3$ also had high VHR (UV) and VHR (HEAT).

Comparative Example 2, Examples 4 to 6

The following LC-B liquid crystal composition was prepared and measured for the physical properties. The components and physical properties of the liquid crystal composition are listed in the table.

TABLE 3

|  | LC-B |
| --- | --- |
| 3-Cy-Cy-V | 20 |
| 3-Cy-Cy-V1 | 10 |
| C-Cy-Ph-Ph-3 | 10 |
| 3-Cy-1O-Ph5-O2 | 8 |
| 1V-Cy-1O-Ph5-O1 | 4 |
| 1V-Cy-1O-Ph5-O2 | 4 |
| 3-Cy-Cy-1O-Ph5-O2 | 9 |
| V-Cy-Cy-1O-Ph5-O2 | 12 |
| 1V-Cy-Cy-1O-Ph5-O1 | 5 |
| 1V-Cy-Cy-1O-Ph5-O2 | 5 |
| 3-Ph-Ph5-Ph-1 | 5 |
| 3-Ph-Ph5-Ph-2 | 8 |
| Total (%) | 100 |
| $T_{NI}$ [° C.] | 91 |
| Δn | 0.115 |
| $\gamma_1$ [mPa · s] | 121 |
| Δε | −4.0 |

In Example 4, 0.05 parts by weight of the compound represented by the formula (I-2-c1) was added to 100 parts by weight of the liquid crystal composition LC-B to prepare a liquid crystal composition LC-4. In Example 5, 0.05 parts by weight of the compound represented by the formula (I-2-e1) was added to 100 parts by weight of the liquid crystal composition LC-B to prepare a liquid crystal composition LC-5. In Example 6, 0.08 parts by weight of the compound represented by the formula (I-2-f1) was added to 100 parts by weight of the liquid crystal composition LC-B to prepare a liquid crystal composition LC-6. A liquid crystal composition composed of 100 parts by weight of LC-B was used as Comparative Example 2. The VHR (UV) and VHR (HEAT) results are listed in the table.

TABLE 4

|  | Comparative example 2 LC-B | Example 4 LC-4 | Example 5 LC-5 | Example 6 LC-6 |
| --- | --- | --- | --- | --- |
| Compound of formula (I-2-c1) (parts by mass) | — | 0.05 |  |  |
| Compound of formula (I-2-e1) (parts by mass) | — | — | 0.05 | — |
| Compound of formula (I-2-f1) (parts by mass) | — | — | — | 0.08 |
| Liquid crystal composition LC-B (parts by mass) | 100 | 100 | 100 | 100 |
| VHR (UV) | 50 | 96 | 94 | 95 |
| VHR (HEAT) | 47 | 82 | 80 | 79 |

Examples 4 to 6 had a sufficiently higher VHR (UV) and VHR (HEAT) than Comparative Example 2. Examples 4 to 6 had no variation in display. The liquid crystal compositions LC-4, LC-5, and LC-6 had the same $T_{ni}$, Δn, Δε, and $\gamma_1$ as the liquid crystal composition LC-B.

Liquid crystal compositions were prepared from the compounds represented by the formulae (I-2-c3), (I-2-e3), and (I-2-f3) instead of the compounds represented by the formulae (I-2-c1), (I-2-e1), and (I-2-f1) in Examples 4 to 6 and were measured for VHR. Compounds in which $R^1$ in the general formula (I) was substituted with —O. also had high VHR (UV) and VHR (HEAT).

Comparative Example 3, Examples 7 to 9

The following LC-C liquid crystal composition was prepared and measured for the physical properties. The components and physical properties of the liquid crystal composition are listed in the table.

TABLE 5

|  | LC-C |
| --- | --- |
| 3-Cy-Cy-V1 | 12 |
| 3-Cy-Cy-2 | 16 |
| 1V-Cy-Cy-1O-Ph5-O2 | 6 |
| 1-Ph-2-Ph-Ph5-O2 | 4 |
| 3-Ph-2-Ph-Ph5-O2 | 6 |
| 3-Cy-Ph5-O2 | 13 |
| 3-Ph-Ph5-O2 | 13 |
| 2-Cy-Cy-Ph5-O2 | 7 |
| 3-Cy-Cy-Ph5-O2 | 7 |
| 2-Cy-Ph-Ph5-O2 | 8 |
| 3-Cy-Ph-Ph5-O2 | 8 |
| Total (%) | 100 |
| $T_{NI}$ [° C.] | 76 |
| Δn | 0.114 |
| $\gamma_1$ [mPa · s] | 117 |
| Δε | −4.4 |

In Example 7, 0.07 parts by weight of the compound represented by the formula (I-2-c1) was added to 100 parts by weight of the liquid crystal composition LC-C to prepare a liquid crystal composition LC-7. In Example 8, 0.03 parts by weight of the compound represented by the formula (I-2-e1) and 0.03 parts by weight of the compound represented by the formula (I-3-a1) were added to 100 parts by weight of the liquid crystal composition LC-C to prepare a liquid crystal composition LC-8. In Example 9, 0.02 parts by weight of the compound represented by the formula (I-2-e1) and 0.05 parts by weight of the compound represented by the formula (I-3-a1) were added to 100 parts by weight of the liquid crystal composition LC-C to prepare a liquid crystal composition LC-9. A liquid crystal composition composed of 100 parts by weight of LC-C was used as Comparative Example 3. The VHR (UV) and VHR (HEAT) results are listed in the table.

TABLE 6

|  | Comparative example 3 LC-C | Example 7 LC-7 | Example 8 LC-8 | Example 9 LC-9 |
| --- | --- | --- | --- | --- |
| Compound of formula (I-2-c1) (parts by mass) | — | 0.07 | — | — |
| Compound of formula (I-2-e1) (parts by mass) | — | — | 0.03 | 0.02 |
| Compound of formula (I-3-a1) (parts by mass) | — | — | 0.03 | 0.05 |
| Liquid crystal composition LC-C (parts by mass) | 100 | 100 | 100 | 100 |
| VHR (UV) | 75 | 97 | 96 | 96 |
| VHR (HEAT) | 68 | 88 | 86 | 87 |

Examples 7 to 9 had a sufficiently higher VHR (UV) and VHR (HEAT) than Comparative Example 3. Examples 7 to 9 had no variation in display. The liquid crystal compositions LC-7, LC-8, and LC-9 had the same $T_{ni}$, Δn, Δε, and $\gamma_1$ as the liquid crystal composition LC-C.

Liquid crystal compositions were prepared from the compounds represented by the formulae (I-2-c2), (I-2-e2), and (I-3-a2) instead of the compounds represented by the formulae (I-2-c1), (I-2-e1), and (I-3-a1) in Examples 7 to 9 and were measured for VHR. Compounds in which $R^1$ in the general formula (I) were substituted with —$CH_3$ also had high VHR (UV) and VHR (HEAT).

Comparative Example 4, Examples 10 to 12

The following LC-D liquid crystal composition was prepared and measured for the physical properties. The components and physical properties of the liquid crystal composition are listed in the table.

TABLE 7

|  | LC-D |
| --- | --- |
| 3-Cy-Cy-V | 28 |
| 1V-Cy-Cy-1O-Ph5-O2 | 6 |
| 1-Ph-2-Ph-Ph5-O2 | 4 |
| 3-Ph-2-Ph-Ph5-O2 | 6 |
| 3-Cy-Ph5-O2 | 13 |
| 3-Ph-Ph5-O2 | 13 |
| 2-Cy-Cy-Ph5-O2 | 7 |
| 3-Cy-Cy-Ph5-O2 | 7 |
| 2-Cy-Ph-Ph5-O2 | 8 |
| 3-Cy-Ph-Ph5-O2 | 8 |
| Total (%) | 100 |
| $T_{NI}$ [° C.] | 73 |
| $\Delta n$ | 0.112 |
| $\gamma_1$ [mPa · s] | 103 |
| $\Delta \varepsilon$ | −4.4 |

In Example 10, 0.08 parts by weight of the compound represented by the formula (I-2-c1) was added to 100 parts by weight of the liquid crystal composition LC-D to prepare a liquid crystal composition LC-10. In Example 11, 0.08 parts by weight of the compound represented by the formula (I-2-d1) was added to 100 parts by weight of the liquid crystal composition LC-D to prepare a liquid crystal composition LC-11. In Example 12, 0.08 parts by weight of the compound represented by the formula (I-2-f1) was added to 100 parts by weight of the liquid crystal composition LC-D to prepare a liquid crystal composition LC-12. A liquid crystal composition composed of 100 parts by weight of LC-D was used as Comparative Example 4. The VHR (UV) and VHR (HEAT) results are listed in the table.

TABLE 8

|  | Comparative example 4 LC-D | Example 10 LC-10 | Example 11 LC-11 | Example 12 LC-12 |
| --- | --- | --- | --- | --- |
| Compound of formula (I-2-c1) (parts by mass) | — | 0.08 | — | — |
| Compound of formula (I-2-d1) (parts by mass) | — | — | 0.08 | — |
| Compound of formula (I-2-f1) (parts by mass) | — | — | — | 0.08 |
| Liquid crystal composition LC-D (parts by mass) | 100 | 100 | 100 | 100 |
| VHR (UV) | 64 | 95 | 94 | 95 |
| VHR (HEAT) | 57 | 84 | 83 | 84 |

Examples 10 to 12 had a sufficiently higher VHR (UV) and VHR (HEAT) than Comparative Example 4. Examples 10 to 12 had no variation in display. The liquid crystal compositions LC-10, LC-11, and LC-12 had the same $T_{ni}$, $\Delta n$, $\Delta \varepsilon$, and $\gamma_1$ as the liquid crystal composition LC-D.

Comparative Example 5, Examples 13 to 15

The following LC-E liquid crystal composition was prepared and measured for the physical properties. The components and physical properties of the liquid crystal composition are listed in the table.

TABLE 9

|  | LC-E |
| --- | --- |
| 3-Cy-Cy-V | 26 |
| 3-Cy-Ph-Ph-2 | 6 |
| V-Cy-Cy-1O-Ph5-O2 | 6 |
| 1-Ph-2-Ph-Ph5-O2 | 4 |
| 3-Cy-Ph5-O2 | 7 |
| 3-Ph-Ph5-O2 | 13 |
| 2-Cy-Cy-Ph5-O2 | 10 |
| 3-Cy-Cy-Ph5-O2 | 10 |
| 2-Cy-Ph-Ph5-O2 | 6 |
| 3-Cy-Ph-Ph5-O2 | 6 |
| 3-Ph-Ph5-Ph-2 | 6 |
| Total (%) | 100 |
| $T_{NI}$ [° C.] | 84 |
| $\Delta n$ | 0.121 |
| $\gamma_1$ [mPa · s] | 106 |
| $\Delta \varepsilon$ | −3.7 |

In Example 13, 0.05 parts by weight of the compound represented by the formula (I-2-c1) and 0.05 parts by weight of the compound represented by the formula (I-2-b1) were added to 100 parts by weight of the liquid crystal composition LC-E to prepare a liquid crystal composition LC-13. In Example 14, 0.03 parts by weight of the compound represented by the formula (I-2-c1), 0.03 parts by weight of the compound represented by the formula (I-1-b1), and 0.03 parts by weight of the compound represented by the formula (I-2-a1) were added to 100 parts by weight of the liquid crystal composition LC-E to prepare a liquid crystal composition LC-14. In Example 15, 0.05 parts by weight of the compound represented by the formula (I-2-c1) and 0.05 parts by weight of the compound represented by the formula (I-2-a1) were added to 100 parts by weight of the liquid crystal composition LC-E to prepare a liquid crystal composition LC-15. A liquid crystal composition composed of 100 parts by weight of LC-E was used as Comparative Example 5. The VHR (UV) and VHR (HEAT) results are listed in the table.

TABLE 10

|  | Comparative example 5 LC-E | Example 13 LC-13 | Example 14 LC-14 | Example 15 LC-15 |
| --- | --- | --- | --- | --- |
| Compound of formula (I-2-c1) (parts by mass) | — | 0.05 | 0.03 | 0.05 |
| Compound of formula (I-1-b1) (parts by mass) | — | — | 0.03 | — |
| Compound of formula (I-2-a1) (parts by mass) | — | — | 0.03 | 0.05 |
| Compound of formula (I-2-b1) (parts by mass) | — | 0.05 | — | — |
| Liquid crystal composition LC-E (parts by mass) | 100 | 100 | 100 | 100 |
| VHR (UV) | 75 | 96 | 94 | 95 |
| VHR (HEAT) | 67 | 85 | 83 | 84 |

Examples 13 to 15 had a sufficiently higher VHR (UV) and VHR (HEAT) than Comparative Example 5. Examples 13 to 15 had no variation in display. The liquid crystal compositions LC-13, LC-14, and LC-15 had the same $T_{ni}$, $\Delta n$, $\Delta \varepsilon$, and $\gamma_1$ as the liquid crystal composition LC-E.

Liquid crystal compositions were prepared from the compounds represented by the formulae (I-2-c4), (I-1-b4), (I-2-a4), and (I-2-b4) instead of the compounds represented by the formulae (I-2-c1), formula (I-1-b1), (I-2-a1), and (I-2-b1) in Examples 13 to 15 and were measured for VHR. Compounds in which $R^1$ in the general formula (I) was substituted with —OH also had high VHR.

Liquid crystal compositions were prepared from the compounds represented by the formulae (I-2-c2), (I-1-b2), (I-2-a2), and (I-2-b2) instead of the compounds represented by the formulae (I-2-c1), formula (I-1-b1), (I-2-a1), and (I-2-b1) in Examples 13 to 15 and were measured for VHR. Compounds in which $R^1$ in the general formula (I) were substituted with —CH$_3$ also had high VHR (UV) and VHR (HEAT).

Comparative Example 6, Examples 16 to 18

The following LC-F liquid crystal composition was prepared and measured for the physical properties. The components and physical properties of the liquid crystal composition are listed in the table.

TABLE 11

|  | LC-F |
|---|---|
| V-Cy-Cy-V | 32 |
| 3-Ph-Ph-1 | 7 |
| 5-Ph-Ph-1 | 4 |
| 3-Cy-Cy-Ph-1 | 7 |
| 3-Cy-1O-Ph5-O2 | 5 |
| 2-Cy-Cy-1O-Ph5-O2 | 12 |
| 3-Cy-Cy-1O-Ph5-O2 | 11 |
| 3-Cy-Ph-Ph5-O3 | 7 |
| 3-Cy-Ph-Ph5-O4 | 9 |
| 4-Cy-Ph-Ph5-O3 | 6 |
| Total (%) | 100 |
| $T_{NI}$ [° C.] | 76 |
| $\Delta n$ | 0.101 |
| $\gamma_1$ [mPa · s] | 74 |
| $\Delta \varepsilon$ | −2.8 |

In Example 16, 0.08 parts by weight of the compound represented by the formula (I-2-c1) was added to 100 parts by weight of the liquid crystal composition LC-F to prepare a liquid crystal composition LC-16. In Example 17, 0.08 parts by weight of the compound represented by the formula (I-2-d1) was added to 100 parts by weight of the liquid crystal composition LC-F to prepare a liquid crystal composition LC-17. In Example 18, 0.03 parts by weight of the compound represented by the formula (I-2-e1) and 0.03 parts by weight of the compound represented by the formula (I-4-a1) were added to 100 parts by weight of the liquid crystal composition LC-F to prepare a liquid crystal composition LC-18. A liquid crystal composition composed of 100 parts by weight of LC-F was used as Comparative Example 6. The VHR (UV) and VHR (HEAT) results are listed in the table.

TABLE 12

|  | Comparative example 6 LC-F | Example 18 LC-16 | Example 17 LC-17 | Example 18 LC-18 |
|---|---|---|---|---|
| Compound of formula (I-2-c1) (parts by mass) | — | 0.08 | — | — |
| Compound of formula (I-2-d1) (parts by mass) | — | — | 0.08 | — |
| Compound of formula (I-2-e1) (parts by mass) | — | — | — | 0.03 |
| Compound of formula (I-4-a1) (parts by mass) | — | — | — | 0.03 |
| Liquid crystal composition LC-F (parts by mass) | 100 | 100 | 100 | 100 |
| VHR (UV) | 51 | 94 | 93 | 92 |
| VHR (HEAT) | 43 | 82 | 80 | 80 |

Examples 16 to 18 had a sufficiently higher VHR (UV) and VHR (HEAT) than Comparative Example 6. Examples 16 to 18 had no variation in display. The liquid crystal compositions LC-16, LC-17, and LC-18 had the same $T_{ni}$, $\Delta n$, $\Delta \varepsilon$, and $\gamma_1$ as the liquid crystal composition LC-F.

Liquid crystal compositions were prepared from the compounds represented by the formulae (I-2-c2), (I-2-d2), (I-2-e2), and (I-4-a2) instead of the compounds represented by the formulae (I-2-c1), (I-2-d1), (I-2-e1), and (I-4-a1) in Examples 16 to 18 and were measured for VHR. Compounds in which $R^1$ in the general formula (I) were substituted with —CH$_3$ also had high VHR (UV) and VHR (HEAT).

Comparative Example 7, Examples 19 to 22

The following LC-G liquid crystal composition was prepared and measured for the physical properties. The components and physical properties of the liquid crystal composition are listed in the table.

TABLE 13

|  | LC-G |
|---|---|
| 3-Cy-Cy-V | 15 |
| 3-Cy-Cy-V1 | 10 |
| 3-Cy-Cy-2 | 9 |
| 3-Cy-Cy-4 | 8 |
| 2-Cy-Ph-Ph5-O2 | 3 |
| 3-Cy-Ph-Ph5-O2 | 8 |
| 3-Ph-Ph5-Ph-2 | 9 |
| 3-Cy-Ph5-O2 | 6 |
| 3-Ph-Ph5-O2 | 14 |
| 3-Cy-Cy-Ph5-O2 | 10 |
| 5-Cy-Cy-Ph5-O2 | 8 |
| Total (%) | 100 |
| $T_{ni}$ [° C.] | 76 |
| $\Delta n$ | 0.105 |
| $\gamma_1$ [mPa · s] | 76 |
| $\Delta \varepsilon$ | −2.6 |

In Example 19, 0.09 parts by weight of the compound represented by the formula (I-2-c1) was added to 100 parts by weight of the liquid crystal composition LC-G to prepare a liquid crystal composition LC-19. In Example 20, 0.09 parts by weight of the compound represented by the formula (I-2-e1) was added to 100 parts by weight of the liquid crystal composition LC-G to prepare a liquid crystal composition LC-20. In Example 21, 0.04 parts by weight of the compound represented by the formula (I-2-f1) and 0.04 parts by weight of the compound represented by the formula (I-3-a1) were added to 100 parts by weight of the liquid crystal composition LC-G to prepare a liquid crystal composition LC-21. In Example 22, 0.03 parts by weight of the compound represented by the formula (I-2-c1), 0.03 parts by weight of the compound represented by the formula (I-2-e1), 0.03 parts by weight of the compound represented by the formula (I-2-f1), and 0.03 parts by weight of the compound represented by the formula (I-3-a1) were added to 100 parts by weight of the liquid crystal composition LC-G to prepare a liquid crystal composition LC-22. A liquid crystal composition composed of 100 parts by weight of LC-G was used as Comparative Example 7. The VHR (UV) and VHR (HEAT) results are listed in the table.

TABLE 14

|  | Comparative example 7 LC-G | Example 19 LC-19 | Example 20 LC-20 | Example 21 LC-21 | Example 22 LC-22 |
|---|---|---|---|---|---|
| Compound of formula (I-2-c1) (parts by mass) |  | 0.09 |  |  | 0.03 |
| Compound of formula (I-2-e1) (parts by mass) |  |  | 0.09 |  | 0.03 |
| Compound of formula (I-2-f1) (parts by mass) |  |  |  | 0.04 | 0.03 |
| Compound of formula (I-3-a1) (parts by mass) |  |  |  | 0.04 | 0.03 |
| Liquid crystal composition LC-G (parts by mass) | 100 | 100 | 100 | 100 |  |
| VHR (UV) | 72 | 95 | 94 | 94 | 95 |
| VHR (HEAT) | 63 | 84 | 83 | 82 | 81 |

Examples 19 to 22 had a sufficiently higher VHR (UV) and VHR (HEAT) than Comparative Example 7. Examples 19 to 22 had no variation in display. The liquid crystal compositions LC-19, LC-20, LC-21, and LC-22 had the same $T_{ni}$, $\Delta n$, $\Delta \varepsilon$, and $\gamma_1$ as the liquid crystal composition LC-G.

Comparative Example 8, Examples 23 to 26

The following LC-H liquid crystal composition was prepared and measured for the physical properties. The components and physical properties of the liquid crystal composition are listed in the table.

TABLE 15

|  | LC-H |
|---|---|
| 3-Cy-Cy-V | 15 |
| 3-Cy-Cy-V1 | 10 |
| 3-Cy-Cy-2 | 9 |
| 5-Ph-Ph-1 | 4 |
| 3-Cy-Ph-Ph-2 | 4 |
| 2-Cy-Ph-Ph5-O2 | 3 |
| 3-Cy-Ph-Ph5-O2 | 8 |
| 3-Ph-Ph5-Ph-2 | 9 |
| 3-Cy-Ph5-O2 | 20 |
| 3-Cy-Cy-Ph5-O2 | 10 |
| 5-Cy-Cy-Ph5-O2 | 8 |
| Total (%) | 100 |
| $T_{NI}$ [° C.] | 76 |
| $\Delta n$ | 0.105 |
| $\gamma_1$ [mPa · s] | 82 |
| $\Delta \varepsilon$ | −2.7 |

In Example 23, 0.09 parts by weight of the compound represented by the formula (I-2-c1) was added to 100 parts by weight of the liquid crystal composition LC-H to prepare a liquid crystal composition LC-23. In Example 24, 0.09 parts by weight of the compound represented by the formula (I-2-e1) was added to 100 parts by weight of the liquid crystal composition LC-H to prepare a liquid crystal composition LC-24. In Example 25, 0.04 parts by weight of the compound represented by the formula (I-2-f1) and 0.04 parts by weight of the compound represented by the formula (I-3-a1) were added to 100 parts by weight of the liquid crystal composition LC-H to prepare a liquid crystal composition LC-25. In Example 26, 0.03 parts by weight of the compound represented by the formula (I-2-c1), 0.03 parts by weight of the compound represented by the formula (I-2-e1), 0.03 parts by weight of the compound represented by the formula (I-2-f1), and 0.03 parts by weight of the compound represented by the formula (I-3-a1) were added to 100 parts by weight of the liquid crystal composition LC-H to prepare a liquid crystal composition LC-26. A liquid crystal composition composed of 100 parts by weight of LC-H was used as Comparative Example 8. The VHR (UV) and VHR (HEAT) results are listed in the table.

TABLE 16

|  | Comparative example 8 LC-H | Example 23 LC-23 | Example 24 LC-24 | Example 25 LC-25 | Example 26 LC-26 |
|---|---|---|---|---|---|
| Compound of formula (I-2-c1) (parts by mass) |  | 0.09 |  |  | 0.03 |
| Compound of formula (I-2-e1) (parts by mass) |  |  | 0.09 |  | 0.03 |
| Compound of formula (I-2-f1) (parts by mass) |  |  |  | 0.04 | 0.03 |
| Compound of formula (I-3-a1) (parts by mass) |  |  |  | 0.04 | 0.03 |
| Liquid crystal composition LC-H (parts by mass) 100 | 100 | 100 | 100 | 100 | 100 |
| VHR (UV) | 76 | 96 | 94 | 95 | 96 |
| VHR (HEAT) | 65 | 85 | 83 | 82 | 83 |

Examples 23 to 26 had a sufficiently higher VHR (UV) and VHR (HEAT) than Comparative Example 8. Examples 23 to 26 had no variation in display. The liquid crystal compositions LC-23, LC-24, LC-25, and LC-26 had the same $T_{ni}$, $\Delta n$, $\Delta \varepsilon$, and $\gamma_1$ as the liquid crystal composition LC-H.

(Examination of Response Speed)

Liquid crystal display devices including the liquid crystal compositions LC-1 to LC-26 had a sufficiently high response speed for use in television sets. The cell thickness was 3.5 μm. The alignment film was JALS2096. The conditions for response speed measurements included Von of 6 V, Voff of 1 V, and a measurement temperature of 25° C. DMS703 from Autronic-Melchers GmbH was used.

(Examination of Polymerizable Monomer Additive Composition)

A liquid crystal composition prepared from 99.6% by mass LC-1 and 0.4% by mass of the polymerizable monomer represented by the formula (XX-2) was used to produce a PSVA liquid crystal display device. The liquid crystal display device had no display defect and had a sufficiently high response speed. Liquid crystal compositions prepared from LC-2 to LC26 instead of LC-1 were used to produce PSVA liquid crystal display devices. The liquid crystal display devices had no display defect and had a sufficiently high response speed.

A liquid crystal composition prepared from 99.6% by mass LC-1 and 0.4% by mass of the polymerizable monomer represented by the formula (XX-4) was used to produce a PSVA liquid crystal display device. The liquid crystal display device had no display defect and had a sufficiently high response speed. Liquid crystal compositions prepared from LC-2 to LC26 instead of LC-1 were used to produce PSVA liquid crystal display devices. The liquid crystal display devices had no display defect and had a sufficiently high response speed.

A liquid crystal composition was prepared from 99.7% LC-1 and 0.3% of the polymerizable monomer represented by (XX-4), and 20 ppm of the antioxidant (H-14) was added to the liquid crystal composition. The liquid crystal composition was used to produce a PSVA liquid crystal display device. The liquid crystal display device had no display defect and had a sufficiently high response speed. Liquid crystal compositions prepared from LC-2 to LC26 instead of LC-1 were used to produce PSVA liquid crystal display devices. The liquid crystal display devices had no display defect and had a sufficiently high response speed.

A liquid crystal composition prepared from 99.6% by mass LC-1 and 0.4% by mass of the polymerizable monomer represented by the formula (P-302) was used to produce a PSVA liquid crystal display device. The liquid crystal display device had no display defect and had a sufficiently high response speed. Liquid crystal compositions prepared from LC-2 to LC26 instead of LC-1 were used to produce PSVA liquid crystal display devices. The liquid crystal display devices had no display defect and had a sufficiently high response speed.

A liquid crystal composition prepared from 99.6% by mass LC-1, 0.4% by mass of the polymerizable monomer represented by the formula (XX-4), and 0.1% by mass of the polymerizable monomer represented by the formula (Ia-31) was used to produce a PSVA liquid crystal display device. The liquid crystal display device had no display defect and had a sufficiently high response speed. Liquid crystal compositions prepared from LC-2 to LC26 instead of LC-1 were used to produce PSVA liquid crystal display devices. The liquid crystal display devices had no display defect and had a sufficiently high response speed.

Comparative Examples 9 to 12, Examples 27 to 29

The following LC-I liquid crystal composition was prepared and measured for the physical properties. The components and physical properties of the liquid crystal composition are listed in the table.

TABLE 17

| | LC-I |
|---|---|
| 3-Cy-Cy-V0 | 43 |
| 3-Cy-Cy-V1 | 12 |
| 1V2-Ph-Ph-1 | 7 |
| 0V-Cy-Cy-Ph-1 | 11.5 |
| V2-Cy-Cy-Ph-1 | 9.5 |
| 3-Ph-Ph1-Ph-2 | 6 |
| 3-Py-Ph-Ph2-CFFO-Ph2-F | 4.5 |
| 3-Ph-Ph1-Ph2-CFFO-Ph2-F | 6 |
| 3-Ph-Ph-Ph1-Ph2-F | 0.5 |
| Total (%) | 100 |
| $T_{NI}$ [° C.] | 81 |
| $\Delta n$ | 0.098 |
| $\gamma_1$ [mPa · s] | 35 |
| $\Delta \varepsilon$ | 2.4 |

In Example 27, 0.10 parts by weight of the compound represented by the formula (I-2-c1) was added to 100 parts by weight of the liquid crystal composition LC-I to prepare a liquid crystal composition LC-27. In Example 28, 0.05 parts by weight of the compound represented by the formula (I-2-c1) was added to 100 parts by weight of the liquid crystal composition LC-I to prepare a liquid crystal composition LC-28. In Example 29, 0.02 parts by weight of the compound represented by the formula (I-2-c1) was added to 100 parts by weight of the liquid crystal composition LC-I to prepare a liquid crystal composition LC-29. A liquid crystal composition composed of 100 parts by weight of LC-I was used as Comparative Example 9. In Comparative Example 10, 0.10 parts by weight of the compound represented by the following formula (HA) was added to 100 parts by weight of the liquid crystal composition LC-I to prepare a liquid crystal composition LC-II. In Comparative Example 11, 0.05 parts by weight of the compound represented by the formula (HA) was added to 100 parts by weight of the liquid crystal composition LC-I to prepare a liquid crystal composition LC-12. In Comparative Example 12, 0.02 parts by weight of the compound represented by the formula (HA) was added to 100 parts by weight of the liquid crystal composition LC-I to prepare a liquid crystal composition LC-I3. The VHR (UV) and VHR (HEAT) results are listed in the table.

[Chem. 124]

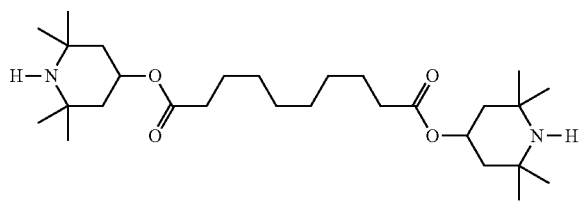

(HA)

TABLE 18

| | Comparative example 9 LC-I | Comparative example 10 LC-I1 | Comparative example 11 LC-I2 | Comparative example 12 LC-I3 | Example 27 LC-27 | Example 28 LC-28 | Example 29 LC-29 |
|---|---|---|---|---|---|---|---|
| Compound of formula (HA) (parts by mass) | — | 0.10 | 0.05 | 0.02 | — | — | — |
| Compound of formula (I-2-c1) (parts by mass) | — | — | — | — | 0.10 | 0.05 | 0.02 |
| Composition LC-I | 100 | 100 | 100 | 100 | 100 | 100 | 100 |
| VHR (UV) | 82 | 83 | 86 | 86 | 88 | 87 | 88 |
| VHR (HEAT) | 48 | 80 | 79 | 79 | 84 | 82 | 83 |

Examples 27 to 29 had a sufficiently higher VHR (UV) and VHR (HEAT) than Comparative Example 9. Examples 27 to 29 had no variation in display. The liquid crystal compositions LC-27, LC-28, and LC-29 had the same $T_{ni}$, $\Delta n$, $\Delta \varepsilon$, and $\gamma_1$ as the liquid crystal composition LC-I. Examples 27 to 29 had VHR (UV) and VHR (HEAT) equal to or higher than those of Comparative Examples 10 to 12, which included the compound having the hindered amine structure represented by the formula (HA).

Comparative Example 13, Examples 30 to 32

The following LC-J liquid crystal composition was prepared and measured for the physical properties. The components and physical properties of the liquid crystal composition are listed in the table.

TABLE 19

|  | LC-J |
| --- | --- |
| 3-Cy-Cy-V0 | 32.5 |
| 3-Cy-Cy-V1 | 2.5 |
| 0V-Cy-Cy-Ph-1 | 10 |
| 5-Cy-Cy-Ph-O1 | 2.5 |
| 3-Cy-Ph-Ph-Cy-3 | 3.5 |
| 3-Cy-Cy-Ph2-F | 8 |
| 3-Ph-Ph2-CFFO-Ph2-F | 9 |
| 3-Cy-Cy-CFFO-Ph2-F | 9.5 |
| 3-Cy-Cy-Ph1-Ph2-F | 4 |
| 3-Py-Ph-Ph2-CFFO-Ph2-F | 8.5 |
| 3-Ph-Ph1-Ph2-CFFO-Ph2-F | 4 |
| 3-Cy-Ph-Ph2-Ph1-OCF3 | 6 |
| Total (%) | 100 |
| $T_{NI}$ [° C.] | 100 |
| Δn | 0.100 |
| $\gamma_1$ [mPa · s] | 72 |
| Δε | 8.1 |

In Example 30, 0.05 parts by weight of the compound represented by the formula (I-2-c1) was added to 100 parts by weight of the liquid crystal composition LC-J to prepare a liquid crystal composition LC-30. In Example 31, 0.05 parts by weight of the compound represented by the formula (I-2-e1) was added to 100 parts by weight of the liquid crystal composition LC-J to prepare a liquid crystal composition LC-31. In Example 32, 0.08 parts by weight of the compound represented by the formula (I-2-f1) was added to 100 parts by weight of the liquid crystal composition LC-J to prepare a liquid crystal composition LC-32. A liquid crystal composition composed of 100 parts by weight of LC-J was used as Comparative Example 13. The VHR (UV) and VHR (HEAT) results are listed in the table.

TABLE 20

|  | Comparative example 13 LC-J | Example 30 LC-30 | Example 31 LC-31 | Example 32 LC-32 |
| --- | --- | --- | --- | --- |
| Compound of formula (I-2-c1) (parts by mass) | — | 0.05 | — | — |
| Compound of formula (I-2-e1) (parts by mass) | — | — | 0.05 | — |
| Compound of formula (I-2-f1) (parts by mass) | — | — | — | 0.08 |
| Composition LC-J | 100 | 100 | 100 | 100 |
| VHR (UV) | 83 | 94 | 92 | 93 |
| VHR (HEAT) | 49 | 81 | 81 | 80 |

Examples 30 to 32 had a sufficiently higher VHR (UV) and VHR (HEAT) than Comparative Example 13. Examples 30 to 32 had no variation in display. The liquid crystal compositions LC-30, LC-31, and LC-32 had the same $T_{ni}$, Δn, Δε, and $\gamma_1$ as the liquid crystal composition LC-J.

Liquid crystal compositions were prepared from the compounds represented by the formulae (I-2-c2) and (I-2-e2) and (I-2-f2) instead of the compounds represented by the formulae (I-2-c1), (I-2-e1), and (I-2-f1) in Examples 30 to 32 and were measured for VHR. Compounds in which $R^1$ in the general formula (I) were substituted with —CH₃ also had high VHR (UV) and VHR (HEAT).

Comparative Example 14, Examples 33 to 35

The following LC-K liquid crystal composition was prepared and measured for the physical properties. The components and physical properties of the liquid crystal composition are listed in the table.

TABLE 21

|  | LC-K |
| --- | --- |
| 3-Cy-Cy-V0 | 44 |
| 3-Cy-Cy-V1 | 16 |
| 5-Ph-Ph-1 | 3.5 |
| 3-Cy-Cy-Ph-1 | 6 |
| 3-Cy-Cy-Ph-3 | 1.5 |
| 3-Cy-Ph-Ph-2 | 7 |
| 2-Ph-Ph1-Ph-2V | 5 |
| 3-Ph1-Np2-F | 4 |
| 3-Cy-Ph1-Np2-F | 6 |
| 2-Ph-Ph1-Np2-F | 5 |
| 2-Cy-Cy-Ph-Ph1-F | 2 |
| Total (%) | 100 |
| $T_{NI}$ [° C.] | 78 |
| Δn | 0.102 |
| $\gamma_1$ [mPa · s] | 38 |
| Δε | 2.3 |

In Example 33, 0.05 parts by weight of the compound represented by the formula (I-2-c1) was added to 100 parts by weight of the liquid crystal composition LC-K to prepare a liquid crystal composition LC-33. In Example 34, 0.03 parts by weight of the compound represented by the formula (I-2-a1) and 0.03 parts by weight of the compound represented by the formula (I-2-b1) were added to 100 parts by weight of the liquid crystal composition LC-K to prepare a liquid crystal composition LC-34. In Example 35, 0.02 parts by weight of the compound represented by the formula (I-2-a1) and 0.05 parts by weight of the compound represented by the formula (I-2-b1) were added to 100 parts by weight of the liquid crystal composition LC-K to prepare a liquid crystal composition LC-35. A liquid crystal composition composed of 100 parts by weight of LC-K was used as Comparative Example 14. The VHR (UV) and VHR (HEAT) results are listed in the table.

TABLE 22

|  | Comparative example 14 LC-K | Example 33 LC-33 | Example 34 LC-34 | Example 35 LC-35 |
| --- | --- | --- | --- | --- |
| Compound of formula (I-2-c1) (parts by mass) | — | 0.05 | — | — |
| Compound of formula (I-2-a1) (parts by mass) | — | — | 0.03 | 0.02 |
| Compound of formula (I-2-b1) (parts by mass) | — | — | 0.03 | 0.05 |
| Composition LC-K | 100 | 100 | 100 | 100 |
| VHR (UV) | 70 | 89 | 87 | 88 |
| VHR (HEAT) | 45 | 79 | 78 | 77 |

Examples 33 to 35 had a sufficiently higher VHR (UV) and VHR (HEAT) than Comparative Example 14. Examples 33 to 35 had no variation in display. The liquid crystal compositions LC-33, LC-34, and LC-35 had the same $T_{ni}$, Δn, Δε, and $\gamma_1$ as the liquid crystal composition LC-K.

Liquid crystal compositions were prepared from the compounds represented by the formulae (I-2-c5), (I-2-a5), and (I-2-b5) instead of the compounds represented by the formulae (I-2-c1), (I-2-a1), and (I-2-b1) in Examples 33 to 35 and were measured for VHR. Compounds in which $R^1$ in the general formula (I) were substituted with —OCH$_3$ also had high VHR (UV) and VHR (HEAT).

Comparative Example 15, Examples 36 to 38

The following LC-L liquid crystal composition was prepared and measured for the physical properties. The components and physical properties of the liquid crystal composition are listed in the table.

TABLE 23

|  | LC-L |
| --- | --- |
| 3-Cy-Cy-V0 | 40 |
| 3-Cy-Cy-2 | 4 |
| 5-Ph-Ph-1 | 1.5 |
| 0V-Cy-Cy-Ph-1 | 5.5 |
| 3-Cy-Ph-Ph-2 | 2 |
| 3-Cy-Cy-Ph2-F | 8 |
| 2-Ph2-O1-Cy-Ph2-Ph2-F | 5.5 |
| 3-Ph2-O1-Cy-Ph2-Ph2-F | 4.5 |
| 3-Ph2-O1-Ph-Np2-F | 10 |
| 3-Ph-Ph2-CFFO-Np2-F | 10 |
| 3-Ph-Ph1-Ph2-CFFO-Np2-F | 4 |
| 4-Ph-Ph1-Ph2-CFFO-Np2-F | 5 |
| Total (%) | 100 |
| $T_{NI}$ [° C.] | 73 |
| Δn | 0.107 |
| $γ_1$ [mPa · s] | 78 |
| Δε | 11.7 |

In Example 36, 0.05 parts by weight of the compound represented by the formula (I-2-c1) was added to 100 parts by weight of the liquid crystal composition LC-L to prepare a liquid crystal composition LC-36. In Example 37, 0.08 parts by weight of the compound represented by the formula (I-2-d1) was added to 100 parts by weight of the liquid crystal composition LC-L to prepare a liquid crystal composition LC-37. In Example 38, 0.08 parts by weight of the compound represented by the formula (I-3-a1) was added to 100 parts by weight of the liquid crystal composition LC-L to prepare a liquid crystal composition LC-38. A liquid crystal composition composed of 100 parts by weight of LC-L was used as Comparative Example 15. The VHR (UV) and VHR (HEAT) results are listed in the table.

TABLE 24

|  | Comparative example 15 LC-L | Example 36 LC-36 | Example 37 LC-37 | Example 38 LC-38 |
| --- | --- | --- | --- | --- |
| Compound of formula (I-2-c1) (parts by mass) | — | 0.05 | — | — |
| Compound of formula (I-2-d1) (parts by mass) | — | — | 0.08 | — |
| Compound of formula (I-3-a1) (parts by mass) | — | — | — | 0.08 |
| Composition LC-L | 100 | 100 | 100 | 100 |
| VHR (UV) | 72 | 90 | 90 | 89 |
| VHR (HEAT) | 47 | 80 | 78 | 79 |

Examples 36 to 38 had a sufficiently higher VHR (UV) and VHR (HEAT) than Comparative Example 15. Examples 36 to 38 had no variation in display. The liquid crystal compositions LC-36, LC-37, and LC-38 had the same $T_{ni}$, Δn, Δε, and $γ_1$ as the liquid crystal composition LC-L.

Liquid crystal compositions were prepared from the compounds represented by the formulae (I-2-c4), (I-2-d4), and (I-3-a4) instead of the compounds represented by the formulae (I-2-c1), (I-2-d1), and (I-3-a1) in Examples 36 to 38 and were measured for VHR. Compounds in which R$^1$ in the general formula (I) was substituted with —OH also had high VHR (UV) and VHR (HEAT).

Comparative Example 16, Examples 39 to 41

The following LC-M liquid crystal composition was prepared and measured for the physical properties. The components and physical properties of the liquid crystal composition are listed in the table.

TABLE 25

|  | LC-M |
| --- | --- |
| 3-Cy-Cy-V0 | 41 |
| 3-Cy-Cy-V1 | 11 |
| 5-Ph-Ph-1 | 2 |
| 3-Cy-Ph-Ph-2 | 6 |
| V-Cy-Ph-Ph-3 | 4 |
| 3-Ph-Ph1-Ph2-O1-V | 15 |
| 3-Cy-Ph-Ph2-O1-Ph2-F | 5 |
| 3-Ph2-O1-Oc-Ph-Ph2-F | 4 |
| 4-Ph2-O1-Oc-Ph-Ph2-F | 4 |
| 3-Ph2-O1-Oc-Ph1-Ph2-F | 5 |
| 5-Ph2-O1-Oc-Ph1-Ph2-F | 3 |
| Total (%) | 100 |
| $T_{NI}$ [° C.] | 87 |
| Δn | 0.117 |
| $γ_1$ [mPa · s] | 54 |
| Δε | 6.3 |

In Example 39, 0.05 parts by weight of the compound represented by the formula (I-1-a1) was added to 100 parts by weight of the liquid crystal composition LC-M to prepare a liquid crystal composition LC-39. In Example 40, 0.03 parts by weight of the compound represented by the formula (I-1-a1), 0.03 parts by weight of the compound represented by the formula (I-1-b1), and 0.03 parts by weight of the compound represented by the formula (I-4-a1) were added to 100 parts by weight of the liquid crystal composition LC-M to prepare a liquid crystal composition LC-40. In Example 41, 0.05 parts by weight of the compound represented by the formula (I-1-a1) and 0.05 parts by weight of the compound represented by the formula (I-4-a1) were added to 100 parts by weight of the liquid crystal composition LC-M to prepare a liquid crystal composition LC-41. A liquid crystal composition composed of 100 parts by weight of LC-M was used as Comparative Example 16. The VHR (UV) and VHR (HEAT) results are listed in the table.

TABLE 26

|  | Comparative example 16 LC-M | Example 39 LC-39 | Example 40 LC-40 | Example 41 LC-41 |
| --- | --- | --- | --- | --- |
| Compound of formula (I-1-a1) (parts by mass) | — | 0.05 | 0.03 | 0.05 |
| Compound of formula (I-1-b1) (parts by mass) | — | — | 0.03 | — |
| Compound of formula (I-4-a1) (parts by mass) | — | — | 0.03 | 0.05 |
| Composition LC-M | 100 | 100 | 100 | 100 |
| VHR (UV) | 73 | 87 | 88 | 88 |
| VHR (HEAT) | 44 | 79 | 80 | 82 |

Examples 39 to 41 had a sufficiently higher VHR (UV) and VHR (HEAT) than Comparative Example 16. Examples 39 to 41 had no variation in display. The liquid crystal compositions LC-39, LC-40, and LC-41 had the same $T_{ni}$, $\Delta n$, $\Delta \varepsilon$, and $\gamma_1$ as the liquid crystal composition LC-M.

Liquid crystal compositions were prepared from the compounds represented by the formulae (I-1-a2), (I-1-b2), and (I-4-a2) instead of the compounds represented by the formulae (I-1-a1), (I-1-b1), and (I-4-a1) in Examples 39 to 41 and were measured for VHR. Compounds in which R1 in the general formula (I) were substituted with —$CH_3$ also had high VHR (UV) and VHR (HEAT). The liquid crystal compositions LC-1 to LC41 according to the present invention left no drop mark on a substrate in the one drop fill (ODF) method. These liquid crystal display devices had no variation in alignment. Furthermore, these liquid crystal display devices had no image sticking during operation.

Comparative Example 17, Examples 42 to 44

The following LC-N liquid crystal composition was prepared and measured for the physical properties. The components and physical properties of the liquid crystal composition are listed in the table.

TABLE 27

|  | LC-N |
|---|---|
| 3-Cy-Cy-V | 25 |
| 3-Cy-Cy-V1 | 3 |
| 3-Ph-Ph-1 | 8 |
| 3-Cy-Ph-Ph-2 | 7 |
| 3-Cy-1O-Ph5-O1 | 3 |
| 3-Cy-1O-Ph5-O2 | 8 |
| 2-Cy-Cy-1O-Ph5-O2 | 13 |
| 3-Cy-Cy-1O-Ph5-O2 | 13 |
| 1V-Cy-Cy-1O-Ph5-O2 | 8 |
| 2-Ph-2-Ph-Ph5-O2 | 6 |
| 3-Ph-2-Ph-Ph5-O2 | 6 |
| Total | 100 |
| $T_{NI}$ [° C.] | 80 |
| $\Delta n$ | 0.107 |
| $\gamma_1$ [mPa·s] | 109 |
| $\Delta \varepsilon$ | −3.9 |
| VHR (UV) | 62 |

In Example 42, 0.15 parts by weight of the compound represented by the formula (I-2-c1) was added to 100 parts by weight of the liquid crystal composition LC-N to prepare a liquid crystal composition LC-42. In Example 43, 0.15 parts by weight of the compound represented by the formula (I-2-a6) was added to 100 parts by weight of the liquid crystal composition LC-N to prepare a liquid crystal composition LC-43. In Example 44, 0.08 parts by weight of the compound represented by the formula (I-2-a6) and 0.08 parts by weight of the compound represented by the formula (I-2-a1) were added to 100 parts by weight of the liquid crystal composition LC-N to prepare a liquid crystal composition LC-44. A liquid crystal composition composed of 100 parts by weight of LC-N was used as Comparative Example 17. The VHR (UV) results are listed in the table.

TABLE 28

|  | Comparative example 17 LC-N | Example 42 LC-42 | Example 43 LC-43 | Example 44 LC-44 |
|---|---|---|---|---|
| Compound of formula (I-2-c1) (parts by mass) | — | 0.15 | — | — |
| Compound of formula (I-2-a6) (parts by mass) | — | — | 0.15 | 0.08 |
| Compound of formula (I-2-a1) (parts by mass) | — | — | — | 0.08 |
| Liquid crystal composition LC-N (parts by mass) | 100 | 100 | 100 | 100 |
| VHR (UV) | 62 | 95 | 93 | 94 |

Examples 42 to 44 had a sufficiently higher VHR (UV) and VHR (HEAT) than Comparative Example 17. Examples 42 to 44 had no variation in display. The liquid crystal compositions LC-42, LC-43, and LC-44 had the same $T_{ni}$, $\Delta n$, $\Delta \varepsilon$, and $\gamma_1$ as the liquid crystal composition LC-N.

Comparative Example 18, Examples 45 to 47

The following LC-O liquid crystal composition was prepared and measured for the physical properties. The components and physical properties of the liquid crystal composition are listed in the table.

TABLE 29

|  | LC-O |
|---|---|
| 3-Cy-Cy-V | 28 |
| 3-Cy-Cy-2 | 8 |
| 5-Ph-Ph-1 | 5 |
| 3-Cy-Ph-Ph-2 | 7 |
| 3-Cy-1O-Ph5-O2 | 8 |
| 3-Ph-Ph5-O2 | 6 |
| 2-Cy-Cy-1O-Ph5-O2 | 13 |
| 3-Cy-Cy-1O-Ph5-O2 | 13 |
| 1-Ph-2-Ph-Ph5-O2 | 6 |
| 3-Ph-2-Ph-Ph5-O2 | 6 |
| Total | 100 |
| $T_{NI}$ [° C.] | 74 |
| $\Delta n$ | 0.100 |
| $\gamma_1$ [mPa·s] | 83 |
| $\Delta \varepsilon$ | −3.0 |
| VHR (UV) | 58 |

In Example 45, 0.1 parts by weight of the compound represented by the formula (I-2-c1) was added to 100 parts by weight of the liquid crystal composition LC-O to prepare a liquid crystal composition LC-45. In Example 46, 0.1 parts by weight of the compound represented by the formula (I-2-a6) was added to 100 parts by weight of the liquid crystal composition LC-O to prepare a liquid crystal composition LC-46. In Example 47, 0.1 parts by weight of the compound represented by the formula (I-2-a1) was added to 100 parts by weight of the liquid crystal composition LC-O to prepare a liquid crystal composition LC-47. A liquid crystal composition composed of 100 parts by weight of LC-O was used as Comparative Example 18. The VHR (UV) results are listed in the table.

TABLE 30

|  | Comparative example 18 LC-O | Example 45 LC-45 | Example 46 LC-46 | Example 47 LC-47 |
|---|---|---|---|---|
| Compound of formula (I-2-c1) (parts by mass) | — | 0.1 | — | — |
| Compound of formula (I-2-a6) (parts by mass) | — | — | 0.1 | — |
| Compound of formula (I-2-a1) (parts by mass) | — | — | — | 0.1 |
| Liquid crystal composition LC-N (parts by mass) | 100 | 100 | 100 | 100 |
| VHR (UV) | 58 | 93 | 92 | 92 |

Examples 45 to 47 had a sufficiently higher VHR (UV) and VHR (HEAT) than Comparative Example 18. Examples 45 to 47 had no variation in display. The liquid crystal compositions LC-45, LC-46, and LC-47 had the same $T_{ni}$, $\Delta n$, $\Delta \varepsilon$, and $\gamma_1$ as the liquid crystal composition LC-0.

The liquid crystal compositions LC-42 to LC47 according to the present invention left no drop mark on a substrate in the one drop fill (ODF) method. These liquid crystal display devices had no variation in alignment. Furthermore, these liquid crystal display devices had no image sticking during operation.

Thus, it was found that a liquid crystal composition according to the present invention had a sufficiently low rotational viscosity ($\gamma_1$), left no drop mark, had no variation in alignment, and had a sufficiently high VHR (UV) and VHR (HEAT), without a decrease in refractive index anisotropy ($\Delta n$) or nematic phase-isotropic liquid phase transition temperature ($T_{ni}$). A liquid crystal display device including a liquid crystal composition according to the present invention had no or few display defects and had high display quality and a high response speed.

The invention claimed is:

1. A liquid crystal composition comprising one or two or more compounds represented by a general formula (I) or a general formula (I-2-a1):

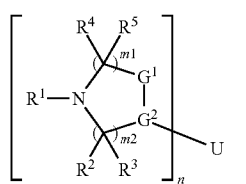

(I)

wherein $R^1$ denotes a hydrogen atom, an alkyl group having 1 carbon atom, or alkoxy group having 1 carbon atom $R^2$, $R^3$, $R^4$, and $R^5$ independently denote a methyl group, -$G^1$-$G^2$- denotes a group represented by

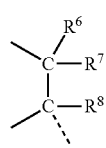

wherein each broken line denotes a bond to U in the general formula (I), $R^6$, $R^7$, and $R^8$ independently denote a hydrogen atom, U denotes a group represented by a general formula (U-1),

wherein $Z^{u1}$ denotes —O—CO—O—, —CO—NH—, —NH—CO—, —CF$_2$O—, —OCF$_2$—, —CH=CH—COO—, —CH=CH—OCO—, —COO—CH=CH—, —OCO—CH=CH—, —COO—CH$_2$CH$_2$—, —CH$_2$CH$_2$—COO—, —CH$_2$CH$_2$—OCO—, —COO—CH$_2$—, —CH$_2$—COO—, —CH$_2$—OCO—, —CH=CH—, —N=N—, —CH=N—, —N=CH—, —CH=N—N=CH—, —CF=CF—, or —C≡C—, $Z^{u2}$ independently denote denotes —O—, —OCH$_2$—, —CH$_2$O—, —CH$_2$CH$_2$—, —CO—, —COO—, —O—CO—O—, —CO—NH—, —NH—CO—, —CF$_2$O—, —OCF$_2$—, —CH=CH—COO—, —CH=CH—OCO—, —COO—CH=CH—, —OCO—CH=CH—, —COO—CH$_2$CH$_2$—, —CH$_2$CH$_2$—COO—, —CH=CH$_2$—OCO—, —COO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond, $A^{u1}$ denotes a group selected from the group consisting of
(a) a 1,4-cyclohexylene group in which one —CH$_2$— or two or more nonadjacent —CH$_2$— groups may be substituted with —O—,
(b) a 1,4-phenylene group in which one —CH= or two or more nonadjacent —CH= groups may be substituted with —N=, and
(c) a naphthalene-2,6-diyl group, a 1,2,3,4-tetrahydronaphthalene-2,6-diyl group, or a decahydronaphthalene-2,6-diyl group wherein one —CH= or two or more nonadjacent —CH= groups in the naphthalene-2,6-diyl group or the 1,2,3,4-tetrahydronaphthalene-2,6-diyl group may be substituted with —N=,
the groups (a), (b), and (c) may be independently substituted with a fluorine atom, a chlorine atom, a bromine atom, an iodine atom, a nitro group, a cyano group, an isocyano group, an amino group, a hydroxy group, a methylamino group, a dimethylamino group, a diethylamino group, a diisopropylamino group, or an alkyl group having 1 to 12 carbon atoms, and one —CH$_2$— or two or more nonadjacent —CH$_2$— groups in the alkyl group may be independently substituted with —O—, —CO—, —COO—, —OCO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, $Sp^{u1}$ denotes a single bond or an alkylene group having 1 to 10 carbon atoms, and one —CH$_2$— or two or more nonadjacent —CH$_2$— groups in the alkylene group not directly bonded to $Z^{u1}$ adjacent to $Sp^{u1}$ may be independently substituted with —O—, —CO—, —COO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, W denotes an organic group having a valence of 1 to 4, the valence of W being identical to n in the formula (I), pu1 denotes an integer in the range of 0 to 8, nu1 denotes an integer in the range of 1 to 4, and nu1 is identical with n in the general formula (I), and pluralities of $Z^{u1}$s, $Z^{u2}$s, $Sp^{u1}$s, and $A^{u1}$s, if present, may be the same or different $Z^{u1}$s, $Z^{u2}$s, $Sp^{u1}$s, and $A^{u1}$s, respectively, m1 and m2 independently denote an integer 1, and n denotes an integer of 1 to 4, and when n is an integer of 1, W denotes a hydrogen atom, a fluorine atom, a chlorine atom, a bromine atom, an iodine atom, a nitro group, an amino group, a hydroxy group, or an alkyl group, having 1-12 carbon atoms, and one —CH$_2$— or two or more nonadjacent —CH$_2$— groups in the alkyl group may be independently substituted with —O—, —CO—, —COO—, —OCO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, when n is an integer of 2, W denotes an alkylene group having 1-10 carbon atoms, and one —CH$_2$— or two or more nonadjacent —CH$_2$— groups in the alkylene group may be independently substituted with —O—, —CO—, —COO—, —OCO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—; or W denotes a group selected from the group consisting of (a) a 1,4-cyclohexylene group in which one —CH$_2$— or two or more nonadjacent —CH$_2$— groups may be substituted with —O—, (b) a 1,4-phenylene group in which one —CH= or two or more nonadjacent —CH= groups may be substituted with —N=, and (c) a naphthalene-2,6-diyl group, a 1,2,3,4-tetrahydronaphthalene-2,6-diyl group, or a decahydronaphthalene-2,6-diyl group, wherein one —CH= or two or more nonadjacent —CH= groups in the naphthalene-2,6-diyl group or the 1,2,3,4-tetrahydronaphthalene-2,6-diyl group may be substituted with —N=, the groups (a), (b), and (c) may be independently substituted with a fluorine atom, a chlorine atom, a bromine atom, an iodine atom, a nitro group, a cyano group, an isocyano group, an amino group, a hydroxy group, a methylamino group, a dimethylamino group, a diethylamino group, a diisopropylamino group, or an alkyl group having 1 to 12 carbon atoms, and one —CH$_2$— or two or more nonadjacent —CH$_2$— groups in the alkyl group may be independently substituted with —O—, —CO—, —COO—, —OCO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, when n is an integer of 3, W denotes a group selected from the groups represented by the formulae (X3-1) to (W3-12),

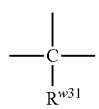
(W3-1)

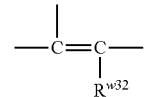
(W3-2)

(W3-3)

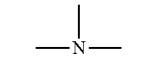
(W3-4)

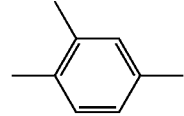
(W3-5)

(W3-6)

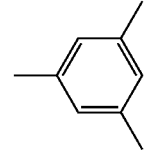
(W3-7)

(W3-8)

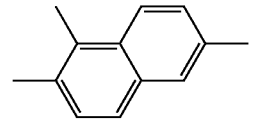
(W3-9)

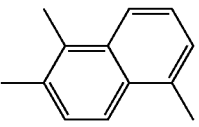
(W3-10)

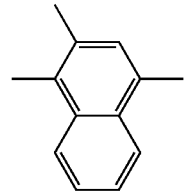
(W3-11)

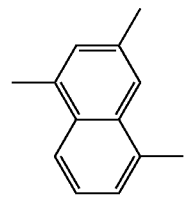
(W3-12)

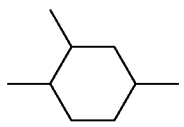

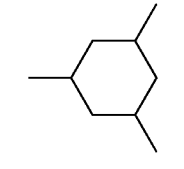

wherein in the formulae, $R^{w31}$ and $R^{w32}$ denote a hydrogen atom, a hydroxy group, or an alkyl group having 1 to 10 carbon atoms, and one or two or more —CH$_2$— groups in the alkyl group may be independently substituted with —O—, —CH=CH—, —C≡C—, —CO—O—, or —O—CO—; wherein a hydrogen atom in a ring structure may be substituted with a fluorine atom, a chlorine atom, a bromine atom, an iodine atom, a nitro group, a cyano group, an isocyano group, an amino group, a hydroxy group, a methylamino group, a dimethylamino group, a diethylamino group, a diisopropylamino group, or an alkyl group having 1 to 12 carbon atoms, and one —CH$_2$— or two or more nonadjacent —CH$_2$— groups in the alkyl group may be independently substituted with —O—, —CO—, —COO—, —OCO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, —OCF$_2$—, —CF$_2$O—, or —C≡C—, when n is an integer of 4, W denotes a group selected from the groups represented by the formulae (W4-1) to (W4-21),

(W4-1)

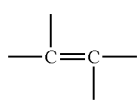
(W4-2)

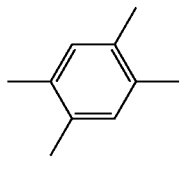
(W4-3)

(W4-4)

(W4-5)

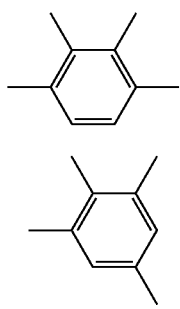

(W4-6)

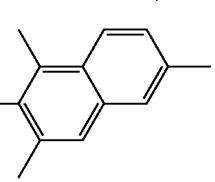

(W4-7)

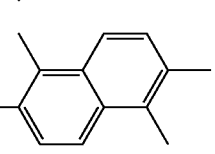

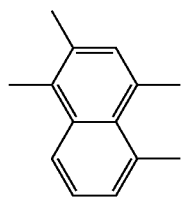
(W4-8)

(W4-9)

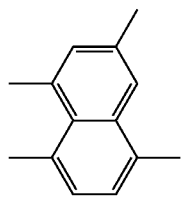

(W4-10)

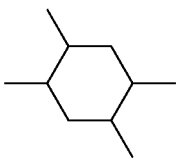

(W4-11)

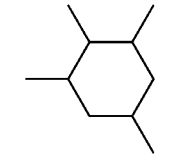

(W4-12)

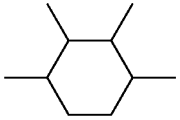

(W4-13)

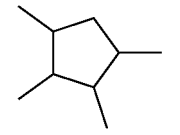

(W4-14)

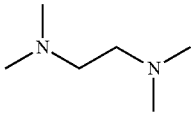

(W4-15)

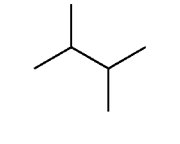

(W4-16)

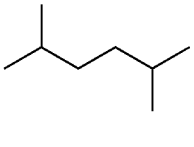

(W4-17)

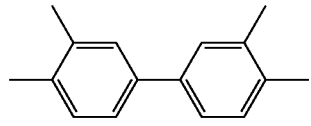

-continued (W4-18)

(W4-19)

(W4-20)

(W4-21)

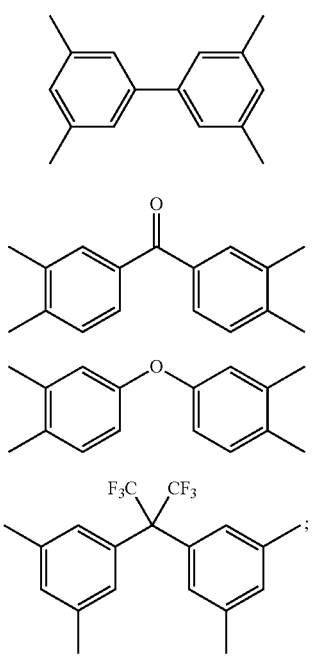

(I-2-a1)

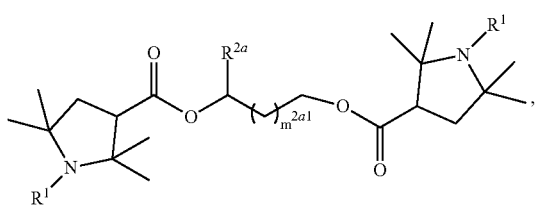

wherein $R^1$ has the same meaning as $R^1$ in the general formula (I), $R^{2a}$ represents an alkyl group having 1 to 10 carbon atoms, and $m^{21}$ denotes an integer in the range of 0 to 9.

2. The liquid crystal composition according to claim 1, further comprising one or two or more compounds represented by a general formula (II),

(II)

wherein $R^{II1}$ denotes an alkyl group having 1 to 10 carbon atoms, and one —$CH_2$— or two or more nonadjacent —$CH_2$— groups in the alkyl group may be independently substituted with —CH=CH—, —C≡C—, —O—, —CO—, —COO—, or —OCO—,
$A^{II1}$ and $A^{II2}$ independently denote a group selected from the group consisting of (a) a 1,4-cyclohexylene group in which one —$CH_2$— or two or more nonadjacent —$CH_2$— groups may be substituted with —O—,
(b) a 1,4-phenylene group in which one —CH= or two or more nonadjacent —CH= groups may be substituted with —N=, and
(c) a naphthalene-2,6-diyl group, a 1,2,3,4-tetrahydronaphthalene-2,6-diyl group, or a decahydronaphthalene-2,6-diyl group wherein one —CH= or two or more nonadjacent —CH= groups in the naphthalene-2,6-diyl group or the 1,2,3,4-tetrahydronaphthalene-2,6-diyl group may be substituted with —N=,
the groups (a), (b), and (c) may be independently substituted with a cyano group, a fluorine atom, or a chlorine atom,
$Z^{II1}$ denotes a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—,
$Y^{II1}$ denotes a hydrogen atom, a fluorine atom, a chlorine atom, a cyano group, or an alkyl group having 1 to 10 carbon atoms, one —$CH_2$— or two or more nonadjacent —$CH_2$— groups in the alkyl group may be independently substituted with —CH=CH—, —C≡C—, —O—, —CO—, —COO—, or —OCO—, and one or two or more hydrogen atoms in the alkyl group may be substituted with a fluorine atom, and
$m^{II1}$ is 1, 2, 3, or 4, and if $m^{II1}$ is 2, 3, or 4, pluralities of $A^{II1}$s and $Z^{II1}$s may be the same or different $A^{II1}$s and $Z^{II1}$s, respectively.

3. The liquid crystal composition according to claim 1, wherein the liquid crystal composition has a negative dielectric constant anisotropy (Δε) at 25° C.

4. The liquid crystal composition according to claim 1, wherein the liquid crystal composition has a positive dielectric constant anisotropy (Δε) at 25° C.

5. The liquid crystal composition according to claim 1, wherein a total amount of compound(s) represented by the general formula (I) in the liquid crystal composition ranges from 0.01% to 5% by mass.

6. The liquid crystal composition according to claim 2, wherein a total amount of compound(s) represented by the general formula (II) in the liquid crystal composition ranges from 10% to 90% by mass.

7. The liquid crystal composition according to claim 1, the liquid crystal composition has a refractive index anisotropy (Δn) in the range of 0.08 to 0.14 at 25° C., a rotational viscosity (γ1) in the range of 60 to 130 mPa·s at 25° C., and a nematic phase-isotropic liquid phase transition temperature ($T_{ni}$) in the range of 60° C. to 120° C.

8. The liquid crystal composition according to claim 1, comprising one or two or more polymerizable compounds and/or antioxidants.

9. A liquid crystal display device comprising the liquid crystal composition according to claim 1.

* * * * *